(12) United States Patent
Tsuchikama et al.

(10) Patent No.: US 12,084,403 B2
(45) Date of Patent: *Sep. 10, 2024

(54) LINKERS FOR ANTIBODY DRUG CONJUGATES

(71) Applicant: THE BOARD OF REGENTS OF THE UNIVERSITY OF TEXAS SYSTEM, Austin, TX (US)

(72) Inventors: Kyoji Tsuchikama, Houston, TX (US); Yasuaki Anami, Houston, TX (US); Chisato Tsuchikama, Houston, TX (US); Ningyang Zhang, Houston, TX (US); Zhiqiang An, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/173,413

(22) Filed: Feb. 23, 2023

(65) Prior Publication Data

US 2024/0059647 A1 Feb. 22, 2024

Related U.S. Application Data

(63) Continuation of application No. 16/616,148, filed as application No. PCT/US2018/034363 on May 24, 2018, now Pat. No. 11,629,122.

(60) Provisional application No. 62/510,505, filed on May 24, 2017, provisional application No. 62/639,894, filed on Mar. 7, 2018.

(51) Int. Cl.
| | |
|---|---|
| C07C 247/04 | (2006.01) |
| A61K 31/40 | (2006.01) |
| A61K 45/06 | (2006.01) |
| A61K 47/68 | (2017.01) |
| A61P 35/00 | (2006.01) |
| C07D 209/20 | (2006.01) |
| C07D 403/12 | (2006.01) |

(52) U.S. Cl.
CPC ............ *C07C 247/04* (2013.01); *A61K 31/40* (2013.01); *A61K 47/6889* (2017.08); *A61P 35/00* (2018.01); *C07D 209/20* (2013.01); *C07D 403/12* (2013.01); *A61K 45/06* (2013.01)

(58) Field of Classification Search
CPC .. C07C 247/04; A61K 31/40; A61K 47/6889; A61K 45/06; A61P 35/00; C07D 209/20; C07D 403/12
See application file for complete search history.

(56) References Cited

U.S. PATENT DOCUMENTS

| | | | |
|---|---|---|---|
| 11,629,122 B2 * | 4/2023 | Tsuchikama | C07D 403/12 424/179.1 |
| 2014/0046030 A1 | 2/2014 | Thanos et al. | |
| 2015/0314007 A1 | 11/2015 | Satomaa et al. | |

FOREIGN PATENT DOCUMENTS

| | | | |
|---|---|---|---|
| CN | 106232131 A | 12/2016 | |
| WO | WO 2006/079641 | 8/2006 | |
| WO | WO 2014/197854 | 12/2014 | |
| WO | WO 2015/061503 | 4/2015 | |
| WO | WO 2016/030791 | 3/2016 | |
| WO | WO-2016030791 A1 * | 3/2016 | ............ A61K 47/64 |
| WO | WO 2017/089890 | 6/2017 | |
| WO | WO 2017/089894 | 6/2017 | |

(Continued)

OTHER PUBLICATIONS

Dib, et al., Results in Chemistry 2022, vol. 4, 100304 (Year: 2022).*

(Continued)

*Primary Examiner* — Julie Wu
*Assistant Examiner* — Sydney Van Druff
(74) *Attorney, Agent, or Firm* — Parker Highlander PLLC

(57) ABSTRACT

In one aspect, the present disclosure provides compounds of the formula:

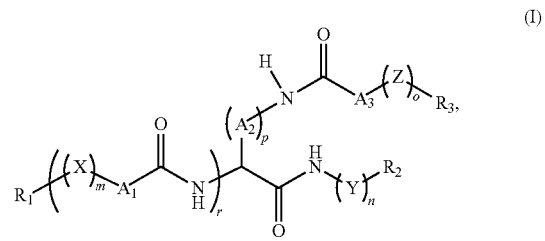

(I)

wherein the variables are as defined herein.
In another aspect, the present disclosure provides compounds of the formula:

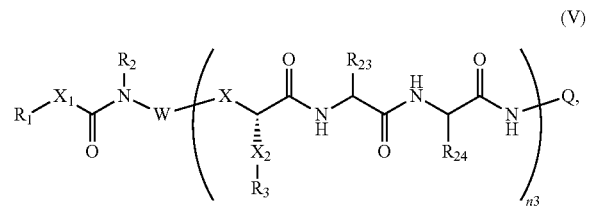

(V)

wherein the variables are as defined herein. In another aspect, the present disclosure also provides methods of preparing the compounds disclosed herein. In another aspect, the present disclosure provides antibody drug conjugates comprising compounds of the present disclosure. In another aspect, the present disclosure also provides phar- (Continued)

maceutical compositions and methods of use of the compounds and anti-body drug conjugates disclosed herein.

19 Claims, 32 Drawing Sheets

(56) References Cited

FOREIGN PATENT DOCUMENTS

| WO | WO 2017/214282 | 12/2017 | | |
|---|---|---|---|---|
| WO | WO-2017214282 A1 | * | 12/2017 | ......... A61K 31/4439 |

OTHER PUBLICATIONS

Nci, et al., Paclitaxel 2006; URL: https://www.cancer.gov/about-cancer/treatment/drugs/paclitaxel ; accessed Jan. 5, 2024 (Year: 2006).*

Akkapeddi et al., "Construction of homogeneous antibody-drug conjugates using site-selective protein chemistry", *Chem. Sci.*, 7:2954-2963, 2016.

International Preliminary Report on Patentability issued in corresponding PCT Application No. PCT/US2018/034363, mailed on Dec. 5, 2019.

International Search Report and Written Opinion issued in corresponding PCT Application No. PCT/US2018/034363, mailed on Oct. 1, 2018.

Stefan et al., "Highly potent, anthracycline-based antibody-drug conjugates generated by enzymatic, site-specific conjugation", *Mol. Cancer Ther.*, 16(5):879-892, 2017.

Partial Search Report and Invitation to Pay Additional Fees issued in corresponding European Application No. 18804968, mailed on Feb. 16, 2021.

Extended European Search Report issued in corresponding European Application No. 18804968, mailed on May 27, 2021.

Reaxys Query Report, dated Jan. 22, 2021, for Kim et al. WO 2017/89894.

Reaxys Query Report, dated Jan. 22, 2021, for Kim et al. WO 2017/89890.

Office Communication issued in corresponding Chinese App. No. 201880049787.7, mailed on Oct. 10, 2022. English Translation.

STN CA RN 1805804-29-8 Registry, dated Sep. 11, 2015.

Dib, Hanna, et al. "PEG-cored phosphorus dendrimers: Synthesis and functionalization." *Results in Chemistry* 4 (2022): 100304.

Cong, Hailin, et al. "Preparation and evaluation of PAMAM dendrimer-based polymer gels physically cross-linked by hydrogen bonding." *Biomaterials science* 7.9 (2019): 3918-3925.

* cited by examiner

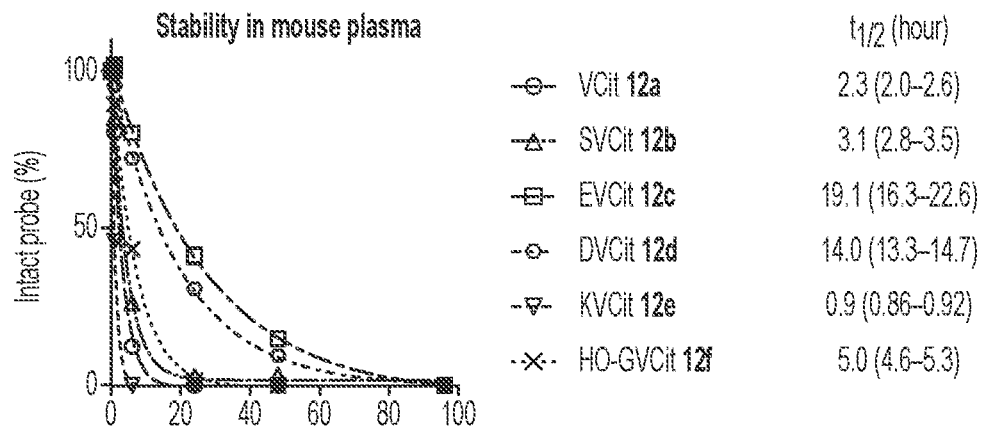
FIG. 13C
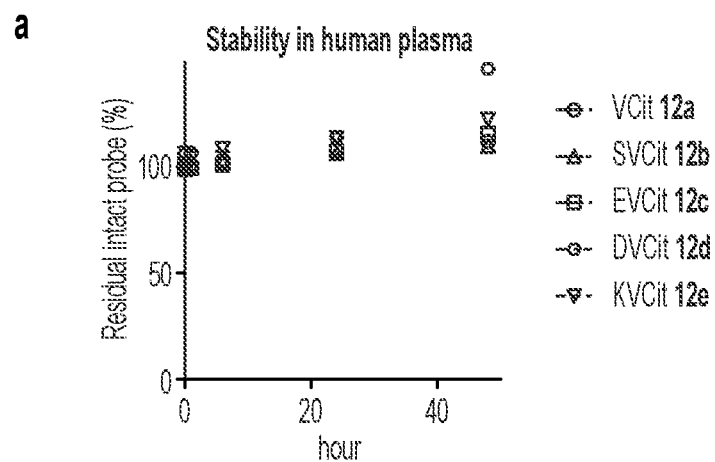
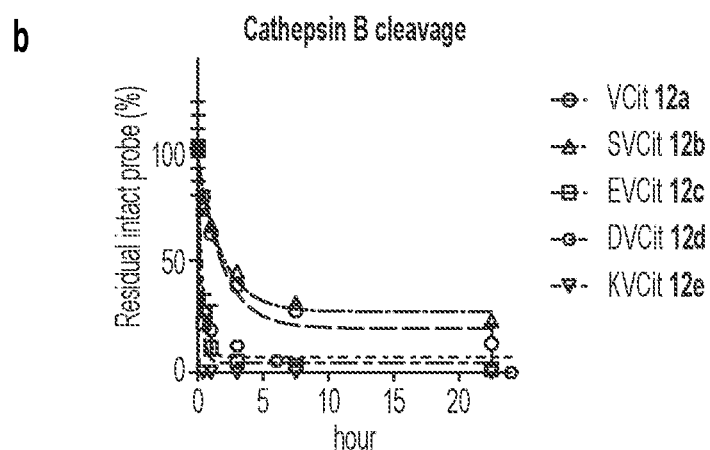
FIGS. 14A-14B

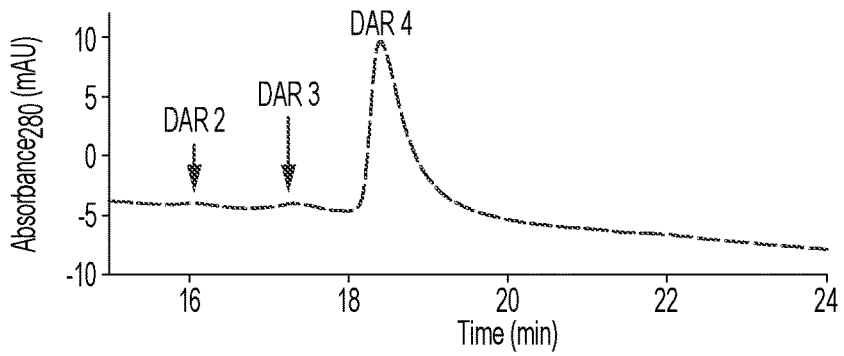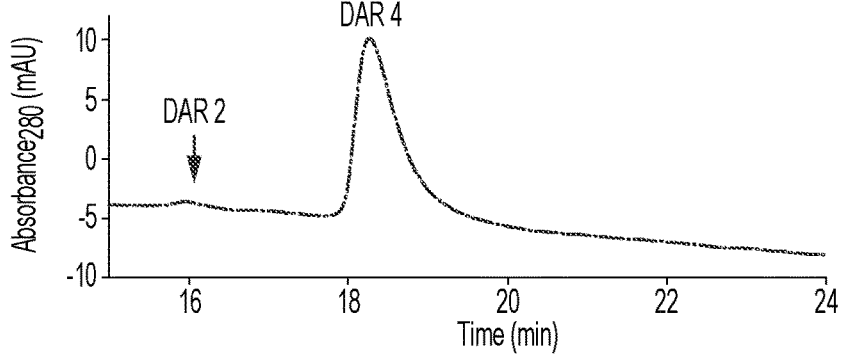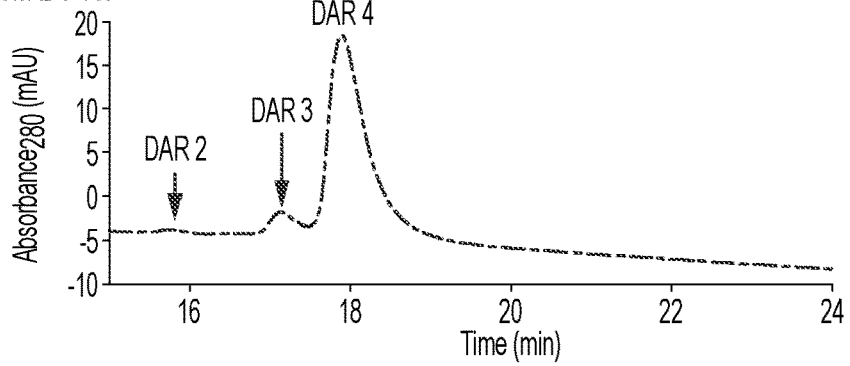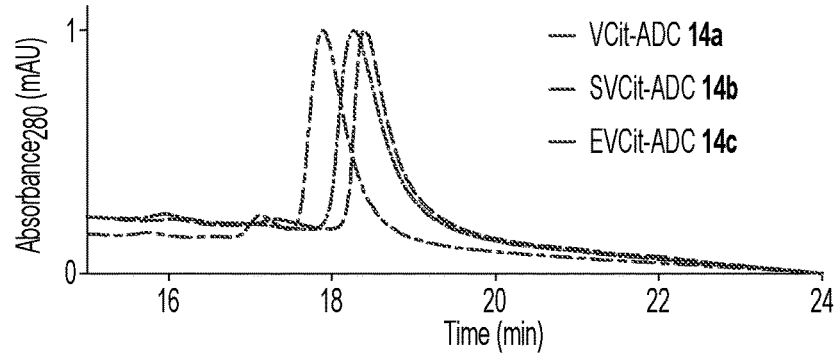
FIGS. 15D-15E a

| | $t_{1/2\beta}$ TOTAL mAb (day) | $t_{1/2\beta}$ ADC (day) | AUC$_{total\ mAb}$ (μg day mL$^{-1}$) | AUC$_{ADC}$ (μg day mL$^{-1}$) |
|---|---|---|---|---|
| N297A anti-HER2 mAb | 14.9 | — | 137.9 (103.2–172.5) | — |
| VCit ADC 14a | 14.5 | 2.0 | 157.3 (138.2–176.4) | 35.13 (31.8–38.4) |
| SVCit ADC 14b | 12.7 | 2.4 | 206.2 (185.4–226.9) | 64.13 (54.9–73.3) |
| EVCit ADC 14c | 14.0 | 12.0 | 162.8 (136.8–188.8) | 200.2 (174.3–226.1) | b

| | $t_{1/2\beta}$ TOTAL mAb (day) | $t_{1/2\beta}$ ADC (day) | AUC$_{total\ mAb}$ (μg day mL$^{-1}$) | AUC$_{ADC}$ (μg day mL$^{-1}$) |
|---|---|---|---|---|
| N297A anti-HER2 mAb | 14.9 | — | 137.9 (103.2–172.5) | — |
| VCit ADC 14a | 14.5 | 2.0 | 157.3 (138.2–176.4) | 35.13 (31.8–38.4) |
| SVCit ADC 14b | 12.7 | 2.4 | 206.2 (185.4–226.9) | 64.13 (54.9–73.3) |
| EVCit ADC 14c | 14.0 | 12.0 | 162.8 (136.8–188.8) | 200.2 (174.3–226.1) | c

| | t$_{1/2\beta}$ total mAb (day) | t$_{1/2\beta}$ ADC (day) | AUC$_{total\ mAb}$ (µg day mL$^{-1}$) | AUC$_{ADC}$ (µg day mL$^{-1}$) |
|---|---|---|---|---|
| N297A anti-HER2 mAb | 14.9 | — | 137.9 (103.2-172.5) | — |
| VCit ADC 14a | 14.5 | 2.0 | 157.3 (138.2-176.4) | 35.13 (31.8-38.4) |
| SVCit ADC 14b | 12.7 | 2.4 | 206.2 (185.4-226.9) | 64.13 (54.9-73.3) |
| EVCit ADC 14c | 14.0 | 12.0 | 162.8 (136.8-188.8) | 200.2 (174.3-226.1) | d

| | t$_{1/2\beta}$ total mAb (day) | t$_{1/2\beta}$ ADC (day) | AUC$_{total\ mAb}$ (µg day mL$^{-1}$) | AUC$_{ADC}$ (µg day mL$^{-1}$) |
|---|---|---|---|---|
| N297A anti-HER2 mAb | 14.9 | — | 137.9 (103.2-172.5) | — |
| VCit ADC 14a | 14.5 | 2.0 | 157.3 (138.2-176.4) | 35.13 (31.8-38.4) |
| SVCit ADC 14b | 12.7 | 2.4 | 206.2 (185.4-226.9) | 64.13 (54.9-73.3) |
| EVCit ADC 14c | 14.0 | 12.0 | 162.8 (136.8-188.8) | 200.2 (174.3-226.1) |

LINKERS FOR ANTIBODY DRUG CONJUGATES

This application is a continuation of U.S. patent application Ser. No. 16/616,148, filed Nov. 22, 2019, as a national phase application under 35 U.S.C. § 371 of International Application No. PCT/US2018/034363, filed May 24, 2018, which claims the benefit of U.S. Provisional Patent Application No. 62/510,505, filed May 24, 2017, and 62/639,894, filed Mar. 7, 2018, the entirety of each of which are incorporated herein by reference.

BACKGROUND

1. Field

This disclosure relates to the fields of medicine, pharmacology, chemistry, and oncology. In particular, compounds, compositions, methods of treatment, and methods of synthesis relating to antibody-drug conjugates (ADCs) are disclosed.

2. Related Art

Antibody-drug conjugates (ADCs), therapeutic monoclonal antibodies tethered to highly cytotoxic molecules (payloads) through chemical linkers, have emerged as a promising therapeutic format that can circumvent severe side effects derived from off-target cytotoxicity of chemotherapeutics in cancer chemotherapy (Polakis, 2016; Tsuchikama and An, 2016). Conjugation methods and chemical linkers are crucial factors determining pharmacokinetic and stability profiles of ADCs (Lu et al., 2016). Traditional conjugation methods are lysine amide coupling and cysteine maleimide coupling (Phillips et al., 2008; Katz et al., 2011). While simple and most frequently used, these methods yield ADCs that differ in conjugation sites and drug-to-antibody ratios (DARs). Such heterogeneous ADCs often suffer from increased clearance rates (Hamblett et al., 2004; Panowski et al., 2013) and require strictly controlled production to minimize DAR variation (Senter et al., 2012). To overcome this problem, site-specific conjugations have emerged as a means to construct homogeneous ADCs. Junutula and co-workers reported the THIOMAB technology, that utilizes two cysteine residues incorporated by genetic engineering for linker conjugation to give ADCs with defined DARs (Junutula et al., 2008). ADCs obtained by this method showed improved PK profiles and in-vivo efficacy compared to heterogeneous ADCs prepared by the traditional cysteine-maleimide coupling. Since then, other methods for constructing homogeneous ADCs including cysteine rebridging (Bryden et al., 2014; Behrens et al., 2015; Maruani et al., 2015; Robinson et al., 2017), incorporation of non-natural amino acids (Axup et al., 2012; Tian et al., 2014; Zimmerman et al., 2014; VanBrunt et al., 2015), and (chemo) enzymatic approaches (Popp et al., 2009; Jeger et al., 2010; Strop et al., 2013; Zhou et al., 2014; van Geel et al., 2015) have been developed. Schibli and co-workers reported an antibody-linker conjugation method using a microbial transglutaminase (MTGase). Through MTGase-mediated transpeptidation, this method covalently tethers ADC linkers containing terminal primary amines to the side chain of glutamine 295 (Q295) of the human IgG heavy chain (FIG. 1a) (Dennler et al., 2014).

Most ADC linkers developed to date only single payloads. Branched linkers that can load multiple payload molecules have yet to be fully explored. A multi-loading strategy allows for increase in DAR with less chemical or enzymatic modification to the antibody structure compared to traditional linkers. This increase in DAR could lead to efficient ADC construction, minimal destabilization of the antibody structure, and enhanced ADC efficacy. To our knowledge, there have previously been only a handful of examples of ADCs equipped with dual-loading linkers (Dubowchik et al., 2002; King et al., 2002; Maruani et al., 2016). A cysteine conjugation-based dual-loading linker enabling modular payload installation was recently developed (Levengood et al., 2017). Thus, there remains a need for ADCs capable of delivering multiple payloads.

In addition, the ADC linker structure and antibody-payload conjugation modality impact ADC homogeneity, cytotoxic potency, tolerability, and pharmacokinetics (PK). These key parameters critically contribute to overall in vivo therapeutic efficacy (Lu et al., 2016, Hamblett et al., 2004, Junutula et al., 2008, and Behrens et al., 2015). Thus, refining linker and conjugation chemistries is of crucial importance to maximize the therapeutic potential and safety profiles of ADCs.

SUMMARY

In some aspects, the present disclosure provides linker groups which may be used to prepare antibody drug conjugates, antibody drug conjugates prepared using these linkers, and compositions and methods of treatment thereof.

In some aspects, the present disclosure provides compounds of the formula:

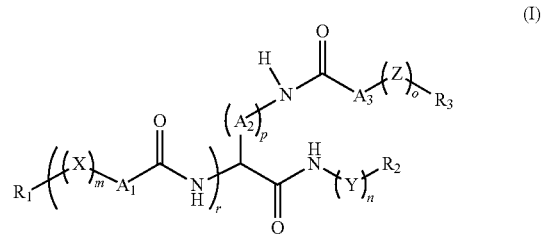

wherein:
 $A_1$, $A_2$, and $A_3$ are each independently alkanediyl$_{C1-12}$, arenediyl$_{C1-12}$, heteroarenediyl$_{C1-12}$, cycloalkanediyl$_{C1-12}$, heterocycloalkanediyl$_{C1-12}$, or a substituted version thereof, or a side chain group of a canonical amino acid;
 X, Y, and Z are each independently —[O(CH$_2$)$_q$]—, —[O(CHW')$_q$]—, or —[O(CW'W")$_q$]—;
 wherein:
  W' and W" are each independently amino, hydroxy, halo, mercapto, alkyl$_{C1-12}$, cycloalkyl$_{C1-12}$, alkenyl$_{C1-12}$, alkynyl$_{C1-12}$, aryl$_{C1-12}$, aralkyl$_{C1-12}$, heteroaryl$_{C1-12}$, heteroaralkyl$_{C1-12}$, heterocycloalkyl$_{C1-12}$, acyl$_{C1-12}$, acyloxy$_{C1-12}$, alkylamino$_{C1-12}$, or a substituted version of thereof;
  q is 1-3;
 m, n, o, and p are each independently 0-12;
 r is 1, 2, or 3;
 $R_1$, $R_2$, and $R_3$ are each independently —NH$_2$, —NHR$_4$, —NR$_4$R$_5$, —N$_3$, or a conjugating group;
 wherein:
  $R_4$ and $R_5$ are each independently alkyl$_{C1-12}$, cycloalkyl$_{C1-12}$, alkenyl$_{C1-12}$, alkynyl$_{C1-12}$, aryl$_{C1-12}$, aralkyl$_{C1-12}$, heteroaryl$_{C1-12}$, heteroaralkyl$_{C1-12}$, heterocycloalkyl$_{C1-12}$, acyl$_{C1-12}$, acyloxy$_{C1-12}$, alkylamino$_{C1-12}$, or a substituted version thereof, or a monovalent amino protecting group; or $R_4$ and $R_5$ are taken together and is a divalent amino protecting group;

provided that at least one of $R_1$, $R_2$, and $R_3$ is —NH$_2$ and at least one of $R_1$, $R_2$, and $R_3$ is —N$_3$;

or a pharmaceutically acceptable salt thereof.

In some embodiments, the compounds are further defined as:

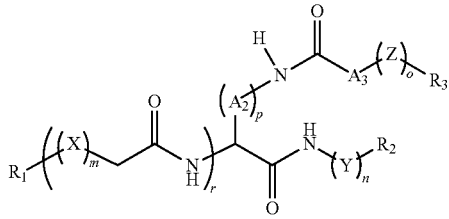

(II)

In some embodiments, the compounds are further defined as:

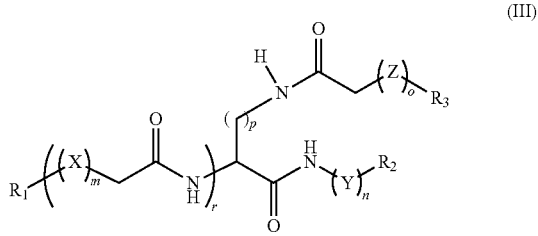

(III)

In some embodiments, X is —[O(CH$_2$)$_q$]— or —[O(CHW')$_q$]—. In some embodiments, Y is —[O(CH$_2$)$_q$]— or —[O(CHW')$_q$]—. In some embodiments, Z is —[O(CH$_2$)$_q$]— or —[O(CHW')$_q$]—. In some embodiments, W' is amino, hydroxy, halo, or mercapto. In other embodiments, W' is alkyl$_{C1-12}$, cycloalkyl$_{C1-12}$, or a substituted version thereof. In some embodiments, W' is alkyl$_{C1-12}$ or substituted alkyl$_{C1-12}$. In other embodiments, W' is acyl$_{C1-12}$, acyloxy$_{C1-12}$, alkylamino$_{C1-12}$, or a substituted version thereof.

In some embodiments, two of $R_1$, $R_2$, and $R_3$ are —N$_3$. In some embodiments, one of $R_1$, $R_2$, and $R_3$ is —NH$_2$, —NHR$_4$, or —NR$_4$R$_5$. In some embodiments, one of $R_1$, $R_2$, and $R_3$ is —NH$_2$. In some embodiments, q is 1. In other embodiments, q is 2. In other embodiments, q is 3.

In some embodiments, the compounds are further defined as:

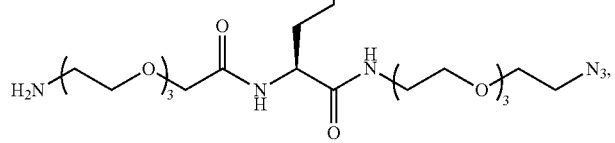

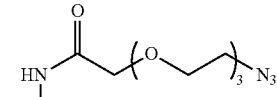

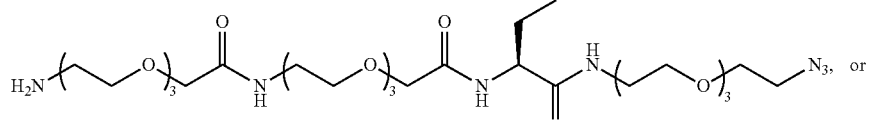

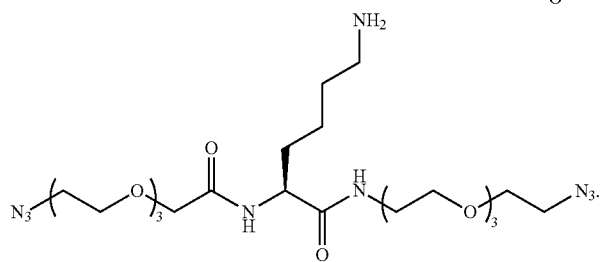

In still yet another aspect, the present disclosure provides conjugates of the formula:

$$(X_1-Z_1)_r-L-A_4 \quad (IV)$$

wherein:
X$_1$ is a drug;
L is a linker described herein;
Z$_1$ is a spacer group;
r is 1-12; and
A$_4$ is a cell targeting moiety.

In some embodiments, X$_1$ is a chemotherapeutic drug such as MMAF. In some embodiments, Z$_1$ comprises a polypeptide cleavable by an intracellular enzyme such as cathepsin B. In some embodiments, Z$_1$ comprises a self-immolating group. In some embodiments, Z$_1$ is a spacer group comprising an alkyne moiety, a polypeptide moiety, and a p-aminobenzyloxycarbonyl (PABC) moiety. In some embodiments, the alkyne is dibenzocyclootyne (DBCO). In some embodiments, the polypeptide is Val-Cit. In some embodiments, A$_4$ is an antibody whose antigen is a tumor associated antigen.

In some embodiments, L is a linker group wherein one of R$_1$, R$_2$, and R$_3$ is a conjugating group. In some embodiments, the conjugating group is linked to a second cell targeting moiety A$_4$'. In some embodiments, A$_4$' is a different cell targeting moiety than A$_4$. In some embodiments, the conjugating group is linked to a second spacer-drug moiety —(Z$_1$'-X$_1$')$_r$. In some embodiments, —(Z$_1$'-X$_1$')$_r$ is a different spacer-drug moiety than —(Z$_1$-X$_1$)$_r$.

In further aspects, the present disclosure provides compounds of the formula:

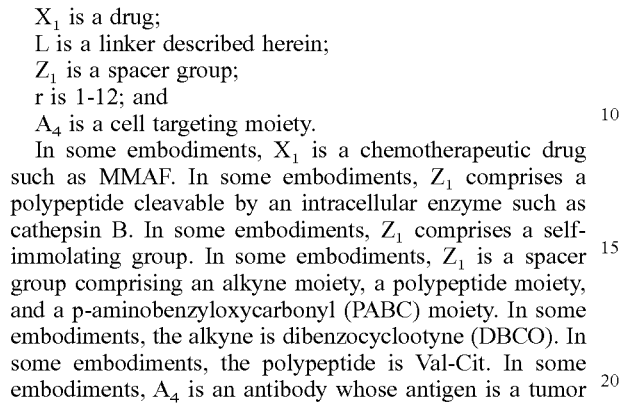

wherein:
X$_1$ is a covalent bond, alkanediyl$_{(C \leq 12)}$, or substituted alkanediyl$_{(C \leq 12)}$;
R$_1$ is hydrogen, —(OCH$_2$CH$_2$)$_{n1}$ZR$_6$, or substituted —(OCH$_2$CH$_2$)$_{n1}$ZR$_6$, wherein:
n1 is 0-50; and
R$_6$ is hydrogen, hydroxy, amine, mercapto, hydroxylamine, hydrazine, or azide; or alkyl$_{(C \leq 12)}$, alkenyl$_{(C \leq 12)}$, alkynyl$_{(C \leq 12)}$, alkylhydrazine$_{(C \leq 12)}$, or a substituted version of any of these groups;
a polyglycine comprising from 1 to 6 glycine units; or
a substructure of the formula:

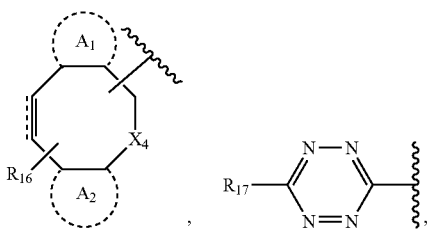

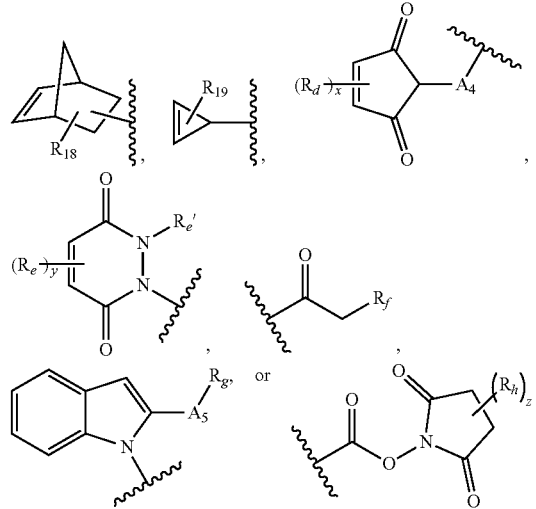

wherein:
A$_1$ and A$_2$ are each independently absent or arenediyl$_{(C \leq 12)}$, substituted arenediyl$_{(C \leq 12)}$, heteroarenediyl$_{(C \leq 12)}$, or substituted heteroarenediyl$_{(C \leq 12)}$, and form a fused arene$_{(C \leq 12)}$, substituted arene$_{(C \leq 12)}$, heteroarene$_{(C \leq 12)}$, or substituted heteroarene$_{(C \leq 12)}$;
A$_4$ or A$_5$ are each independently selected from a covalent bond, alkanediyl$_{(C \leq 8)}$, or substituted alkanediyl$_{(C \leq 8)}$;
R$_d$, R$_e$, R$_e$', and R$_h$ are each independently selected from hydrogen, halo, sulfate, tosylate, mesylate, aryl$_{(C \leq 8)}$, or substituted aryl$_{(C \leq 8)}$;
R$_f$ is halo;
R$_g$ is amine, hydrazine, alkylamino$_{(C \leq 8)}$, substituted alkylamino$_{(C \leq 8)}$, dialkylamino$_{(C \leq 8)}$, substituted dialkylamino$_{(C \leq 8)}$, alkylhydrazine$_{(C \leq 8)}$, or substituted alkylhydrazine$_{(C \leq 8)}$;
X$_4$ is O, N, CH$_2$, or X$_4$ is alkanediyl$_{(C \leq 8)}$ or substituted alkanediyl$_{(C \leq 8)}$ and is taken together to form a fused cycloalkane group consisting of 3 to 8 ring atoms;
R$_{16}$ is hydroxy, amino, or oxo;
R$_{17}$ is carboxy; or
alkyl$_{(C \leq 12)}$, amido$_{(C \leq 12)}$, aryl$_{(C \leq 12)}$, heteroaryl$_{(C \leq 12)}$, —C(O)NR$_{20}$R$_{20}$', or a substituted version of any of these groups wherein:
R$_{20}$ and R$_{20}$' are each independently hydrogen; or alkyl$_{(C \leq 12)}$, aryl$_{(C \leq 12)}$, or a substituted version of either of these groups;
R$_{18}$ and R$_{19}$ are each independently hydroxy, amino, halo; or alkyl$_{(C \leq 12)}$, aryl$_{(C \leq 12)}$, or a substituted version of either of these groups;
Z is a covalent bond, alkanediyl$_{(C \leq 12)}$, —C(O)-alkanediyl$_{(C \leq 12)}$, —C(O)-alkanediyl$_{(C \leq 12)}$—C(O)NH—, or a substituted version of any of these groups;
R$_2$ is hydrogen, alkyl$_{(C \leq 12)}$, substituted alkyl$_{(C \leq 12)}$, acyl$_{(C \leq 12)}$, substituted acyl$_{(C \leq 12)}$, or a monovalent amino protecting group;
W is a covalent bond or a polyvalent polymer having 2-21 connection points;
n3 is 1 to 20 provided that when W is a covalent bond then n3 is 1 and when W is a polyvalent polymer then n3 is less than or equal to one less than the number of connection points;

Each X is independently a covalent bond, alkanediyl$_{(C \leq 12)}$, or substituted alkanediyl$_{(C \leq 12)}$.

Each $X_2$ is independently alkanediyl$_{(C \leq 12)}$ or substituted alkanediyl$_{(C \leq 12)}$;

Each $R_3$ is independently hydroxy, or amino; or
  alkoxy$_{(C \leq 12)}$, acyloxy$_{(C \leq 12)}$, alkylamino$_{(C \leq 12)}$, dialkylamino$_{(C \leq 12)}$, amido$_{(C \leq 12)}$, heteroaryl$_{(C \leq 12)}$, or a substituted version of any of these groups; or
  —$X_9$—C(O)$R_7$, wherein:
    $X_9$ is O, —NR$_b$—, or a covalent bond;
      $R_b$ is hydrogen, alkyl$_{(C \leq 6)}$, substituted alkyl$_{(C \leq 6)}$, or a monovalent amino protecting group;
    $R_7$ is hydroxy or amino; or
      alkoxy$_{(C \leq 12)}$, alkylamino$_{(C \leq 12)}$, dialkylamino$_{(C \leq 12)}$, or a substituted version of any of these groups; or
  $A_3SO_2NR_{21}R_{21}'$, -$A_3P(O)(OH)OR_{22}$, or -$A_3SO_2OR_{22}'$, wherein:
    $A_3$ is O, —NR$_c$—, or a covalent bond;
      $R_c$ is hydrogen, alkyl$_{(C \leq 6)}$, substituted alkyl$_{(C \leq 6)}$, or a monovalent amino protecting group;
    $R_{21}$, $R_{21}'$, $R_{22}$, and $R_{22}'$ are each independently hydrogen, alkyl$_{(C \leq 12)}$, cycloalkyl$_{(C \leq 12)}$, aryl$_{(C \leq 12)}$, heteroaryl$_{(C \leq 12)}$, aralkyl$_{(C \leq 12)}$, heteroaralkyl$_{(C \leq 12)}$, or a substituted version of any of these groups;

Each $R_{23}$ is independently the side chain moiety of alanine, valine, leucine, isoleucine, phenylalanine, tyrosine, tryptophan, a hydroxyl-protected version of tyrosine, or an amino-protected version of tryptophan; and Each $R_{24}$ is independently the side chain moiety of alanine, ornithine, lysine, arginine, citrulline, or an amino-protected version thereof;

Each Q is independently a group of the formula:

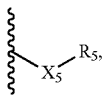

wherein:
  Each $R_5$ is independently hydrogen or —C(O)—$R_8$, wherein:
    $R_8$ is a chemotherapeutic agent;
  Each $X_5$ is independently a covalent bond, O, S, —NH—, alkanediyl$_{(C \leq 12)}$, substituted alkanediyl$_{(C \leq 12)}$, —(OCH$_2$CH$_2$)$_{n2}$—, or substituted —(OCH$_2$CH$_2$)$_{n2}$—, wherein:
    n2 is 0-50; or
  a group of the formula:

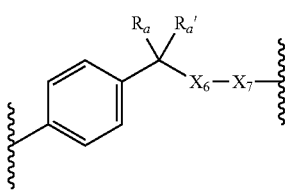

wherein:
  $R_a$ and $R_a'$ are each independently hydrogen, alkyl$_{(C \leq 12)}$, or substituted alkyl$_{(C \leq 12)}$;
  $X_6$ is O or —NR$_{26}$R$_{26}'$—, wherein:
    $R_{26}$ and $R_{26}'$ are each independently alkyl$_{(C \leq 12)}$ or substituted alkyl$_{(C \leq 12)}$;
  $X_7$ is a covalent bond, O, S, —NH—, —(OCH$_2$CH$_2$)$_{n3}$—, or substituted —(OCH$_2$CH$_2$)$_{n3}$—, wherein:
    n3 is 0-50; or
  a group of the formula:

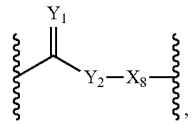

wherein:
  $Y_1$ is O or S;
  $Y_2$ is O, S, —NH—, or —NR$_{27}$—, wherein:
    $R_{27}$ is alkyl$_{(C \leq 12)}$ or substituted alkyl$_{(C \leq 12)}$; and
  $X_8$ is a covalent bond, O, S, —NH—, —(OCH$_2$CH$_2$)$_{n3}$—, or substituted —(OCH$_2$CH$_2$)$_{n3}$—;

or a pharmaceutically acceptable salt thereof.

In some embodiments, W is a polyvalent polymer such as a dendrimer. In some embodiments, the polyvalent polymer has 3 connection points. In some embodiments, n3 is greater than 1. In other embodiments, the polyvalent polymer has 2 connection points. In other embodiments, W is a covalent bond. In some embodiments, X is a covalent bond. In some embodiments, $X_1$ is alkanediyl$_{(C \leq 12)}$, or substituted alkanediyl$_{(C \leq 12)}$. In further embodiments, $X_1$ is alkanediyl$_{(C \leq 12)}$ such as methylene.

In some embodiments, $R_{24}$ is the side chain moiety of citrulline or an amino-protected version thereof. In further embodiments, $R_{24}$ is the side chain moiety of citrulline. In some embodiments, $R_{23}$ is the side chain moiety of valine. In some embodiments, $X_2$ is alkanediyl$_{(C \leq 12)}$. In further embodiments, $X_2$ is alkanediyl$_{(C \leq 6)}$ such as methylene or ethanediyl. In some embodiments, $R_3$ is hydroxy, amino, alkoxy$_{(C \leq 12)}$, substituted alkoxy$_{(C \leq 12)}$, alkylamino$_{(C \leq 12)}$, dialkylamino$_{(C \leq 12)}$, amido$_{(C \leq 12)}$, or —$X_9$—C(O)$R_7$. In further embodiments, $R_3$ is hydroxy. In other embodiments, $R_3$ is amino. In other embodiments, $R_3$ is alkoxy$_{(C \leq 12)}$ such as tert-butoxy. In other embodiments, $R_3$ is —$X_9$—C(O)$R_7$. In some embodiments, $X_9$ is —NH— or a covalent bond. In further embodiments, $X_9$ is a covalent bond. In some embodiments, $R_7$ is hydroxy. In other embodiments, $R_7$ is alkoxy$_{(C \leq 12)}$ or substituted alkoxy$_{(C \leq 12)}$. In further embodiments, $R_7$ is alkoxy$_{(C \leq 12)}$ such as tert-butoxy.

In some embodiments, $R_5$ is hydrogen. In other embodiments, $R_5$ is a —C(O)—$R_8$, wherein $R_8$ is a chemotherapeutic agent. In further embodiments, the chemotherapeutic agent is monomethyl auristatin E (MMAE), auristatin F (MMAF), or a derivative of auristatin, dolastatine, maytansine, duocarmycin, tubulysin, chalicheamicin, pyrrobenzodiazepine dimer, anthracycline, paclitaxel, vinblastine, or amanitin. In still further embodiments, the chemotherapeutic agent is MMAF. In some embodiments, $X_5$ is a group of the formula:

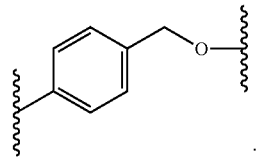 [SMILES: *OCc1ccc(*)cc1]

In some embodiments, $R_1$ is —(OCH$_2$CH$_2$)$_{n1}$ZR$_6$, or substituted —(OCH$_2$CH$_2$)$_{n1}$ZR$_6$. In some embodiments, $R_6$ is hydroxy. In other embodiments, $R_6$ is a substructure of the formula:

In some embodiments, Z is —C(O)-alkanediyl$_{(C\leq12)}$—C(O)NH— or a substituted —C(O)-alkanediyl$_{(C\leq12)}$—C(O)NH—. In further embodiments, Z is —C(O)-alkanediyl$_{(C\leq12)}$—C(O)NH— such as —C(O)-ethanediyl-C(O)NH—. In some embodiments, n1 is 0-10. In further embodiments, n1 is 0-5 such as 3. In yet further embodiments, n1 is not 0.

In other aspects, the present disclosure provides conjugates of the formula:

T-L    (VI)

wherein:
T is a cell targeting moiety; and
L is a linker of the present disclosure. In some embodiments, L comprises a chemotherapeutic drug such as MMAF. In some embodiments, T is an antibody. In further embodiments, the antibody is an antibody whose antigen is a tumor associated antigen.

In still other aspects, the present disclosure provides compounds of the formula:

(VII)

wherein:
$X_1$ is alkyl$_{(C\leq12)}$ or substituted alkyl$_{(C\leq12)}$;
$R_2$ is hydrogen, alkyl$_{(C\leq12)}$, substituted alkyl$_{(C\leq12)}$, acyl$_{(C\leq12)}$, substituted acyl$_{(C\leq12)}$, or a monovalent amino protecting group;
W is a covalent bond or a polyvalent polymer having 2-21 connection points;
n3 is 1 to 20 provided that when W is a covalent bond n3 is 1 and when W is a polyvalent polymer n3 is less than or equal to one less than the number of connection points;
Each X is independently a covalent bond, alkanediyl$_{(C\leq12)}$, or substituted alkanediyl$_{(C\leq12)}$.
Each $X_2$ is independently alkanediyl$_{(C\leq12)}$ or substituted alkanediyl$_{(C\leq12)}$;
Each $R_3$ is independently hydroxy, or amino; or
alkoxy$_{(C\leq12)}$, acyloxy$_{(C\leq12)}$, alkylamino$_{(C\leq12)}$, dialkylamino$_{(C\leq12)}$, amido$_{(C\leq12)}$, heteroaryl$_{(C\leq12)}$, or a substituted version of any of these groups; or —$X_9$—C(O)R$_7$, wherein:
$X_9$ is O, —NR$_b$—, or a covalent bond;
$R_b$ is hydrogen, alkyl$_{(C\leq6)}$, substituted alkyl$_{(C\leq6)}$, or a monovalent amino protecting group;
$R_7$ is hydroxy or amino; or
alkoxy$_{(C\leq12)}$, alkylamino$_{(C\leq12)}$, dialkylamino$_{(C\leq12)}$, or a substituted version of any of these groups; or
-A$_3$SO$_2$NR$_{21}$R$_{21}$', -A$_3$P(O)(OH)OR$_{22}$, or -A$_3$SO$_2$OR$_{22}$', wherein:
$A_3$ is O, —NR$_c$—, or a covalent bond;
$R_c$ is hydrogen, alkyl$_{(C\leq6)}$, substituted alkyl$_{(C\leq6)}$, or a monovalent amino protecting group;
$R_{21}$, $R_{21}$', $R_{22}$, and $R_{22}$' are each independently hydrogen, alkyl$_{(C\leq12)}$, cycloalkyl$_{(C\leq12)}$, aryl$_{(C\leq12)}$, heteroaryl$_{(C\leq12)}$, aralkyl$_{(C\leq12)}$, heteroaralkyl$_{(C\leq12)}$, or a substituted version of any of these groups;

Each $R_{23}$ is independently the side chain moiety of alanine, valine, leucine, isoleucine, phenylalanine, tyrosine, tryptophan, a hydroxyl-protected version of tyrosine, or an amino-protected version of tryptophan; and Each $R_{24}$ is independently the side chain moiety of alanine, ornithine, lysine, arginine, citrulline, or an amino-protected version thereof;

Each Q is independently a group of the formula:

wherein:
Each $R_5$ is independently hydrogen or —C(O)—R$_8$, wherein:
$R_8$ is a chemotherapeutic agent;
Each $X_5$ is independently a covalent bond, O, S, —NH—, alkanediyl$_{(C\leq12)}$, substituted alkanediyl$_{(C\leq12)}$, —(OCH$_2$CH$_2$)$_{n2}$—, or substituted —(OCH$_2$CH$_2$)$_{n2}$—, wherein:
n2 is 0-50; or
a group of the formula:

wherein:
$R_a$ and $R_a$' are each independently hydrogen, alkyl$_{(C\leq12)}$, or substituted alkyl$_{(C\leq12)}$;
$X_6$ is O or —NR$_{26}$R$_{26}$'—, wherein:
$R_{26}$ and $R_{26}$' are each independently alkyl$_{(C\leq12)}$ or substituted alkyl$_{(C\leq12)}$;

X$_7$ is a covalent bond, O, S, —NH—, —(OCH$_2$CH$_2$)$_{n3}$—, or substituted —(OCH$_2$CH$_2$)$_{n3}$—, wherein:
n3 is 0-50; or
a group of the formula:

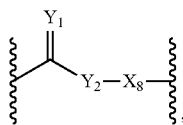

wherein:
Y$_1$ is O or S;
Y$_2$ is O, S, —NH—, or —NR$_{27}$—, wherein:
R$_{27}$ is alkyl$_{(C≤12)}$ or substituted alkyl$_{(C≤12)}$; and
X$_8$ is a covalent bond, O, S, —NH—, —(OCH$_2$CH$_2$)$_{n3}$—, or substituted —(OCH$_2$CH$_2$)$_{n3}$—;
or a pharmaceutically acceptable salt thereof.

In some embodiments, W is a polyvalent polymer such as a dendrimer. In some embodiments, the polyvalent polymer has 3 connection points. In some embodiments, n3 is greater than 1. In other embodiments, the polyvalent polymer has 2 connection points. In other embodiments, W is a covalent bond. In some embodiments, X is a covalent bond. In some embodiments, X$_1$ is alkyl$_{(C≤12)}$ such as ethyl or methyl. In some embodiments, R$_{24}$ is the side chain moiety of citrulline or an amino-protected version thereof. In further embodiments, R$_{24}$ is the side chain moiety of citrulline. In some embodiments, R$_{23}$ is the side chain moiety of valine. In some embodiments, X$_2$ is alkanediyl$_{(C≤12)}$. In further embodiments, X$_2$ is alkanediyl$_{(C≤6)}$ such as methylene or ethanediyl.

In some embodiments, R$_3$ is hydroxy, amino, alkoxy$_{(C≤12)}$, substituted alkoxy$_{(C≤12)}$, alkylamino$_{(C≤12)}$, dialkylamino$_{(C≤12)}$, amido$_{(C≤12)}$, or —X$_9$—C(O)R$_7$. In further embodiments, R$_3$ is hydroxy. In other embodiments, R$_3$ is amino. In still other embodiments, R$_3$ is alkoxy$_{(C≤12)}$ such as tert-butoxy. In yet other embodiments, R$_3$ is —X$_9$—C(O)R$_7$. In some embodiments, X$_9$ is —NH— or a covalent bond. In further embodiments, X$_9$ is a covalent bond. In some embodiments, R$_7$ is hydroxy. In other embodiments, R$_7$ is alkoxy$_{(C≤12)}$ or substituted alkoxy$_{(C≤12)}$. In still further embodiments, R$_7$ is alkoxy$_{(C≤12)}$ such as tert-butoxy. In some embodiments, R$_5$ is hydrogen. In other embodiments, R$_5$ is a —C(O)—R$_8$, wherein R$_8$ is a chemotherapeutic agent. In further embodiments, the chemotherapeutic agent is monomethyl auristatin E (MMAE), auristatin F (MMAF), or a derivative of auristatin, dolastatine, maytansine, duocarmycin, tubulysin, chalicheamicin, pyrrobenzodiazepine dimer, anthracycline, paclitaxel, vinblastine, or amanitin. In still further embodiments, the chemotherapeutic agent is MMAF. In some embodiments, X$_5$ is a group of the formula:

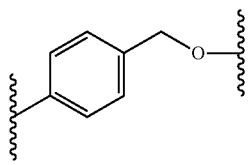

In still yet another aspect, the present disclosure provides pharmaceutical compositions comprising a conjugate described herein and an excipient. In some embodiments, the pharmaceutical composition is formulated for oral, intraadiposal, intraarterial, intraarticular, intracranial, intradermal, intralesional, intramuscular, intranasal, intraocular, intrapericarial, intraperitoneal, intrapleural, intraprostatical, intrarectal, intrathecal, intratracheal, intratumoral, intraumbilical, intravaginal, intravenous, intravesicularal, intravitreal, liposomal, local, mucosal, parenteral, rectal, subconjunctival, subcutaneous, sublingual, topical, transbuccal, transdermal, vaginal, via a catheter, via a lavage, via continuous infusion, via infusion, via inhalation, via injection, via local delivery, or via localized perfusion administration.

In still yet another aspect, the present disclosure provides methods of treating a disease or disorder in a patient comprising administering to the patient a therapeutically effective amount of a conjugate or pharmaceutical composition described herein. In some embodiments, the disease or disorder is cancer such as a carcinoma, sarcoma, lymphoma, leukemia, melanoma, mesothelioma, multiple myeloma, or seminoma or is a cancer of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid.

In other embodiments, the disease or disorder is a microbial infection. In other embodiments, the disease or disorder is an autoimmune disease. In other embodiments, the disease or disorder is associated with inflammation. In some embodiments, the methods further comprise administering a second therapy. In some embodiments, the patient is a mammal such as a human. In some embodiments, the conjugate or composition is administered once. In other embodiments, the conjugate or composition is administered two or more times.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE FIGURES

The following drawings form part of the present specification and are included to further demonstrate certain aspects of the present disclosure. The disclosure may be better understood by reference to one or more of these drawings in combination with the detailed description.

FIGS. 13A-13C show structures and plasma stability of cathepsin B-responsive cleavable peptides. (FIG. 13A) VCit and EVCit-based ADC linkers. VCit linkers are unstable in mouse plasma due to susceptibility to the extracellular carboxylesterase Ces1c. This instability often triggers premature release of payload during circulation. In contrast, VCit-based tripeptide sequences with high polarity such as EVCit are responsive to cathepsin-B mediated cleavage but highly stable in mouse plasma. (FIG. 13B) Structures of pyrene-based small-molecule probes containing a VCit (12a), SVCit (12b), EVCit (12c), DVCit (12d), KVCit (12e), or hydroxy-GVCit (12f) cleavable sequence. (FIG. 13C) Stability of probes 1a-f in undiluted BALB/c mouse plasma at 37° C. EVCit and DVCit probes 12c-12d showed great plasma stability tested while highly responsive to cathepsin B-mediated cleavage. Plasma stability data shown are representative of more than two independent trials performed in technical duplicate. Error bars represent SEM and values in parentheses are 95% confidential intervals.

FIGS. 14A & 14B show (FIG. 14A) Human cathepsin B-mediated cleavage of probed 12a-12e at 37° C. Left panel: the VCit and SVCit probes were not completely cleaved because a limited amount of cathepsin B was used to accurately monitor the highly responsive EVCit, DVCit, and KVCit probes. Right panel: VCit and SVCit probes were almost cleaved by 10 times cathepsin B as much as limited conditions (left panel). (FIG. 14B) Stability of probes 12a-12e in human plasma at 37° C. All assays were performed in duplicate and error bars represent SEM.

FIGS. 15A-15E show construction and characterization of ADCs 14a-c. (FIG. 15A) Construction of ADCs 14a-c by MTGase-mediated branched linker conjugation and following strain-promoted azide-alkyne cycloaddition (spark: PEG spacer-cleavable linker-MMAF module). (FIG. 15B) Deconvoluted ESI-mass spectra. Top panel: N297A anti-HER2 mAb. Second panel: antibody-branched linker conjugate. Third-fifth panels: highly homogeneous ADCs 14a-c. Asterisk (*) indicates a fragment ion detected in ESI-MS analysis. (FIG. 15C) Size-exclusion chromatography (SEC) traces of ADCs 3a-c. (FIG. 15D) Hydrophobic interaction chromatography (HIC) analysis of ADCs 3a-c under physiological conditions (phosphate buffer, pH 7.4). (FIG. 15E) Overlay of the three HIC traces. DAR, drug-to-antibody ratio; DBCO, dibenzocyclooctyne; MMAF, monomethyl auristatin F; MTGase, microbial transglutaminase; PABC, p-aminobenzyloxycarbonyl; PEG, polyethylene glycol.

(FIG. 20A) stability in human plasma. (FIG. 20B) stability in mouse plasma. Cell killing potency in the breast cancer cell lines KPL-4 (FIG. 20C), JIMT-1 (FIG. 20D), and MDA-MB-231 (FIG. 20E). Unconjugated N297A anti-HER2 mAb (black), VCit-ADC 14a, SVCit-ADC 14b, EVCit-ADC 14c, non-cleavable ADC 15, and isotype control ADC containing EVCit 16 (non-targeting control). All assays were performed in quadruplicate. Error bars represent SEM.

(FIGS. 23A and 23B) PK of VCit, EVCit, and SVCit ADCs 14a-c in BALB/c female mice (n=3). At the indicated time points, blood was collected to quantify total antibody (conjugated and unconjugated, FIG. 23A) and ADC (conjugated only, FIG. 23B) by sandwich ELISA. EVCit-ADC 3c exhibited greater stability in mice than VCit- and hydroxy-functionalized SVCit ADCs 14a and 14b. (FIGS. 23C and 23D) Antitumor activity of anti-HER2 ADCs 3a and 3c in the JIMT-1 (FIG. 23C) and KPL-4 (FIG. 23D) breast xenograft models in female NCr nude mice (n=4 for vehicle in the JIMT-1 model; n=3 for vehicle in the KPL-4 model; n=5 for ADCs). A single dose of each ADC (1 or 3 mg/kg) was administered to mice when a mean tumor volume reached ~100 mm³ (indicated with a black arrow). (FIGS. 23E and 23F) Changes in the percentages of surviving mice over time in the JIMT-1 (FIG. 23E) and KPL-4 (FIG. 23F) models. Mice were euthanized at the pre-defined endpoint (see the Method). EVCit-based ADC 14c (3 mg/kg; 1 mg/kg) exerted much greater treatment efficacy than VCit variant 14a (3 mg/kg) in both models. Error bars represent SEM. * p<0.025,  p<0.01, * p<0.005.

DESCRIPTION OF ILLUSTRATIVE EMBODIMENTS

Figure 1:
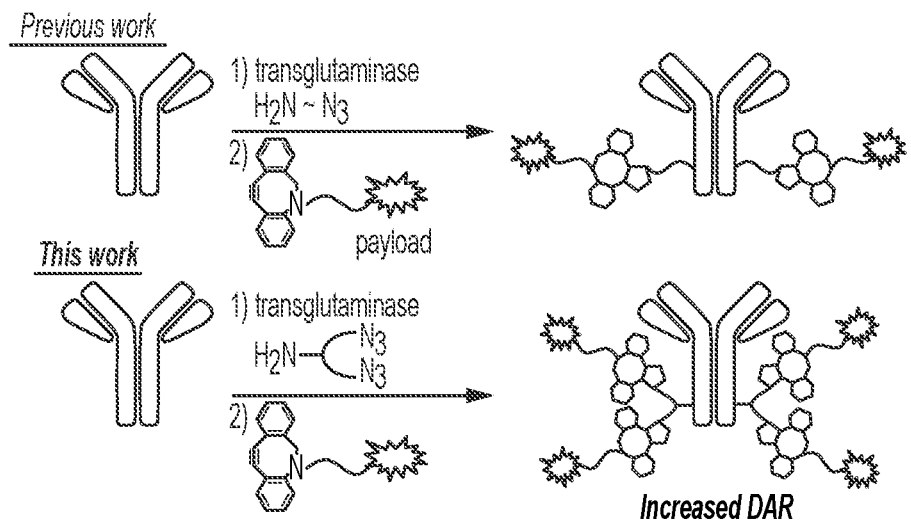
FIG. 1. MTGase-mediated antibody¬-drug conjugation using linear or branched linkers. Azide-containing linkers are conjugated to the side chain of Q295 of the IgG heavy chain using MTGase, followed by installation of payload by strain-promoted azide-alkyne cyclization to afford an ADC with a DAR of 2 (linear linker) or 4 (branched linker).

The present disclosure provides ADC constructed from branch linkers or linkers exhibiting improved properties. These compounds may be used in the treatment of cancer or other diseases, wherein the ADC is used to deliver a chemical payload. In some aspects, the compounds show improved activity or other pharmacological characteristics relative to known ADCs.

Also provided herein are methods of preparing ADCs with branched linkers which allow for the incorporation of multiple therapeutic compounds. Using MTGase, antibodies could be coupled with amines comprised of pendant diazide functionality. The azide moieties could then be further functionalized through azide-alkyne cycloaddition to incorporate a chemical payload.

In other aspects, the present disclosure provides linkers for use in the construction of antibody drug conjugates which show improved therapeutic profiles in vivo such as improved stability and increased specificity of cleavage by the desired peptidase. Antibody drug conjugates often use a peptide based linker which is capable of being cleaved by peptidases in vivo and is often based upon a Val-Cit dipeptide. As described herein, the peptide based linker may further a third amino acid residue with a polar side chain such as glutamic acid or aspartic acid. These changes in the peptide based linker may lead to the decreased cleavage from the non-target peptidase and improve the overall stability of the antibody drug conjugate until it reaches its desired and therapeutically effective location. These peptide based linkers may be used in any potential antibody drug conjugate. These and more details are described herein.

I. Delivery of Therapeutic Agents Via ADCs

A. Drugs for Conjugation to a Polypeptide

Any of a number of drugs are suitable for use, or can be modified to be rendered suitable for use, as a reactive partner to conjugate to a polypeptide. Examples of drugs include small molecule drugs and peptide drugs. Thus, the present disclosure provide drug-antibody conjugates.

"Small molecule drug" as used herein refers to a compound, e.g., an organic compound, which exhibits a pharmaceutical activity of interest and which is generally of a molecular weight of 800 Da or less, or 2000 Da or less, but can encompass molecules of up to 5 kDa and can be as large as 10 kDa. A small inorganic molecule refers to a molecule containing no carbon atoms, while a small organic molecule refers to a compound containing at least one carbon atom.

"Peptide drug" as used herein refers to amino-acid containing polymeric compounds, and is meant to encompass naturally-occurring and non-naturally-occurring peptides, oligopeptides, cyclic peptides, polypeptides, and proteins, as well as peptide mimetics. The peptide drugs may be obtained by chemical synthesis or be produced from a genetically encoded source (e.g., recombinant source). Peptide drugs can range in molecular weight, and can be from 200 Da to 10 kDa or greater in molecular weight.

It is contemplated that ADCs constructed from the compounds of the present disclosure can be used to deliver a drugs. In some embodiments, the drug is a cancer chemotherapeutic agent. For example, where the polypeptide is an antibody (or fragment thereof) that has specificity for a tumor cell, the antibody can be modified as described herein to include a modified amino acid, which can be subsequently conjugated to a cancer chemotherapeutic agent. Cancer chemotherapeutic agents include non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (*vinca*) alkaloids, and steroid hormones. Peptidic compounds can also be used.

Suitable cancer chemotherapeutic agents include dolastatin and active analogs and derivatives thereof: and auristatin and active analogs and derivatives thereof. See, e.g., WO 96/33212, WO 96/14856, and U.S. Pat. No. 6,323,315. For example, dolastatin 10 or auristatin PE can be included in an antibody-drug conjugate of the present disclosure. Suitable cancer chemotherapeutic agents also include maytansinoids and active analogs and derivatives thereof (see, e.g., EP 1391213; and Liu et al. 1996): and duocarmycins and active analogs and derivatives thereof (e.g., including the synthetic analogues. KW-2189 and CB 1-TMI).

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine, (CY-TOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, lO-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics. e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin: anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafme, cyclophosphamide, ifosamide, and droloxafme.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives. docetaxel (Taxotere®) thiocolchicine (NSC 361792), trityl cysterin, vinblastine sulfate, vincristine sulfate, natural and synthetic epothilones including but not limited to, eopthilone A, epothilone B, discodermolide: estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17a-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines. e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fiuorophenylamino)-7-methoxy-6-(3-(4-morpholinyl)propoxy)quinazoline); etc.

Taxanes are suitable for use. "Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (17402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α: (7) IFN-γ; (8) colony-stimulating factors; and (9) inhibitors of angiogenesis.

B. Methods for Modification of Drugs to Contain a Reactive Partner

Drugs to be conjugated to a polypeptide may be modified to incorporate a reactive partner for reaction with the polypeptide. Where the drug is a peptide drug, the reactive moiety (e.g., aminooxy or hydrazide can be positioned at an N-terminal region, the N-terminus, a C-terminal region, the C-terminus, or at a position internal to the peptide. For example, an example of a method involves synthesizing a peptide drug having an aminooxy group. In this example, the peptide is synthesized from a Boc-protected precursor. An amino group of a peptide can react with a compound comprising a carboxylic acid group and oxy-N-Boc group. As an example, the amino group of the peptide reacts with 3-(2,5-dioxopyrrolidin-1-yloxy)propanoic acid. Other variations on the compound comprising a carboxylic acid group and oxy-N-protecting group can include different number of carbons in the alkylene linker and substituents on the alkylene linker.

The reaction between the amino group of the peptide and the compound comprising a carboxylic acid group and oxy-N-protecting group occurs through standard peptide coupling chemistry. Examples of peptide coupling reagents that can be used include, but not limited to, DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl-3-ethyl-carbodiimide hydrochloride), cyanuric fluoride, cyanuric chloride, TFFH (tetramethyl fluoroformamidinium hexafluorophosphate). DPPA (diphenylphosphorazidate), BOP (benzotriazol-1-yloxytris(dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N',N-tetramethyluronium tetrafluoroborate). TSTU (0-(N-succinimidyl)-N,N,N'-N'-tetramethyluronium tetrafluoroborate), HATU (N-[(dimethylamino)-1-H-1,2,3-triazolo[4,5,6]-pyridin-1-ylmethylene]-N-methylmethanaminium hexafluorophosphate N-oxide), BOP-Cl (bis(2-oxo-3-oxazolidinyl)phosphinic chloride), PyBOP ((1-H-1,2,3-benzotriazol-1-yloxy)-tris(pyrrolidino) phosphonium tetrafluorophopsphate), BrOP (bromotris(dimethylamino)phosphonium hexafluorophosphate). DEPBT (3-(diethoxyphosphoryloxy)-1,2,3-benzotriazin-4(3H)-one) PyBrOP (bromotris(pyrrolidino)phosphonium hexafluorophosphate). As a non-limiting example, HOBt and DIC can be used as peptide coupling reagents.

Deprotection to expose the amino-oxy functionality is performed on the peptide comprising an N-protecting group. Deprotection of the N-oxysuccinimide group, for example, occurs according to standard deprotection conditions for a cyclic amide group. Deprotecting conditions can be found in Greene and Wuts, Protective Groups in Organic Chemistry, 3rd Ed., 1999. John Wiley & Sons. NY and Harrison et al. Certain deprotection conditions include a hydrazine reagent, amino reagent, or sodium borohydride. Deprotection of a Boc protecting group can occur with TFA. Other reagents for deprotection include, but are not limited to, hydrazine, methylhydrazine, phenylhydrazine, sodium borohydride, and methylamine. The product and intermediates can be purified by conventional means, such as HPLC purification.

The ordinarily skilled artisan will appreciate that factors such as pH and steric hindrance (i.e., the accessibility of the amino acid residue to reaction with a reactive partner of interest) are of importance, Modifying reaction conditions to provide for optimal conjugation conditions is well within the skill of the ordinary artisan, and is routine in the art. Where conjugation is conducted with a polypeptide present in or on a living cell, the conditions are selected so as to be physiologically compatible. For example, the pH can be dropped temporarily for a time sufficient to allow for the reaction to occur but within a period tolerated by the cell (e.g., from about 30 min to 1 hour). Physiological conditions for conducting modification of polypeptides on a cell surface can be similar to those used in a ketone-azide reaction in modification of cells bearing cell-surface azides (see, e.g., U.S. Pat. No. 6,570,040).

Small molecule compounds containing, or modified to contain, a nucleophilic group that serves as a reactive partner with a compound or conjugate disclosed herein are also contemplated for use as drugs in the polypeptide-drug conjugates of the present disclosure. General methods are known in the art for chemical synthetic schemes and conditions useful for synthesizing a compound of interest (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry. Including Qualitative Organic Analysis. Fourth Edition, New York: Longman, 1978).

C. Peptide Drugs

In some cases, a conjugate comprises a covalently linked peptide. Suitable peptides include, but are not limited to, cytotoxic peptides; angiogenic peptides; anti-angiogenic peptides; peptides that activate B cells; peptides that activate T cells; anti-viral peptides; peptides that inhibit viral fusion; peptides that increase production of one or more lymphocyte populations; anti-microbial peptides; growth factors; growth hormone-releasing factors; vasoactive peptides; anti-inflammatory peptides; peptides that regulate glucose metabolism: an anti-thrombotic peptide; an anti-nociceptive peptide; a vasodilator peptide; a platelet aggregation inhibitor: an analgesic: and the like.

In some embodiments, the peptide can be chemically synthesized to include a group reactive with an amino acid residue or a modified amino acid residue of the polypeptide. A suitable synthetic peptide has a length of from 5 amino acids to 100 amino acids, or longer than 100 amino acids; e.g., a suitable peptide has a length of from 5 amino acids (aa) to 10 aa, from 10 aa to 15 aa, from 15 aa to 20 aa, from 20 aa to 25 aa, from 25 aa to 30 aa, from 30 aa to 40 aa, from 40 aa to 50 aa, from 50 aa to 60 aa, from 60 aa to 70 aa, from 70 aa to 80 aa, from 80 aa to 90 aa, or from 90 aa to 100 aa.

In certain embodiments, a peptide can be modified to contain a nucleophile-containing moiety (e.g., an aminooxy or hydrazide moiety). e.g., can be reacted with an fGly-containing polypeptide to yield a conjugate in which the polypeptide and peptide are linked by a hydrazone or oxime bond, respectively. Examples of methods of synthesizing a peptide, such that the synthetic peptide comprising a reactive group reactive with an amino acid residue or a modified amino acid residue of the polypeptide, are described above.

Suitable peptides include, but are not limited to, hLF-11 (an 11-amino acid N-terminal fragment of lactoferrin), an anti-microbial peptide: granulysin, an anti-microbial peptide; Plectasin (NZ21 14; SAR 215500), an anti-microbial peptide; viral fusion inhibitors such as Fuzeon (enfuvirtide), TRI-1249 (T-1249; see, e.g., Matos et al., 2010), TRI-2635 (T-2635: see, e.g., Eggink et al., 2(X9), T651, and TRI-1144; C5a receptor inhibitors such as PMX-53. JPE-1375, and JSM-7717: POT-4, a human complement factor C3 inhibitor; Pancreate (an INGAP derivative sequence, a HIP-human proislet protein); somatostatin; a somatostatin analog such as DEBIO 8609 (Sanvar), octreotide, octreotide (C2L), octreotide QLT, octreotide LAR, Sandostatin LAR, SomaLAR, Somatuline (lanreotide), see, e.g., Deghenghi et al., 2001; TH9507 (Tesamorelin, a growth hormone-releasing factor); POL7080 (a protegrin analog, an anti-microbial peptide); relaxin; a corticotropin releasing factor agonist such as urotensin, sauvagine, and the like; a heat shock protein derivative such as DiaPep277; a human immunodeficiency virus entry inhibitor; a heat shock protein-20 mimic such as AZX100; a thrombin receptor activating peptide such as TP508 (Chrysalin); a urocortin 2 mimic (e.g., a CRF2 agonist) such as urocortin-2; an immune activator such as Zadaxin (thymalfasin; thymosin-al), see, e.g., Sjogren (2004) J. Gastroenterol. Hepatol, 19:569; a hepatitis C virus (HCV) entry inhibitorE2 peptide such as HCV3; an atrial natriuretic peptide such as HANP (Sun 4936; carperitide); an annexin peptide; a defensin (anti-microbial peptide) such as hBD2-4: a defensin (anti-microbial peptide) such as hBD-3; a defensin (antimicrobial peptide) such as PMX-30063; a histatin (anti-microbial peptide) such as histatin-3, histatin-5, histatin-6, and histatin-9; a histatin (anti-microbial peptide) such as PAC-113; an indolicidin (anti-microbial peptide) such as MX-594AN (Omniganin; CLSOOI); an indolicidin (anti-microbial peptide) such as Omnigard (MBI-226; CPI-226); an anti-microbial peptide such as an insect cecropin; an anti-microbial peptide such as a lactoferrin (talactoferrin): an LL-37/cathelicidin derivative (an anti-microbial peptide) such as P60.4 (OP-145); a magainin (an anti-microbial peptide) such as Pexiganan (MSI-78: Suponex); a protegrin (an anti-microbial peptide) such as IB-367 (Iseganan); an agan peptide; a beta-natriuretic peptide such as Natrecor, or Noratak (Nesiritide), or ularitide; bivalarudin (Angiomax), a thrombin inhibitor, a C peptide derivative; a calcitonin such as Miacalcin (Fortical); an enkephalin derivative; an erythropoiesis-stimulating peptide such as Hematide; a gap junction modulator such as Danegaptide (ZP1609): a gastrin-releasing peptide; a ghrelin; a glucagon-like peptide; a glucagon-like peptide-2 analog such as ZP1846 or ZP1848; a glucosaminyl muramyl dipeptide such as GMDP; a glycopeptide antibiotic such as Oritavancin; a teicoplanin derivative such as Dalbavancin; a gonadotropin releasing hormone (GnRH) such as Zoladex (Lupon) or Triptorelin; a histone deacetylase (HiDAC) inhibitor depsipeptide such as PM02734 (Irvalec); an integrin such as eptifibatide; an insulin analog such as Humulog; a kahalalide depsipeptide such as PM02734; a kallikrein inhibitor such as Kalbitor (ecallantide); an antibiotic such as Telavancin; a lipopeptide such as Cubicin or MX-2401; a lutenizing hormone releasing hormone (LHRH) such as goserelin; an LHRH synthetic decapeptide agonist analog such as Treistar (triptorelin pamoate); an LHRH such as Eligard; an M2 protein channel peptide inhibitor, metreleptin; a melanocortin receptor agonist peptide such as bremalanotide/PT-141; a melanocortin; a muramyl tripeptide such as Mepact (mifamurtide); a myelin basic protein peptide such as MBP 8298 (dirucotide); an N-type voltage-gated calcium channel blocker such as Ziconotide (Prialt); a parathyroid hormone peptide; a parathyroid analog such as 768974: a peptide hormone analog such as UGP281; a prostaglandin F2-a receptor inhibitor such as PDC31; a protease inhibitor such as PPL-100; surfaxin; a thromnobspondin-1 (TSP-1) mimetic such as CVX-045 or ABT 510: a vasoactive intestinal peptide; vasopressin; a Y2R agonist peptide such as RG7089; obinepeptide; and TM30339.

II. Linkers

In some aspects, the present disclosure provides linkers which may be used to connect one or more different drugs and/or cell targeting moieties to a drug molecule. In some embodiments, the linker may be a compound of the formula:

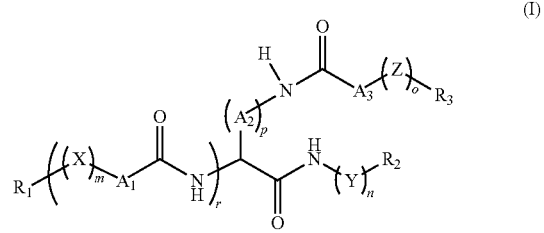

(I)

wherein:
A$_1$, A$_2$, and A$_3$ are each independently alkanediyl$_{C1-12}$, arenediyl$_{C1-12}$, heteroarenediyl$_{C1-12}$, cycloalkanediyl$_{C1-12}$, heterocycloalkanediyl$_{C1-12}$, or a substituted version thereof, or a side chain group of a canonical amino acid;
X, Y, and Z are each independently —[O(CH$_2$)$_q$]—, —[O(CHW')$_q$]—, or —[O(CW'W'')$_q$]—;
wherein:
W' and W'' are each independently amino, hydroxy, halo, mercapto, alkyl$_{C1-12}$, cycloalkyl$_{C1-12}$, alkenyl$_{C1-12}$, alkynyl$_{C1-12}$, aryl$_{C1-12}$, aralkyl$_{C1-12}$, heteroaryl$_{C1-12}$, heteroaralkyl$_{C1-12}$, heterocycloalkyl$_{C1-12}$, acyl$_{C1-12}$, acyloxy$_{C1-12}$, alkylamino$_{C1-12}$, or a substituted version of thereof;
q is 1-3;
m, n, o, and p are each independently 0-12;
r is 1, 2, or 3;
R$_1$, R$_2$, and R$_3$ are each independently —NH$_2$, —NHR$_4$, —NR$_4$R$_5$, —N$_3$, or a conjugating group;
wherein:
R$_4$ and R$_5$ are each independently alkyl$_{C1-12}$, cycloalkyl$_{C1-12}$, alkenyl$_{C1-12}$, alkynyl$_{C1-12}$, aryl$_{C1-12}$, aralkyl$_{C1-12}$, heteroaryl$_{C1-12}$, heteroaralkyl$_{C1-12}$, heterocycloalkyl$_{C1-12}$, acyl$_{C1-12}$, acyloxy$_{C1-12}$, alkylamino$_{C1-12}$, or a substituted version thereof, or a monovalent amino protecting group; or R$_4$ and R$_5$ are taken together and is a divalent amino protecting group;

provided that at least one of R$_1$, R$_2$, and R$_3$ is —NH$_2$ and at least one of R$_1$, R$_2$, and R$_3$ is —N$_3$;

or a pharmaceutically acceptable salt thereof.

In another aspect, the present disclosure provides linkers which may be used to connect one or more different drugs and/or cell targeting moieties to a drug molecule. In some embodiments, the linker may be a compound of the formula:

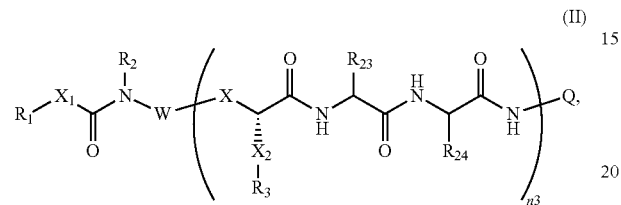

(II)

wherein:
X$_1$ is a covalent bond, alkanediyl$_{(C≤12)}$, or substituted alkanediyl$_{(C≤12)}$;

R$_1$ is hydrogen, —(OCH$_2$CH$_2$)$_{n1}$ZR$_6$, or substituted —(OCH$_2$CH$_2$)$_{n1}$ZR$_6$, wherein:
n1 is 0-50; and R$_6$ is hydrogen, hydroxy, amine, mercapto, hydroxylamine, hydrazine, or azide; or alkyl$_{(C≤12)}$, alkenyl$_{(C≤12)}$, alkynyl$_{(C≤12)}$, alkylhydrazine$_{(C≤12)}$, or a substituted version of any of these groups;

a polyglycine comprising from 1 to 6 glycine units; or a substructure of the formula:

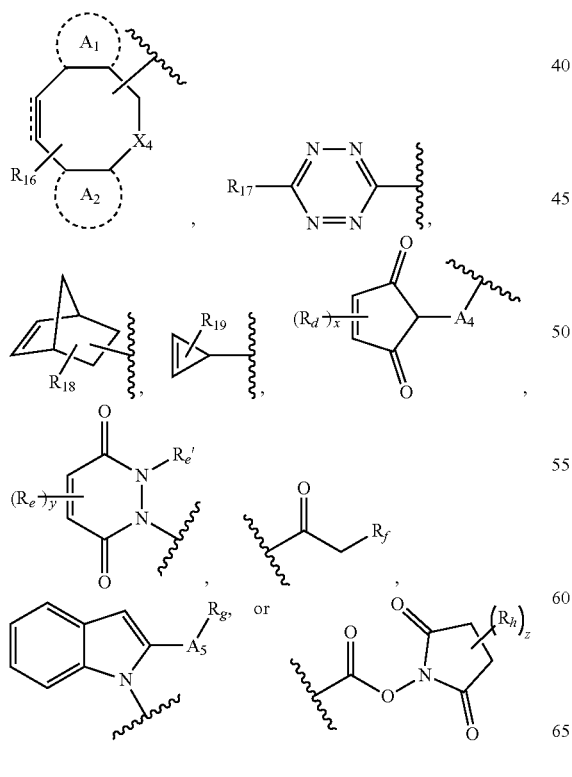

wherein:
A$_1$ and A$_2$ are each independently absent or arenediyl$_{(C≤12)}$, substituted arenediyl$_{(C≤12)}$, heteroarenediyl$_{(C≤12)}$, or substituted heteroarenediyl$_{(C≤12)}$, and form a fused arene$_{(C≤12)}$, substituted arene$_{(C≤12)}$, heteroarene$_{(C≤12)}$, or substituted heteroarene$_{(C≤12)}$;

A$_4$ or A$_5$ are each independently selected from a covalent bond, alkanediyl$_{(C≤8)}$, or substituted alkanediyl$_{(C≤8)}$;

R$_d$, R$_e$, R$_e$', and R$_h$ are each independently selected from hydrogen, halo, sulfate, tosylate, mesylate, aryl$_{(C≤8)}$, or substituted aryl$_{(C≤8)}$;

R$_f$ is halo;

R$_g$ is amine, hydrazine, alkylamino$_{(C≤8)}$, substituted alkylamino$_{(C≤8)}$, dialkylamino$_{(C≤8)}$, substituted dialkylamino$_{(C≤8)}$, alkylhydrazine$_{(C≤8)}$, or substituted alkylhydrazine$_{(C≤8)}$;

X$_4$ is O, N, CH$_2$, or X$_4$ is alkanediyl$_{(C≤8)}$ or substituted alkanediyl$_{(C≤8)}$ and is taken together to form a fused cycloalkane group consisting of 3 to 8 ring atoms;

R$_{16}$ is hydroxy, amino, or oxo;

R$_{17}$ is carboxy; or
alkyl$_{(C≤12)}$, amido$_{(C≤12)}$, aryl$_{(C≤12)}$, heteroaryl$_{(C≤12)}$, —C(O)NR$_{20}$R$_{20}$', or a substituted version of any of these groups wherein:
R$_{20}$ and R$_{20}$' are each independently hydrogen; or alkyl$_{(C≤12)}$, aryl$_{(C≤12)}$, or a substituted version of either of these groups;

R$_{18}$ and R$_{19}$ are each independently hydroxy, amino, halo; or
alkyl$_{(C≤12)}$, aryl$_{(C≤12)}$, or a substituted version of either of these groups;

Z is a covalent bond, alkanediyl$_{(C≤12)}$, —C(O)-alkanediyl$_{(C≤12)}$, —C(O)-alkanediyl$_{(C≤12)}$—C(O)NH—, or a substituted version of any of these groups;

R$_2$ is hydrogen, alkyl$_{(C≤12)}$, substituted alkyl$_{(C≤12)}$, acyl$_{(C≤12)}$, substituted acyl$_{(C≤12)}$, or a monovalent amino protecting group;

W is a covalent bond or a polyvalent polymer having 2-21 connection points;

n3 is 1 to 20 provided that when W is a covalent bond then n3 is 1 and when W is a polyvalent polymer then n3 is less than or equal to one less than the number of connection points;

Each X is independently a covalent bond, alkanediyl$_{(C≤12)}$, or substituted alkanediyl$_{(C≤12)}$.

Each X$_2$ is independently alkanediyl$_{(C≤12)}$ or substituted alkanediyl$_{(C≤12)}$; Each R$_3$ is independently hydroxy, or amino; or
alkoxy$_{(C≤12)}$, acyloxy$_{(C≤12)}$, alkylamino$_{(C≤12)}$, dialkylamino$_{(C≤12)}$, amido$_{(C≤12)}$, heteroaryl$_{(C≤12)}$, or a substituted version of any of these groups; or —X$_9$—C(O)R$_7$, wherein:
X$_9$ is O, —NR$_b$—, or a covalent bond;
R$_b$ is hydrogen, alkyl$_{(C≤6)}$, substituted alkyl$_{(C≤6)}$, or a monovalent amino protecting group;
R$_7$ is hydroxy or amino; or
alkoxy$_{(C≤12)}$, alkylamino$_{(C≤12)}$, dialkylamino$_{(C≤12)}$, or a substituted version of any of these groups; or -A₃SO₂NR₂₁R₂₁', -A₃P(O)(OH)OR₂₂, or -A₃SO₂OR₂₂', wherein:
  A₃ is O, —NR$_c$—, or a covalent bond;
    R$_c$ is hydrogen, alkyl$_{(C≤6)}$, substituted alkyl$_{(C≤6)}$, or a monovalent amino protecting group;
  R₂₁, R₂₁', R₂₂, and R₂₂' are each independently hydrogen, alkyl$_{(C≤12)}$, cycloalkyl$_{(C≤12)}$, aryl$_{(C≤12)}$, heteroaryl$_{(C≤12)}$, aralkyl$_{(C≤12)}$, heteroaralkyl$_{(C≤12)}$, or a substituted version of any of these groups;
Each R₂₃ is independently the side chain moiety of alanine, valine, leucine, isoleucine, phenylalanine, tyrosine, tryptophan, a hydroxyl-protected version of tyrosine, or an amino-protected version of tryptophan; and
Each R₂₄ is independently the side chain moiety of alanine; or ornithine, lysine, arginine, citrulline, or an amino-protected version thereof;
Each Q is independently a group of the formula:

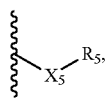

wherein:
  Each R₅ is independently hydrogen or —C(O)—R₈, wherein:
    R₈ is a chemotherapeutic agent;
  Each X₅ is independently a covalent bond, O, S, —NH—, alkanediyl$_{(C≤12)}$, substituted alkanediyl$_{(C≤12)}$, —(OCH₂CH₂)$_{n2}$—, or substituted —(OCH₂CH₂)$_{n2}$—, wherein:
    n2 is 0-50; or
  a group of the formula:

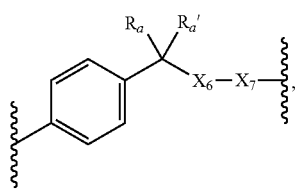

wherein:
  R$_a$ and R$_a$' are each independently hydrogen, alkyl$_{(C≤12)}$, or substituted alkyl$_{(C≤12)}$;
  X₆ is O or —NR₂₆R₂₆'—, wherein:
    R₂₆ and R₂₆' are each independently alkyl$_{(C≤12)}$ or substituted alkyl$_{(C≤12)}$;
  X₇ is a covalent bond, O, S, —NH—, —(OCH₂CH₂)$_{n3}$—, or substituted —(OCH₂CH₂)$_{n3}$—, wherein:
    n3 is 0-50; or
  a group of the formula:

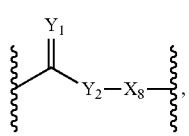

wherein:
  Y₁ is O or S;
  Y₂ is O, S, —NH—, or —NR₂₇—, wherein:
    R₂₇ is alkyl$_{(C≤12)}$ or substituted alkyl$_{(C≤12)}$; and
  X₈ is a covalent bond, O, S, —NH—, —(OCH₂CH₂)$_{n3}$—, or substituted —(OCH₂CH₂)$_{n3}$—;
or a pharmaceutically acceptable salt thereof.

In other aspects, the linker may further comprise one or more spacer groups. The spacer groups may comprise an amino acid sequence which is recognized by a peptidase in vivo and result in the cleavage of the cell targeting moiety from the drug. In some embodiments, the peptidase is a endosomal or lysosomal peptidase. In other embodiments, the peptidase is an extracellular peptidase such as a matrix metalloproteases, thimet oligopeptidase, or CD10. One example is the amino acid sequence valine-citrulline which is cleavable by cathepsin B. Other non-limiting examples of peptide sequences that are cleavable include valine-alanine, valine-lysine, valine-ornithine, phenylalanine-alanine, phenylalanine-lysine, and phenylalanine-ornithine. Additionally, it is contemplated that other functional moieties may be added into the spacer group which can be used to achieve decoupling of the drug and the cell targeting moieties including but not limited to hydrazones, disulfide bonds, or esters. It is also contemplated that the space group may further comprise one or more self-immolating groups. As used herein, a self immolating group is a group which undergoes decomposition once cleaved at one functional group. Self immolating groups are well known with the context of ADC's and are taught by Carl et al., 1981; WO 81/01145; Dubowchik et al., 1999; U.S. Pat. No. 6,214,345; Told et al., 2002; Doronina et al., 2003 (erratum, p. 941); U.S. Pat. No. 7,691,962; US 2008/0279868; WO 2008/083312; U.S. Pat. No. 7,375,078 B2; US 2003/0096743; Burke et al., 2017; Staben et al., 2016, the entirety of which are incorporated by reference. One particular example of a self-immolating group is para-aminobenzyl alcohol or para-aminobenzyloxycarbonyl.

III. Compounds and Formulations Thereof

A. Compounds

The compounds provided by the present disclosure are shown, for example, above in the summary section and in the examples and claims below. They may be made using the methods outlined in the Examples section. The ADCs described herein can be synthesized according to the methods described, for example, in the Examples section below. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The ADCs described herein may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration.

Chemical formulas used to represent the ADCs described herein will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

The ADCs described herein may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the ADCs described herein are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

The ADCs herein may also exist in prodrug form. Since prodrugs are known to enhance numerous desirable qualities of pharmaceuticals (e.g., solubility, bioavailability, manufacturing, etc.), the compounds employed in some methods of the disclosure may, if desired, be delivered in prodrug form. Thus, the disclosure contemplates prodrugs of compounds of the present disclosure as well as methods of delivering prodrugs. Prodrugs of the ADCs described herein may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the ADCs described herein are within the scope of the disclosure. It will also be appreciated by those skilled in organic chemistry that many organic compounds can exist in more than one crystalline form. For example, crystalline form may vary from solvate to solvate. Thus, all crystalline forms of the ADCs or precursors described herein are within the scope of the present disclosure.

B. Formulations

In some embodiments of the present disclosure, the ADCs are included in a pharmaceutical formulation. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Formulations for oral use include tablets containing the active ingredient(s) (e.g., the ADCs herein) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinyl-pyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate may be employed.

IV. Indications

A. Hyperproliferative Diseases

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, the ADCs described herein may be used to lead to decreased cell counts and as such can potentially be used to treat a variety of types of cancer lines. In some aspects, it is anticipated that the ADCs described herein may be used to treat virtually any malignancy.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

B. Microbial Infection

The compositions of the present disclosure may provide antimicrobial effect to a target microbial organism and can be used to treat a disease or infection associated with the target microbial organism. An antimicrobial effect includes inhibiting the growth or killing of the target microbial organisms, or interfering with any biological functions of the target microbial organisms. In general, the compositions of the present disclosure can be used to treat a disease or infection at any place in a host, e.g., at any tissue including surfaces of any tissue or implant. In one embodiment, the compositions are used to specifically kill or inhibit bacterial target microbial organisms in body fluid (e.g., blood, sputum).

Compositions of the present disclosure may be effective against bacteria including Gram-positive and Gram-negative cocci, Gram-positive and Gram-negative straight, curved and helical/vibroid and branched rods, sheathed bacteria, sulfur-oxidizing bacteria, sulfur or sulfate-reducing bacteria, spirochetes, actinomycetes and related genera, myxobacteria, mycoplasmas, rickettsias and chlamydias, cyanobacteria, archea, fungi, parasites, viruses and algae. For example, the target microbial organisms of the present disclosure include, without limitation, *Escherichia coli, Candida, Salmonella, Staphylococcus*, and *Pseudomonas, Campylobacter jejuni, Candida albicans, Candida krusei, Chlamydia trachomatis, Clostridium difficile, Cryptococcus neoformans, Haempohilus influenzae, Helicobacter pylori, Moraxella catarrhalis, Neisseria gonorrhoeae, Pseudomonas aeroginosa, Salmonella typhimurium, Shigella disenteriae, Staphylococcus aureus*, and *Streptococcus pneumoniae*. In addition, the composition may be used to treat chronic skin ulcers, infected acute wounds or burn wounds, infected skin eczema, impetigo, atopic dermatitis, acne, external otitis, vaginal infections, seborrhoic dermatitis, oral infections, paradontitis, conjunctivitis or pneumonia.

Compositions of the present disclosure may be effective against gram-negative bacteria. Gram-positive and Gram-negative cocci include, but are not limited to, *Aerococcus, Enterococcus, Halococcus, Leuconostoc, Micrococcus*, Mobiluncus, *Moraxella catarrhalis, Neisseria* (including *N. gonorrheae* and *N. meningitidis*), *Pediococcus, Peptostreptococcus, Staphylococcus* species (including *S. aureus*, methicillin-resistant *S. aureus*, coagulase-negative *S. aureus*, and *S. saprophyticus*), *Streptococcus* species (including *S. pyogenes, S. agalactiae, S. bovis, S. pneumoniae, S. mutans, S. sanguis, S. equi, S. equinus, S. thermophilus, S. morbillorum, S. hansenii, S. pleomorphus*, and *S. parvulus*), and *Veillonella*.

The Gram-positive and Gram-negative straight, curved, helical/vibroid and branched rods include, but are not limited to, *Acetobacter, Acinetobacter, Actinobacillus equuli, Aeromonas, Agrobacterium, Alcaligenes, Aquaspirillum, Arcanobacterium haemolyticum, Bacillus* species (including *B. cereus* and *B. anthracis*), *Bacteroides* species (including *B. fragilis*), *Bartonella, Bordetella* species (including *B. pertussis*), *Brochothrix, Brucella, Burkholderia cepacia, Calymmatobacterium granulomatis, Campylobacter* species (including *C. jejuni*), *Capnocytophaga, Caulobacter, Chromobacterium violaceum, Citrobacter, Clostridium* species (including *C. perfringens, C. tetani* and *C. difficile*), *Comamonas, Curtobacterium, Edwardsiella, Eikenella, Enterobacter, Erwinia, Erysipelothrix, Escherichia* species (including *E. coli*), *Flavobacterium* species (including *E. meninosepticum*), *Francisella* species (including *E. tularensis*), *Fusobacterium* (including *E. nucleatum*), *Gardnerella* species (including *G. vaginalis*), *Gluconobacter, Haemophilus* species (including *H. influenzae* and *H. ducreyi*), *Hafnia, Helicobacter* (including *H. pylori*), *Herpetosiphon, Klebsiella* species (including *K. pneumoniae*), *Kluyvera, Lactobacillus, Legionella* species (including *E. pneumophila*), *Leptotrichia, Listeria* species (including *E. monocytogenes*), *Microbacterium, Morganella, Nitrobacter, Nitrosomonas, Pasteurella* species (including *P. multocida*), *Pectinatus, Porphyromonas gingivalis, Proteus* species (including *E. mirabilis*), *Providencia, Pseudomonas* species (including *E. aeruginosa, P. mallei, P. pseudomallei* and *E. solanacearum*), *Rahnella, Renibacterium salmoninarum, Salmonella, Serratia, Shigella, Spirillum, Streptobacillus* species (including *S. moniliformis*), *Vibrio* species (including *V. cholerae* and *V. vulnificus*), *Wolinella, Xanthobacter, Xenorhabdus, Yersinia* species (including *Y. pestis* and *Y. enter ocoliticd*), *Zanthomonas* and *Zymomonas*.

The clinical diseases or infections caused by Gram-positive and/or Gram-negative bacteria, treatable with the present disclosure include abscesses, bacteremia, contamination of peritoneal dialysis fluid, endocarditis, pneumonia, meningitis, osteomyelitis, cellulitis, pharyngitis, otitis media, sinusitis, scarlet fever, arthritis, urinary tract infection, laryngotracheitis, erysipeloid, gas gangrene, tetanus, typhoid fever, acute gastroenteritis, bronchitis, epiglottitis, plague, sepsis, chancroid, wound and burn infection, cholera, glanders, periodontitis, genital infections, empyema, granuloma inguinale, Legionnaire's disease, paratyphoid, bacillary dysentary, brucellosis, diphtheria, pertussis, botulism, toxic shock syndrome, mastitis, rheumatic fever, cystic fibrosis, eye infections, plaque, and dental caries. Other uses include swine erysipelas, peritonitis, abortion, encephalitis, anthrax, nocardiosis, pericarditis, mycetoma, peptic ulcer, melioidosis, HaverhiU fever, tularemia, Moko disease, galls (e.g., crown, cane and leaf), hairy root, bacterial rot, bacterial blight, bacterial brown spot, bacterial wilt, bacterial fin rot, dropsy, columnaris disease, pasteurellosis, furunculosis, enteric redmouth disease, vibriosis offish, and fouling of medical devices.

Compounds and compositions of the present disclosure may be effective against influenza virus, cytomegalovirus, avian leukosis-sarcoma virus, Rous Sarcoma virus, Mammalian C-type Murine leukemia virus, Feline leukemia virus, simian sarcoma virus, B-type Mouse mammary tumor virus, D-type virus Mason-Pfizer monkey virus, simian AIDS virus, Human T-cell leukemia virus, Simian T-cell leukemia virus, bovine leukemia virus, Human immunodeficiency virus, Simian immunodeficiency virus, Feline immunodeficiency virus, Visna/maedi virus, Equine infectious anemia virus, Caprine arthritis-encephalitis virus, spumavirus, foamy virus, endogenous retrovirus, papilloma virus, respiratory syncytial virus, poliomyelitis virus, pox virus, measles virus, arbor virus, Coxsackie virus, herpes virus, hantavirus, hepatitis virus, baculovirus, mumps virus, circovirus, arenavirus, rotavirus, Colorado Tick Fever CTF virus, Eyach virus, Langat virus, Powassan virus, Omsk hemorrhagic fever virus, Crimean-Congo hemorrhagic fever virus, Yellow fever virus, Encephalitis virus, St. Louis Encephalitis virus, Venezualan equine encephalitis virus, Western equine encephalitis virus, Chikungunya virus, Japanese encephalitis virus, West Nile virus, Kyasanur forest disease virus, Dengue fever virus, California encephalitis virus, adenovirus, Korean haemorrhagic fever virus, hantavirus, Argentine haemorrhagic fever virus, Junin virus, Aujeszky disease virus, Pseudorabies virus, Herpesvirus, Chikungunya virus, cowpox virus, ebolavirus, Ganjam virus, herpesvirus simiae, Lassa fever virus, Louping ill virus, Lymphocytic choriomeningitis virus, Marburg virus, Milkers nodule virus, Newcastle disease virus, Omsk haemorrhagic fever virus, Orf virus, Parvovirus, Poliovirus, Pseudorabies, Rabies virus, Rift Valley fever virus, Russian Spring-Summer encephalitis virus, Sabia virus, vaccinia virus, vesicular stomatitis virus, Western equine encephalitis virus, or Yelllow fever virus.

C. Autoimmune Diseases

Compounds and compositions of the present disclosure may be effective in the treatment or prevention of autoimmune disease. Non-limiting examples of auto-immune diseases include Addison's disease, Agammaglobulinemia, Alopecia areata, Amyloidosis, Ankylosing spondylitis, Anti-GBM/Anti-TBM nephritis, Antiphospholipid syndrome (APS), Autoimmune hepatitis, Autoimmune inner ear disease (AIED), Axonal & neuronal neuropathy (AMAN), Behcet's disease, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss, Cicatricial pemphigoid/benign mucosal pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hypogammalglobulinemia, IgA Nephropathy, IgG4-related sclerosing disease, Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multiple sclerosis (MS), Myasthenia gravis, Myositis, Narcolepsy, Neuromyelitis optica, Neutropenia, Ocular cicatricial pemphigoid, Optic neuritis, Palindromic rheumatism (PR), PANDAS (Pediatric Autoimmune Neuropsychiatric Disorders Associated with *Streptococcus*), Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome (polyneuropathy, organomegaly, endocrinopathy, monoclonal gammopathy, skin changes), Polyarteritis nodosa, Polymyalgia rheumatic, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Reiter's syndrome, Relapsing polychondritis, Restless legs syndrome (RLS), Retroperitoneal fibrosis, Rheumatic fever, Rheumatoid arthritis (RA), Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, Vitiligo, and Wegener's granulomatosis (now termed Granulomatosis with Polyangiitis (GPA).

D. Inflammation

Inflammation is a biological process that provides resistance to infectious or parasitic organisms and the repair of damaged tissue. Inflammation is commonly characterized by localized vasodilation, redness, swelling, and pain, the recruitment of leukocytes to the site of infection or injury, production of inflammatory cytokines such as TNF-α and IL-1, and production of reactive oxygen or nitrogen species such as hydrogen peroxide, superoxide and peroxynitrite. In later stages of inflammation, tissue remodeling, angiogenesis, and scar formation (fibrosis) may occur as part of the wound healing process. Under normal circumstances, the inflammatory response is regulated and temporary and is resolved in an orchestrated fashion once the infection or injury has been dealt with adequately. However, acute inflammation can become excessive and life-threatening if regulatory mechanisms fail. Alternatively, inflammation can become chronic and cause cumulative tissue damage or systemic complications.

Many serious and intractable human diseases involve dysregulation of inflammatory processes, including diseases such as cancer, atherosclerosis, and diabetes, which were not traditionally viewed as inflammatory conditions. In the case of cancer, the inflammatory processes are associated with tumor formation, progression, metastasis, and resistance to therapy. Atherosclerosis, long viewed as a disorder of lipid metabolism, is now understood to be primarily an inflammatory condition, with activated macrophages playing an important role in the formation and eventual rupture of atherosclerotic plaques. Activation of inflammatory signaling pathways has also been shown to play a role in the development of insulin resistance, as well as in the peripheral tissue damage associated with diabetic hyperglycemia Chronic organ failure such as renal failure, heart failure, liver failure, and chronic obstructive pulmonary disease is closely associated with the presence of chronic oxidative stress and inflammation, leading to the development of fibrosis and eventual loss of organ function. Oxidative stress in vascular endothelial cells, which line major and minor blood vessels, can lead to endothelial dysfunction and is believed to be an important contributing factor in the development of systemic cardiovascular disease, complications of diabetes, chronic kidney disease and other forms of organ failure, and a number of other aging-related diseases including degenerative diseases of the central nervous system and the retina. Many other disorders involve oxidative stress and inflammation in affected tissues, including inflammatory bowel disease; inflammatory skin diseases; mucositis related to radiation therapy and chemotherapy; eye diseases such as uveitis, glaucoma, macular degeneration, and various forms of retinopathy; transplant failure and rejection; ischemia-reperfusion injury; chronic pain; degenerative conditions of the bones and joints including osteoarthritis and osteoporosis; asthma and cystic fibrosis; seizure disorders; and neuropsychiatric conditions including schizophrenia, depression, bipolar disorder, post-traumatic stress disorder, attention deficit disorders, autism-spectrum disorders, and eating disorders such as anorexia nervosa. Dysregulation of inflammatory signaling pathways is believed to be a major factor in the pathology of muscle wasting diseases including muscular dystrophy and various forms of cachexia.

A variety of life-threatening acute disorders also involve dysregulated inflammatory signaling, including acute organ failure involving the pancreas, kidneys, liver, or lungs, myocardial infarction or acute coronary syndrome, stroke, septic shock, trauma, severe burns, and anaphylaxis.

Many complications of infectious diseases also involve dysregulation of inflammatory responses. Although an inflammatory response can kill invading pathogens, an excessive inflammatory response can also be quite destructive and in some cases can be a primary source of damage in infected tissues. Furthermore, an excessive inflammatory response can also lead to systemic complications due to overproduction of inflammatory cytokines such as TNF-α and IL-1. This is believed to be a factor in mortality arising from severe influenza, severe acute respiratory syndrome, and sepsis.

V. Cell Targeting Moieties

In some aspects, the present disclosure provides compounds conjugated directly or through linkers to a cell targeting moiety. In some embodiments, the conjugation of the compound to a cell targeting moiety increases the efficacy of the compound in treating a disease or disorder. Cell targeting moieties according to the embodiments may be, for example, an antibody, a growth factor, a hormone, a peptide, an aptamer, a small molecule such as a hormone, an imaging agent, or cofactor, or a cytokine. It has been demonstrated that the gp240 antigen is expressed in a variety of melanomas but not in normal tissues. Thus, in some embodiments, the compounds of the present disclosure may be used in conjugates with an antibody for a specific antigen that is expressed by a cancer cell but not in normal tissues.

In certain additional embodiments, it is envisioned that cancer cell targeting moieties bind to multiple types of cancer cells. For example, the 8H9 monoclonal antibody and the single chain antibodies derived therefrom bind to a glycoprotein that is expressed on breast cancers, sarcomas and neuroblastomas (Onda, et al., 2004). Another example is the cell targeting agents described in U.S. Patent Publication No. 2004/005647 and in Winthrop, et al. (2003) that bind to MUC-1, an antigen that is expressed on a variety cancer types. Thus, it will be understood that in certain embodiments, cell targeting constructs according the embodiments may be targeted against a plurality of cancer or tumor types.

Additionally, certain cell surface molecules are highly expressed in tumor cells, including hormone receptors such as human chorionic gonadotropin receptor and gonadotropin releasing hormone receptor (Nechushtan et al., 1997). Therefore, the corresponding hormones may be used as the cell-specific targeting moieties in cancer therapy. Additionally, the cell targeting moiety that may be used include a cofactor, a sugar, a drug molecule, an imaging agent, or a fluorescent dye. Many cancerous cells are known to over express folate receptors and thus folic acid or other folate derivatives may be used as conjugates to trigger cell-specific interaction between the conjugates of the present disclosure and a cell (Campbell, et al., 1991; Weitman, et al., 1992).

Since a large number of cell surface receptors have been identified in hematopoietic cells of various lineages, ligands or antibodies specific for these receptors may be used as cell-specific targeting moieties. IL-2 may also be used as a cell-specific targeting moiety in a chimeric protein to target IL-2R+ cells. Alternatively, other molecules such as B7-1, B7-2 and CD40 may be used to specifically target activated T cells (The Leucocyte Antigen Facts Book, 1993, Barclay, et al. (eds.), Academic Press). Furthermore, B cells express CD19, CD40 and IL-4 receptor and may be targeted by moieties that bind these receptors, such as CD40 ligand, IL-4, IL-5, IL-6 and CD28. The elimination of immune cells such as T cells and B cells is particularly useful in the treatment of lymphoid tumors.

Other cytokines that may be used to target specific cell subsets include the interleukins (IL-1 through IL-15), granulocyte-colony stimulating factor, macrophage-colony stimulating factor, granulocyte-macrophage colony stimulating factor, leukemia inhibitory factor, tumor necrosis factor, transforming growth factor, epidermal growth factor, insulin-like growth factors, and/or fibroblast growth factor (Thompson (ed.), 1994, The Cytokine Handbook, Academic Press, San Diego). In some aspects, the targeting polypeptide is a cytokine that binds to the Fn14 receptor, such as TWEAK (see, e.g., Winkles, 2008; Zhou, et al., 2011 and Burkly, et al., 2007, incorporated herein by reference).

A skilled artisan recognizes that there are a variety of known cytokines, including hematopoietins (four-helix bundles) (such as EPO (erythropoietin), IL-2 (T-cell growth factor), IL-3 (multicolony CSF), IL-4 (BCGF-1, BSF-1), IL-5 (BCGF-2), IL-6 IL-4 (IFN-β2, BSF-2, BCDF), IL-7, IL-8, IL-9, IL-11, IL-13 (P600), G-CSF, IL-15 (T-cell growth factor), GM-CSF (granulocyte macrophage colony stimulating factor), OSM (OM, oncostatin M), and LIF (leukemia inhibitory factor)); interferons (such as IFN-γ, IFN-α, and IFN-β); immunoglobin superfamily (such as B7.1 (CD80), and B7.2 (B70, CD86)); TNF family (such as TNF-α (cachectin), TNF-3 (lymphotoxin, LT, LT-α), LT-β, CD40 ligand (CD40L), Fas ligand (FasL), CD27 ligand (CD27L), CD30 ligand (CD30L), and 4-1BBL)); and those unassigned to a particular family (such as TGF-β, IL 1α, IL-1β, IL-1 RA, IL-10 (cytokine synthesis inhibitor F), IL-12 (NK cell stimulatory factor), MIF, IL-16, IL-17 (mCTLA-8), and/or IL-18 (IGIF, interferon-γinducing factor)). Furthermore, the Fc portion of the heavy chain of an antibody may be used to target Fc receptor-expressing cells such as the use of the Fc portion of an IgE antibody to target mast cells and basophils.

Furthermore, in some aspects, the cell-targeting moiety may be a peptide sequence or a cyclic peptide. Examples, cell- and tissue-targeting peptides that may be used according to the embodiments are provided, for instance, in U.S. Pat. Nos. 6,232,287; 6,528,481; 7,452,964; 7,671,010; 7,781,565; 8,507,445; and 8,450,278, each of which is incorporated herein by reference.

Thus, in some embodiments, cell targeting moieties are antibodies or avimers. Antibodies and avimers can be generated against virtually any cell surface marker thus, providing a method for targeted to delivery of GrB to virtually any cell population of interest. Methods for generating antibodies that may be used as cell targeting moieties are detailed below. Methods for generating avimers that bind to a given cell surface marker are detailed in U.S. Patent Publications Nos. 2006/0234299 and 2006/0223114, each incorporated herein by reference.

Additionally, it is contemplated that the compounds described herein may be conjugated to a nanoparticle or other nanomaterial. Some non-limiting examples of nanoparticles include metal nanoparticles such as gold or silver nanoparticles or polymeric nanoparticles such as poly-L-lactic acid or poly(ethylene) glycol polymers. Nanoparticles and nanomaterials which may be conjugated to the instant compounds include those described in U.S. Patent Publications Nos. 2006/0034925, 2006/0115537, 2007/0148095, 2012/0141550, 2013/0138032, and 2014/0024610 and PCT Publication No. 2008/121949, 2011/053435, and 2014/087413, each incorporated herein by reference.

VI. Therapies

A. Pharmaceutical Formulations and Routes of Administration

Where clinical applications are contemplated, it will be necessary to prepare pharmaceutical compositions in a form appropriate for the intended application. In some embodiments, such formulation with the ADCs of the present disclosure is contemplated. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present disclosure comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Such routes include oral, nasal, buccal, rectal, vaginal or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the ADCs described herein may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA's Division of Biological Standards and Quality Control of the Office of Compliance and Biologics Quality.

B. Methods of Treatment

In particular, the compositions that may be used in treating a disease or disorder, such as cancer, in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells or killing microbes). Toxicity and therapeutic efficacy of the compositions utilized in methods of the disclosure can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that induces death of cancerous cells (e.g., induces apoptosis of a cancer cell), as assayed by identifying a reduction in hematological parameters (complete blood count—CBC), or cancer cell growth or proliferation. In some embodiments, amounts of the ADCs used to induce apoptosis of the cancer cells is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the ADCs may be more efficacious and thus a smaller dose is required to achieve a similar effect. Such a dose is typically administered once a day for a few weeks or until sufficient reducing in cancer cells has been achieved.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In some embodiments, the disclosure provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer (e.g., leukemia) in which the subject has been administered a therapeutic amount of a composition as described herein. The level of marker determined in the method can be compared to known levels of marker in either healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

C. Combination Therapies

It is envisioned that the ADCs described herein may be used in combination therapies with one or more therapies or a compound which mitigates one or more of the side effects experienced by the patient. It is common in the field of medical therapy to combine therapeutic modalities. The following is a general discussion of therapies that may be used in conjunction with the therapies of the present disclosure.

To treat certain diseases or disorders using the methods and compositions of the present disclosure, one would generally contact the subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the ADCs described herein may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours.

In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are also contemplated.

VII. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof, "mercapto" means —SH; and "thio" means =S; "sulfonyl" means —S(O)$_2$—; and "sulfinyl" means —S(O)—.

In the context of chemical formulas, the symbol "-" means a single bond, "=" means a double bond, and "≡" means triple bond. The symbol "----" represents an optional bond, which if present is either single or double. The symbol "⫀" represents a single bond or a double bond. Thus, the formula

covers, for example,

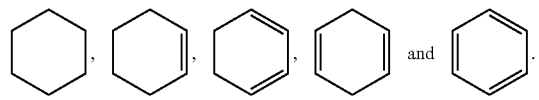

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "⌇⌇⌇", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◄" means a single bond where the group attached to the thick end of the wedge is "out of the page." The symbol "⫼⫼⫼" means a single bond where the group attached to the thick end of the wedge is "into the page". The symbol "⌇⌇⌇" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

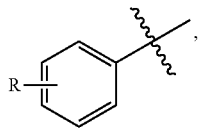

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

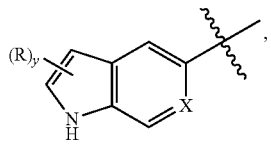

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefincs" are all synonymous. When any of the chemical groups or compound classes defined herein is modified by the term "substituted", any carbon atom(s) in the moiety replacing a hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$(i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$(isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more aromatic ring structure, wherein the ring atoms are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

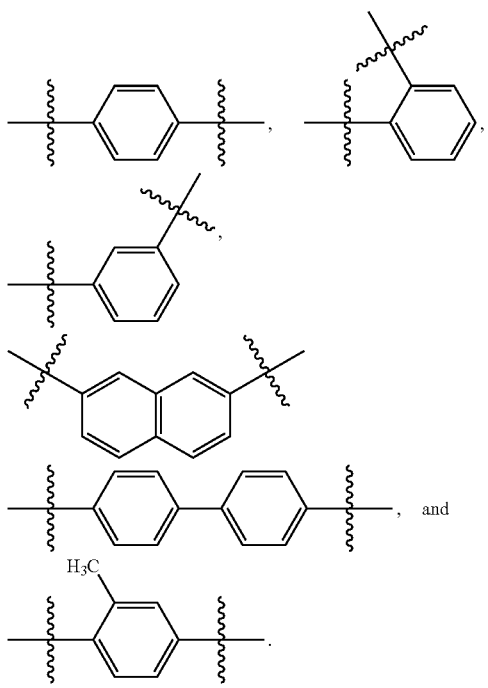

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group-alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. Unfused rings are connected with a covalent bond. As used herein, the term heteroaryl does not preclude the presence of one or more alkyl or aryl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolinyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings are connected with a covalent bond. As used herein, the term heteroarenediyl does not preclude the presence of one or more alkyl or aryl groups (carbon number limitation permitting) attached to the aromatic ring or aromatic ring system. Non-limiting examples of heteroarenediyl groups include:

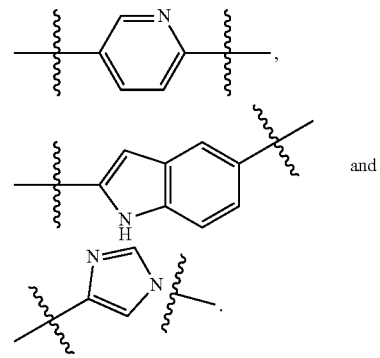
and

The term "heterocycloalkanediyl" when used without the "substituted" modifier refers to an divalent cyclic group, with two carbon atoms, two nitrogen atoms, or one carbon atom and one nitrogen atom as the two points of attachment, said atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings are connected with a covalent bond. As used herein, the term heterocycloalkanediyl does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

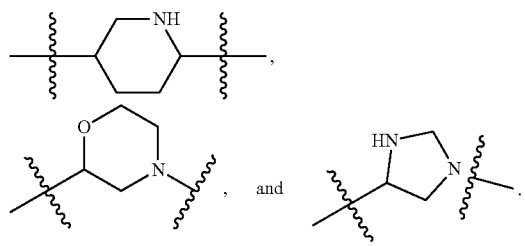

The terms "alkylsulfonyl" and "alkylsulfinyl" when used without the "substituted" modifier refers to the groups —S(O)$_2$R and —S(O)R, respectively, in which R is an alkyl, as that term is defined above. The terms "cycloalkylsulfonyl", "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O) CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC (O)CH$_3$, —S(O)$_2$OH, or —S(O)$_2$NH$_2$.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O) CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC (O)CH$_3$, —S(O)$_2$OH, or —S(O)$_2$NH$_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

An "active ingredient" (AI) (also referred to as an active compound, active substance, active agent, pharmaceutical agent, agent, biologically active molecule, or a therapeutic compound) is the ingredient in a pharmaceutical drug or a pesticide that is biologically active. The similar terms active pharmaceutical ingredient (API) and bulk active are also used in medicine, and the term active substance may be used for pesticide formulations.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical agent, pharmaceutical preparation, pharmaceutical composition, pharmaceutical formulation, pharmaceutical product, medicinal product, medicine, medication, medicament, or simply a drug) is a drug used to diagnose, cure, treat, or prevent disease. An active ingredient (AI) (defined above) is the ingredient in a pharmaceutical drug or a pesticide that is biologically active. The similar terms active pharmaceutical ingredient (API) and bulk active are also used in medicine, and the term active substance may be used for pesticide formulations. Some medications and pesticide products may contain more than one active ingredient. In contrast with the active ingredients, the inactive ingredients are usually called excipients (defined above) in pharmaceutical contexts.

The "polyvalent polymer" describes a linking group which contains two or more open valent points that can be used to connect different components together. Some non-limiting examples of polyvalent polymers include polymers with side chains that are capable of reacting with the component, dendrimers, dendrons, or fragments thereof. In one embodiment, the polyvalent polymer is a dendrimer or dendron.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-p-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

An "amine protecting group" is well understood in the art. An amine protecting group is a group which prevents the reactivity of the amine group during a reaction which modifies some other portion of the molecule and can be easily removed to generate the desired amine. Amine protecting groups can be found at least in Greene and Wuts, 1999, which is incorporated herein by reference. Some non-limiting examples of monovalent amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth). When used herein, a "protected amino group", is a group of the formula $PG_{MA}NH-$ or $PG_{DA}N-$ wherein $PG_{MA}$ is a monovalent amine protecting group, which may also be described as a "monvalently protected amino group" and $PG_{DA}$ is a divalent amine protecting group as described above, which may also be described as a "divalently protected amino group".

A "hydroxyl protecting group" is well understood in the art. A hydroxyl protecting group is a group which prevents the reactivity of the hydroxyl group during a reaction which modifies some other portion of the molecule and can be easily removed to generate the desired hydroxyl. Hydroxyl protecting groups can be found at least in Greene and Wuts, 1999, which is incorporated herein by reference. Some non-limiting examples of hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. When used herein, a protected hydroxy group is a group of the formula $PG_HO-$ wherein $PG_H$ is a hydroxyl protecting group as described above.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

As used herein, average molecular weight refers to the weight average molecular weight (Mw) determined by static light scattering.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, $-[-CH_2CH_2-]_n-$, the repeat unit is $-CH_2CH_2-$. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in metal organic frameworks, modified polymers, thermosetting polymers, etc.

The term "conjugating group" refers to a chemical group capable of coupling with the functional group of another compound to form a covalent bond under mild conditions and which is stable under physiological conditions. In some embodiments, the conjugating group can form the covalent bond via an $S_N2$ reaction, a Diels-Alder reaction, or a conjugate addition reaction. Examples of conjugating groups include, but are not limited to, diene groups (such as tetrazinyl), alkene groups (such as trans-cyclooctenyl and norbornyl), and —SH.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

VIII. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Assessment of Cleavage of Branched Linkers, Synthesis of Branched Linkers, and Payload Installation and Stability Study A. Assessment of Cathepsin B-mediated Cleavage of the Branched Linkers Herein is disclosed that branched cleavable ADC linkers can be efficiently installed on therapeutic monoclonal antibodies by MTGase-mediated conjugation. This methodology enables modular installation of payload molecules and construction of homogeneous ADCs with an increased DAR (FIG. 1). Upon antigen recognition and internalization to target cancer cells, the cathepsin B-responsive peptide sequences incorporated in our branched linkers undergo lysosomal cleavage to liberate two cytotoxic payloads per linker, leading to effective cell killing. To identify rational design of branched ADC linkers that can release two payloads inside the target cancer cell, a series of linear and branched fluorescent probes 1-4 (Scheme 1 and Schemes 3-6) was synthesized.

Scheme 1. Structures of fluorescent probes 1-4 containing tryptophan (fluorophore) and EdDnp groups (quencher) for the FRET assay (See the Examples below for synthesis detail). The Val-Cit sequence undergoes cathepsin B-mediated cleavage (depicted with an arrow) to release the EdDnp from the probes, enablling fluorescence detection derived from the tryptophan (excitation: 280 nm, emission: 360 nm).

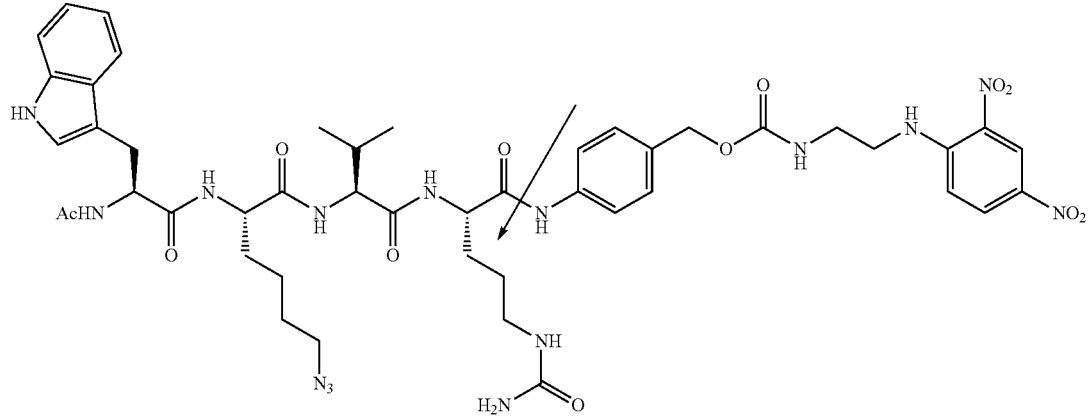

1

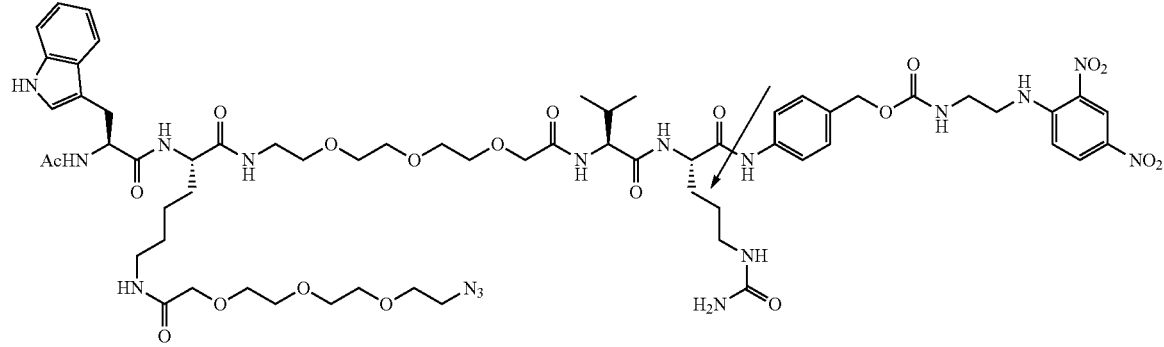

2

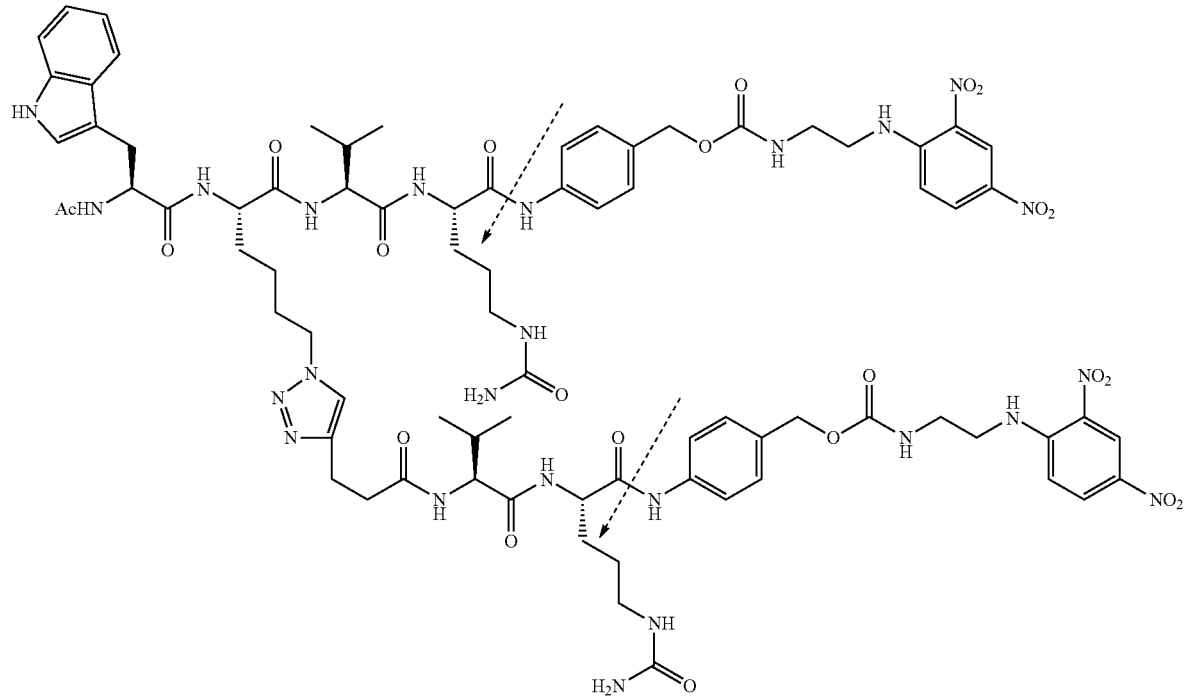

3

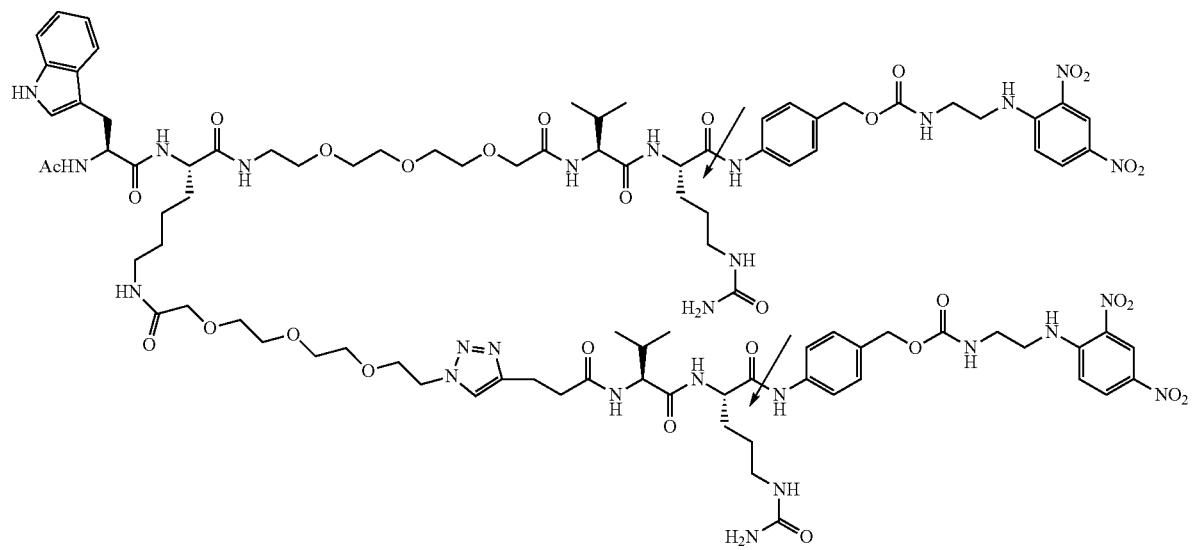

4

These model linker units consisted of cathepsin B-cleavable valine-citrulline (Val-Cit) with or without polyethyleneglycol (PEG) spacers. This dipeptide sequence has been used in many successful ADCs including the FDA-approved ADC Adcetris® (Katz et al., 2011). The sequence is stable in circulation but in lysosomes undergoes cathepsin B-mediated cleavage, resulting in intracellular release of payload (Dubowchik et al., 2002). Tryptophan and 2,4-dinitrophenylethylenediamine (EdDnp) were installed as a fluorophore/quencher(s) pair, which is commonly used in the Förster resonance energy transfer (FRET) assay. The release of EdDnp from each synthetic model linker unit in the presence of human cathepsin B (Table 1 and Scheme 3) was assessed. It was found that Linear PEG (+) probe 2 released EdDnp more efficiently than Linear PEG (−) 1. The release rate of branched PEG (+) probe 4 was comparable to that of linear PEG (+) probe 2. In contrast, branched PEG (−) probe 3 showed marginal release of EdDnp. Without wishing to be bound by any theory, it is surmised that the structural congestion of branched probe 3 due to the lack of PEG spacers prevents cathepsin B accessing Val-Cit moieties. These results clearly illustrate that the spacer is a component for retaining the high responsiveness of the Val-Cit containing linkers to cathepsin B-mediated cleavage, especially in the branched linker format.

TABLE 1

Rates of cathepsin B-mediated cleavage of linear and branched probes 1-4 in FRET Assay[a]

| | Slope (RFU/sec) |
|---|---|
| Linear PEG (−) 1 | 1.30 ± 0.07 |
| Linear PEG (+) 2 | 1.81 ± 0.07 |
| Branched PEG (−) 3 | 0.03 ± 0.06 |
| Branched PEG (+) 4 | 1.56 ± 0.05 |

[a]Each slope reflecting the quencher release rate was calculated by the linear regression method using Graph Pad Prism 7 software. All assays were performed in triplicate. RFU, relative fluorescence units.

Synthesis and Conjugation of the Branched Linkers. With the rational linker design in hand, construction of ADCs containing branched linkers commenced. First, branched linkers 5-7 (Scheme 2) were designed and synthesized. These linkers contained 1) a L-lysine scaffold as a branching point, 2) PEG spacers, 3) a primary amine for MTGase-mediated antibody-linker conjugation, and 4) two azide groups as reaction handles for the following payload installation by the azide-alkyne click reaction (Agard et al., 2004) (vide infra). These linkers were constructed by sequential amide couplings of each component (Scheme 7). The azide and primary amine were spatially sequestered with PEG spacers to minimize the steric congestion of the linker arms. In addition, it was envisaged that highly hydrophilic PEG spacers could help reduce the hydrophobicity of the ADCs to be constructed, which may prevent protein aggregation and fast clearance from the body (Adem et al., 2014). Indeed, PEG chains installed on the payload or the linker reportedly prevent ADCs forming non-covalent oligomers (King et al., 2002; Lyon et al., 2015).

Scheme 2. Structures of branched linkers 5-7.

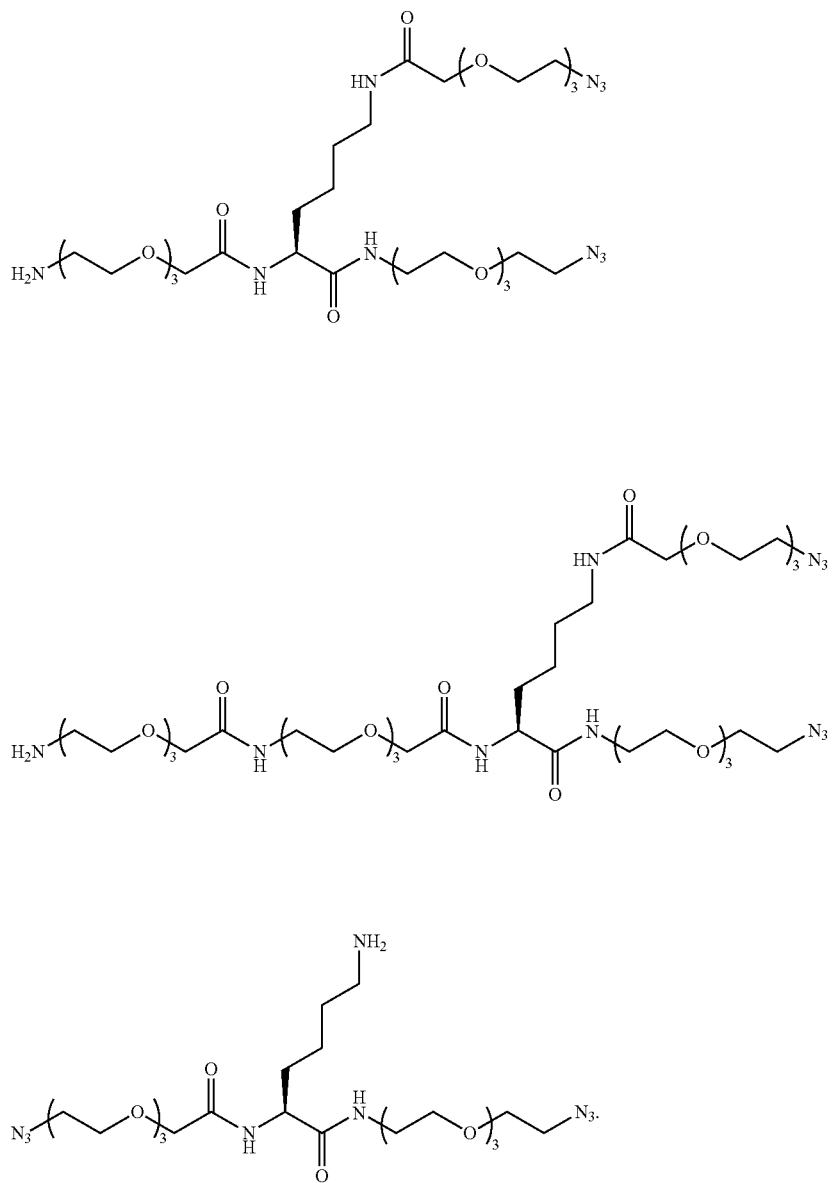

Next, conjugation of the branched linkers synthesized to the anti-HER2 IgG1 antibody was performed. In this study, an engineered anti-HER2 monoclonal antibody (mAb) with a mutation of the asparagine 297 of the heavy chain into alanine (N297A) was employed. It has been reported that this mutation does not alter the HER2 binding profile of the anti-HER2 mAb (Shi et al., 2014). In addition, this mutation allowed for the omission of the removal of the N-glycan chain on the asparagine 297, a required step for MTGase-mediated antibody-linker conjugation (Dennler et al., 2014). Installation of branched linkers 5-7 onto the N297A anti-HER2 mAb was attempted according to the reported protocol (linker: 80 equiv., antibody: 1.0 mg/mL, MTGase: 6.7 unit/mg antibody) (Dennler et al., 2014). However, the conversion rates were unsatisfactory (50-79%, entries 1-3 in Table 2 and Schemes 4-5), resulting in mixtures of somewhat heterogeneous antibody-linker conjugates. The bulkiness of primary amine-containing molecules often leads to low efficiency in MTGase-mediated protein labeling ((Dennler et al., 2015). Indeed, Schibli and co-workers used a simple linear linker for ADC construction to achieve quantitative conversion (Dennler et al., 2014). This finding inspired the optimization of the reaction conditions to attach the bulky branched linkers to the N297A anti-HER2 mAb in an efficient manner. Thus, various reaction conditions were screened using branched linker 5, the most reactive linker of the three. It was found that the amount of MTGase did not show a significant impact on the conversion rate (entry 4). In contrast, a higher concentration of the N297A anti-HER2 mAb substantially improved the conjugation efficiency (entry 5). In addition, increasing the amount of linker 5 turned out to be effective for improving the conversion rate (entries 6 and 7). Various reaction conditions were further examined, and finally effective conditions enabling nearly quantitative conjugation (entries 8 and 9) were identified. Incubation of the reaction mixture at 37° C. overnight afforded by-products that may be derived from protein denaturing or overreaction with the glutamine residues other than Q295 whereas such side reactions were not observed at room temperature. Thus, it was decided to perform the linker conjugation in the following sections at room temperature. The optimal reaction conditions also enabled highly efficient conjugation of branched linkers 6 and 7 to the N297A anti-HER2 mAb (entries 10 and 11). This success demonstrates that the MTGase-based transpeptidation can efficiently conjugate even bulky linkers to antibodies under optimal conditions. In addition, this finding is encouraging because additional modifications of linker structure may be used to fine-tune ADC physicochemical properties and further increase DARs. The results also indicate that the MTGase-mediated transpeptidation could be used more generally for various protein modifications.

TABLE 2

MTGase-mediated antibody-branched linker conjugation

| entry | linker (equiv.) | linker | antibody (mg/mL) | temperature (° C.) | conversion[b] (%) |
|---|---|---|---|---|---|
| 1 | 80 | 5 | 1.0 | 37 | 79 |
| 2 | 80 | 6 | 1.0 | 37 | 52 |
| 3 | 80 | 7 | 1.0 | 37 | 50 |
| 4[a] | 80 | 5 | 1.0 | 37 | 77 |
| 5 | 80 | 5 | 2.0 | 37 | 86 |
| 6 | 200 | 5 | 2.0 | 37 | 90 |
| 7 | 400 | 5 | 2.0 | 37 | 90 |
| 8 | 400 | 5 | 6.2 | 37 | >95[c] |
| 9 | 400 | 5 | 6.2 | r.t. | >95 |
| 10 | 400 | 6 | 6.2 | r.t. | 94 |
| 11 | 400 | 7 | 6.2 | r.t. | >95 |

[a]MTGase (26.9 U/mg antibody).
[b]Determined based on deconvoluted ESI-mass spectra.
[c]After 3 h.
Partial loss of the product was observed after overnight incubation, which is probably due to protein denaturing and/or overreaction with glutamine residues other than Q295.

Payload Installation by Click Chemistry and Stability Study.

Figure 2:
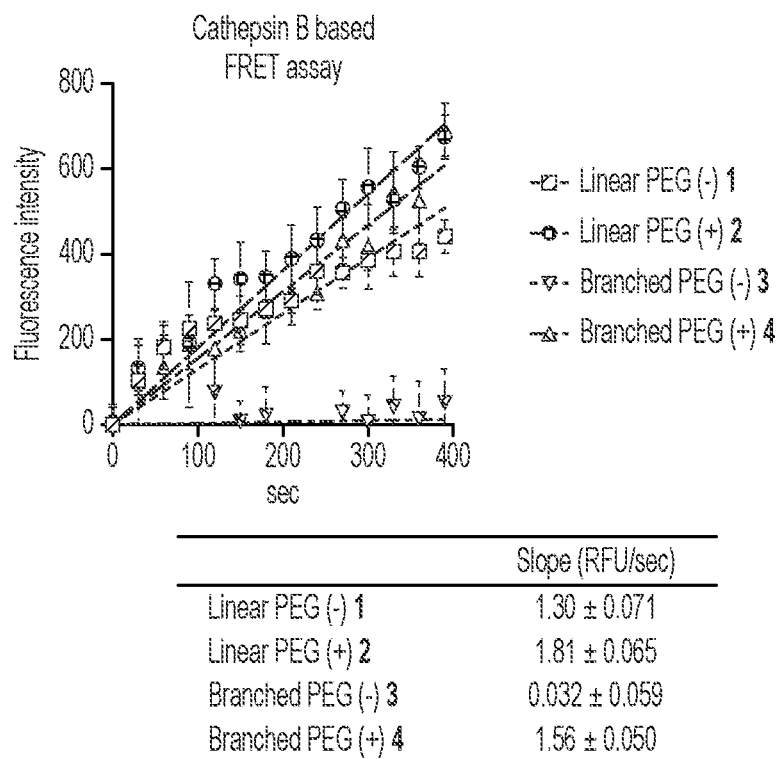
FIG. 2. Quencher release rate determination in Förster resonance energy transfer (FRET) assay. Each slope reflecting drug (quencher) release rate was calculated by linear regression using Graph Pad Prism 7 software. Values of branched probes 3 and 4 were doubled for plotting because those probes possess two quencher moieties. All assays were performed in triplicate and error bars represent SEM.
Figure 3A:
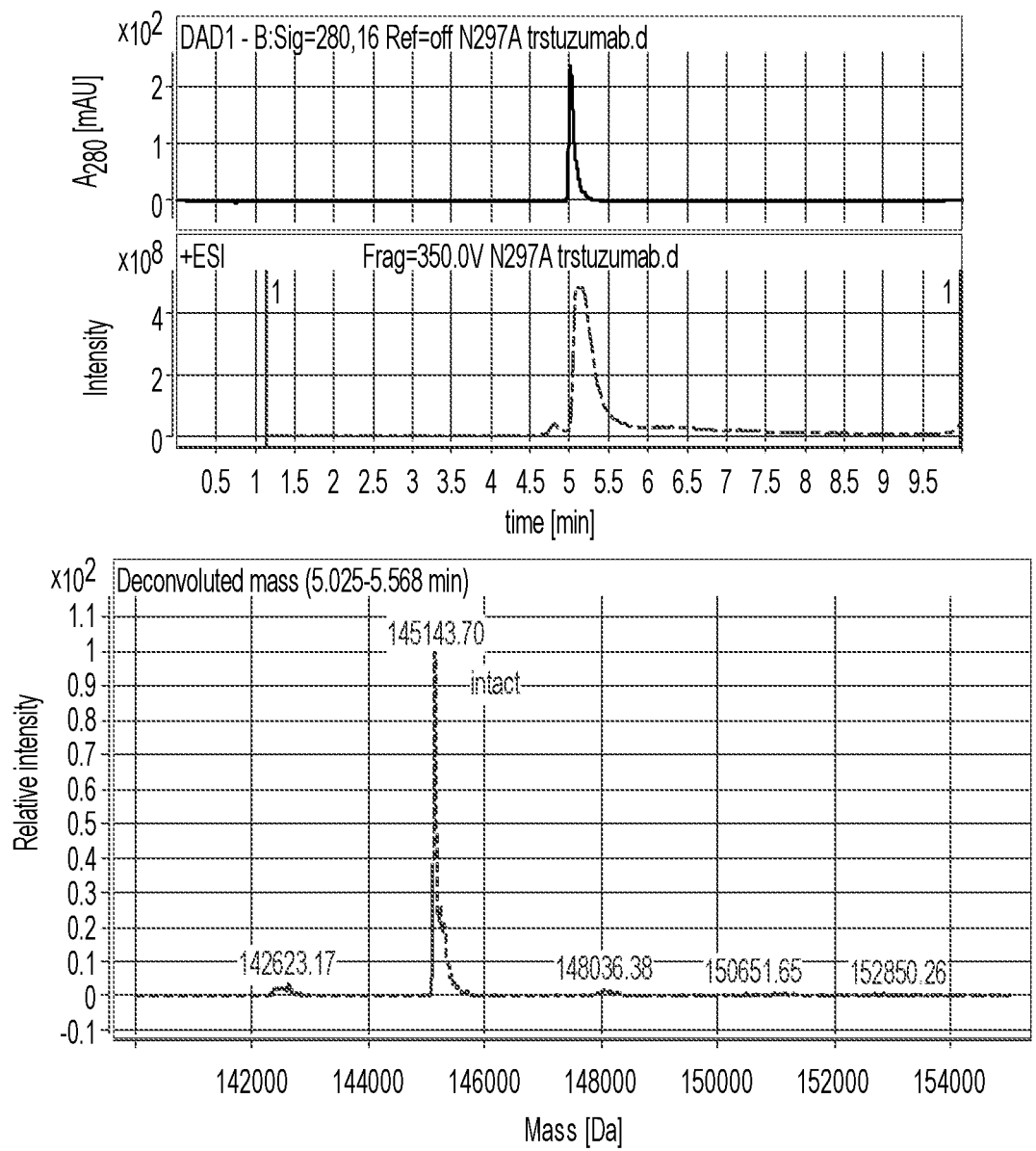
FIGS. 3A & 3B. (a) UV trace at 280 nm, total ion chromatogram, and deconvoluted mass spectra of the intact N297A anti-HER2 antibody. (b) UV trace at 280 nm, total ion chromatogram, and deconvoluted mass spectrum of the DTT-reduced N297A anti-HER2 antibody (heavy and light chains).
Figure 3B:
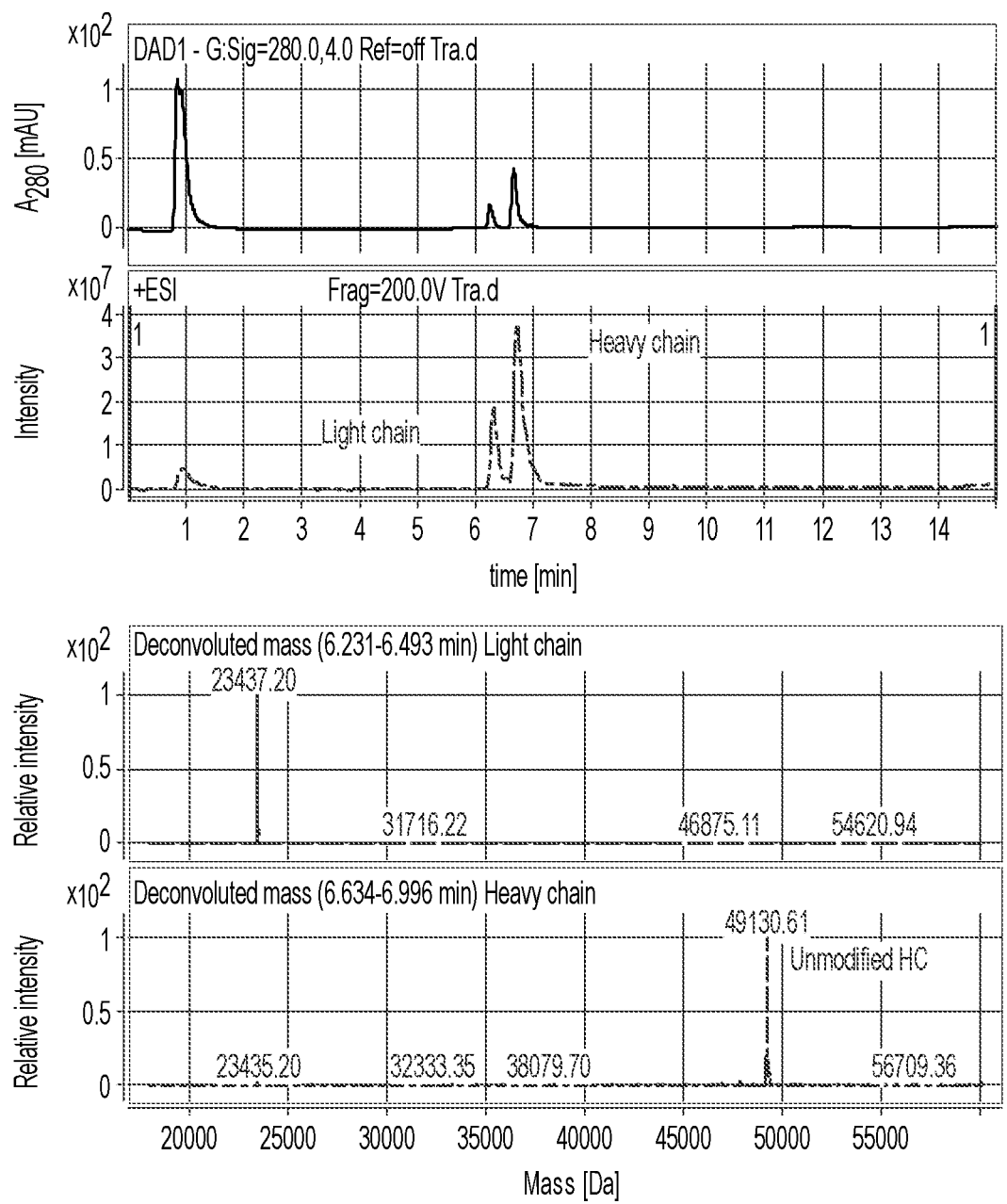

Finally, the N297A anti-HER2 mAb-branched linker 5 conjugate obtained and the potent antimitotic agent monomethyl auristatin F (MMAF) were coupled. The strain-promoted azide-alkyne cycloaddition (copper-free click reaction) (Agard et al., 2004) was employed using MMAF module 8 containing dibenzocyclooctyne (DBCO), PEG spacer, Val-Cit, and p-aminobenzyloxycarbonyl (PABC) (FIG. 2a). The PABC was incorporated to allow for traceless release of the MMAF upon cathepsin B-mediated cleavage of the Val-Cit. The anti-HER2 mAb-linker 5 conjugate (4.0 mg/mL) was incubated with DBCO-MMAF 8 (1.5 equiv. per reaction site) in PBS/4% DMSO. The click reaction reached full completion within 1 h to give nearly homogeneous ADC 9 with an average DAR of 3.9 (FIG. 2b-2c and Schemes 6-7). Two control ADCs were also prepared in the same manner: N297A anti-HER2 mAb-MMAF conjugate containing linear linkers (linear ADC 10, DAR: 1.9) (Dennler et al., 2004) and a N297A non-targeting IgG conjugated with MMAF through the branched linker 5 (non-targeting branched ADC 11, DAR: 3.9).

Notably, size-exclusion chromatography (SEC) analysis revealed that ADC 9 existed predominantly in monomer form (FIG. 2d), likely due to the multiple hydrophilic PEG spacers incorporated within the ADC scaffold. Furthermore, the cleavable branched linkers installed on ADC 9 were stable under physiological conditions; no significant degradation of the linkers was observed in human plasma at 37° C. for 7 days, indicating that the DAR did not significantly changed during incubation (Scheme 8). These results support the validity of the linker design from a drug development perspective.

Example 2—General Methods and Materials

Unless otherwise noted, all materials were purchased from commercial suppliers (Acros Organics, Chem-Impex International, Fisher Scientific, Sigma Aldrich, and TCI America) and used as received. All anhydrous solvents were purchased and stored over activated molecular sieves under argon atmosphere.

Analytical thin-layer chromatography (TLC) was performed using silica gel plates (Merck Kieselgel 60F$_{254}$, 0.25 mm for TLC) and visualization was conducted with ultraviolet light (254 nm) or by ninhydrin staining. Flash column chromatography was performed using silica gel (TCI America, spherical, particle size 60 μm).

Nuclear magnetic resonance (NMR) spectra were recorded on a Bruker DPX spectrometer ($^1$H: 300 MHz) using methanol-d$_4$ (CD$_3$OD) as deuterated solvent. Chemical shifts (δ) in $^1$H NMR spectra were reported in parts per million (ppm) relative to CD$_3$OD (δ=3.34 ppm. Coupling constants (J) in all NMR spectra are reported in Hertz (Hz).

Analytical Reverse-phase high performance liquid chromatography (RP-HPLC) was performed using an Agilent LC-MS system consisting of a 1100 HPLC and a 1946D single quadrupole electrospray ionization (ESI) mass spectrometer equipped with a C18 reverse-phase column (50×3 mm, 2.6 micron; Accucore C18, Thermo Scientific). Standard analysis conditions for organic molecules were as follows: flow rate=0.5 mL/min; solvent A=water containing 0.1% formic acid; solvent B=acetonitrile containing 0.1% formic acid. Compounds were analyzed using a linear gradient and monitored with UV detection at 210 and 254 nm. Preparative HPLC was performed using a Breeze HPLC system (Waters) equipped with a C18 reverse-phase column (19×150 mm, 5.0 micron; SunFire Prep C18 OBD, Waters). Standard purification conditions were as follows: flow rate=10 mL/min; solvent A=water containing 0.05% trifluoroacetic acid (TFA); solvent B=acetonitrile containing 0.05% TFA. Compounds were analyzed using a linear gradient and monitored with UV detection at 210 and 254 nm. In all cases, fractions were analyzed off-line using the LC-MS for purity confirmation.

High-resolution mass spectra were obtained using an Agilent 6530 Accurate Mass Q-TOF LC/MS. Absorbance and fluorescence were measured on a Cytation 5 Cell Imaging Multi-Mode Reader (Biotek).

Example 3—Branched-Linker Compound Characterization

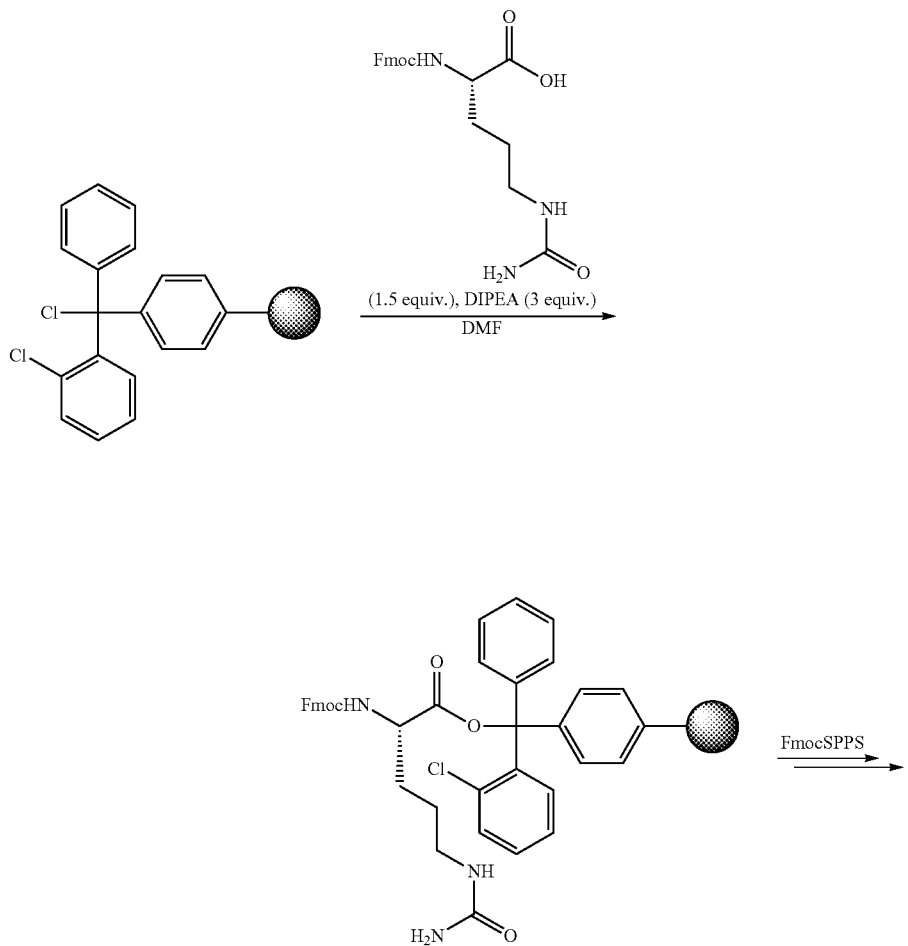

Scheme 3. Synthesis of linear probe 1.

-continued
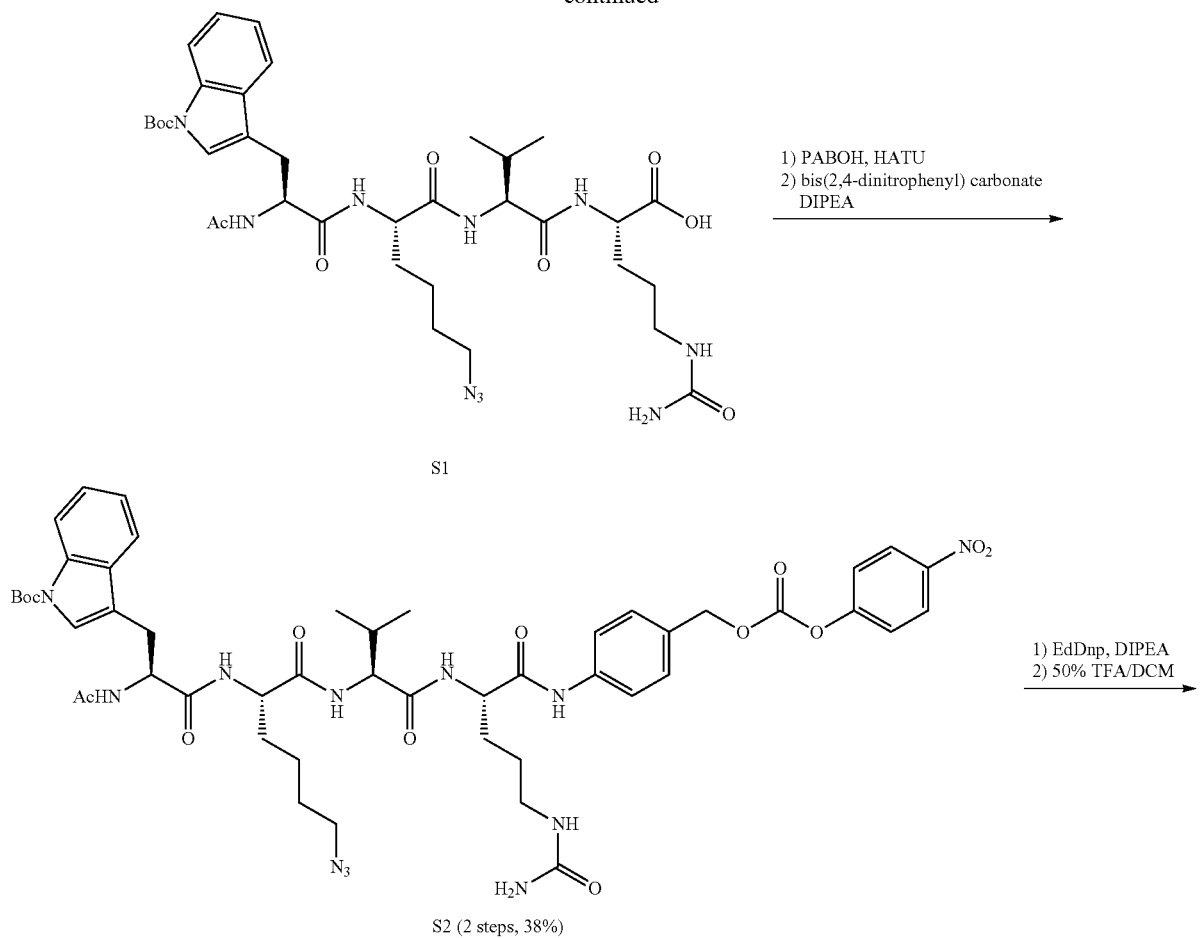
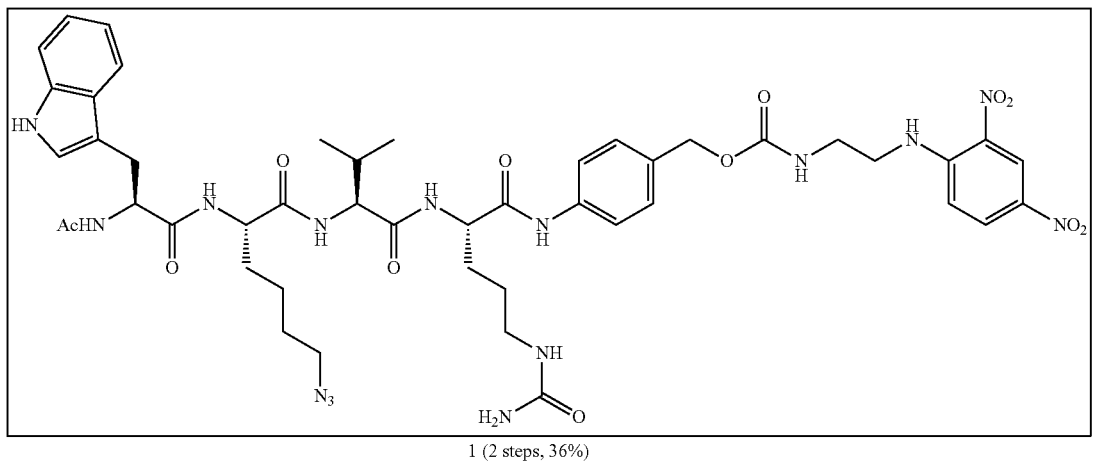
FmocSPPS
Conditions
Coupling: Fmoc-amino acid (2 equiv)
HATU (2 equiv.)
DIPEA (3 equiv.)
Fmoc deprotection: 20% piperidine in DMF
Resin cleavage: 1% TFA in DCM

Synthesis of Ac-Trp(Boc)-Lys(N3)-Val-Cit-OH S1

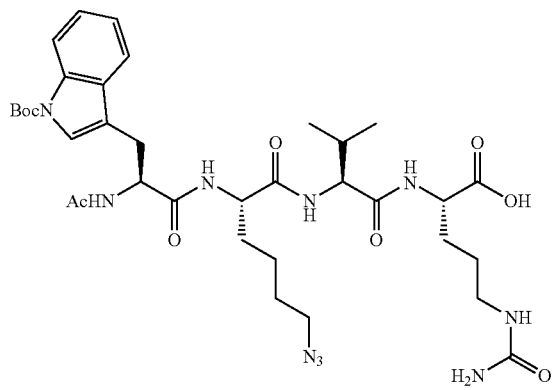 [SMILES: CC(=O)N[C@@H](Cc1cn(C(=O)OC(C)(C)C)c2ccccc12)C(=O)N[C@@H](CCCCN=[N+]=[N-])C(=O)N[C@H](C(=O)N[C@@H](CCCNC(N)=O)C(=O)O)C(C)C]

Chlorotrityl chloride resin (500 mg, 0.76 mmol) and Fmoc-citrulline-OH (453 mg, 1.14 mmol) were taken to a manual solid-phase reactor containing N,N-diisopropylethylamine (DIPEA, 397 µL, 2.28 mmol) and dimethylfolmamide (DMF, 3 mL) and agitated for 2 h. Methanol (MeOH, 600 µL, 1.52 mmol) was added to the resin and agitated for 20 min, the solution was drained and the resin was washed with DMF (5×3 mL) and dichloromethane (DCM, 5×3 mL). To remove the Fmoc-protecting group after each coupling, the resin was treated with piperidine (5 mL of 20% in DMF, 20 min) and washed with DMF (5×3 mL) and DCM (5×3 mL). Fmoc-protected amino acid (2 equiv.) was pre-activated using 1-[bis(dimethylamino)methylene]-1H-1,2,3-triazolo[4,5-b]pyridinium 3-oxid hexafluorophosphate (HATU, 2 equiv.) and DIPEA (3 equiv.) in DMF for 3 min, and the cocktail was added to the resin. The resin was agitated for 1 h at room temperature. The completion of the coupling was verified by the Kaiser test. After each coupling step, the coupling cocktail was drained and the resin was washed with DMF (5×3 mL) and DCM (5×3 mL). After elongation of the peptide, the resin was treated with acetic anhydride (2 equiv.) and DIPEA (3 equiv.) in DMF for 1 h and then washed with DMF (5×3 mL) and DCM (5×3 mL). The resulting protected peptide resin was treated with cocktail of 1% trifluoroacetic acid (TFA)/DCM at room temperature for 1 h. The solution was concentrated in vacuo and the crude peptide was precipitated with cold diethyl ether (5-6 mL) followed by centrifugation at 500×g for 5 min (3 times). The resulting crude peptide S1 was dried in vacuo and then used immediately in the next step without purification.

Synthesis of Ac-Trp(Boc)-Lys(N$_3$)-Val-Cit-PABC-PNP S2

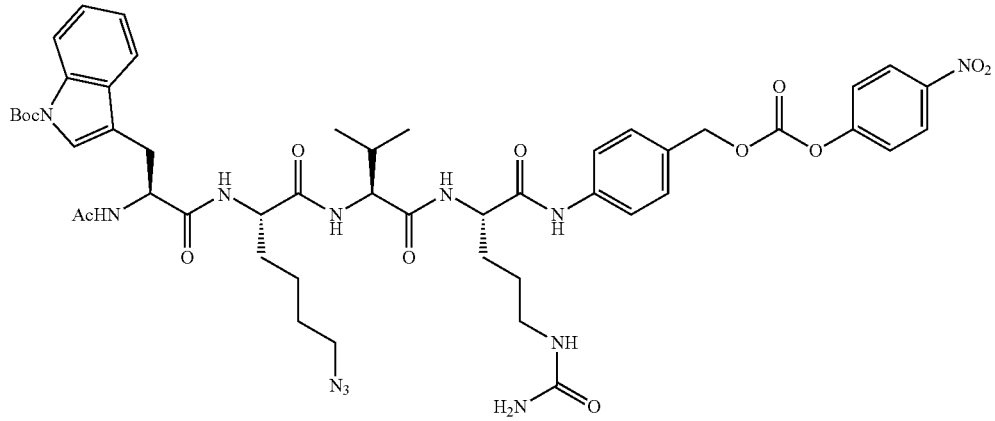 [SMILES: CC(=O)N[C@@H](Cc1cn(C(=O)OC(C)(C)C)c2ccccc12)C(=O)N[C@@H](CCCCN=[N+]=[N-])C(=O)N[C@H](C(=O)N[C@@H](CCCNC(N)=O)C(=O)Nc1ccc(COC(=O)Oc2ccc([N+](=O)[O-])cc2)cc1)C(C)C]

To a solution of peptide S1 (20 mg, 0.026 mmol) in DMF (1 mL) was added HATU (13.0 mg, 0.034 mmol), DIPEA (6 µL, 0.04 mmol), and p-aminobenzyl alcohol (PABOH, 4.9 mg, 0.04 mmol), and the mixture was stirred at room temperature for 1.5 h in the dark. The solution was directly concentrated in vacuo and the crude peptide was precipitated with cold diethyl ether (5-6 mL) followed by centrifugation at 500×g for 5 min (3 times). The resulting crude peptide was dried in vacuo for 90 min at least and then used immediately in the next step without purification. To a solution of this crude mixture in DMF (2 mL) was added bis(2,4-dinitrophenyl) carbonate (40.2 mg, 0.13 mmol) and DIPEA (23 µL, 0.13 mmol), and the mixture was stirred overnight at room temperature. The crude peptide S2 was purified by preparative RP-HPLC to give analytically pure peptide S2 (10.2 mg, 38% for the 2 steps). Off-white powder. HRMS (ESI) Calcd. For $C_{49}H_{62}N_{12}O_{13}Na$ [M+Na]$^+$: 1049.4452. Found: 1049.4462.

Synthesis of Ac-Trp-Lys(N₃)-Val-Cit-PABC-EdDnp 1

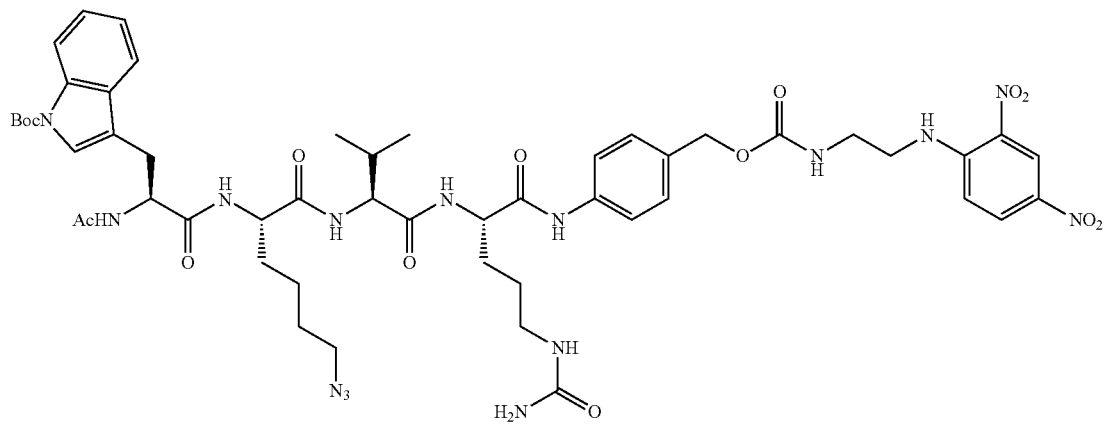 [SMILES: CC(=O)N[C@@H](Cc1cn(C(=O)OC(C)(C)C)c2ccccc12)C(=O)N[C@@H](CCCCN=[N+]=[N-])C(=O)N[C@H](C(=O)N[C@@H](CCCNC(N)=O)C(=O)Nc1ccc(COC(=O)NCCNc2ccc([N+](=O)[O-])cc2[N+](=O)[O-])cc1)C(C)C]

Peptide S2 (4.6 mg, 0.0045 mmol) was treated with N'-(2,4-dinitrophenyl)ethane-1,2-diamine (EdDnp, 1.53 mg, 0.0068 mmol) and DIPEA (1 μL, 0.0045 mmol) in DMF (0.5 mL) at room temperature for 3.5 h. The solution was directly concentrated in vacuo to get the crude peptide. The crude peptide was then dissolved in DCM (0.5 mL) and TFA (0.5 mL) was added to the solution at 0° C. After 1 h, the solution was directly concentrated in vacuo and purified by preparative RP-HPLC to give analytically pure peptide 1 (1.66 mg, 36% for the 2 steps). Yellow powder. HRMS (ESI) Calcd. For $C_{46}H_{59}N_{15}O_{12}Na$ $[M+Na]^+$: 1036.4360. Found: 1036.4357.

Scheme 4. Synthesis of alkyne peptide S4.

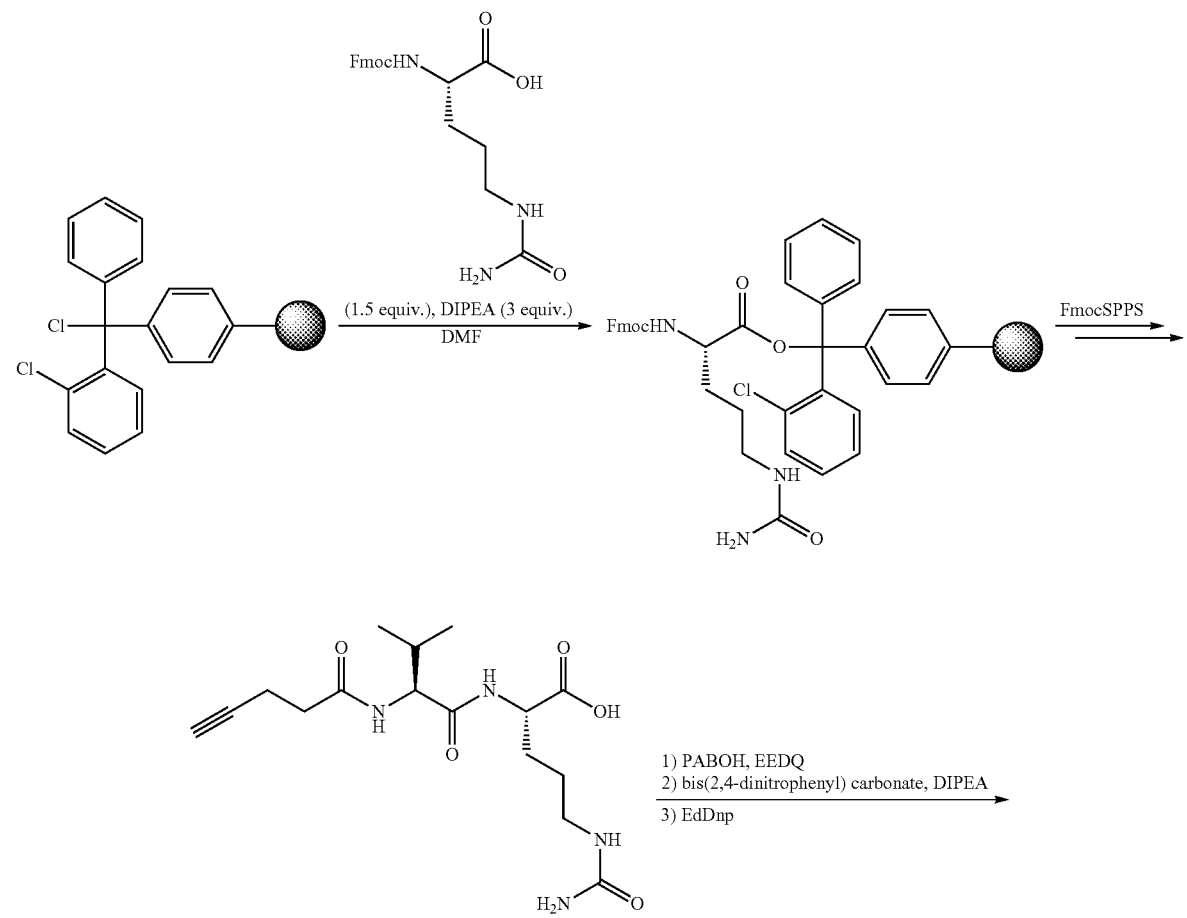

-continued

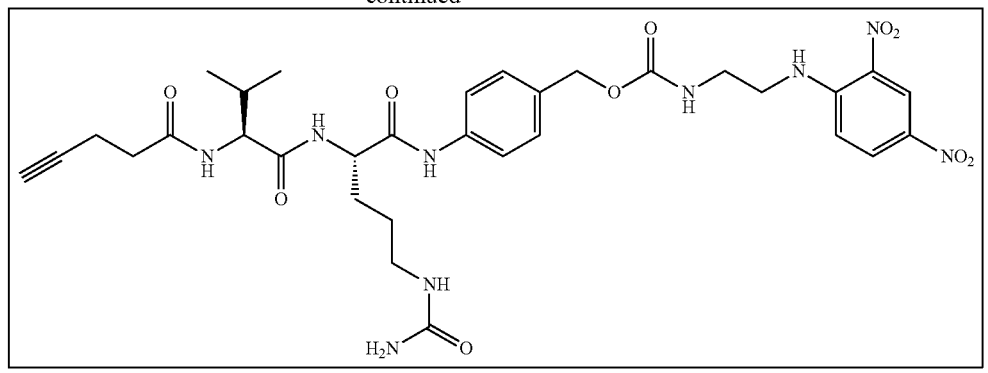

S4 (3 steps, 16%)

FmocSPPS

Conditions
Coupling: Fmoc-amino acid (2 equiv.)
HATU (2 equiv.)
DIPEA (3 equiv.)
Fmoc deprotection: 20% piperidine in DMF
Resin cleavage: 1% TFA in DCM Synthesis of alkyne-Val-Cit-OH S3

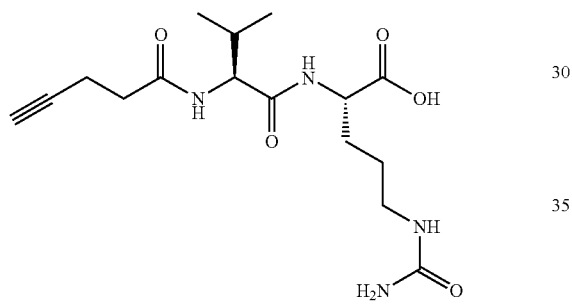

Fmoc-Val-Cit-resin was synthesized in the same manner as preparation of S1. After elongation of the peptide, the resin was treated with 4-pentynoic acid (2 equiv.), HATU (2 equiv.), and DIPEA (3 equiv.) in DMF for 1 h and then washed with DMF (5×1 mL) and DCM (5×1 mL). The resulting peptide resin was treated with cocktail of 1% TFA/DCM at room temperature for 1 h. The solution was concentrated in vacuo and the crude peptide was precipitated with cold diethyl ether (5-6 mL) followed by centrifugation at 500×g for 5 min (3 times). The resulting crude peptide S3 was dried in vacuo and then used immediately in the next step without purification.

Synthesis of alkyne-Val-Cit-PABC-EdDnp S4

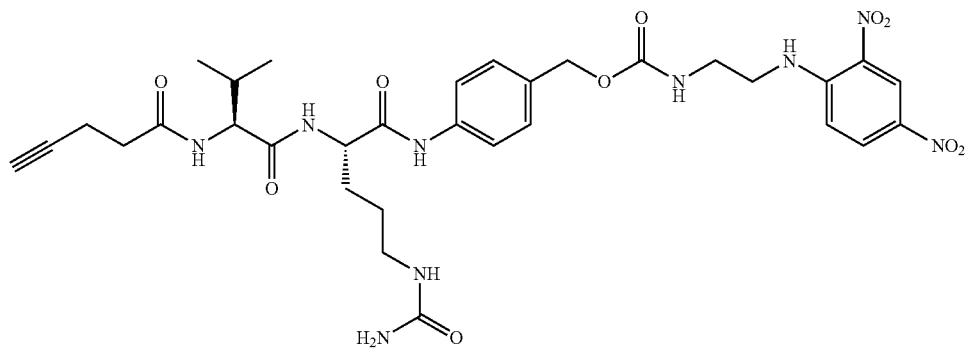 [SMILES: C#CCCC(=O)N[C@H](C(=O)N[C@@H](CCCNC(N)=O)C(=O)Nc1ccc(COC(=O)NCCNc2ccc([N+](=O)[O-])cc2[N+](=O)[O-])cc1)C(C)C]

To a solution of peptide S3 (21.8 mg, 0.062 mmol) in MeOH/DCM (1.5 mL, 1:2) was added PABOH (15.3 mg, 0.12 mmol) and N-ethoxycarbonyl-2-ethoxy-1,2-dihydroquinoline (EEDQ, 30.7 mg, 0.12 mmol), and the mixture was stirred overnight at room temperature in the dark. The solution was directly concentrated in vacuo and the crude peptide was precipitated with cold diethyl ether (5-6 mL) followed by centrifugation at 500×g for 5 min (3 times). The resulting crude peptide was dried in vacuo and then used immediately in the next step without purification.

To a solution of crude peptide in DMF (1 mL) was added bis(2,4-dinitrophenyl) carbonate (106 mg, 0.35 mmol) and DIPEA (36 µL, 0.21 mmol) and the mixture was stirred for 2 h at room temperature. Afterwards, EdDnp (31.7 mg, 0.14 mmol) was added to the mixture and the mixture was stirred for 3 h at room temperature. The additional EdDnp (55 mg, 0.25 mmol) was added and the mixture was further stirred for 1 h at room temperature. The reaction was quenched with 15% citric acid and extracted with ethyl acetate. The organic layer was washed with brine, dried over $Na_2SO_4$, and concentrated in vacuo. The crude peptide was purified by preparative RP-HPLC to give analytically pure peptide S4 (6.7 mg, 16% for the 3 steps). Yellow powder. HRMS (ESI) Calcd. For $C_{32}H_{41}N_9O_{10}Na$ $[M+Na]^+$: 734.2869. Found: 734.2871.

Scheme 5. Synthesis of linear probe containing PEG spacer 2.

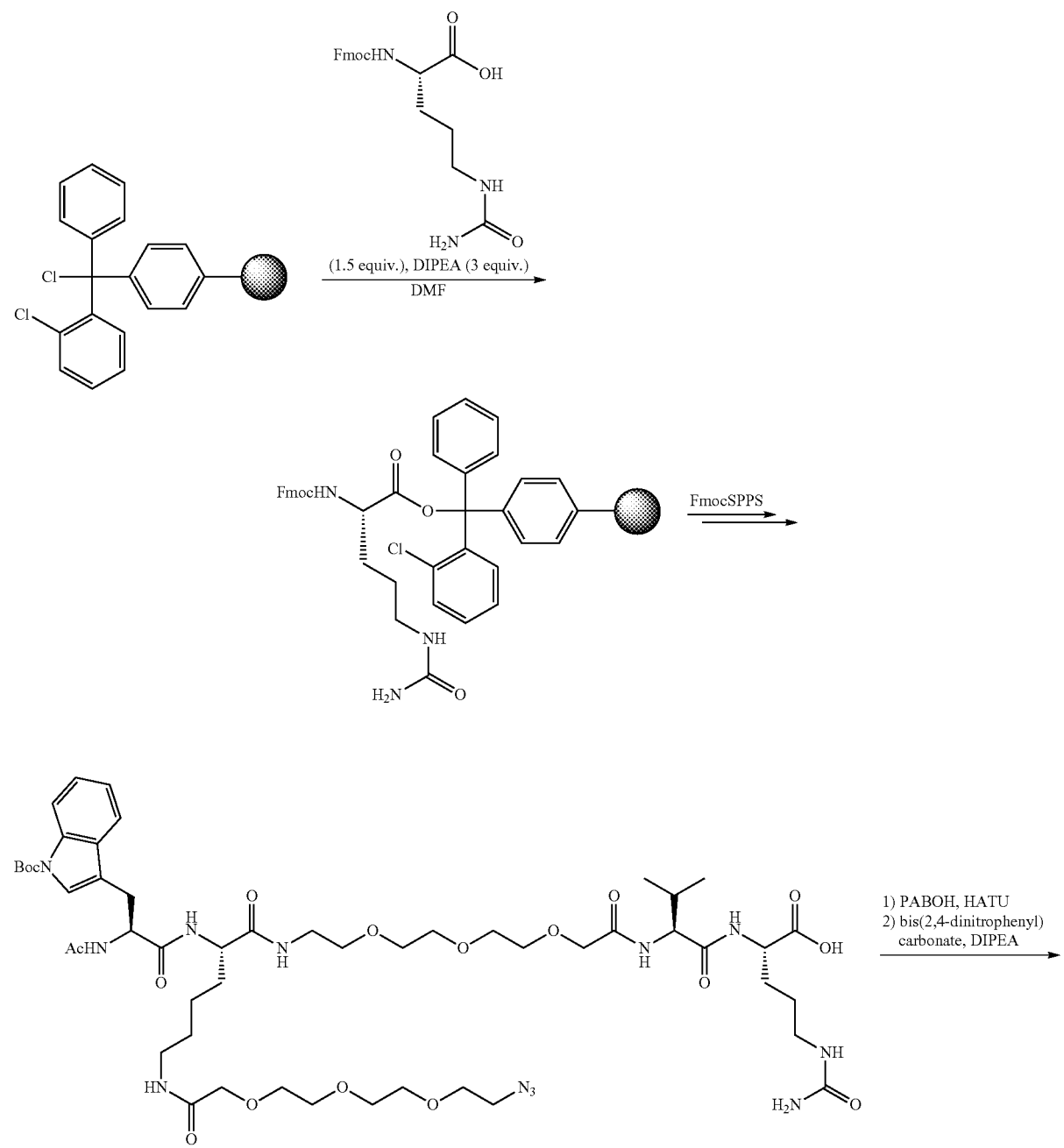

S5

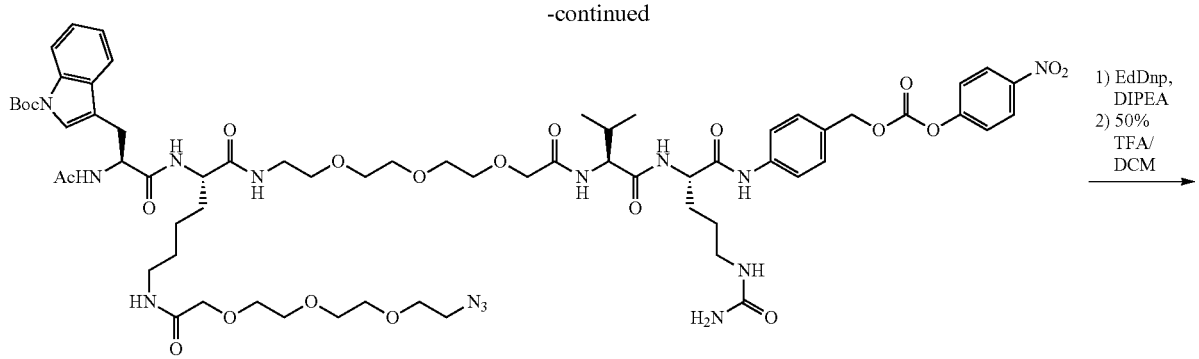
S6 (2 steps, 14%)
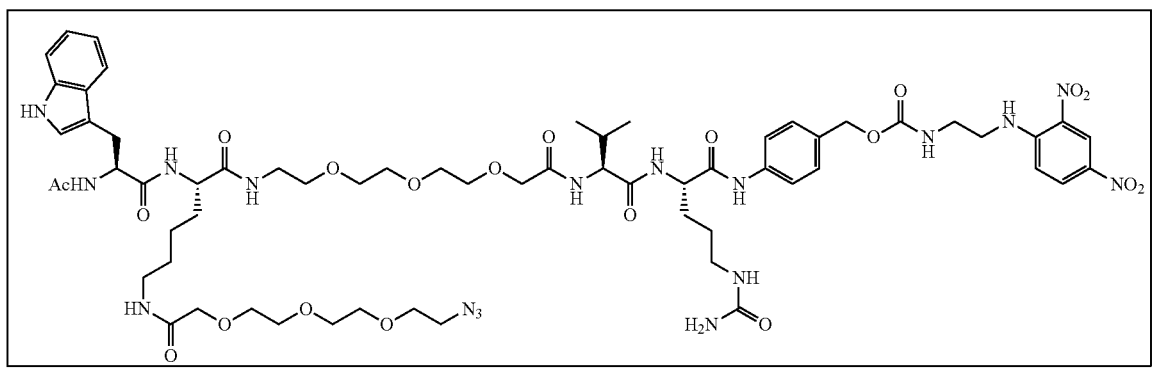
2 (2 steps, 34%)
FmocSPPS
Conditions
Coupling: Fmoc-amino acid (2 equiv)
HATU (2 equiv.)
DIPEA (3 equiv.)
Fmoc deprotection: 20% piperidine in DMF
Alloc deprotection: Pd(PPh$_3$)$_4$, PhSiH$_3$
Resin cleavage: 1% TFA in DCM
Synthesis of Ac-Trp(Boc)-Lys(-PEG$_3$-N$_3$)-PEG$_3$-Val-Cit-OH S5
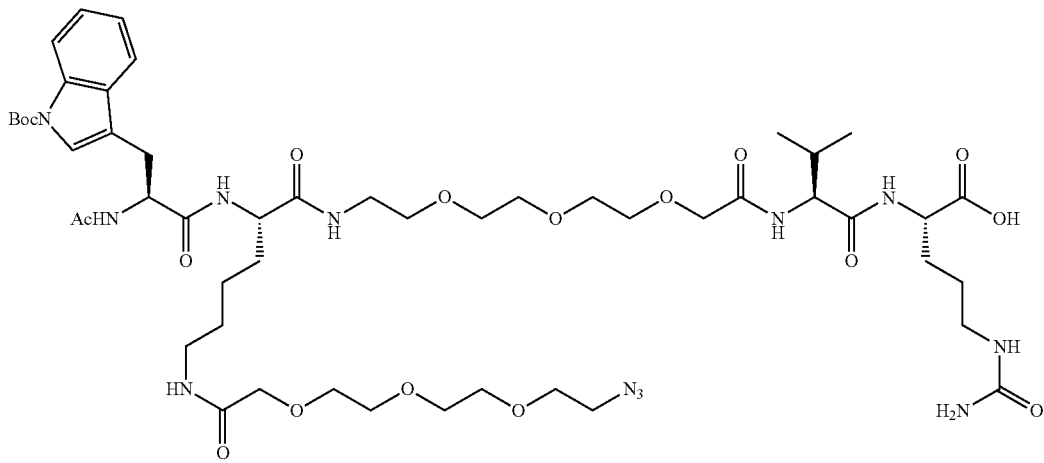 [SMILES: CC(=O)N[C@@H](Cc1cn(C(=O)OC(C)(C)C)c2ccccc12)C(=O)N[C@@H](CCCCNC(=O)COCCOCCOCCN=[N+]=[N-])C(=O)NCCOCCOCCOCC(=O)N[C@H](C(=O)N[C@@H](CCCNC(N)=O)C(=O)O)C(C)C]

Ac-Trp(Boc)-Lys(-PEG$_3$-N$_3$)-PEG$_3$-Val-Cit-OH was synthesized in the same manner as preparation of S1. The resulting peptide resin was treated with cocktail of 1% TFA/DCM at room temperature for 1 h. The solution was concentrated in vacuo and the crude peptide was precipitated with cold diethyl ether (5-6 mL) followed by centrifugation at 500×g for 5 min (3 times). The resulting crude peptide S5 was dried in vacuo and then used immediately in the next step without purification.

Synthesis of Ac-Trp(Boc)-Lys(-PEG$_3$-N$_3$)-PEG$_3$-Val-Cit-PABC-PNP S6

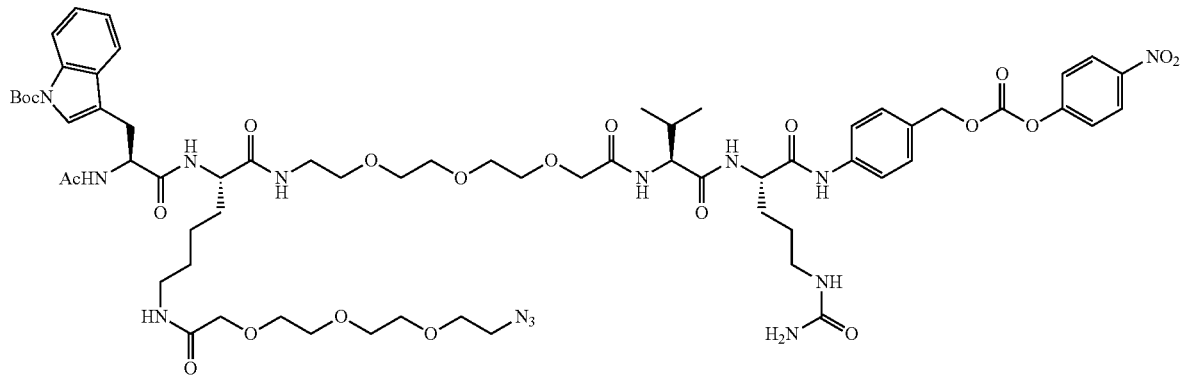 [SMILES: CC(=O)N[C@@H](Cc1cn(C(=O)OC(C)(C)C)c2ccccc12)C(=O)N[C@@H](CCCCNC(=O)COCCOCCOCCN=[N+]=[N-])C(=O)NCCOCCOCCOCC(=O)N[C@H](C(=O)N[C@@H](CCCNC(N)=O)C(=O)Nc1ccc(COC(=O)Oc2ccc([N+](=O)[O-])cc2)cc1)C(C)C]

To a solution of peptide S5 (24 mg, 0.021 mmol) in DMF (1 mL) was added HATU (10.4 mg, 0.027 mmol), DIPEA (4.8 μL, 0.027 mmol), and PABOH (3.9 mg, 0.032 mmol), and the mixture was stirred at room temperature for 2 h in the dark. The solution was directly concentrated in vacuo and the crude peptide was precipitated with cold diethyl ether (5-6 mL) followed by centrifugation at 500×g for 5 min (3 times). The resulting crude peptide was dried in vacuo for 90 min at least and then used immediately in the next step without purification. To a solution of this crude peptide in DMF (1 mL) was added bis(2,4-dinitrophenyl) carbonate (32 mg, 0.11 mmol) and DIPEA (18 μL, 0.11 mmol), and the mixture was stirred overnight at room temperature. The crude peptide S6 was purified by preparative RP-HPLC to give analytically pure peptide S6 (4.0 mg, 14% for the 2 steps). Off-white powder. HRMS (ESI) Calcd. For C$_{65}$H$_{92}$N$_{14}$O$_{21}$Na [M+Na]$^+$: 1427.6454. Found: 1427.6454.

Synthesis of Ac-Trp-Lys(-PEG$_3$-N$_3$)-PEG$_3$-Val-Cit-PABC-EdDnp 2

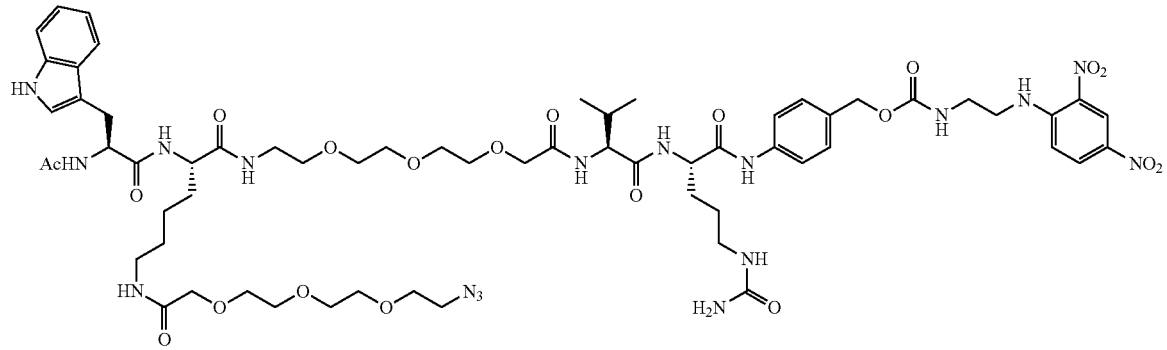 [SMILES: CC(=O)N[C@@H](Cc1c[nH]c2ccccc12)C(=O)N[C@@H](CCCCNC(=O)COCCOCCOCCN=[N+]=[N-])C(=O)NCCOCCOCCOCC(=O)N[C@H](C(=O)N[C@@H](CCCNC(N)=O)C(=O)Nc1ccc(COC(=O)NCCNc2ccc([N+](=O)[O-])cc2[N+](=O)[O-])cc1)C(C)C]

Peptide S6 (3.2 mg, 0.0023 mmol) was treated with EdDnp (0.78 mg, 0.0035 mmol) in DMF (0.5 mL) at room temperature for 2 h and the solution was directly concentrated in vacuo. The crude peptide was then dissolved in in DCM (1 mL) and TFA (1 mL) was added to the solution at 0° C. After 1 h, the solution was directly concentrated in vacuo and the crude peptide was precipitated with cold diethyl ether (5-6 mL) followed by centrifugation at 500×g for 5 min (3 times). The crude peptide was purified by preparative RP-HPLC to give analytically pure peptide 2 (1.1 mg, 34% for the 2 steps). Yellow powder. HRMS (ESI) Calcd. For $C_{62}H_{89}N_{17}O_{20}Na$ $[M+Na]^+$: 1414.6362. Found: 1414.6349.

Scheme 6. Synthesis of branched probes 3 and 4.

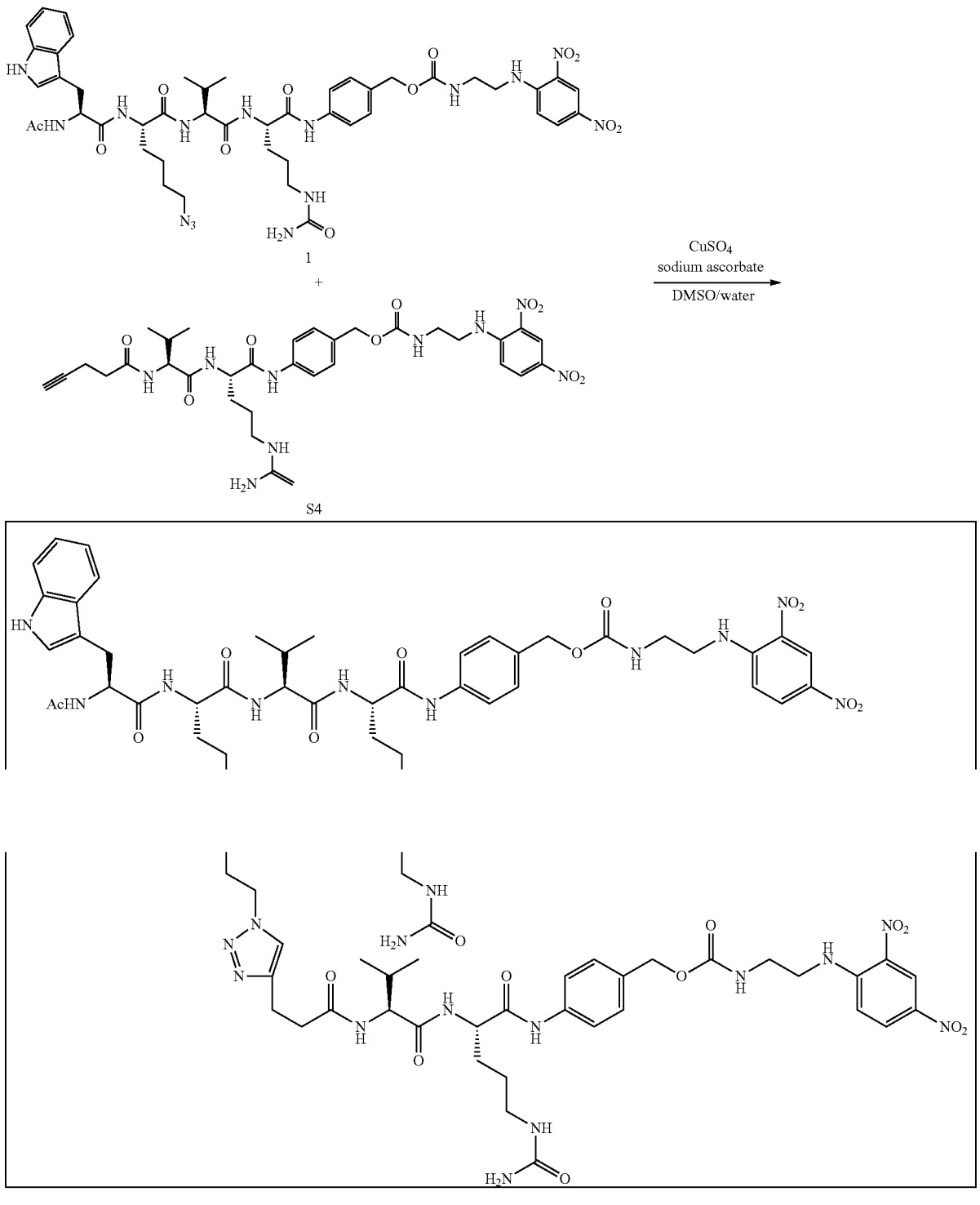

-continued
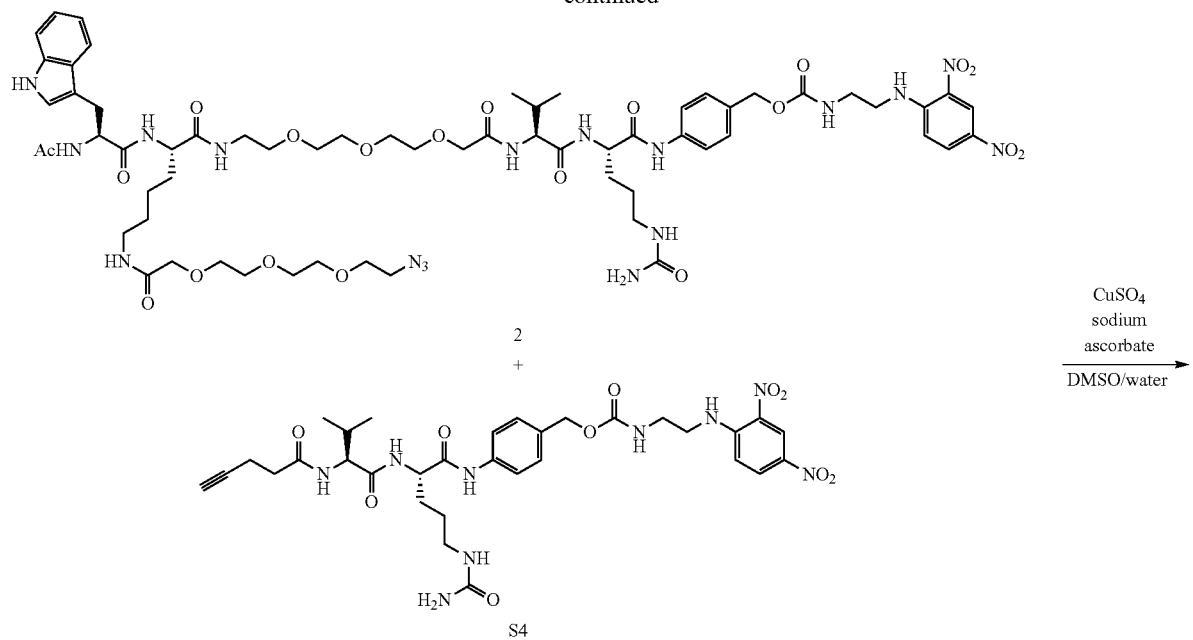
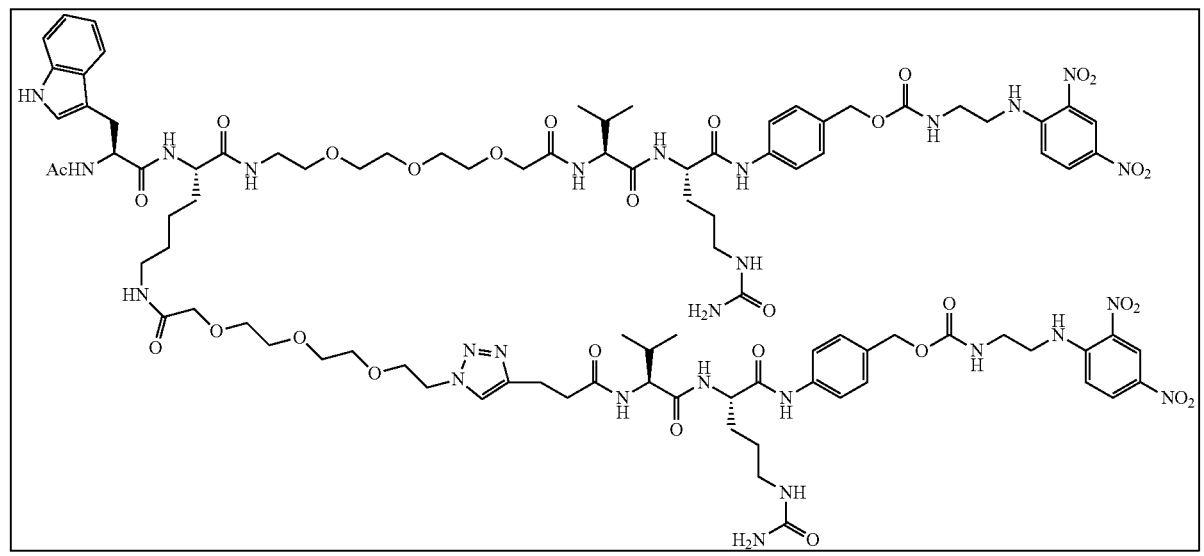
4 (30%)

Synthesis of FRET Compound 3

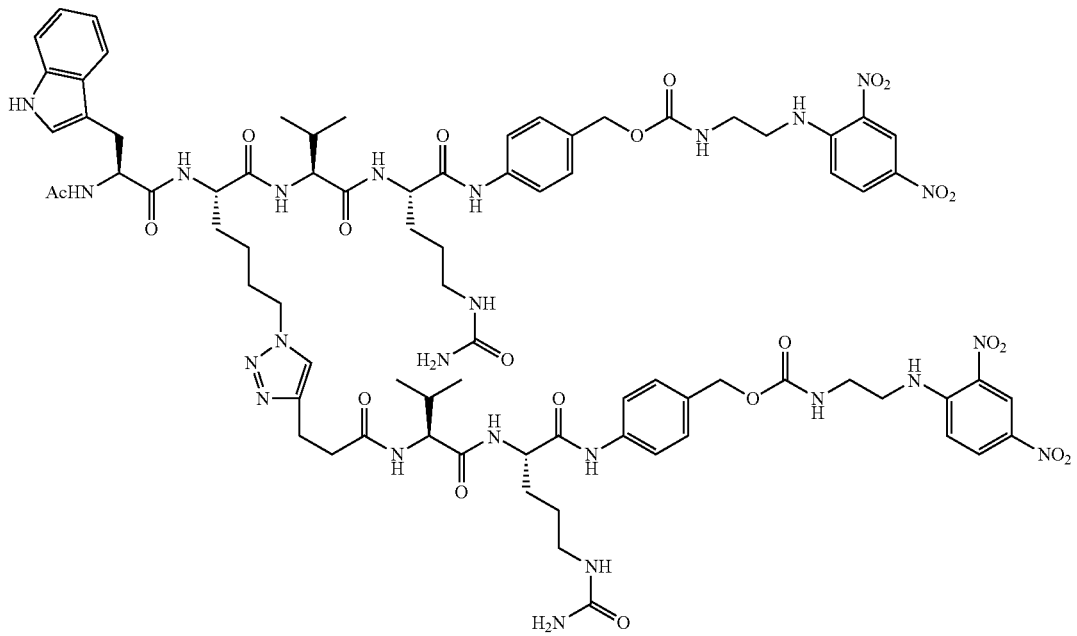 [SMILES: CC(=O)N[C@@H](Cc1c[nH]c2ccccc12)C(=O)N[C@@H](CCCCn1cc(CCC(=O)N[C@H](C(=O)N[C@@H](CCCNC(N)=O)C(=O)Nc2ccc(COC(=O)NCCNc3ccc([N+](=O)[O-])cc3[N+](=O)[O-])cc2)C(C)C)nn1)C(=O)N[C@H](C(=O)N[C@@H](CCCNC(N)=O)C(=O)Nc1ccc(COC(=O)NCCNc2ccc([N+](=O)[O-])cc2[N+](=O)[O-])cc1)C(C)C]

A mixture of alkyne peptide S4 (100 μL, 10 mM in DMSO) and azide peptide 1 (130 μL, 10 mM in DMSO) in DMSO (620 μL) was treated with a mixture of CuSO$_4$ (50 μL, 100 mM in DI water) and sodium ascorbate (100 μL, 100 mM in DI water) and stirred overnight at room temperature. Additional alkyne peptide S4 (20 μL, 10 mM in DMSO), CuSO$_4$ (50 μL, 100 mM in DI water) and sodium ascorbate (100 μL, 100 mM in DI water) were added to the reaction mixture, and further stirred at room temperature for 6.5 h. The crude peptide was purified by preparative RP-HPLC to give analytically pure peptide 3 (970 μg, 43%). Yellow powder. HRMS (ESI) Calcd. For $C_{78}H_{100}N_{24}O_{22}Na_2$ [M+2Na]$^{2+}$: 885.3614. Found: 885.3626.

Synthesis of FRET Compound 4

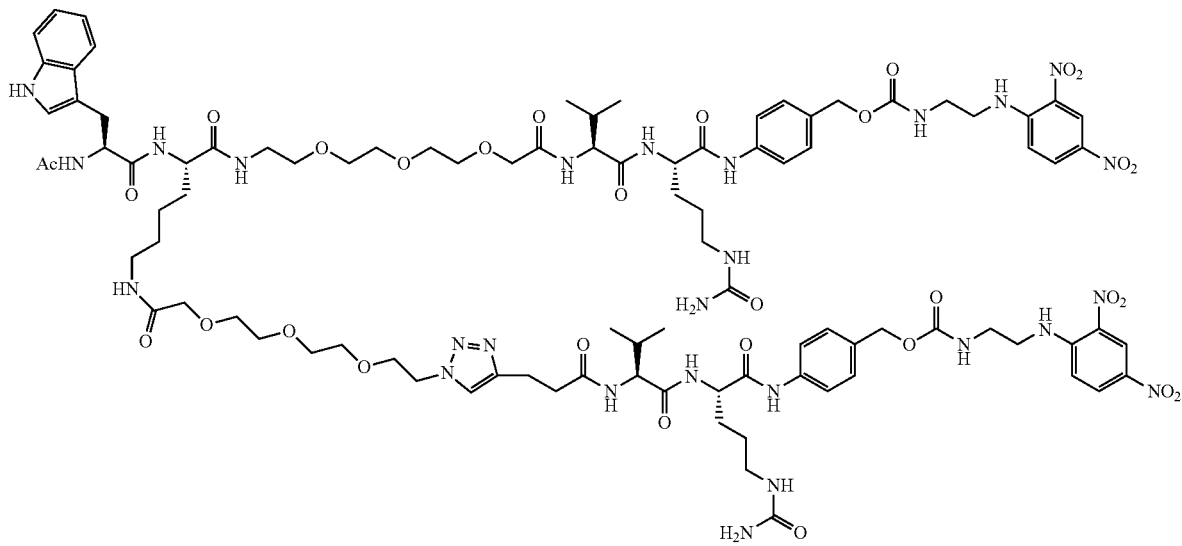 [SMILES: CC(=O)N[C@@H](Cc1c[nH]c2ccccc12)C(=O)N[C@@H](CCCCNC(=O)COCCOCCOCCn1cc(CCC(=O)N[C@H](C(=O)N[C@@H](CCCNC(N)=O)C(=O)Nc2ccc(COC(=O)NCCNc3ccc([N+](=O)[O-])cc3[N+](=O)[O-])cc2)C(C)C)nn1)C(=O)NCCOCCOCCOCC(=O)N[C@H](C(=O)N[C@@H](CCCNC(N)=O)C(=O)Nc1ccc(COC(=O)NCCNc2ccc([N+](=O)[O-])cc2[N+](=O)[O-])cc1)C(C)C]

A mixture of alkyne peptide S4 (135 μL, 10 mM in DMSO) and azide peptide 2 (79 μL, 10 mM in DMSO) in DMSO (600 μL) was treated with a mixture of CuSO₄ (39 μL, 100 mM in DI water) and sodium ascorbate (79 μL, 100 mM in DI water) and stirred at room temperature for 8 h. The crude peptide was purified by preparative RP-HPLC to give analytically pure peptide 4 (500 μg, 30%). Yellow powder. HRMS (ESI) Calcd. For $C_{94}H_{13}MN_{26}O_{30}Na$ [M+Na]⁺: 2126.9367. Found: 2126.9345.

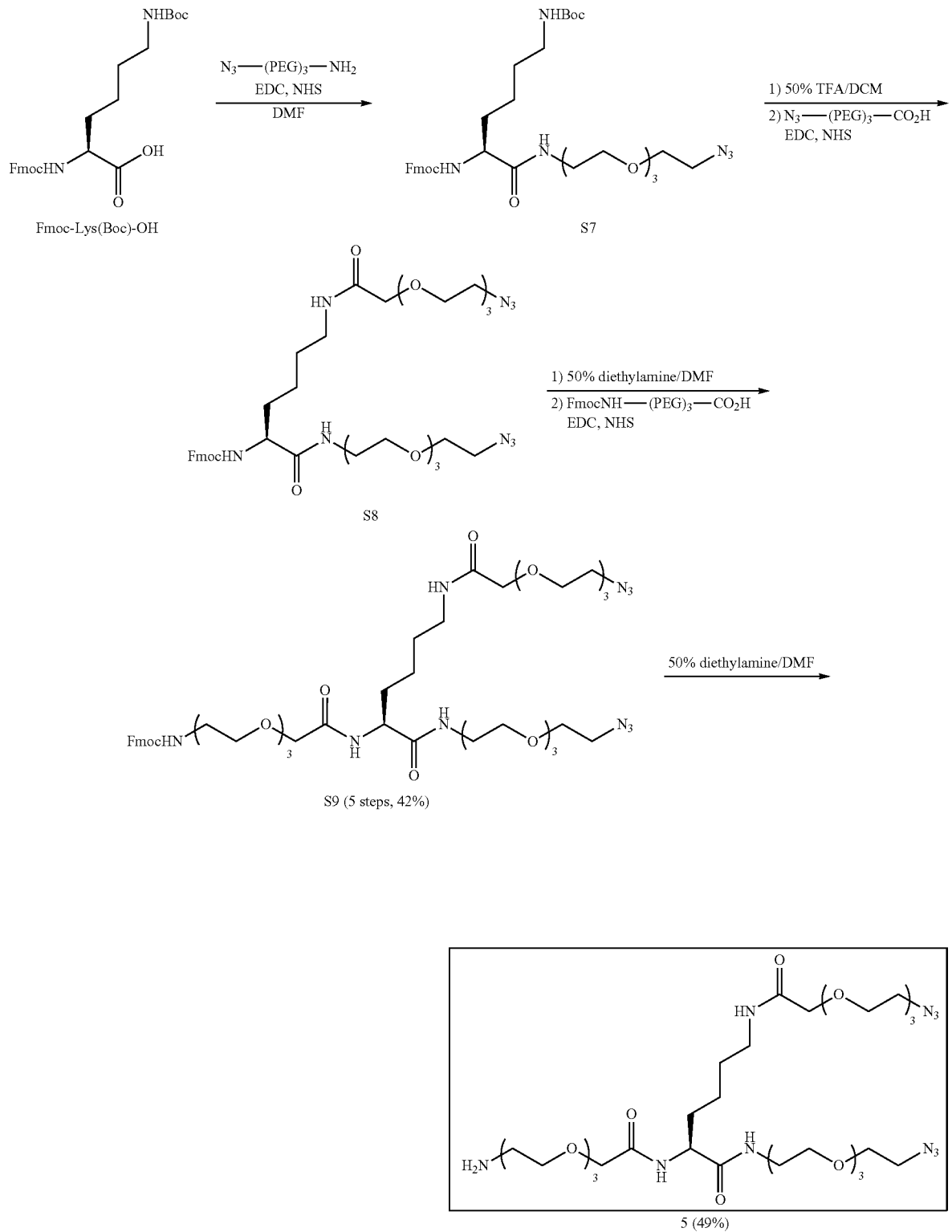

Scheme 7. Synthesis of branched linker compounds 5-7.

-continued

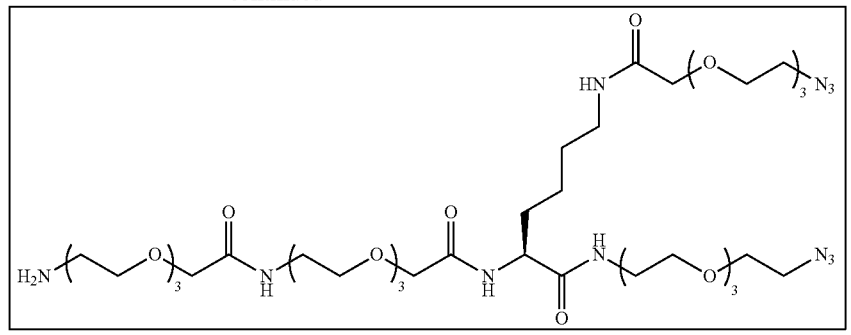

6 (3 steps, 65%)

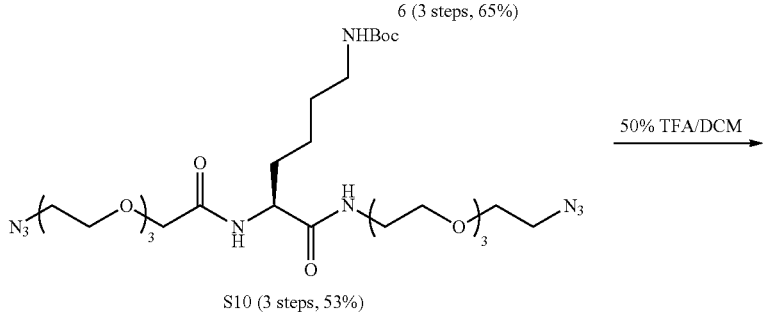

S10 (3 steps, 53%)

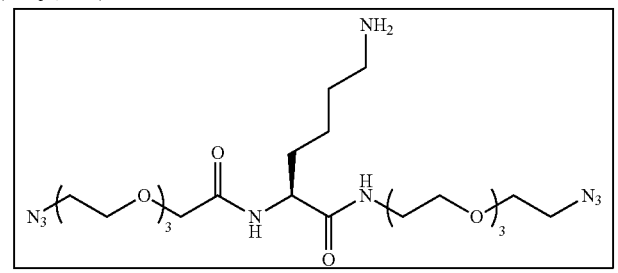

7 (81%)

Synthesis of Fmoc-Lys(Boc)-PEG$_3$-N$_3$ S7

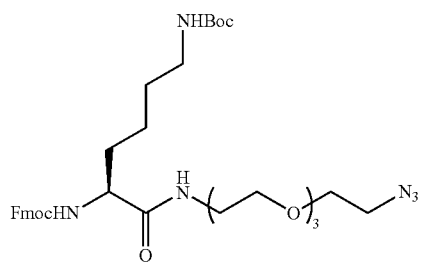

Fmoc-Lys(Boc)-OH (217.5 mg, 0.46 mmol) in DMF (3 mL) was treated with N-hydroxysuccinimide (NHS, 105.9 mg, 0.92 mmol) and N-(3-dimethylaminopropyl)-N'-ethyl-carbodiimide hydrochloride (EDC-HCl, 176.4 mg, 0.92 mmol) at room temperature. Afterwards, to this mixture was added 11-azido-3,6,9-trioxaundecan-1-amine (130.5 mg, 0.60 mmol) and stirred overnight at room temperature. The reaction was quenched with 15% citric acid and extracted with ethyl acetate. The organic layer was washed with brine, dried over Na$_2$SO$_4$, and concentrated. The crude compound S7 was immediately used without further purification.

Synthesis of Fmoc-Lys(PEG$_3$-N$_3$)-PEG$_3$-N$_3$ S8

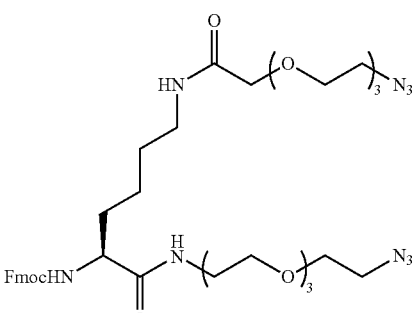

The crude compound S7 was dissolved in DCM (2 mL) and TFA (2 mL) was added to the solution at room temperature. After 1 h, the mixture was concentrated and the Boc-deprotected compound was afforded. In other flask, a mixture of 11-azido-3,6,9-trioxaundecanoic acid (129 mg, 0.55 mmol), NHS (127.1 mg, 1.10 mmol) and EDC-HCl (211.6 mg, 1.10 mmol) in DMF (1 mL) was prepared and the mixture was added to the Boc-deprotected compound in DMF (3 mL) and DIPEA (80 µL, 0.46 mmol). After 18 h, the reaction was quenched with 15% citric acid and extracted Synthesis of Fmoc-PEG$_3$-Lys(PEG$_3$-N$_3$)-PEG$_3$-N$_3$ S9

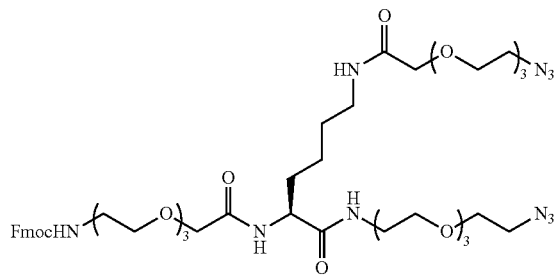

The crude compound S8 was dissolved in DMF (1 mL) and diethylamine (1 mL) was added to the solution at room temperature. After 1 h, the mixture was concentrated and the Fmoc-deprotected compound was afforded. In other flask, a mixture of Fmoc-11-amino-3,6,9-trioxaundecanoic acid (217.3 mg, 0.51 mmol, Broadpharm), NHS (116.5 mg, 1.01 mmol) and EDC-HCl (194.0 mg, 1.01 mmol) in DMF (2 mL) was prepared and the mixture was added to the Fmoc-deprotected compound in DMF (2 mL). After 15 h, the reaction was quenched with 15% citric acid and extracted with ethyl acetate. The organic layer was washed with brine, dried over Na$_2$SO$_4$, and concentrated. The residue was chromatographed on silica gel (20 g) with DCM/MeOH (50:1 to 10:1) to afford S9 (186.1 mg, 42% for the 5 steps). Pale yellow oil. HRMS (ESI) Calcd. For C$_{45}$H$_{69}$N$_{10}$O$_{14}$ [M+H]$^+$: 973.4989. Found: 973.4981. $^1$H NMR (300 MHz, CD$_3$OD) δ 7.80 (d, J=7.7 Hz, 2H), 7.65 (d, J=7.5 Hz, 2H), 7.39 (t, J=7.0 Hz, 2H), 7.31 (t, J=7.5 Hz, 2H), 4.45-4.31 (m, 3H), 4.21 (t, J=6.7 Hz, 1H), 4.01 (s, 2H), 3.95 (s, 2H), 3.72-3.56 (m, 27H), 3.51 (t, J=5.3 Hz, 3H), 3.36 (td, J=4.8, 3.2 Hz, 6H), 3.22 (t, J=7.0 Hz, 2H), 1.90-1.62 (m, 2H), 1.60-1.46 (m, 2H), 1.45-1.32 (m, 3H), 1.29 (s, 2H), 0.97-0.82 (m, 1H).

Synthesis of amine-PEG$_3$-Lys(PEG$_3$-N$_3$)-PEG$_3$-N$_3$ 5

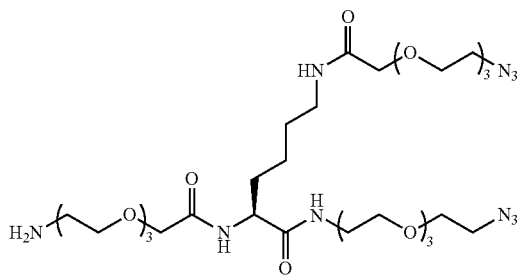

The compound S9 (42.0 mg, 0.043 mmol) was dissolved in DMF (0.4 mL) and diethylamine (0.4 mL) was added to the solution at room temperature. After 1 h, the mixture was concentrated and the Fmoc-deprotected compound was afforded. The residue was chromatographed on silica gel (5 g) with DCM/MeOH (30:1 to 5:1) to afford 5 (15.6 mg, 49%). Pale yellow oil. HRMS (ESI) Calcd. For C$_{30}$H$_{59}$N$_{10}$O$_{12}$ [M+H]$^+$: 751.4308. Found: 751.4319. $^1$H NMR (300 MHz, CD$_3$OD) δ 7.96 (s, 1H), 4.43 (dd, J=8.3, 5.6 Hz, 1H), 4.06 (s, 2H), 3.98 (s, 2H), 3.78-3.60 (m, 28H), 3.55 (t, J=5.4 Hz, 2H), 3.42-3.36 (m, 6H), 3.28-3.21 (m, 2H), 3.19-3.12 (m, 2H), 2.84 (d, J=15.3 Hz, 1H), 2.69 (d, J=15.4 Hz, 1H), 1.89-1.65 (m, 2H), 1.64-1.50 (m, 2H), 1.46-1.34 (m, 3H), 1.29 (s, 2H), 0.95-0.78 (m, 1H).

Synthesis of amine-PEG$_3$-PEG$_3$-Lys(PEG$_3$-N$_3$)-PEG$_3$-N$_3$ 6

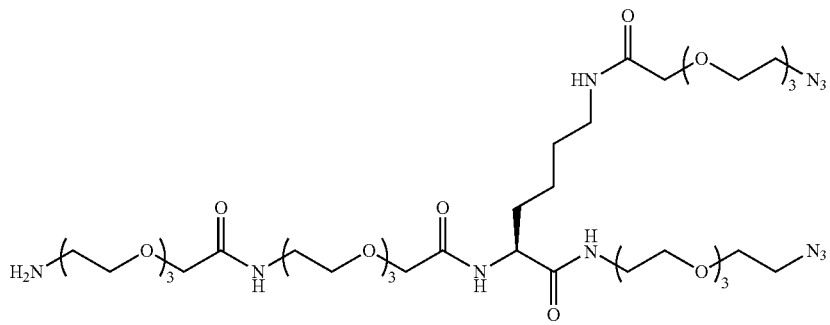

The compound S9 (17.1 mg, 0.018 mmol) was dissolved in DMF (0.4 mL) and diethylamine (0.4 mL) was added to the solution at room temperature. After 1 h, the mixture was concentrated and the Fmoc-deprotected compound was afforded. In other flask, a mixture of Fmoc-11-amino-3,6,9-trioxaundecanoic acid (7.6 mg, 0.018 mmol, Broadpharm), NHS (3.0 mg, 0.026 mmol) and EDC-HCl (5.1 mg, 0.026 mmol) in DMF (0.4 mL) was prepared and the mixture was added to the Fmoc-deprotected compound in DMF (0.8 mL). After 16 h, the reaction was quenched with 15% citric acid and extracted with ethyl acetate. The organic layer was washed with brine, dried over Na$_2$SO$_4$, and concentrated. The crude compound was immediately used without further purification.

The crude compound was dissolved in DMF (0.4 mL) and diethylamine (0.4 mL) was added to the solution at room temperature. After 1 h, the mixture was concentrated and the Fmoc-deprotected compound was afforded. The residue was chromatographed on silica gel (3 g) with DCM/MeOH (30:1 to 5:1) to afford 6 (10.8 mg, 65% for the 3 steps). Pale yellow oil. HRMS (ESI) Calcd. For C$_{38}$H$_{73}$N$_{11}$O$_{16}$Na [M+Na]$^+$:

962.5129. Found: 962.5129. $^1$H NMR (300 MHz, CD$_3$OD) δ 4.42 (dd, J=8.5, 5.6 Hz, 1H), 4.08 (s, 2H), 4.05 (s, 2H), 4.00 (s, 2H), 3.79-3.54 (m, 42H), 3.47 (t, J=5.4 Hz, 3H), 3.43-3.37 (m, 5H), 3.27 (t, J=7.1 Hz, 2H), 3.17 (t, J=5.0 Hz, 2H), 1.91-1.68 (m, 3H), 1.64-1.53 (m, 2H), 1.49-1.33 (m, 3H), 1.32 (s, 2H), 0.99-0.83 (m, 1H).

Synthesis of azide-PEG$_3$-Lys(Boc)-PEG$_3$-N$_3$ S10

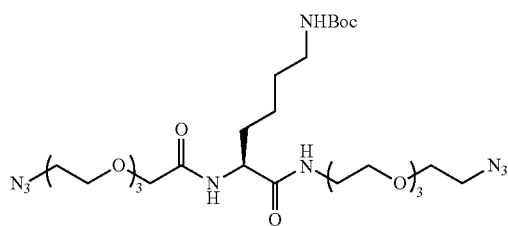

The crude compound S7 was dissolved in DMF (2.5 mL) and diethylamine (2.5 mL) was added at room temperature. After 1 h, the mixture was concentrated and the Fmoc-deprotected compound was afforded. In other flask, the mixture of 11-azido-3,6,9-trioxaundecanoic acid (133.0 mg, 0.57 mmol), NHS (131.7 mg, 1.14 mmol) and EDC·HCl (219.3 mg, 1.14 mmol) in DMF (1.5 mL) was prepared and the mixture was added to the Fmoc-deprotected compound in DMF (3.5 mL). After 21 h, the reaction was quenched with 15% citric acid and extracted with ethyl acetate. The residue was chromatographed on silica gel (20 g) with DCM/MeOH (50:1 to 20:1) to afford S10 (154.7 mg, 53% for the 3 steps). Pale yellow oil. HRMS (ESI) Calcd. For C$_{27}$H$_{52}$N$_9$O$_{10}$ [M+H]$^+$: 662.3832. Found: 662.3836. $^1$H NMR (300 MHz, CD$_3$OD) δ 8.16 (t, J=5.6 Hz, 1H), 7.88 (d, J=8.1 Hz, 1H), 4.43 (td, J=8.3, 5.6 Hz, 1H), 4.06 (s, 2H), 3.78-3.61 (m, 20H), 3.57 (t, J=5.4 Hz, 2H), 3.40 (t, J=5.1 Hz, 6H), 3.10-2.99 (m, 2H), 1.91-1.65 (m, 2H), 1.59-1.48 (m, 3H), 1.45 (s, 9H), 1.43-1.32 (m, 2H).

Synthesis of azide-PEG$_3$-Lys-PEG$_3$-N$_3$ 7

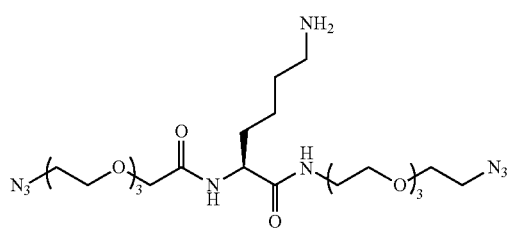

The crude compound S10 (6.7 mg, 0.010 mmol) was dissolved in DCM (0.4 mL) and TFA (0.4 mL) was added to the solution at room temperature. After 1 h, the mixture was concentrated and the Boc-deprotected compound was afforded. The crude compound was purified by preparative RP-HPLC to give analytically pure compound 7 (4.6 mg, 81%). Colorless oil. HRMS (ESI) Calcd. For C$_{22}$H$_{43}$N$_9$O$_8$Na [M+Na]$^+$: 584.3127. Found: 584.3133. $^1$H NMR (300 MHz, CD$_3$OD) δ 8.15 (t, J=5.5 Hz, 1H), 7.94 (d, J=8.2 Hz, 1H), 4.47 (td, J=8.3, 5.6 Hz, 1H), 4.07 (s, 2H), 3.78-3.61 (m, 20H), 3.58 (t, J=5.4 Hz, 2H), 3.45-3.36 (m, 6H), 2.94 (t, J=7.6 Hz, 2H), 1.97-1.83 (m, 1H), 1.82-1.60 (m, 3H), 1.58-1.36 (m, 2H), 1.31 (s, 1H), 0.98-0.83 (m, 1H).

Example 4—Biological Evaluation and Data

Figures 4A, 4B, 4C, 4D, 4E, 4F:
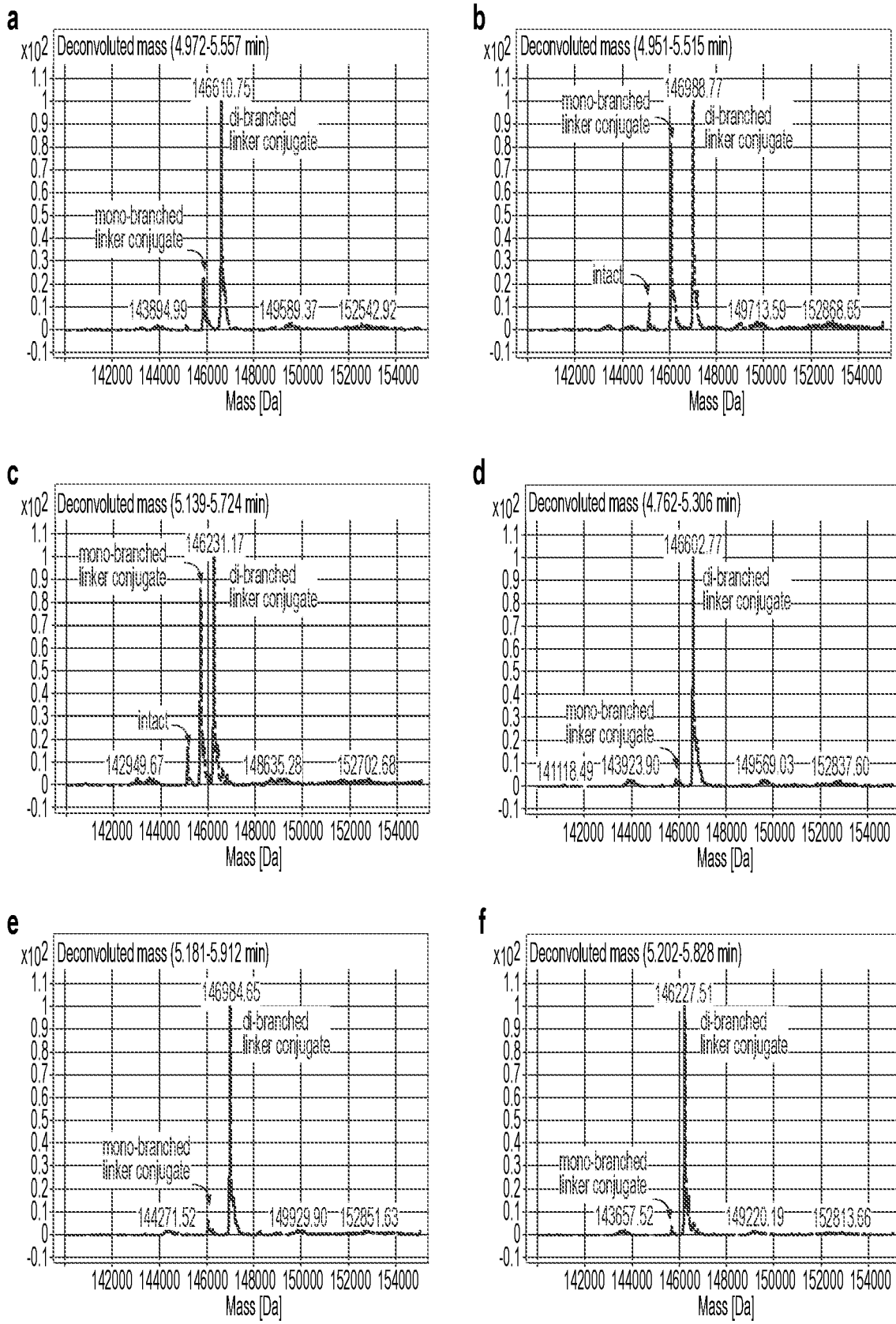
FIGS. 4A-F. Deconvoluted mass spectra of the N297A anti-HER2 antibody conjugate containing branched linker 5 (a and d), 6 (b and e), or 7 (c and f) obtained under the reaction conditions reported by Schibli and coworkers (Polakis, 2016) (a-c) or the optimal conditions reported in this article (d-e). The conversion rates shown in Table 2 were determined based on the mass intensities of these deconvoluted peaks.
Figure 5A:
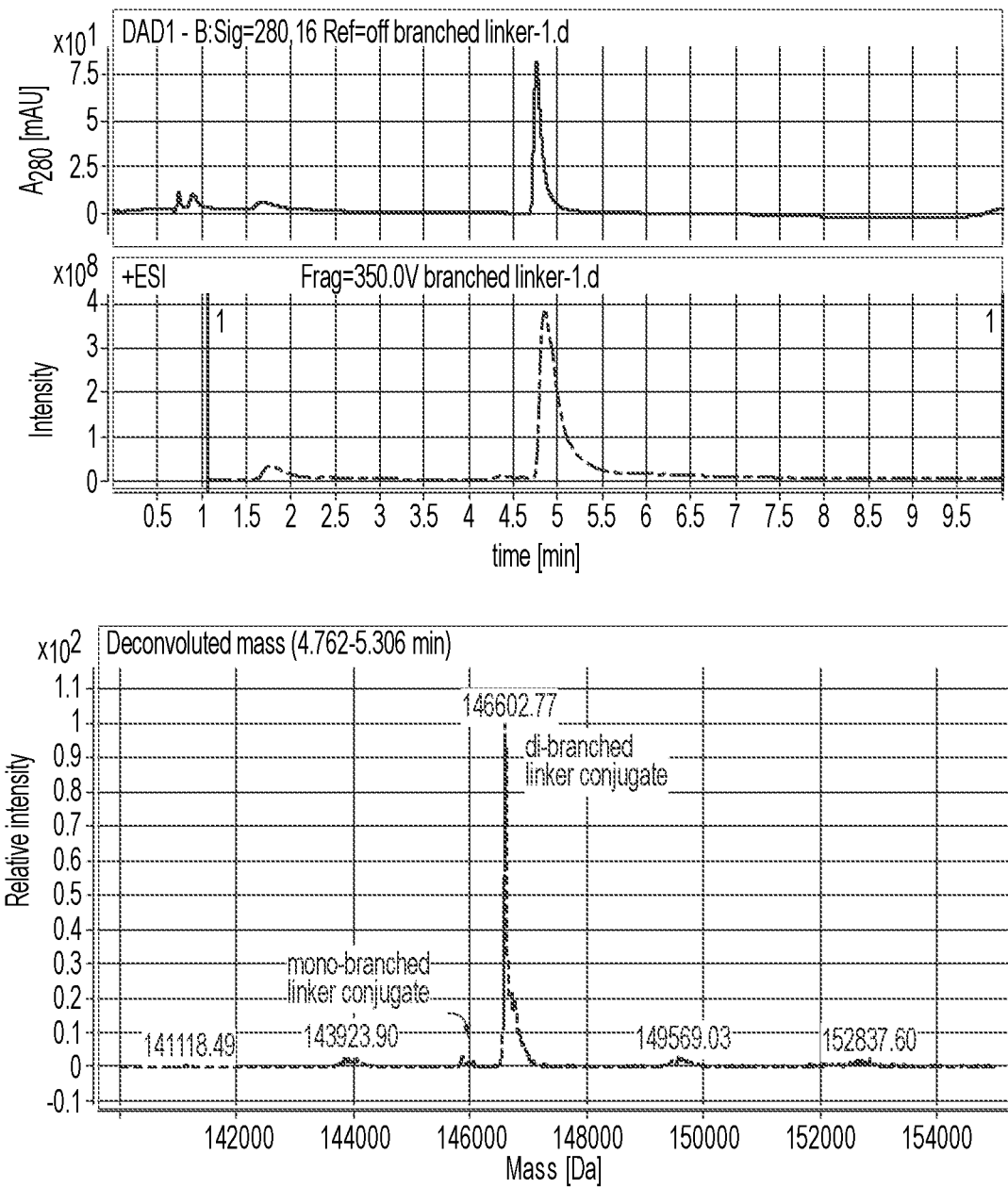
FIGS. 5A & 5B (a) UV trace at 280 nm, total ion chromatogram, and deconvoluted mass spectra of the N297A anti-HER2 antibody-branched linker 5 conjugate. (b) UV trace at 280 nm, total ion chromatogram, and deconvoluted mass spectrum of the DTT-reduced N297A anti-HER2 antibody-branched linker 5 conjugate (heavy and light chains).
Figure 5B:
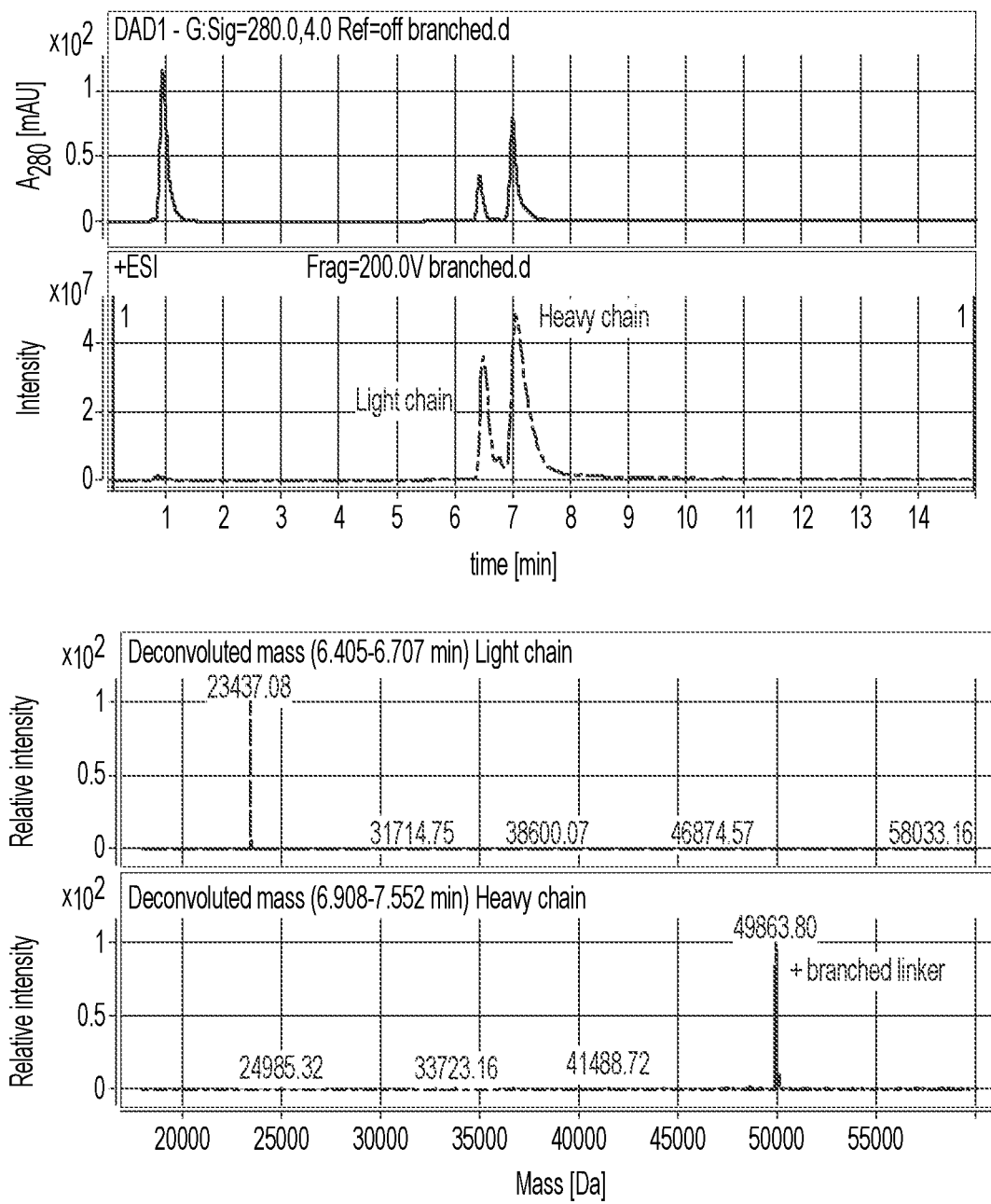

Evaluation of the ADCs for Antigen Binding and Cytotoxicity. Anti-HER2 ADCs 9 and 10 were evaluated for binding affinity and specificity to the human epidermal growth factor receptor 2 (HER2) in cell-based ELISA assays using the human breast cancer cell lines SKBR-3 (HER2 positive) and MDA-MB-231 (HER2 negative) (FIGS. 4 and 5). Branched ADC 9 showed a high binding affinity to SKBR-3, comparable to those of linear ADC 10 and the parent N297A anti-HER2 mAb ($K_D$=0.98, 1.12, and 0.64 nM, respectively). In contrast, non-targeting ADC 11 did not show HER-2 specific binding. None of the ADCs bound to MDA-MB-231. These results demonstrate that the branched linker-MMAF moieties within ADC 9 do not impact the antigen recognition and specificity of the parent N297A anti-HER2 mAb. As previously reported (Dennler et al., 2014), the conjugation site Q295 in the Fc moiety is distant from the antigen recognition site in the Fab region, allowing for the MTGase-based conjugation of linker-payload components at this position without detrimental effects on the antigen binding. The disclosed results are consistent with this observation.

Figure 6A:
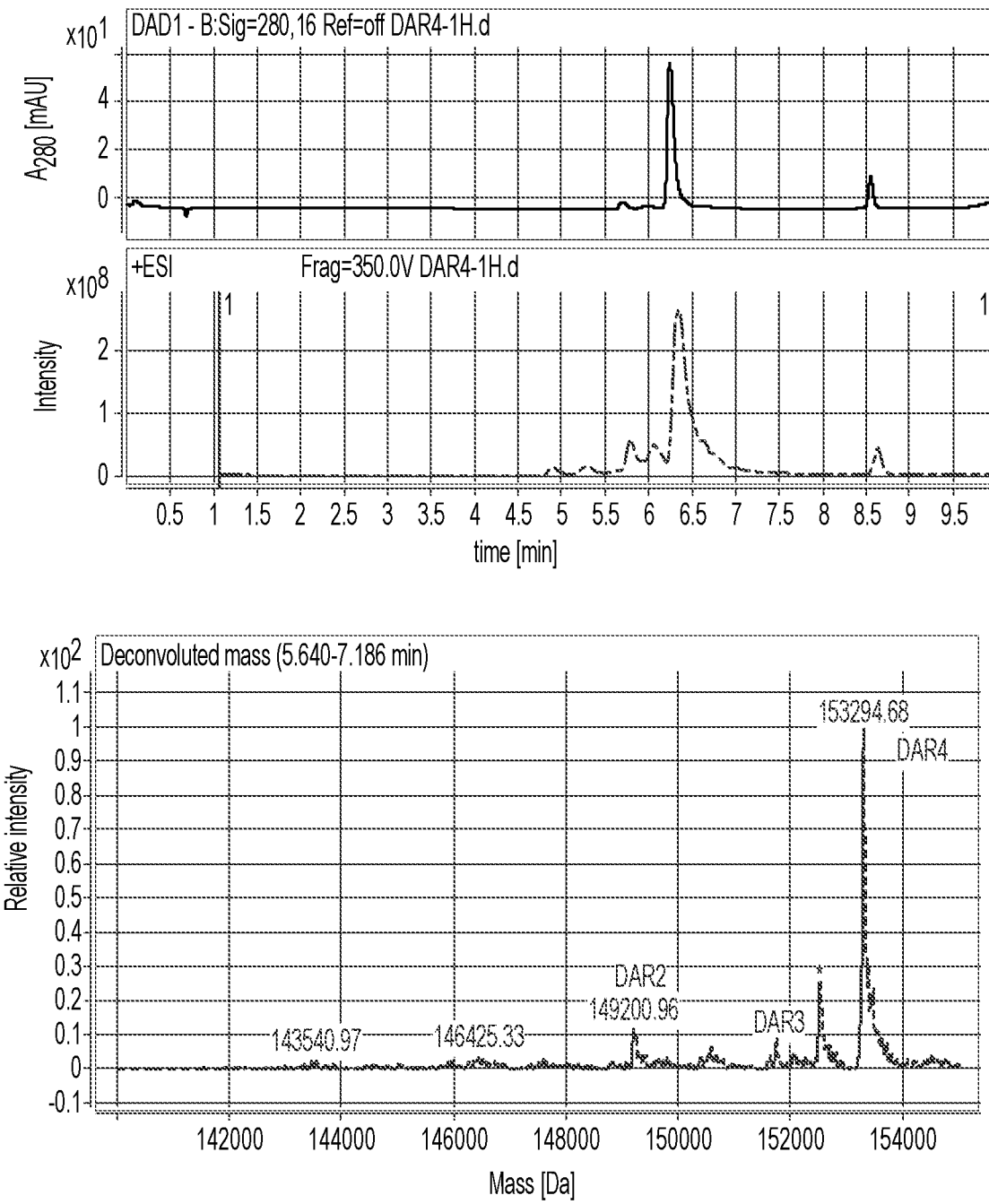
FIGS. 6A-C (a) UV trace at 280 nm, total ion chromatogram, and deconvoluted mass spectra of the N297A anti-HER2 antibody-MMAF conjugate 9. Asterisked peak (152523.82 Da) indicates an ion fragment derived from the DAR-4 species (153294.68 Da), which corresponds to a loss of ~770.86 Da. (b) UV trace at 280 nm, total ion chromatogram, and deconvoluted mass spectra of heavy and light chain of N297A the DTT-reduced ADC 9 (heavy and light chains). Asterisked peak (52436.27 Da) indicates an ion fragment derived from the heavy chain-MMAF (53208.63 Da), which corresponds to a loss of ~772.36 Da. (c) SEC chromatogram of crude ADC 9 before purification (UV: 280 nm). The weak peak around 15.552 min is derived from high molecular weight proteins (protein aggregates). This chromatogram clearly indicates that ADC 9 was >99% monomeric.
Figure 6B:
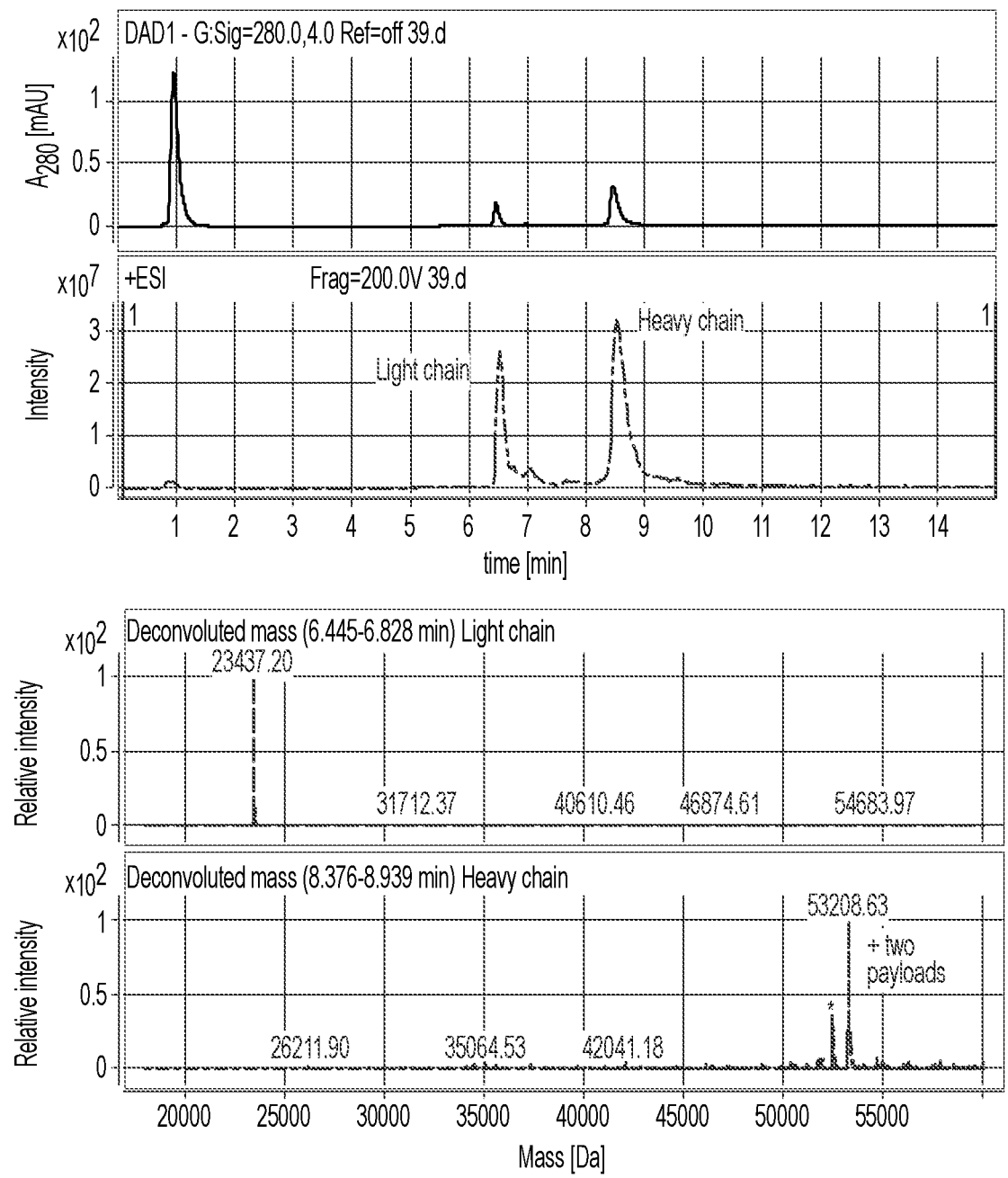
Figure 6C:
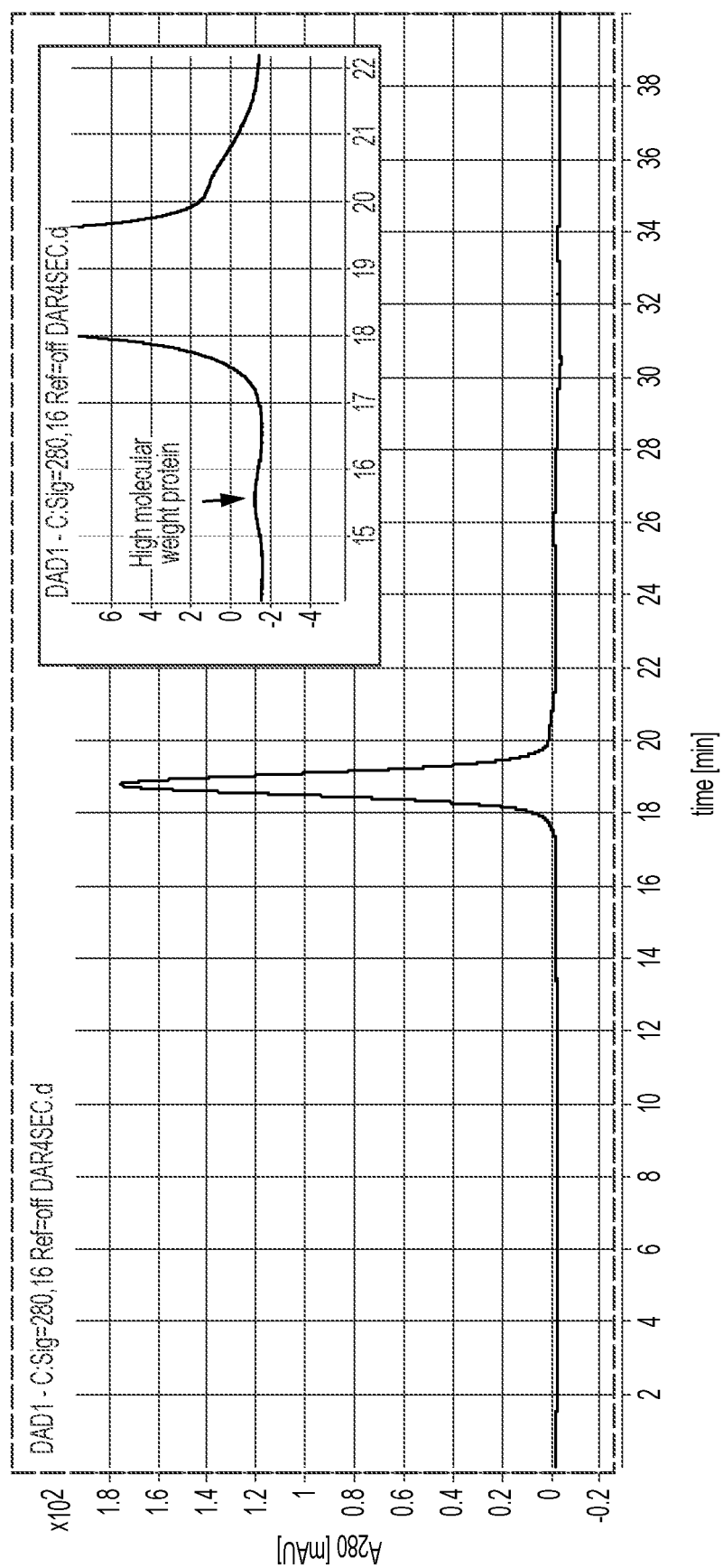
Figure 7A:
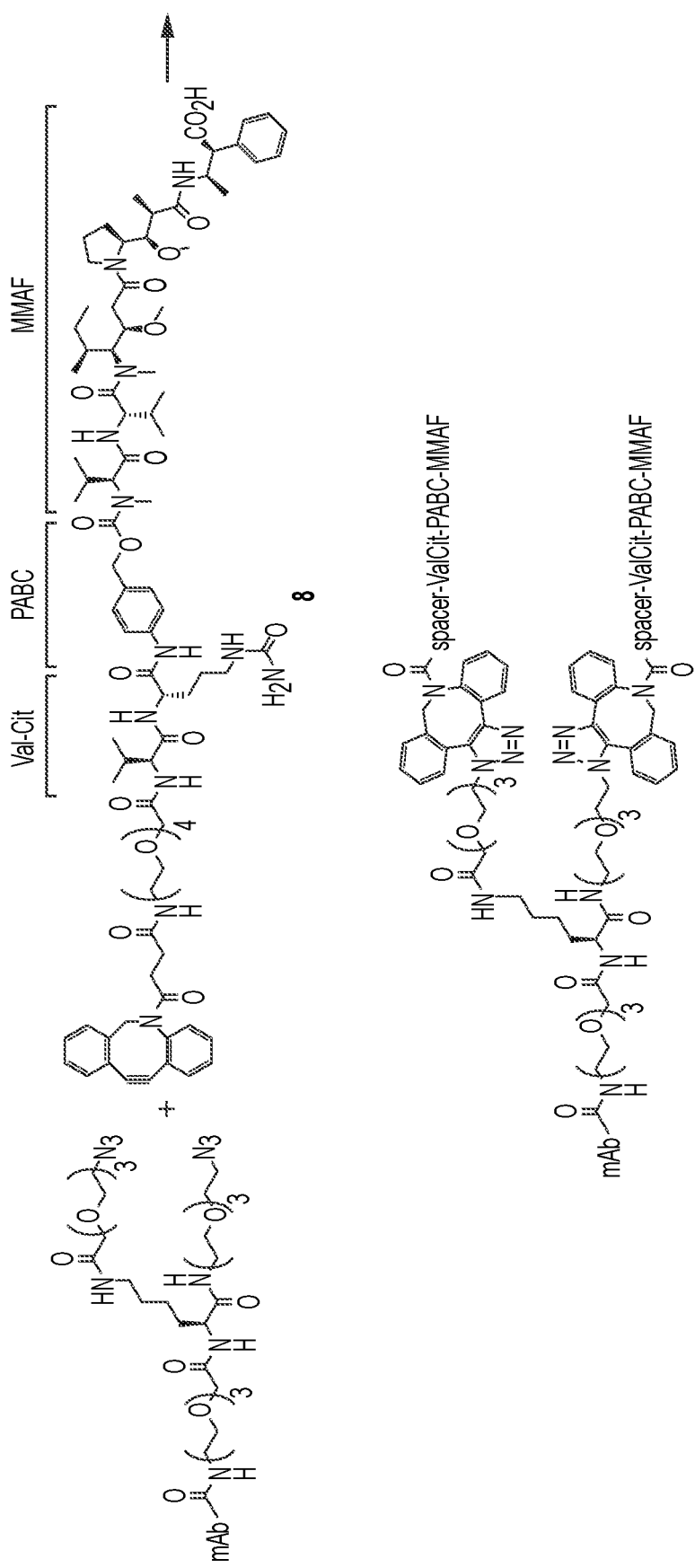
FIGS. 7A-D shows the synthesis and characterization of branched ADC 9. (a) Antibody-payload conjugation by strain-promoted azide-alkyne cyclization (copper-free click reaction). (b) Deconvoluted ESI-mass spectra. Top panel: N297A anti-HER2 mAb. Middle panel: antibody-branched linker conjugate. Antibody-linker di-conjugate was the major product and very small amount of mono-conjugate was detected. Bottom panel: antibody-MMAF (star) conjugate 9. The click reaction afforded an ADC with a DAR of 4 as the major product and small amount of ADCs with lower DARs (2 and 3). Asterisk (*) indicates a fragment ion derived from the DAR-4 product (See FIG. 3). (c) Reverse-phase HPLC trace (UV: 280 nm) of ADC 9. The average DAR was determined to be 3.9 based on the peak areas of each DAR species. (d) SEC trace (UV: 280 nm) of crude ADC 9 (before purification). The small peak at 15.6 min is derived from high molecular weight proteins (protein aggregates), indicating that the monomer content of ADC 9 is >99%.
Figure 7B:
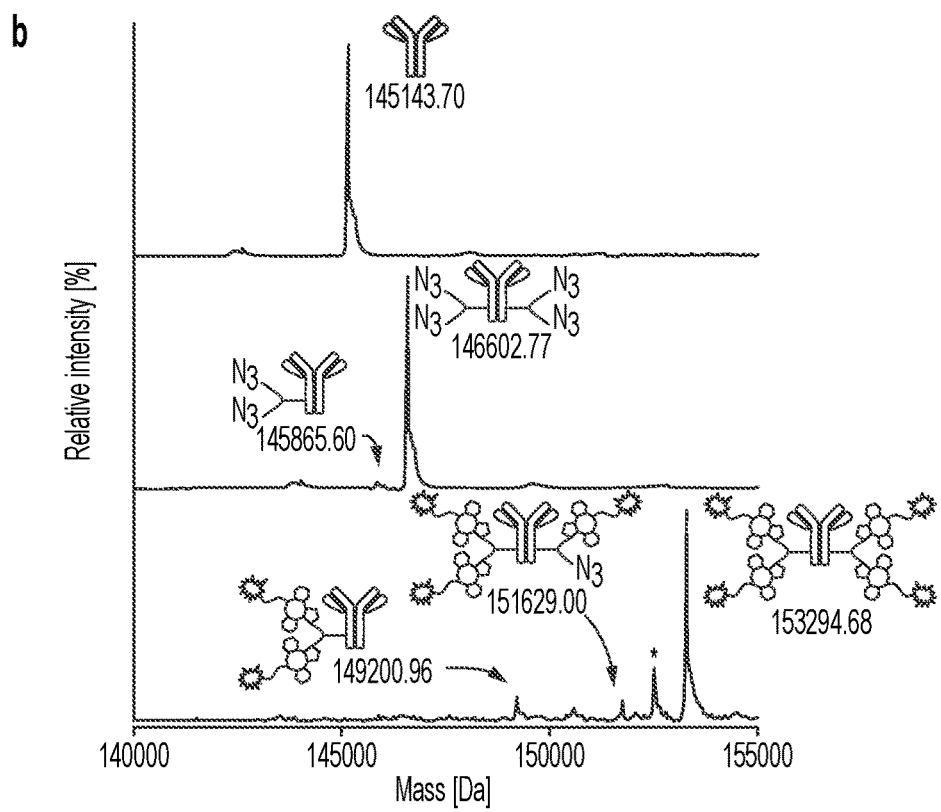
Figure 7C:
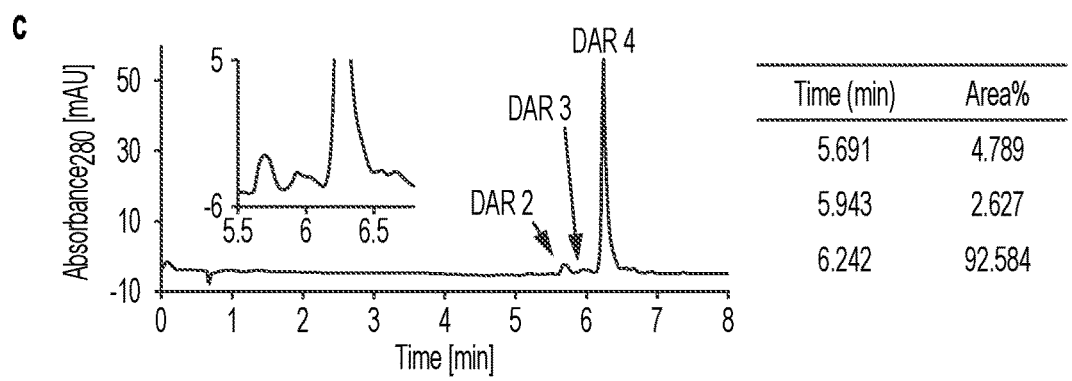
Figure 7D:
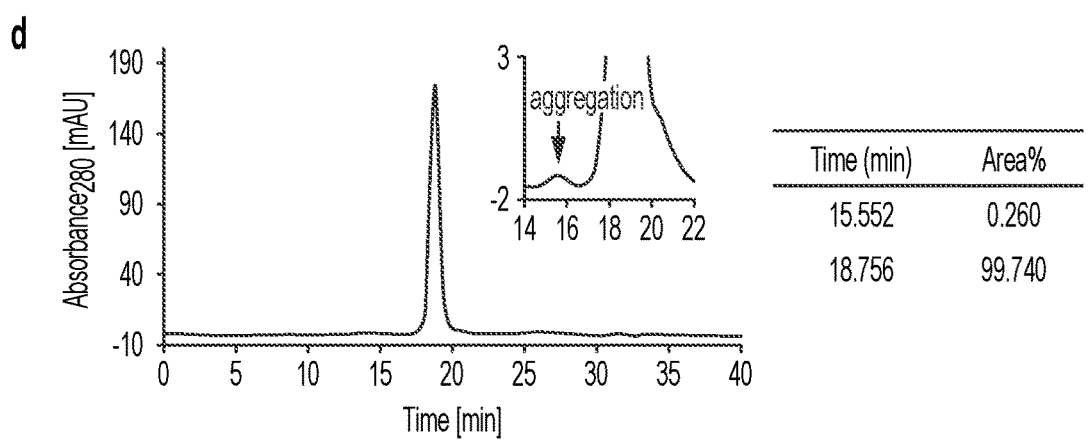
Figure 8:
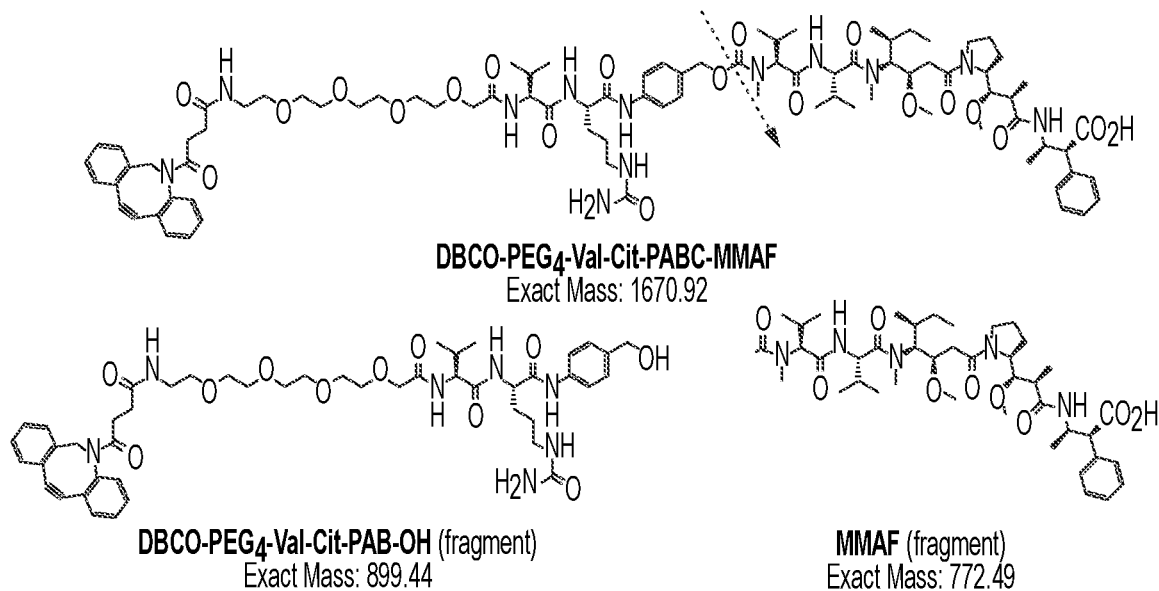
FIG. 8 shows the predicted fragment. The exact mass of DBCO-PEG4-Val-Cit-PABC-MMAF is 1670.92 Da and that of DBCO-PEG4-Val-Cit-PAB-OH is 899.44 Da. The difference between these two is 771.48 Da. This value is consistent to the observed values of the ion fragments in FIG. S5.
Figure 9:
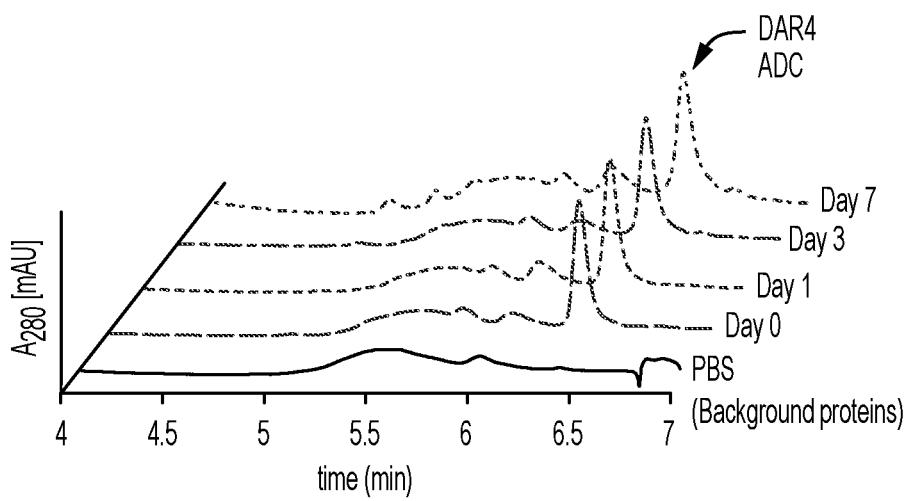
FIG. 9 shows the stability of ADC 9 in human plasma at 37° C. (performed in duplicate). No significant reduction of the DAR was observed after 7 days.
Figure 10:
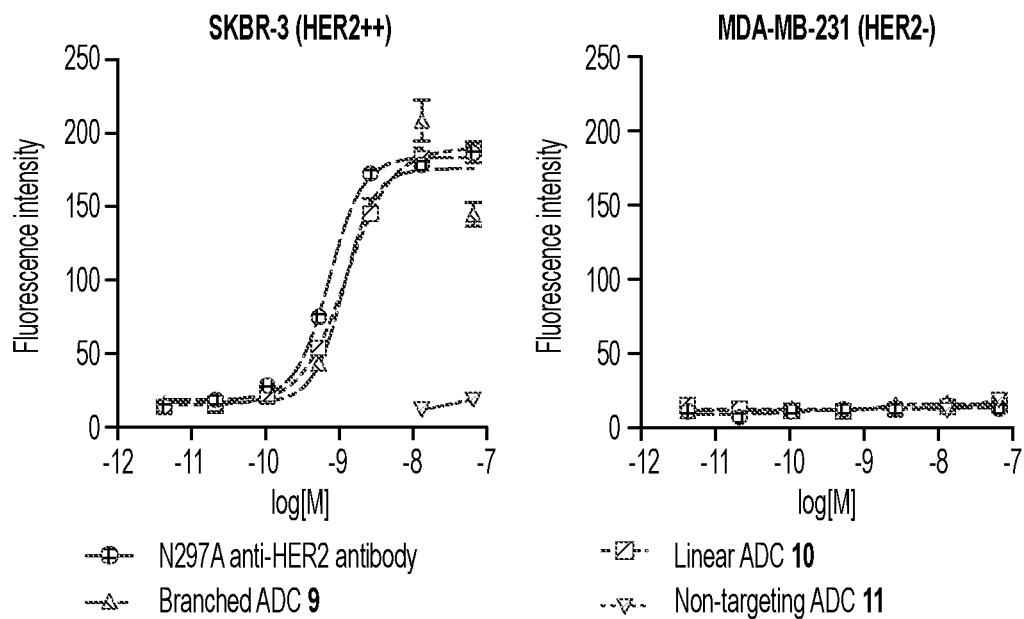
FIG. 10 shows the cell-based ELISA using the SKBR-3 (HER2 positive, left) and MDA-MB-231 (HER2 negative, right) cell lines. Binding affinities of unconjugated N297A anti-HER2 mAb (circle) and ADCs 9 (delta), 10 (square), and 11 (nabla) against HER2 were measured. All assays were performed in triplicate. Error bars represent SEM and values in parentheses are 95% confidential intervals. All of the antibodies tested showed HER2-dependent cell binding.
Figure 11:
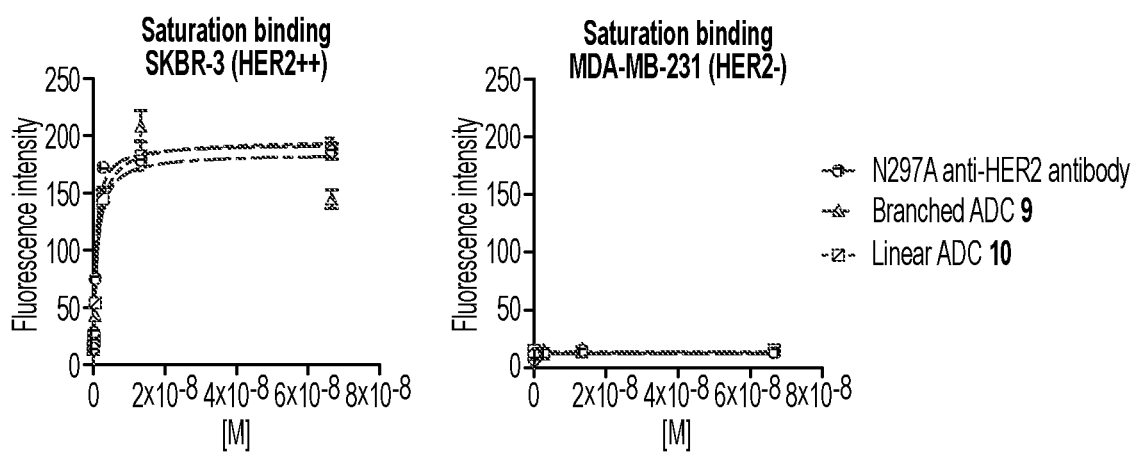
FIG. 11 shows the saturation-binding curves obtained by cell-based ELISA All assays were performed in triplicate and error bars represent SEM. The N297A anti-HER2 antibody and ADCs 9-10 bound to SKBR-3 cells (HER2 positive, left) with comparable binding affinities but not to MDA-MB-231 cells (HER2 negative, right).
Figure 12:
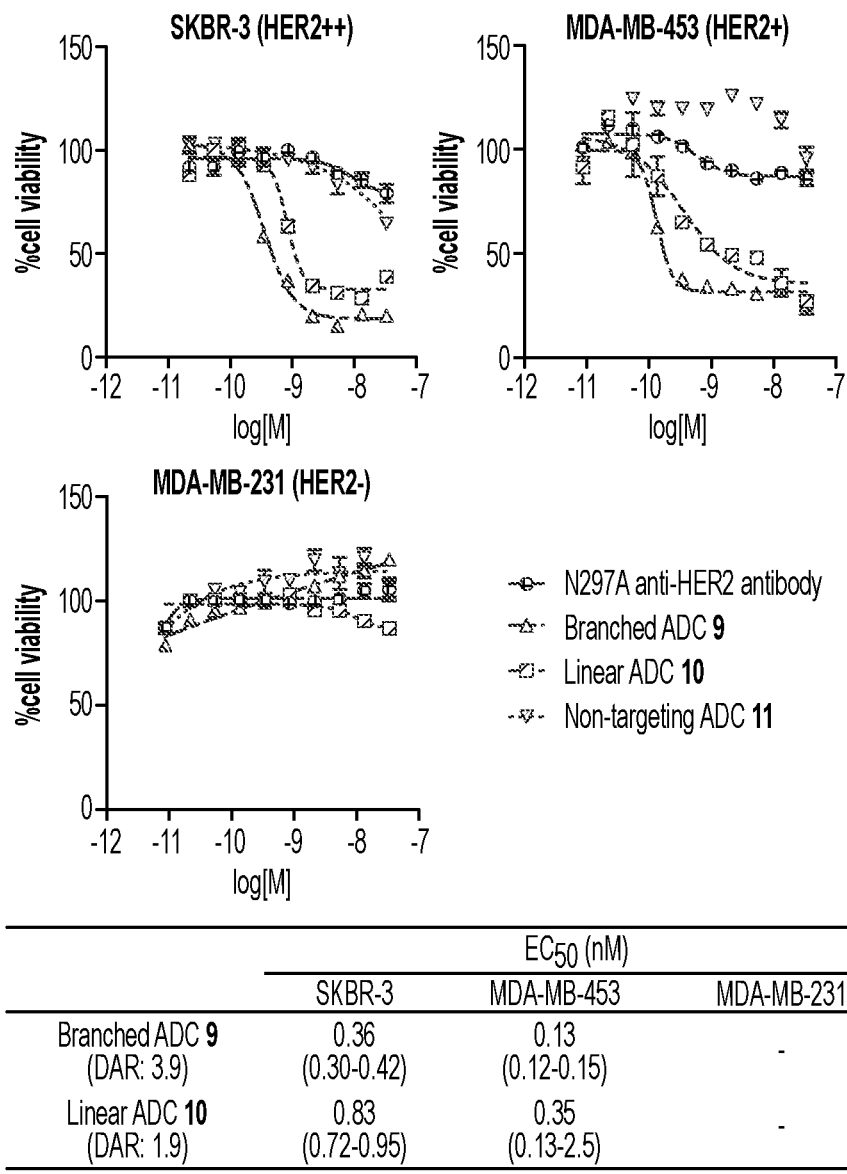
FIG. 12 shows the in vitro cytotoxicity of unconjugated N297A anti-HER2 mAb (circle) and ADCs 9 (delta), 10 (square), and 11 (nabla). All assays were performed in triplicate. Error bars represent SEM and values in parentheses are 95% confidential intervals. Branched ADC 9 showed the greatest cell killing potency both in the SKBR-3 and MDA-MB-453 of the antibodies tested. None of the antibodies tested showed significant cell killing in MDA-MB-231.

To investigate how the branched linker-based conjugation influences cell killing potency, ADCs 9-11 and the parent N297A anti-HER2 mAb were tested in cell-based assays using three human cell lines with varying HER2 expression levels: SKBR-3 (HER2++), MDA-MB-453 (HER2+), and MDA-MB-231 (HER2-) (FIG. 6). Branched ADC 9 (DAR: 3.9) exerted greater potency than linear ADC 10 (DAR: 1.9) in SKBR-3 (EC$_{50}$: 0.36 nM and 0.83 nM, respectively) whereas non-targeting ADC 11 and the 297A anti-HER2 mAb showed marginal cytotoxicity. In addition, the maximum cell killing effect of ADC 9 (85% cell killing at 5.3 nM) was higher than that of ADC 10 (71% cell killing at 13.3 nM) with a statistically significant difference (Student's t test, p<0.005). Intriguingly, the difference of the EC$_{50}$ values of ADCs 9 and 10 was 2.3 fold, which is greater than the 2-fold difference of the DARs. We observed more drastic enhancement of ADC efficacy by the branched linker strategy in the moderately HER2-positive cell line MDA-MB-453; the dose-response curve of branched ADC 9 clearly shifted towards the lower concentration side compared to that of linear ADC 10, resulting in EC$_{50}$ values of 0.13 nM and 0.35 nM, respectively (2.7-fold difference in potency).

The observed lower EC$_{50}$ values in MDA-MB-453 than those in highly HER2-expressing SKBR-3 may indicate that MDA-MB-453 is more sensitive to MMAF than SKBR-3. Indeed, it has been reported that the highest level of HER2 expression does not necessarily lead to maximal HER2-targeting ADC cell killing effect (Chooniedass et al., 2016). The dose-response curve of branched ADC 9 in MDA-MB-453 is steeper than that of linear ADC 10 (Hill slope: -3.5 and -1.0, respectively), reflecting the effectiveness of the branched linker-based payload delivery. As anticipated, all ADCs tested showed no cytotoxicity to the HER2-negative MDA-MB-231. Collectively, these results clearly demonstrated that the increased DAR by our branched linker contributed to the enhancement of the ADC efficacy without impairing the cell binding and specificity of the parent antibody.

Example 5—Discussion of Linkers with Increased Stability

Valine-citrulline (VCit) dipeptide linkers are commonly used as enzymatically cleavable linkers for antibody-drug conjugates (ADCs). While stable in human plasma, VCit linkers are unstable in mouse plasma due to susceptibility to an extracellular carboxylesterase. This instability often triggers premature release of drugs during circulation and makes it a challenge to design VCit-based ADCs without compromising in vivo stability. Disclosed herein are glutamic acid-valine-citrulline (EVCit) linkers responsive to cathepsin B-mediated cleavage but which undergo no premature cleavage during circulation in mice. An EVCit-based anti-HER2 ADC exhibited much greater treatment efficacy in xenograft mouse models than a VCit variant. Notably, the stable ADCs contained long spacers facilitating the access of any proteases to the EVCit moiety, indicating EVCit linkers likely assure exceptional in vivo stability regardless of the degree of exposure. The use of EVCit linkers may expand flexibility in designing ADCs and minimize failure rates in pre-clinical studies due to linker instability.

Figure 13A:
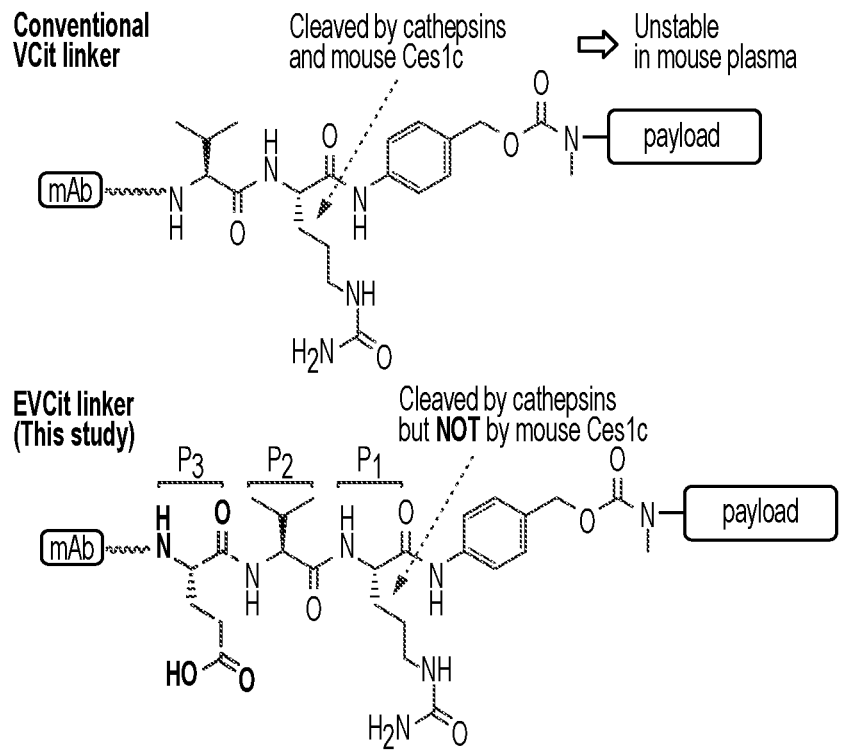

In addition to acid-labile hydrazone linkers and reducible disulfide linkers, valine-citrulline (VCit) dipeptide linkers connecting a payload with a p-aminobenzyloxycarbonyl (PABC) group are the standard cleavable linkers widely used in many successful ADCs including the FDA-approved ADC Adcetris (Tsuchikama et al., 2018, Katz et al., 2011, and Gordon et al., 2015). VCit linkers are cleaved upon internalization of given ADCs and following cathepsin B-mediated cleavage to release unmodified payloads inside the target cancer cell (FIG. 13A, Lu et al., 2016). While highly stable in cynomolgus monkey and human plasma, it has been reported that the extracellular carboxylesterase 1c (Ces1c) found in mouse plasma can hydrolyze VCit linkers, resulting in premature release of toxic payloads during circulation prior to reaching tumors in mouse models (Dorywalska et al., 2016). As demonstrated with several ADCs constructed using VCit linkers (Dorywalska et al., 2016, Shen et al., 2012, and Lhospice et al., 2015), this linker instability can be ameliorated by carefully selecting the linker attachment sites within an antibody and limiting the length of the VCit linker to minimize the exposure of the vulnerable moiety to extracellular enzymes. However, it has also been confirmed that installation of VCit linkers at exposed conjugation sites and extending the linker structure result in rapid premature loss of payload during circulation (Dorywalska et al., 2016, Lhospice et al., 2015, Elgersma et al., 2015, Dorywalska et al. 2015, and Dal Corso et al., 2017). Given that almost all preclinical studies in drug development are initially performed using mouse models, this instability issue makes it a challenge to evaluate the true therapeutic potential and safety profiles of VCit-based ADCs, and significantly limits flexibility in the choice of conjugation sites and linker design. Indeed, ADCs constructed using the multi-loading VCit linker are unstable in mouse plasma and show poor treatment efficacy in mouse breast tumor models.

Disclosed herein are VCit-based tripeptide sequences with high polarity, such as glutamic acid-VCit (EVCit) and aspartic acid-VCit (EVCit) provide exceptionally high stability in mouse and human plasma while capable of releasing the free payload upon cathepsin B-mediated cleavage. Disclosed herein are ADCs constructed using the acidic EVCit linker, which exhibits by far greater in vivo stability and antitumor efficacy in xenograft mouse models bearing human breast cancer than is possible with a VCit-based variant. These results indicate that the use of these linkers, in particular the EVCit linker may expand flexibility in designing ADCs and minimize failure rates in pre-clinical studies using mouse models caused by linker instability. These improved linkers may also provide a broadly applicable solution for enhancing stability and efficacy of other molecular classes of drug conjugates for targeted cancer therapy.

Example 6—Results Using Linkers with Improved Stability

Impact of introducing a highly polar functional group on plasma stability and reactivity to cathepsin B-mediated cleavage. Introducing a chemical modification to the N-terminus of the valine residue ($P_3$ position, FIG. 13A) significantly impacts the plasma stability of VCit linker-based ADCs (Dorywalska et al., 2016). It was demonstrated that VCit linkers with a hydrophilic group at the P3 position, such as hydroxyl groups, confers ADCs with increased stability in mouse plasma without impairing the reactivity to intracellular cathepsin B-mediated cleavage. Based on these findings, it was speculated that installation of a highly polar functional group at the P3 position could further enhance the resistance to Ces1c-mediated degradation.

Figure 13B:
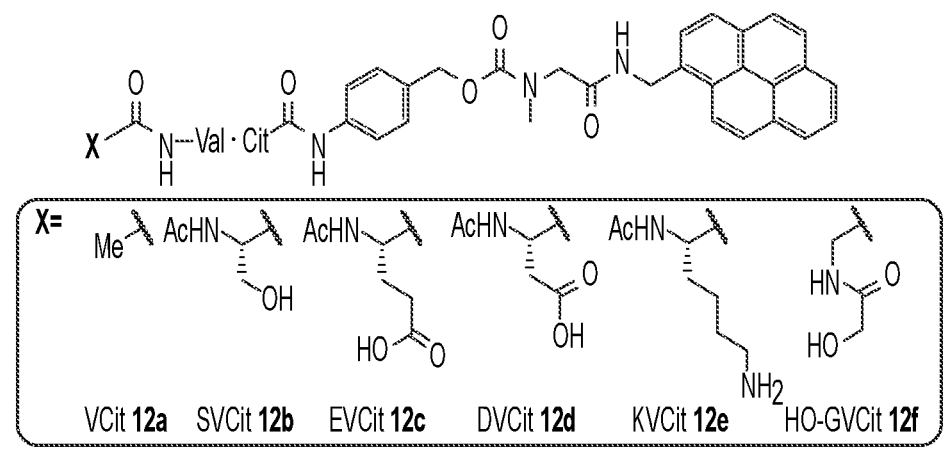

To test this hypothesis, a panel of peptide probes containing a various amino acid at the P3 position were evaluated for plasma stability at the small-molecule level (FIG. 13B). VCit- and tripeptide probes 12a-f were first synthesized by standard solid- and liquid-phase peptide synthesis and following carbamate formation. These model probes consisted of a XVCit-PABC unit where X is none (12a), serine (12b), glutamic acid (12c), aspartic acid (12d), lysine (12e), or hydroxyacetylglycine (12f). It was assumed that serine and hydroxyacetylglycine would serve as a mimic of the hydroxy-functionalized tripeptide ADC linker with increased mouse plasma stability reported by Dorywalska et al (Dorywalska et al., 2016). In particular, the 2-hydroxyacetamide group within probe 12f is the modifier that provided the greatest stability in their report. These linkers were covalently linked to 1-pyrenemethylamine, a surrogate of hydrophobic payloads with distinct UV absorbance at 341 nm (van Geel et al., 2015). Subsequently, probes 12a-f were incubated in undiluted BALB/c plasma at 37° C. and the amount of each probe was monitored by HPLC (FIG. 13C). As anticipated, VCit probe 12a exhibited a very short half-life ($t_{1/2}$=2.3 h). SVCit probe 12b was slightly more stable ($t_{1/2}$=3.1 h) than VCit probe 12a but the increase in stability was not as significant as what had been anticipated based on the previous report on the hydroxy-functionalized stable ADC linker (Dorywalska et al., 2016). Intriguingly, EVCit and DVCit probes 12c and 12d showed greatly extended half-lives ($t_{1/2}$=19.1 h and 14.0 h, respectively). In contrast, basic KVCit probe 12e showed the shortest half-life of all probes ($t_{1/2}$=0.9 h). These results indicate that an acidic or neutral side chain with high polarity at the P3 position can effectively repel the access of Ces1c. Taking into account that all probes tested were stable in human plasma and no significant degradation was observed after 2 days (FIG. 14A), the accelerated degradation observed in KVCit probe 12e may indicate that a basic side chain at the P3 position provides an additional interaction with Ces1c leading to fast bond cleavage. 2-Hydroxyacetamide probe 12f was slightly more stable ($t_{1/2}$=5.0 h) than SVCit probe 12b but much less stable than EVCit and DVCit probes 12c,d. Thus, the stabilizing effect of a neutral carbonyl group at the $P_3$ position was not as significant as that of a negatively charged carboxylic acid side chain.

Next, all probes were tested for responsiveness to human cathepsin B-mediated cleavage (FIG. 14B). SVCit probe 12b showed a cleavage rate comparable with that of VCit probe 12a. In contrast, faster bond cleavage was observed in EVCit DVCit, and KVCit probes 12c-e than in VCit- and SVCit probes 12a and 12b. These results demonstrated at the small-molecule level that the polar EVCit and DVCit linker systems provided enhanced stability in mouse plasma without impairing cathepsin B-mediated payload release.

Figure 15A:
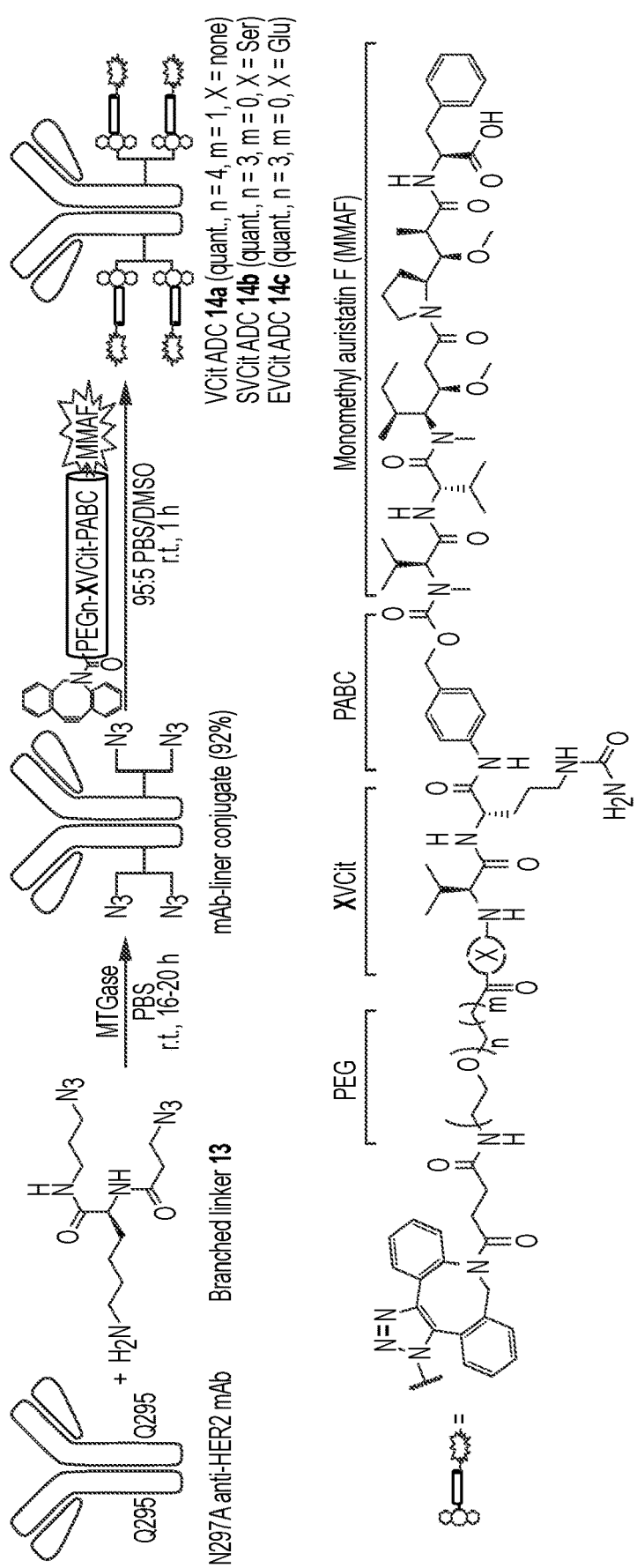
Figure 15B:
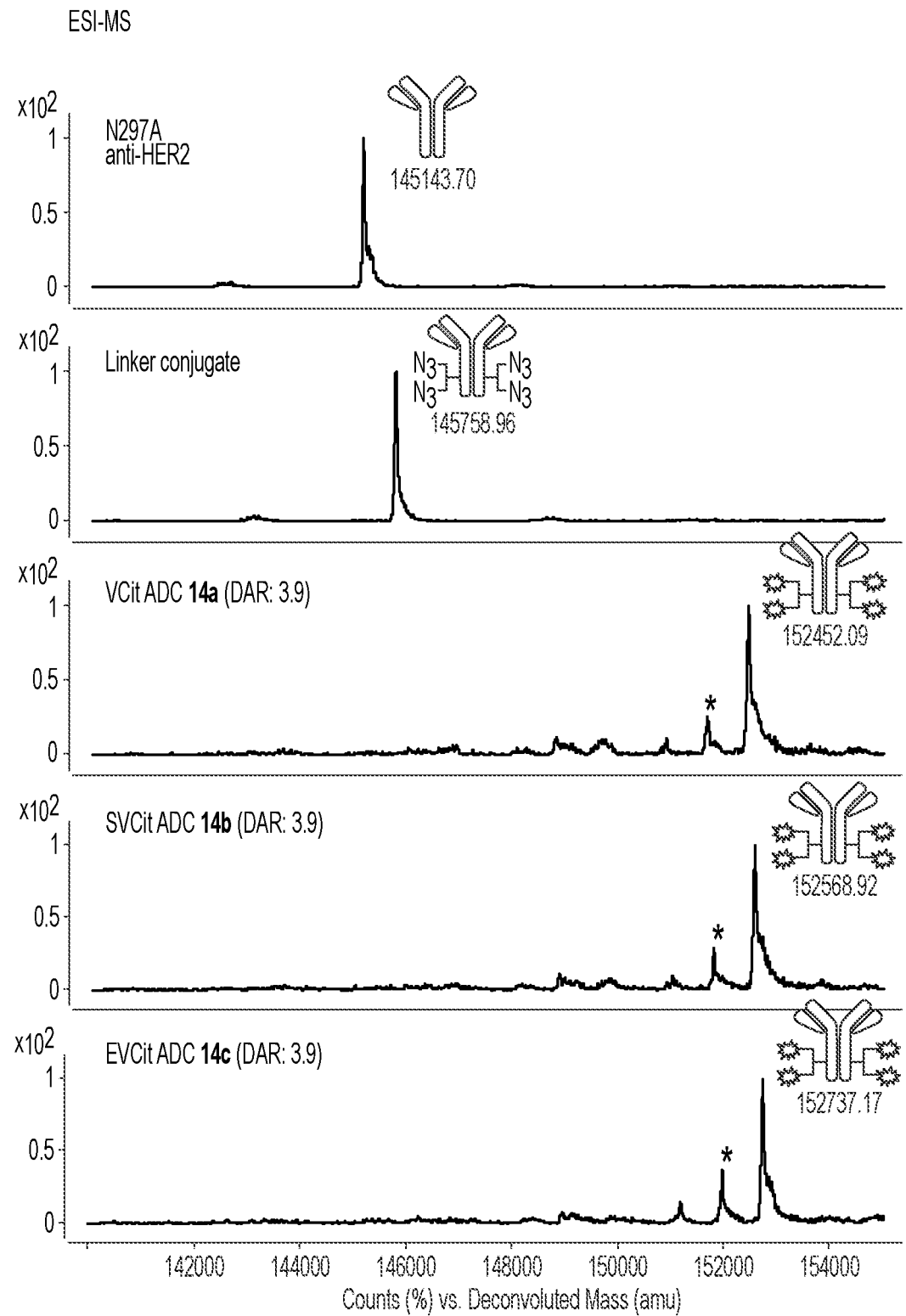
Figure 15C:
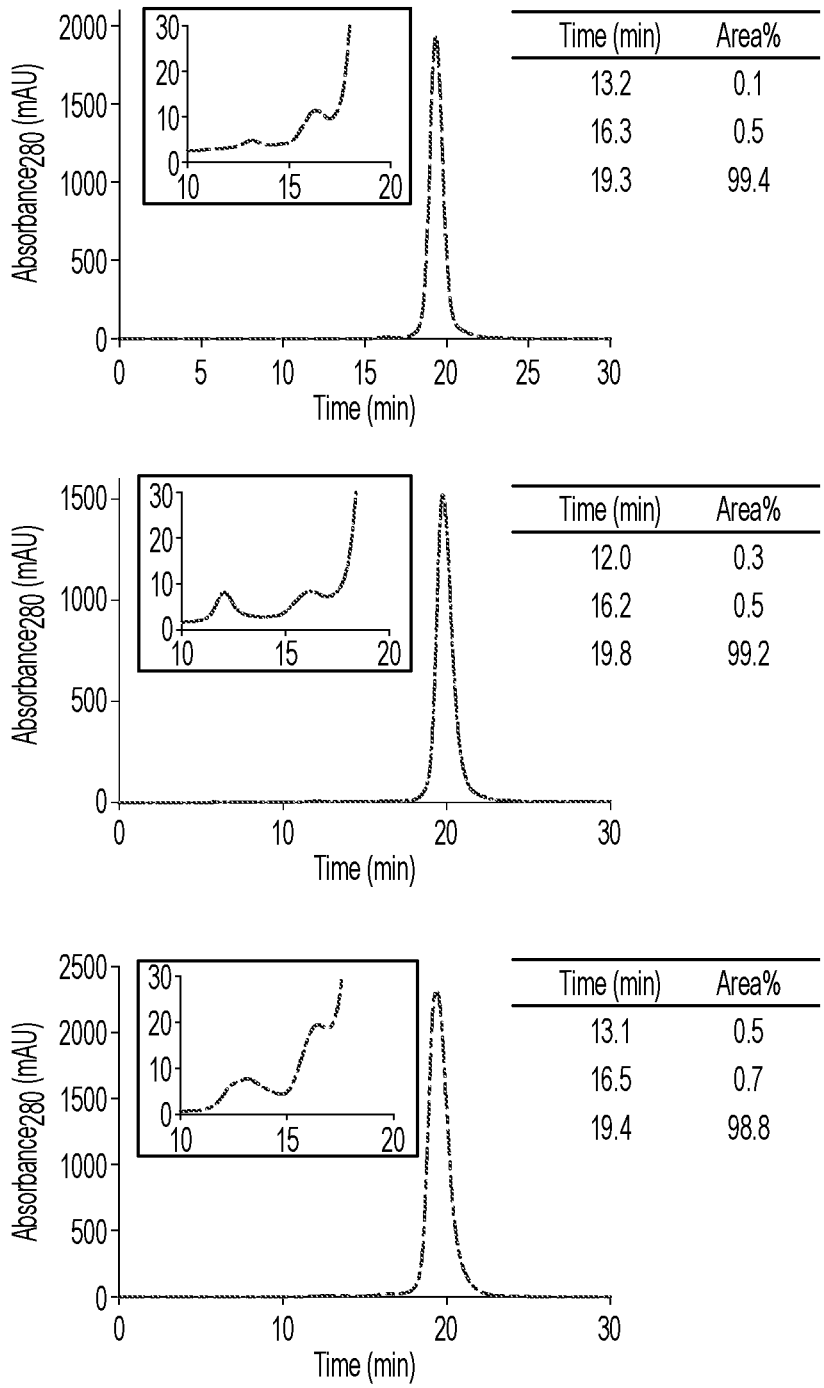
Figure 16A:
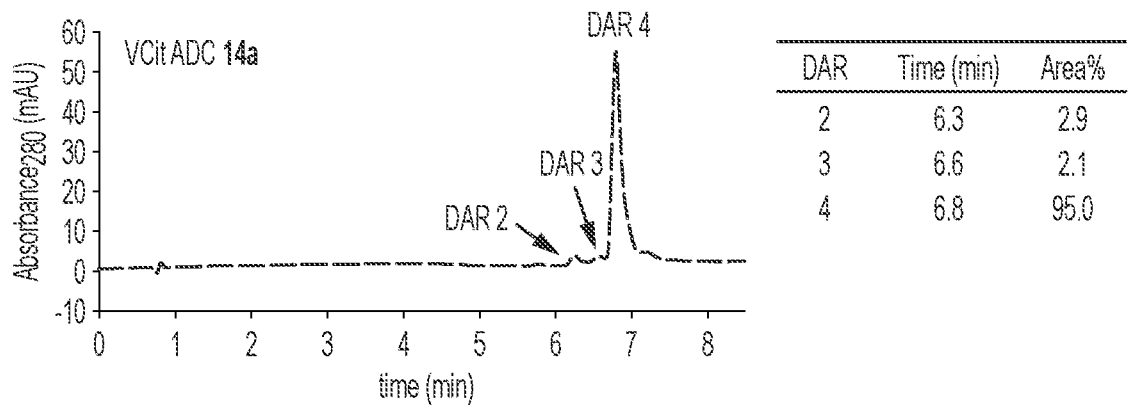
FIGS. 16A-16C show the reverse-phase HPLC traces (UV: 280 nm) of (FIG. 16A) VCit-, (FIG. 16B) SVCit-, and (FIG. 16C) EVCit-ADCs 14a-c.
Figure 16B:
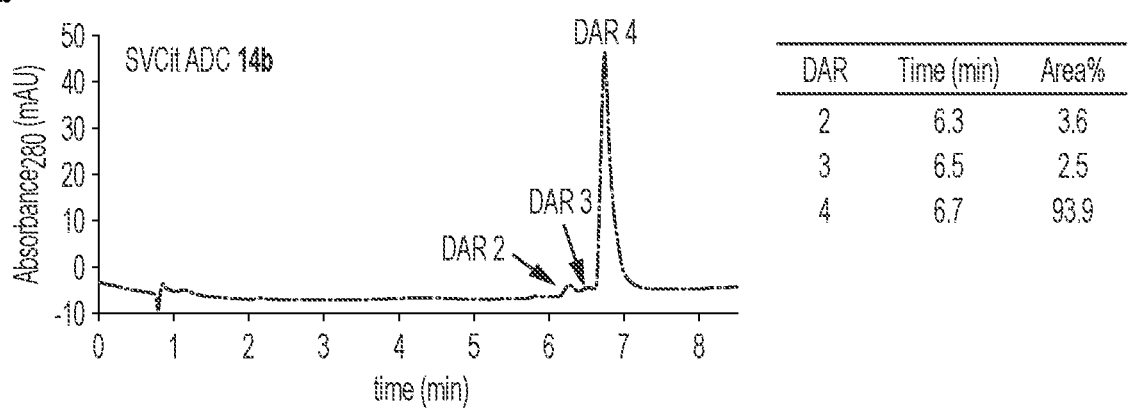
Figure 16C:
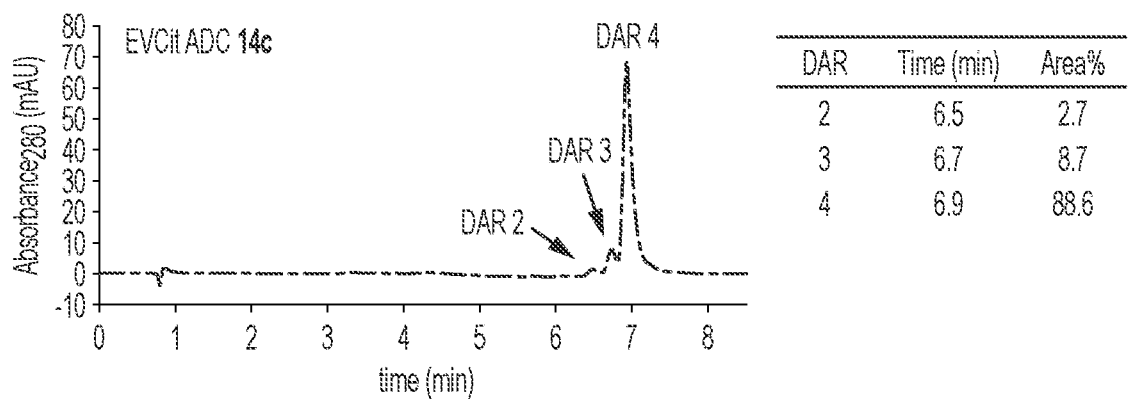
Figures 17A, 17B, 17C, 17D:
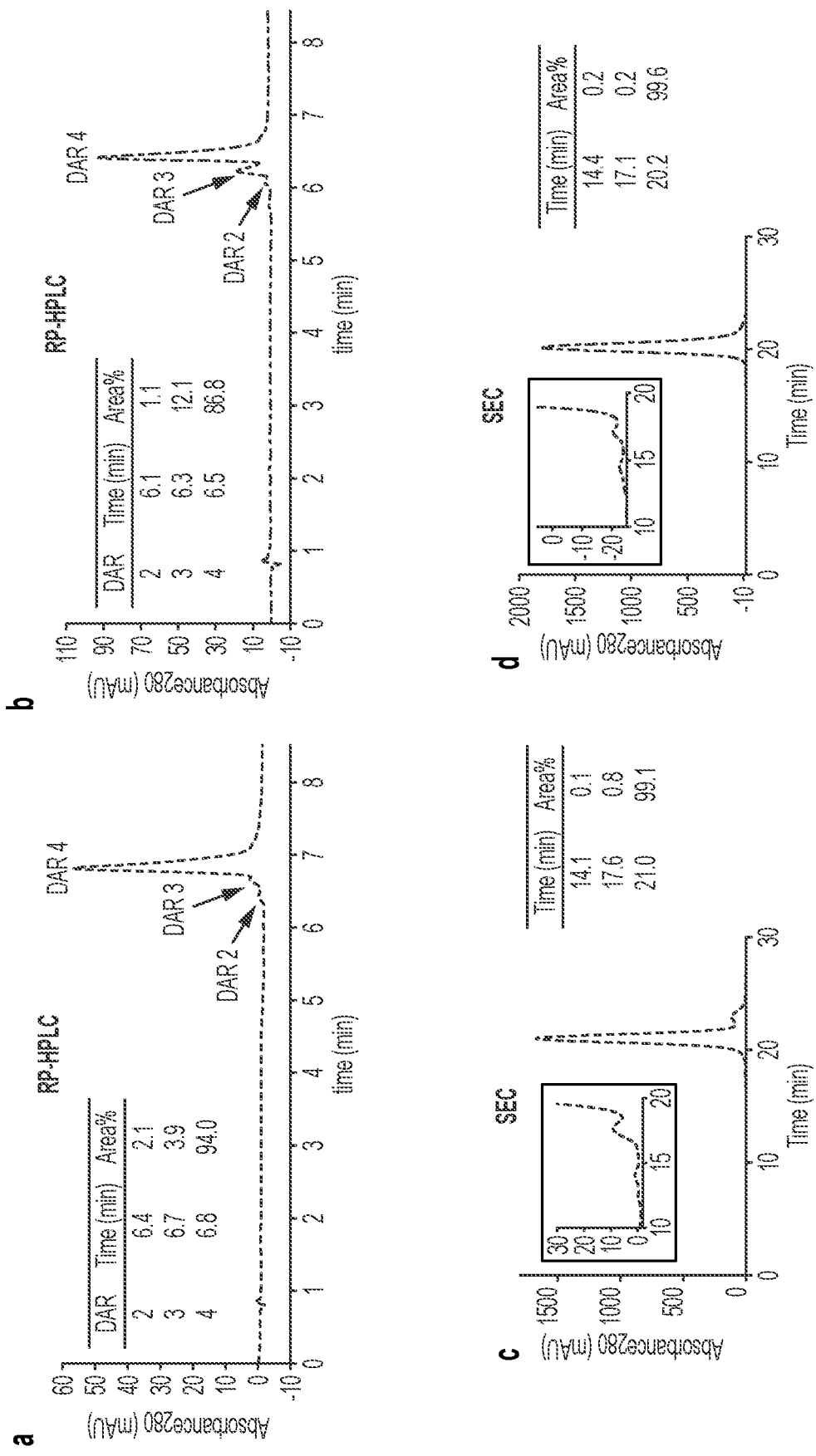
FIGS. 17A-17D show HPLC and size-exclusion chromatography (SEC) traces of non-cleavable ADC 15 (FIGS. 17A & 17C, respectively), and isotype control ADC containing EVCit 16 (non-targeting control) (FIGS. 17B & 17D, respectively).
Figures 18A, 18B, 18C:
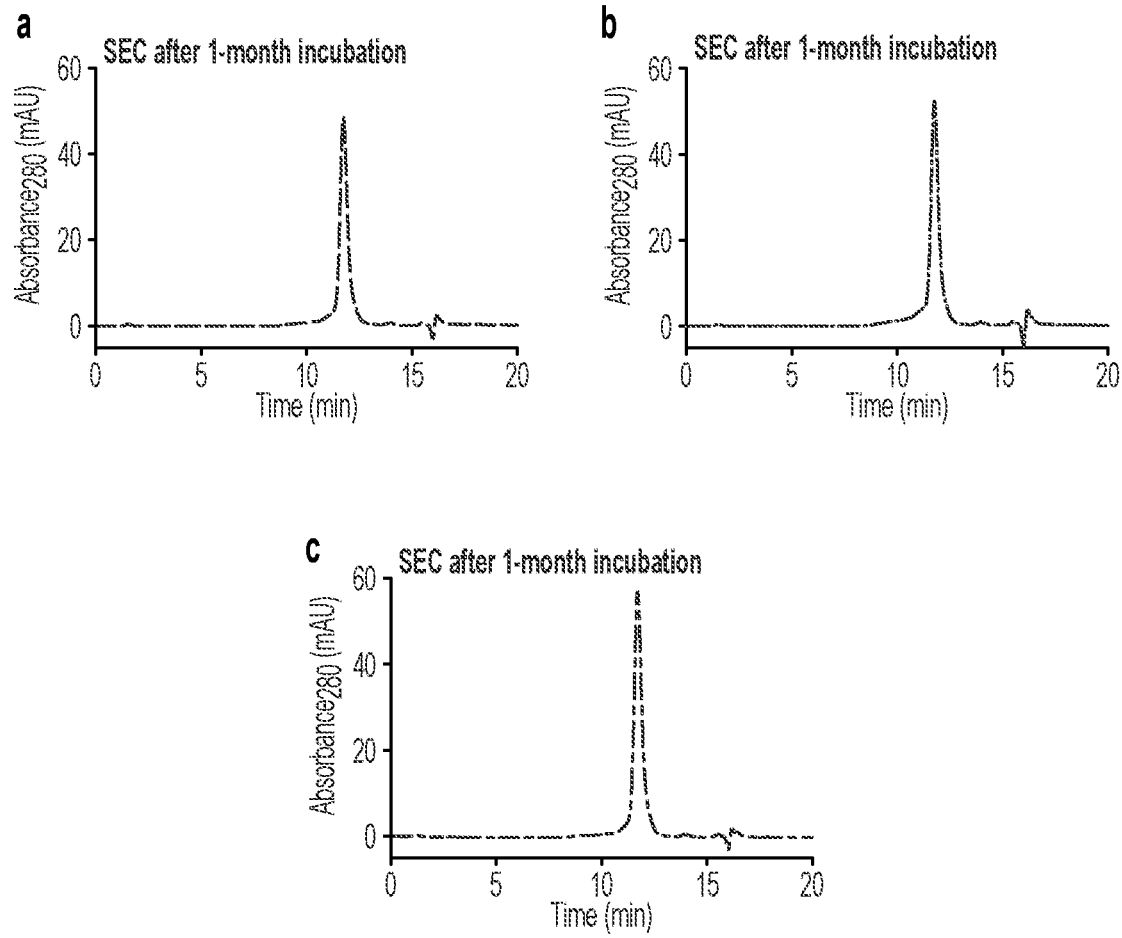
FIGS. 18A-18C show the degree of aggregation of each ADC after one-month incubation of 37° C. No aggregation was observed in either case (VCit-ADC 14a, FIG. 18A; SVCit-ADC 14b, FIG. 18B; EVCit-ADC 14c, FIG. 18C).

Construction of homogeneous ADCs using VCit, SVCit, and EVCit linkers. To investigate whether the above-mentioned observation holds true for the ADC format, ADCs construed using VCit-, SVCit-, and EVCit-based cleavable linkers were evaluated. An anti-HER2 monoclonal antibody (mAb)-branched linker conjugate was first prepared by transglutaminase-mediated conjugation according to the reported protocol with minor modifications (FIGS. 15A and 15B, Anami et al., 2017). The anti-HER2 mAb used for linker conjugation contained a mutation of the asparagine 297 within the heavy chain into alanine (N297A, Shi et al., 2014), which allows to omit the removal of the N-glycan chain on N297, a required step for MTGase-mediated antibody-linker conjugation (Dennler et al., 2014). The conjugation afforded a homogeneous mAb-branched linker conjugate in high yield. In parallel, EVCit- and SVCit-based modules were synthesized containing polyethylene glycol (PEG) spacer, MMAF, and dibenzocyclooctyne (DBCO) as a reaction handle for following strain-promoted azide-alkyne click reaction. The DBCO-VCit module was obtained from a commercial source. The number of PEG units in each module was adjusted so that all MMAF modules were similar in length. Each "clickable" module could be quantitatively conjugated to the common mAb-branched linker conjugate to give highly homogeneous ADCs with an average DAR 3.9 (determined by reverse-phase HPLC, FIG. 15B and FIG. 16). Non-cleavable branched ADC 15 (DAR: 3.9) and an isotype control constructed using the EVCit-MMAF module (16, DAR: 3.9) were also prepared in the same manner (FIG. 17). Size-exclusion chromatography (SEC) analysis revealed that all ADCs produced existed predominantly in the monomer form (FIG. 15C). Long-term stability was evaluated by incubating each ADC at 37° C. in PBS (pH 7.4) for 28 days. (FIG. 18). No significant degradation and aggregation of each ADC was observed by SEC analysis.

To assess how a chemical modification at the P3 modification impacts the ADC hydrophilicity, hydrophobic interaction chromatography (HIC) analysis was performed under the physiological conditions (phosphate buffer at pH 7.4, FIG. 15D). Highly polar EVCit-ADC 14c was detected earlier in retention time than VCit-ADC 14a whereas the hydroxy group within SVCit-ADC 14b marginally affected the ADC hydrophobicity (FIG. 15E). These results demonstrate that constructing ADCs using carboxy-functionalized EVCit linkers can reduce the ADC hydrophobicity at physiological pH. This feature is advantageous for the construction of ADCs, especially high-DAR ADCs because the ADC hydrophobicity is known to trigger aggregation and fast clearance from the body (Lyon et al., 2015).

Figures 20A, 20B, 20C:
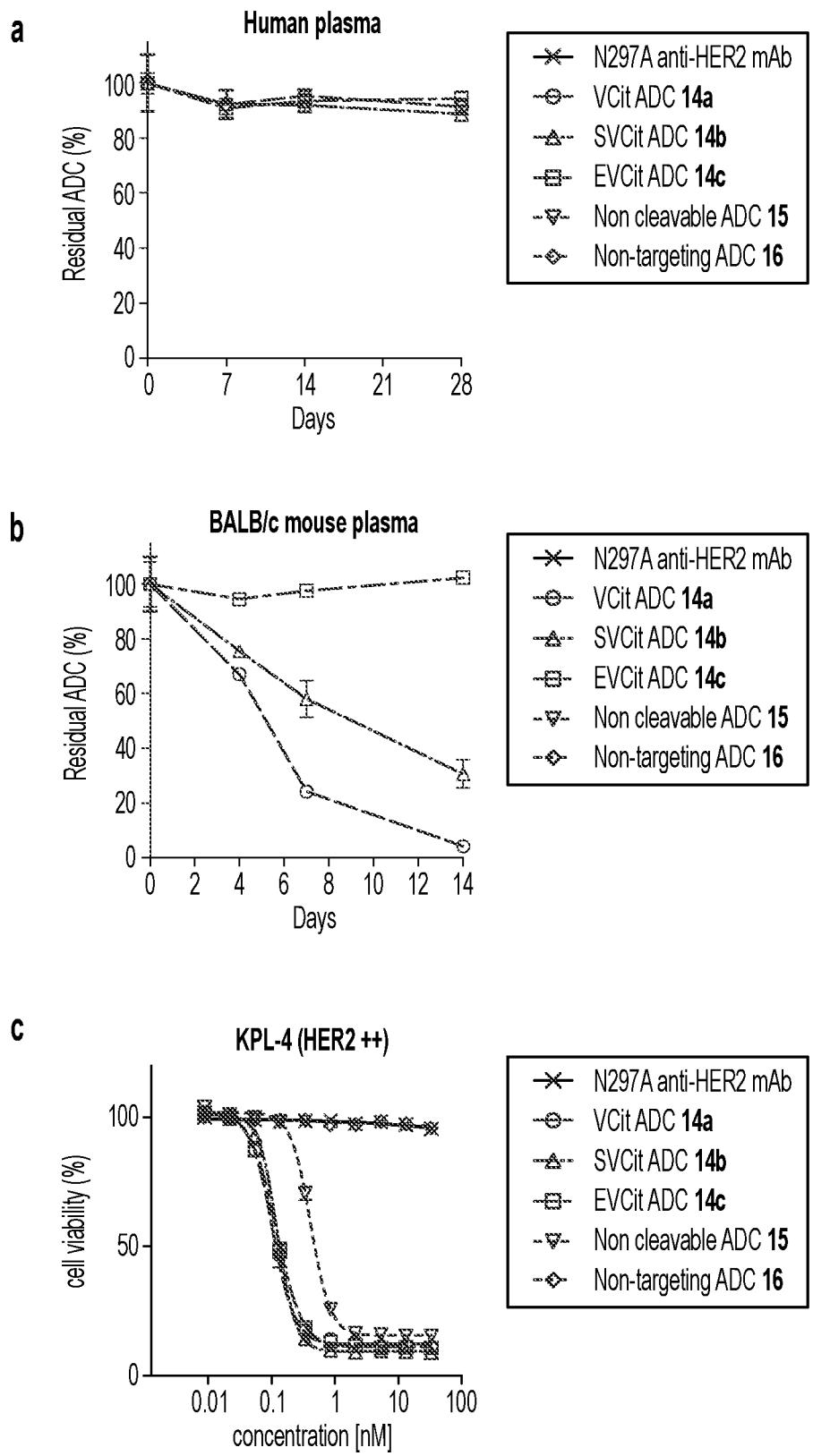
FIGS. 20A-20E show the plasma stability and in vitro cytotoxicity.

Validation of ADCs in vitro. To investigate how ADC in vitro properties are modulated by a chemical modification to the P3 position, ADCs 14a-c were first evaluated for cathepsin B-mediated cleavage. Each ADC was incubated in the presence of human liver cathepsin B at 37° C. The half-lives of VCit-ADC 14a, SVCit-ADC 14b, and EVCit-ADC 14c were determined to be 4.6 h, 5.4 h, and 2.8 h, respectively (FIG. 7). This result illustrates that EVCit linkers conjugated to a mAb are more sensitive to cathepsin B-mediated cleavage than VCit and SVCit linkers, which is consistent with the responsiveness of pyrene probes 12a-c (FIG. 13B). Next, the ADCs were assessed for stability in human and mouse plasma. No significant degradation was observed in all ADCs after 1-month incubation in human plasma at 37° C. (FIG. 20A). In contrast, EVCit-ADC 14c showed almost no linker cleavage even after 14-day incubation in undiluted BALB/c mouse plasma whereas VCit- and SVCit-ADCs 14a,b lost >95% and ~70% of the conjugated MMAF, respectively, after the same period of time (FIG. 20B). This tendency is also consistent with what was observed in the small-molecule probes (FIG. 13C). Given that the PEG spacer within the linker scaffold most likely facilitates the access of any enzymes to the linker-payload moiety, these results indicate that the acidic EVCit linker provides not only reactivity to cathepsin B-mediated cleavage but also high stability in plasma regardless of the degree of payload exposure.

Figure 19:
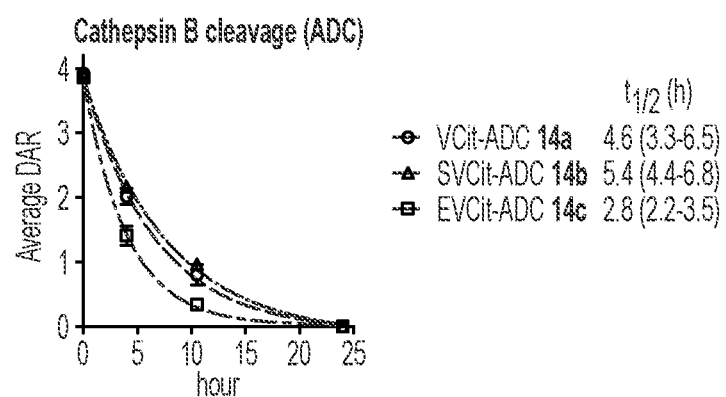
FIG. 19 shows human cathepsin B-mediated cleavage of ADCs at 37° C. Error bars represent SEM and values in parentheses are 95% confidential intervals.
Figures 20D, 20E:
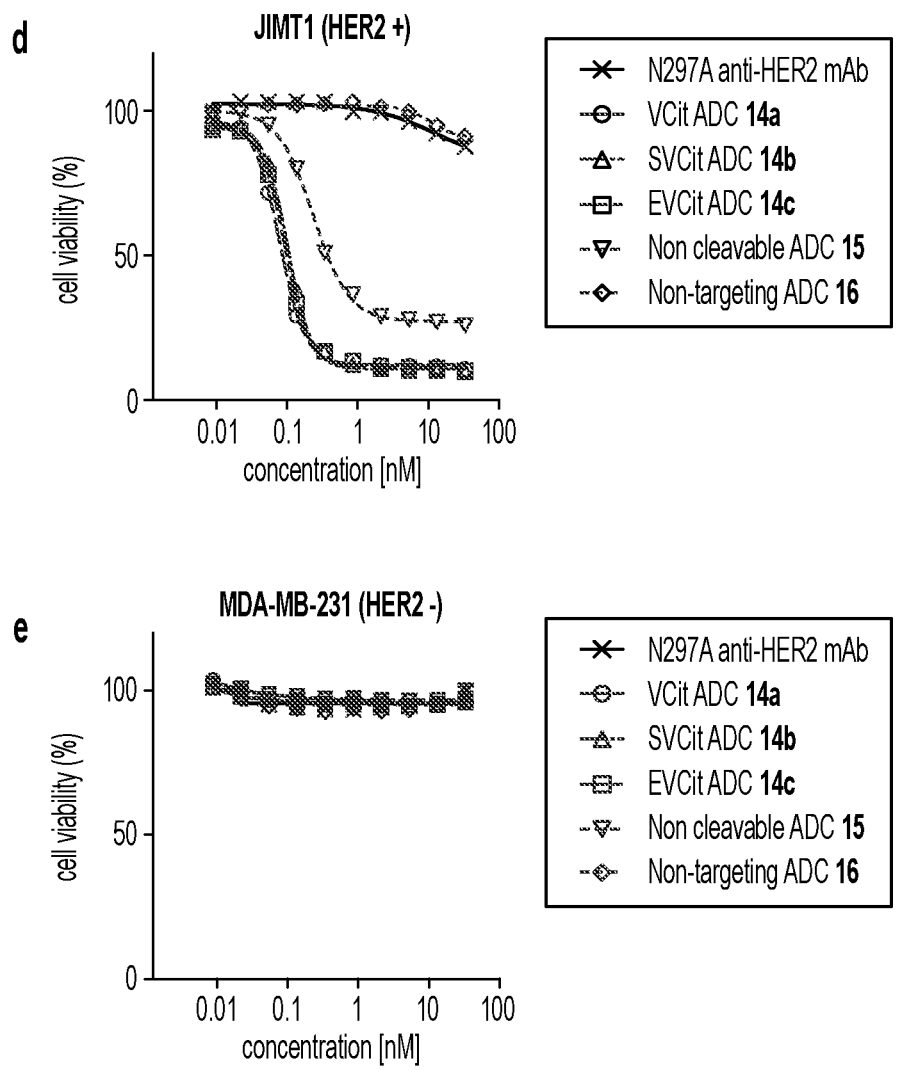
Figure 21:
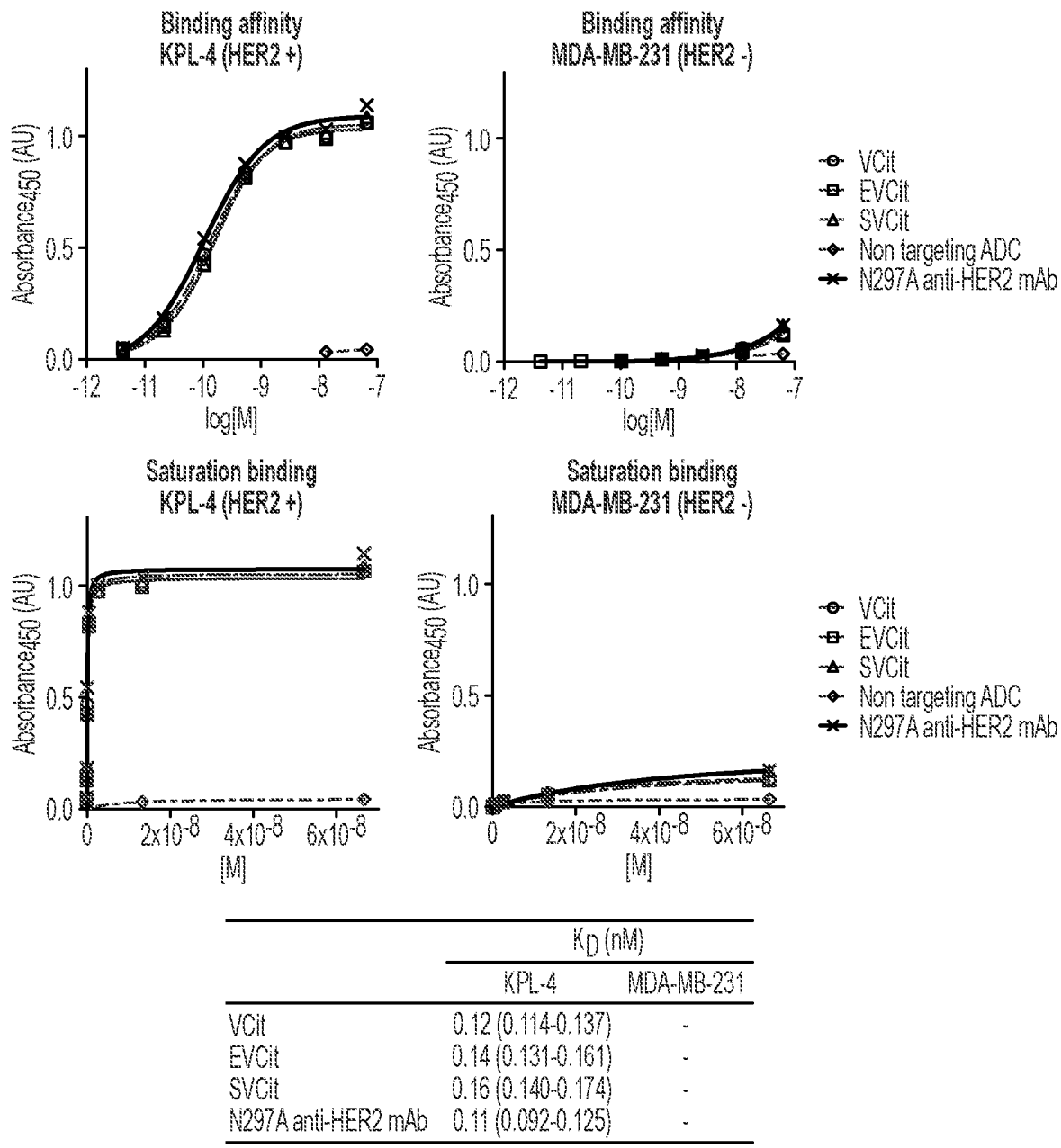
FIG. 21 shows sigmoidal-binding curves and saturation-binding curves obtained by cell-based ELISA. All assays were performed in triplicate and error bars represent SEM. Values in parentheses are 95% confidential intervals. The N297A anti-HER2 antibody and ADCs bound to KPL-4 cells (HER2 positive, left) with comparable binding affinities but not to MDA-MB-231 cells (HER2 negative, right).
Figure 22:
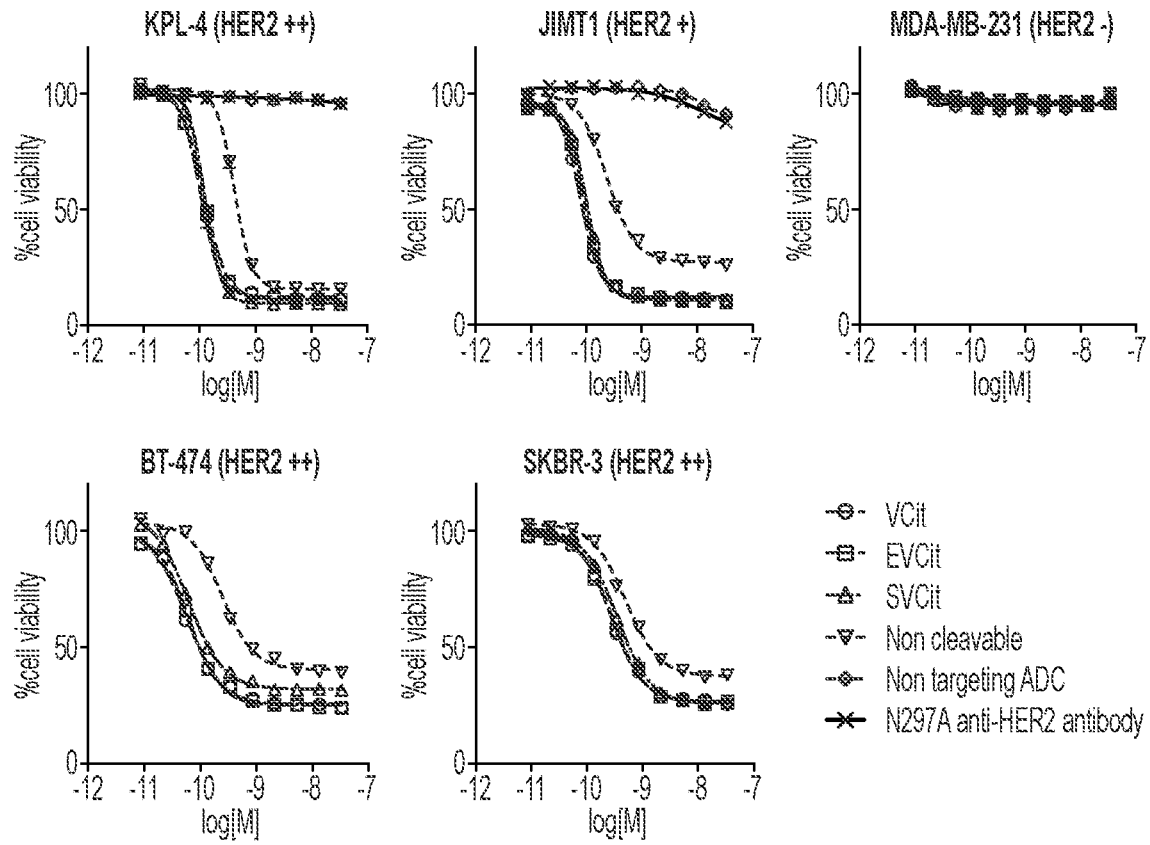
FIG. 22 shows detailed in vitro cytotoxicity profiles of unconjugated N297A anti-HER2 mAb (star) and VCit-ADC (circle), EVCit-ADC (square), SVCit-ADC (delta), non-cleavable ADC (nabla) and non-targeting EVCit-ADC (diamond). All assays were performed in triplicate. Error bars represent SEM and values in parentheses are 95% confidential intervals.

Subsequently, the anti-HER2 ADCs were tested for antigen binding affinity and specificity using the human breast cancer cell lines KPL-4 (HER2 positive) and MDA-MB-231 (HER2 negative) (FIG. 21). ADCs 14a-c showed high binding affinity to KPL-4 ($K_D$: 0.12-0.16 nM) but not to MDA-MB-231, which are comparable with the parental anti-HER2 mAb. Non-targeting control 16 showed no binding to either cell line. These results indicate that installation of glutamic acid or serine at the $P_3$ position do not impact the antigen recognition and specificity. These ADCs were also evaluated for in vitro cytotoxicity using HER2 positive-(KPL-4, JIMT-1, BT-474, and SKBR-3) and negative (MDA-MB-231) breast cancer cell lines (FIGS. 20C-20F and FIG. 22). Cathepsin B-cleavable ADCs 14a-c exhibited subnanomolar-level cell killing potency in the HER2-positive cell lines, but no cytotoxicity in HER2-negative MDA-MB-231 under the assay conditions. A significant difference in cell killing potency was not observed among the three cleavable ADCs (ranges of the $EC_{50}$ values in KPL-4: 0.10-0.12 nM; in JIMT-1: 0.078-0.10 nM; in BT-474: 0.058-0.063 nM; and in SKBR-3: 0.27-0.34 nM, FIG. 22), indicating that the slightly accelerated cathepsin B-mediated cleavage in EVCit ADC 14c (FIG. 19) does not drastically impact the cell killing potency. However, non-cleavable ADC 15, which lacks a cathepsin B-cleavable sequence within the linker scaffold, showed 1.8-4.2-fold higher $EC_{50}$ values than those of cleavable ADC 14a (FIGS. 20C & 20D and FIG. 22). These results suggest that existence of a cleavage mechanism is a key to maximize cell killing potency of ADCs constructed using the branched linker.

Figures 23A, 23B, 23C, 23D:
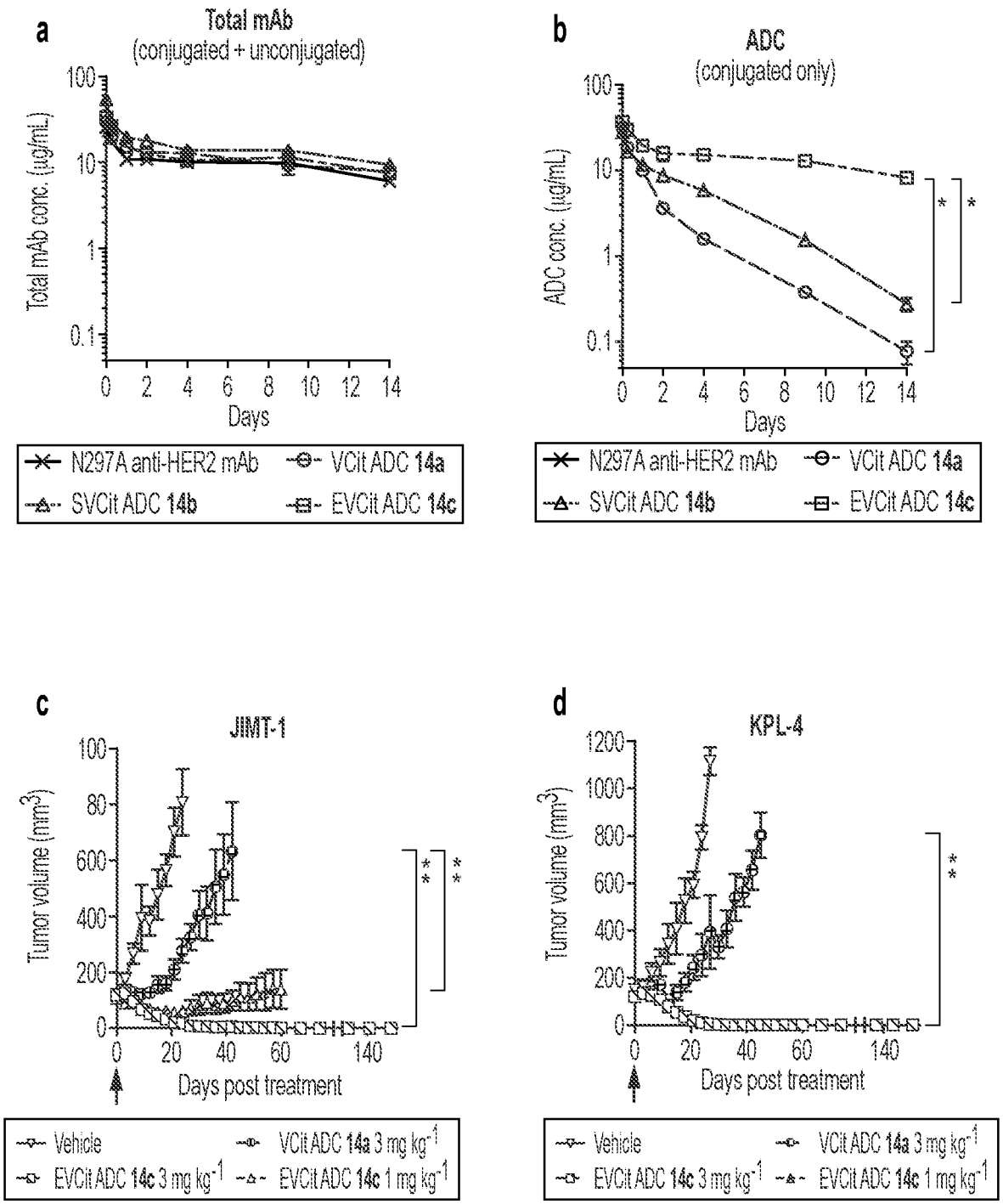
FIGS. 23A-23F show in vivo pharmacokinetics (PK) and antitumor activity.

Validation of ADCs in vivo. The ADCs were evaluated for in vivo properties using mouse models. PK profiles of VCit-, SVCit-, and EVCit-ADCs 14a-c were assessed using BALB/c mice. Mice were intravenously injected with each ADC or the parental N297A anti-HER2 mAb (3 mg/kg) and blood was collected periodically via the tail vein. Concentrations of total mAb (both conjugated and unconjugated) and intact ADC (conjugated only) in blood were determined by sandwich ELISA (FIGS. 23A & 23B and FIG. 24). All ADCs showed similar clearance rates as that of the parental mAb ($t_{1/2\beta}$=14.9 days), indicating that installing glutamic acid or serine at the P3 position did not negatively impact the clearance profile (FIG. 23A). As expected, EVCit-ADC 14c showed almost no loss of payload caused by premature cleavage during circulation ($t_{1/2\beta}$=12.0 days, FIG. 23B and FIG. 24D). In contrast, VCit- and SVCit-ADCs 14a,b quickly lost MMAF ($t_{1/2\beta}$=2.0 days and 2.4 days, respectively), demonstrating that the VCit and SVCit sequences installed on the mAb-branched linker system were unstable in circulation.

Figure 23E:
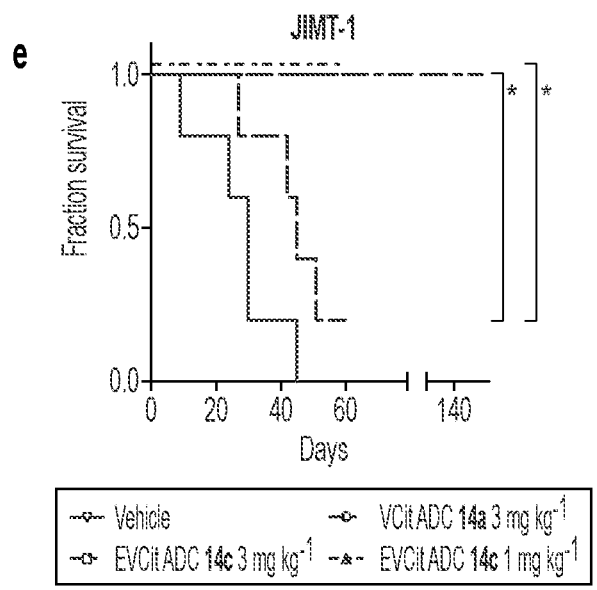
Figure 23F:
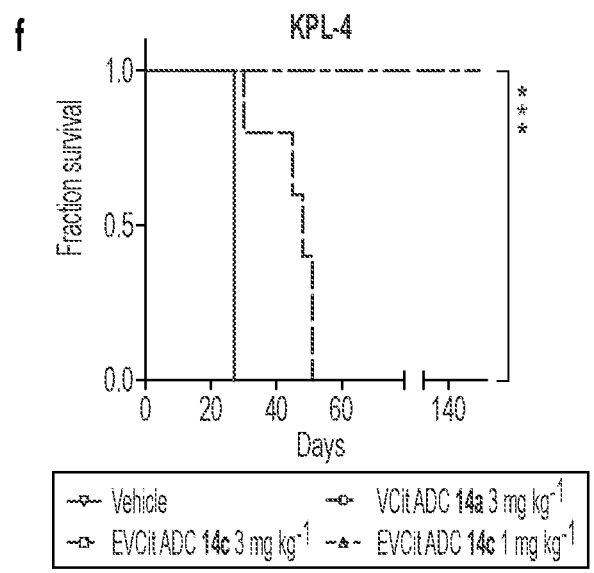
Figure 24A:
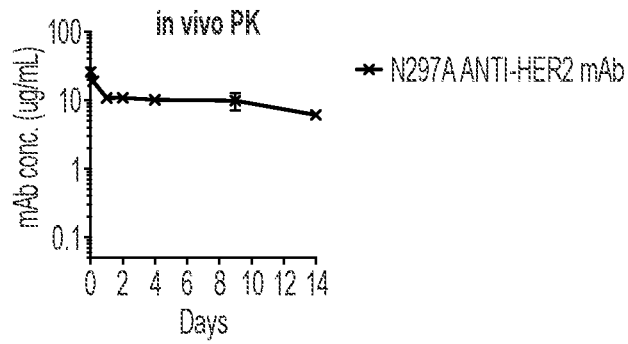
FIGS. 24A-24D show detailed in vivo pharmacokinetics (PK) profiles of (FIG. 24A) unmodified N297A anti-HER2 mAb, (FIG. 24B) VCit-ADC 14a, (FIG. 24C) SVCit-ADC 14b, and (FIG. 24D) EVCit-ADC 14c in female BALB/c mice (n=3). At the indicated time points, blood was collected to quantify concentrations of total antibody (conjugated and unconjugated, solid line) and ADC (conjugated only, dashed line) by sandwich ELISA. AUC, area under the curve; Cl, clearance.
Figure 24B:
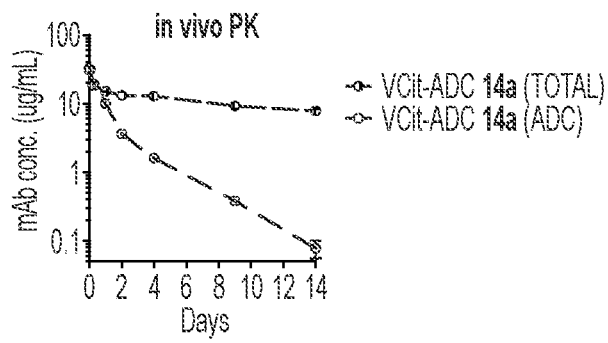
Figure 24C:
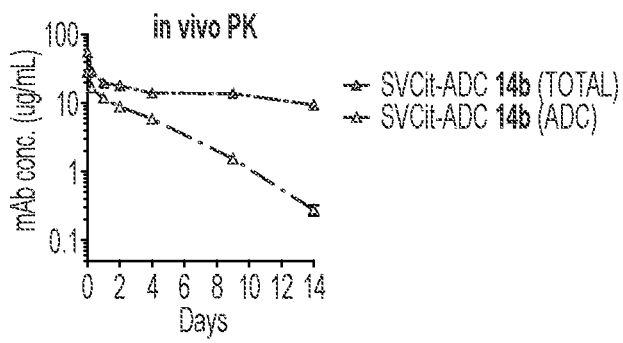
Figure 24D:
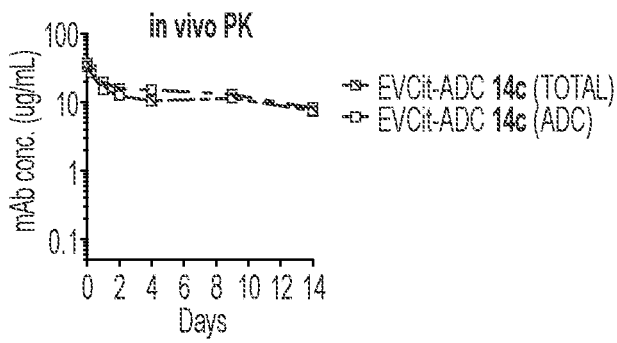
Figures 25A, 25B:
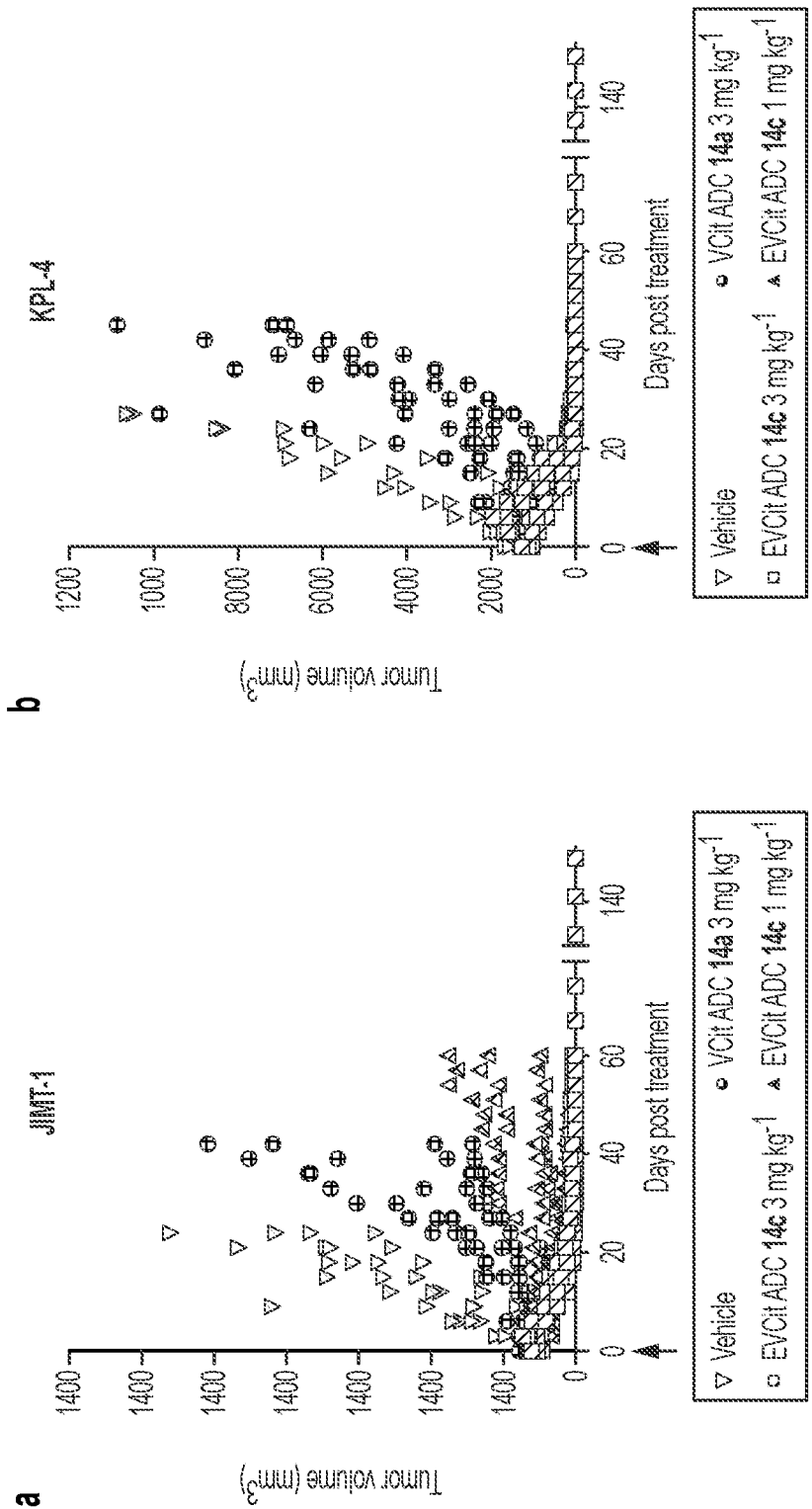
FIGS. 25A & 25B show dot plots of tumor volume after treatment in the JIMT-1 (FIG. 25A) and KPL-4 (FIG. 25B) breast xenograft models (NCr nude mice, n=4 for vehicle in the JIMT-1 model; n=3 for vehicle in the KPL-4 model; n=5 for ADCs). Each dot represents the individual mouse treated with vehicle (nabla), 3 mg/kg VCit-ADC 14a (circle), 3 mg/kg EVCit-ADC 14c (square), or 1 mg/kg 3c (delta). A single dose of each ADC (1 or 3 mg/kg) or vehicle was administered intravenously to mice when a mean tumor volume reached ~100 mm³ (indicated with an arrow). Tumor volume and body weight were monitored every 3 days until Day 60. Mice treated with 3 mg/kg EVCit-ADC 14 (square) were then monitored every 7 days until Day 148. Mice were euthanized when the tumor volume exceeded 1000 mm3, the tumor size exceeded 2 cm in diameter, greater than 15% weight loss was observed, or mice showed signs of distress.

Encouraged by this finding, VCit- and EVCit-ADC 14a,c were tested for in vivo treatment efficacy in the JIMT-1 and KPL-4 xenograft mouse models (FIGS. 23C-23F and FIG. 25) Because it was reported that athymic nude mice could quickly clear exogenously introduced IgGs (Reddy et al., 1998), tumor-bearing mice were preconditioned by intravenous administration of human IgGs (30 mg/kg) to prevent fast clearance of ADCs to be administered (Stefan et al., 2017 and Nanna et al., 2017). Tumor-bearing mice were injected intravenously with a single dose of each ADC (1 or 3 mg/kg) or vehicle control and the tumor volume was monitored every 3 days. A single dose of EVCit-based ADC 14c at 3 mg/kg was completely curative and no tumor regrowth was visually observed in both models study for about 4 months (between Day 30 and Day 148) (FIGS. 23C-23F). Furthermore, ADC 14c was highly potent even at a lower dose level (1 mg/kg) in the JIMT-1 model and all five mice survived over the course of study (FIGS. 23C & 23E). In contrast, VCit-ADC 14a exhibited only partial inhibition of tumor growth despite the high in vitro cell killing potency, and almost all mice died or reached a humane endpoint before the end of study (four out of five mice dead in the JIMT-1 model; all five mice dead in the KPL-4 model) (FIGS. 23C-23F). Taking into account the molecular structure of ADC 14c, these results demonstrate that the EVCit cleavable linker system can fully elicit the therapeutic potential of ADCs in mouse models even if it is spatially sequestered from the mAb through a long spacer.

In summary, it is disclosed herein that VCit-containing neutral or acidic tripeptides with highly polarity, in particular an acidic EVCit tripeptide sequence show enhanced stability in mouse and human plasma while remaining susceptible to intracellular cathepsin B-mediated proteolytic cleavage. Notably, the small molecule-based stability assay clearly demonstrates that a carboxylic acid side chain at the $P_3$ position provides much greater stabilization effect than does a 2-hydroxyacetamide group, the modifier that reportedly conferred the VCit sequence with the highest stability in mouse plasma (Dorywalska et al., 2016). These features make this sequence ideal cleavable ADC linker design for increasing the hydrophilicity under physiological conditions, maximizing the therapeutic potential and minimizing risks of systemic toxicity in mouse models caused by premature loss of payload. Indeed, a homogeneous anti-HER2 ADC constructed using an EVCit-PABC linker along with branched linker technology (Anami et al., 2017) exhibited higher hydrophilicity and by far greater long-term in vivo stability than those of ADCs equipped with a conventional VCit or SVCit, an analogue of the hydroxy-functionalized tripeptide ADC linker that reportedly exhibited increased stability in mouse plasma (Dorywalska et al., 2016). In addition, the stable EVCit-ADC led complete remission in two xenograft mouse models of HER2-positive breast cancer whereas the unstable VCit-ADC showed poor therapeutic effect. Taking into account that both ADCs contained long PEG spacers within the linker scaffold for fully exposing the cleavable peptide moiety, the EVCit linker system likely provides great resistance to degradation in mouse models regardless of the degree of exposure. Although the EVCit sequence appears to be promising in its present form, future structure-activity relationship studies on the interaction between an EVCit sequence and the mouse Ces1c may provide in-depth insights into the observed in vivo stability leading to further improved ADC linker design.

The use of EVCit or similar peptide linkers (e.g., DVCit, EVA, DVA) may serve as a simple but powerful solution to salvage many types of ADCs that have previously been abandoned due to linker instability in mouse models. The high polarity of the EVCit linker could also help to some extent mitigate the hydrophobicity of high-DAR ADCs that often face aggregation and fast clearance issues (Sun et al., 2017). In addition, EVCit linkers may be preferentially chosen over non-cleavable linkers in the future design of various ADCs. Non-cleavable linkers are designed to withstand proteolytic degradation during circulation and have been successfully used for constructing potent ADCs along with MMAF (Doronina et al., 2006), monomethyl auristatin D (MMAD, Strop et al., 2015), and emtansine (DM1, LoRusso et al., 2011 and Verma et al., 2012). However, the use of non-cleavable linkers reportedly attenuated or nullified ADC potency of several payload classes including doxorubicin (Doronina et al., 2006), monomethyl auristatin E (MMAE) (Doronina et al., 2006 and Caculitan et al., 2017), a hydrophilic derivative of MMAF (Mendelsohn et al., 2017), and a pyrrolobenzodiazepine dimer (PBD, Caculitan et al., 2017). This is because non-cleavable linkers lack a defined cleavage mechanism and final active metabolites after intracellular protein degradation still retain the linker component. Although it has been demonstrated that this drawback can be circumvented in some cases by fine-tuning the chemical structures of the linker and payload (Gregson et al., 2017 and Christie et al., 2017), such efforts may not necessarily lead to success depending on the choice of the linker installation sites, conjugation modality, and payload. Indeed, as demonstrated in our previous (Anami et al., 2017) and this reports, branched linker technology requires both adequate spacers (e.g., $PEG_3$) and cleavable mechanisms within the liker scaffold for maximal ADC potency; these components are critical to alleviate the structural congestion and to ensure rapid payload release in an active form from each linker arm.

Taken together, it is envisaged that the linker technology disclosed herein will boost up efforts for developing next-generation ADCs and other drug conjugates by allowing for flexible molecular design and minimizing the risk of stumbling at the pre-clinical stage due to linker instability or poor potency. Although further validation is necessary, it is envisaged that this linker technology may benefit a diverse array of conjugation methods and linker systems developed to date, including but not limited to conventional couplings at lysine or cysteine residues, site-specific conjugations at solvent accessible moieties (e.g., conjugation at the C-terminus of the antibody heavy chain) (Rabuka et al. 2012, Beerli et al., 2015, and Drake et al., 2014), and novel branched ADC linkers for heterologous payload loading (Maruani et al., 2015 and Levengood et al., 2017). Furthermore, considering the long half-life of EVCit and DVCit probes 12c,d, these linkers may also be useful for constructing small molecule-based drug conjugates for targeted therapy (Srinivasarao et al., 2015 and Cazzamalli et al., 2017).

Example 7—Synthesis of Linkers with Improved Stability
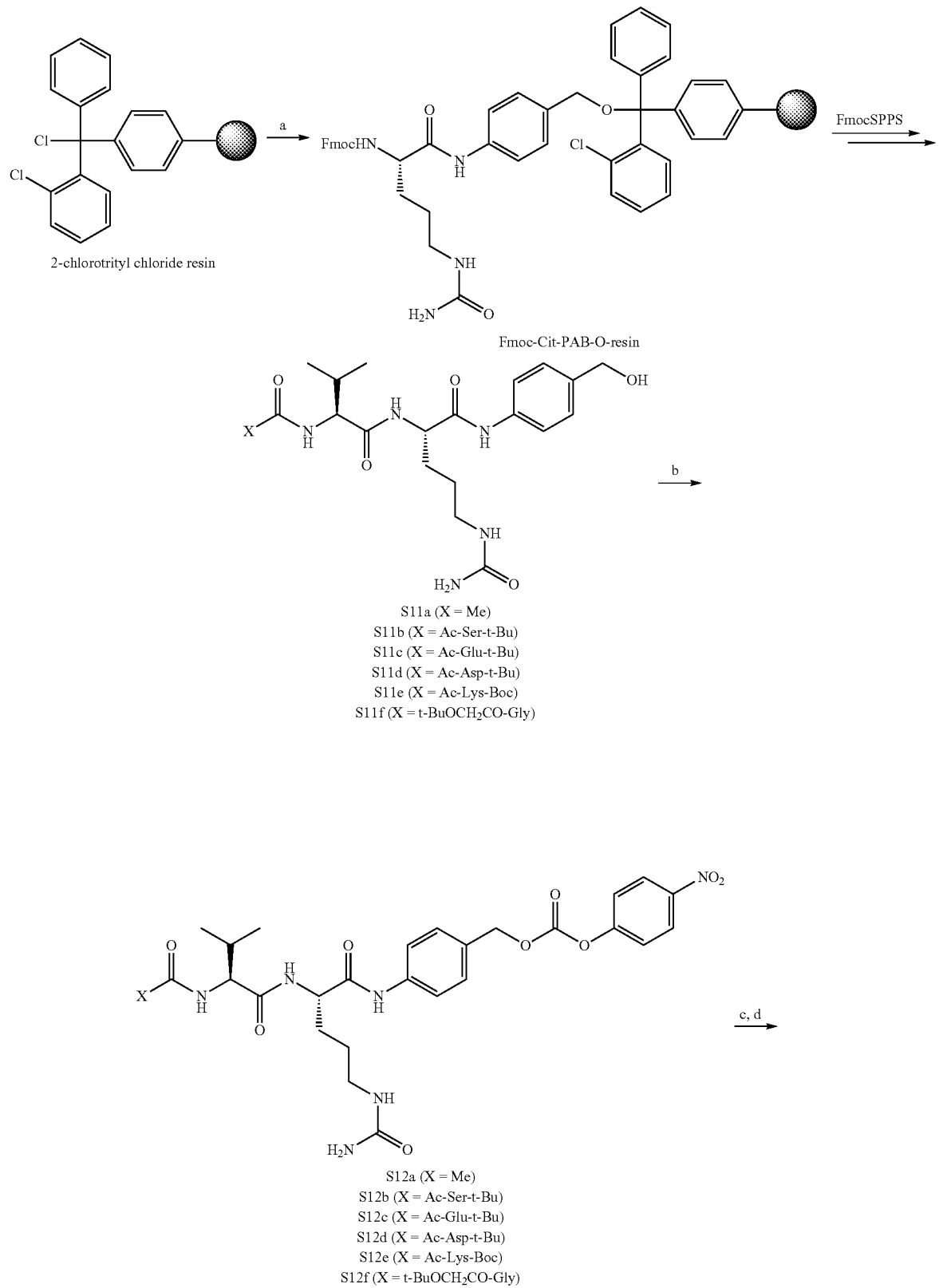
Scheme 8. Synthesis of pyrene probes 12a-f.

-continued

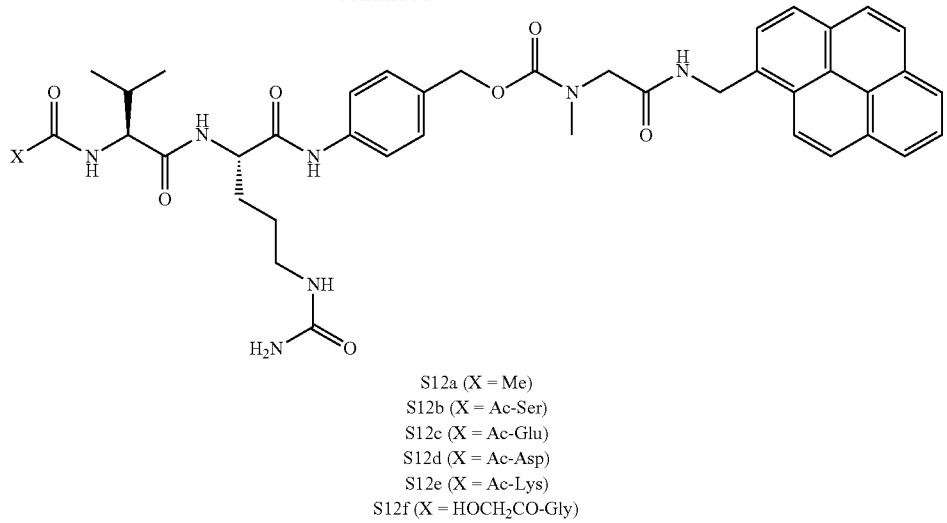

S12a (X = Me)
S12b (X = Ac-Ser)
S12c (X = Ac-Glu)
S12d (X = Ac-Asp)
S12e (X = Ac-Lys)
S12f (X = HOCH$_2$CO-Gly)

FmocSPPS

Conditions
Coupling: Fmoc-amino acid (4 equiv.)
　　　　　HATU (4 equiv.)
　　　　　DIPEA (6 equiv.)
Acetyl capping: Ac$_2$O (4 equiv.)
　　　　　　　DIPEA (6 equiv.)
Fmoc deprotection: 20% piperidine in DMF
Resin cleavage: 1% TFA in DCM

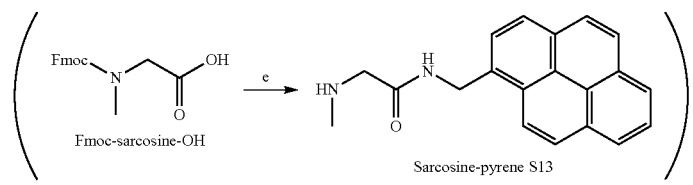

Fmoc-sarcosine-OH

Sarcosine-pyrene S13

Reagents and conditions: (a) Fmoc-citrulline-PABOH, pyridine, 55° C., overnight; (b) bis(4-nitrophenyl) carbonate, DIPEA (for S12a-c, and S12e) or DMAP (for S12d and S12f), DMF, room temp, overnight; (c) sarcosine-pyrene S13, DIPEA, DMAP, DMF, 37° C., 2 h; (d) TFA, DCM, TIPS, room temp, 1 h for 12-b-f; (e) HATU, DIPEA, DMF, room temp, 2 h then 50% diethylamine/DMF, room temp, 1 h.

Synthesis of Compounds and Conjugates.
Preparation of Fmoc-Cit-PAB-O-resin.

Chlorotrityl chloride resin (1 g, 1.6 mmol) was mixed with a solution of Fmoc-citrulline-PABOH (U.S. Pat. No. 9,487,556, 2.4 g, 4.8 mmol) in pyridine (783 µL, 9.6 mmol), tetrahydrofuran (THF, 30 mL), and dimethylformamide (DMF, 3 mL) and agitated overnight at 55° C. After the solution was cooled, methanol (MeOH) was added and agitated for 30 min at room temperature. The solution was drained and the resin was washed with DMF (5×5 mL) and dichloromethane (DCM, 5×5 mL). The loading rate was determined to be 10% (0.16 mmol/g resin) by small-scale resin cleavage using 1% trifluoroacetic acid (TFA)/DCM.

Fmoc Solid-Phase Peptide Synthesis (Fmoc SPPS) for Acetyl-Capped Compounds (S11a-f).

To remove a Fmoc-protecting group after each coupling, resin (100-150 mg) was treated with piperidine (5 mL of 20% in DMF) for 20 min and washed with DMF (5×5 mL) and DCM (5×5 mL). Fmoc-protected amino acid (4 equiv.) was pre-activated by being mixed with 1-[bis(dimethylamino)methylene]-1H-1,2,3-triazolo[4,5-b]pyridinium 3-oxid hexafluorophosphate (HATU, 4 equiv.) and N,N-diisopropylethylamine (DIPEA, 6 equiv.) in DMF for 2-5 min, and the cocktail was used for coupling (conditions: room temperature, 1 h). The completion of the coupling was verified by the Kaiser test. After each coupling step, the coupling cocktail was drained and the resin was washed with DMF (5×5 mL) and DCM (5×5 mL). After completion of peptide elongation, the resin was treated with acetic anhydride (4 equiv.) and DIPEA (6 equiv.) in DMF for 1 h and then washed with DMF (5×5 mL) and DCM (5×5 mL). The acetyl-capped resin containing protected peptides was treated with 1% TFA/DCM at room temperature for 1 h. The solution was concentrated in vacuo and the crude peptides were precipitated with cold diethyl ether (5-6 mL) followed by centrifugation at 1,000 g for 5 min (3 times). The peptide pellet was dried in vacuo and used immediately in the next step without purification.

Ac-Val-Cit-PABC-PNP (S12a).

To a solution of crude S11a (3.6 mg, approximately 0.008 mmol) in DMF (0.3 mL) were added bis(2,4-dinitrophenyl) carbonate (12.8 mg, 0.042 mmol) and DIPEA (4.4 µL, 0.025 mmol). After being mixed overnight at room temperature, the crude products were purified by preparative RP-HPLC under acidic conditions to afford peptide S12a (2.9 mg, total yield: 62%, based on the resin loading rate). Purity was confirmed by LC-MS under acidic conditions. Off-white powder. HRMS (ESI) Calcd. For $C_{27}H_{34}N_6O_9Na$ [M+Na]$^+$: 609.2279. Found: 609.2286. Peptides S12b-f were synthesized from S11b-f in a similar manner.

Ac-Ser(t-Bu)-Val-Cit-PABC-PNP (S12b).

3.9 mg, total yield: 66% (based on the loading rate). Off-white powder. HRMS (ESI) Calcd. For $C_{34}H_{47}N_7O_{11}Na$ [M+Na]$^+$: 752.3226. Found: 752.3240.

Ac-Glu(t-Bu)-Val-Cit-PABC-PNP (S12c).

4.8 mg, total yield: 78% (based on the loading rate). Off-white powder. HRMS (ESI) Calcd. For $C_{36}H_{49}N_7O_{12}Na$ [M+Na]$^+$: 794.3331. Found: 794.3351.

Ac-Asp(t-Bu)-Val-Cit-PABC-PNP (S12d).

DMAP (2 equiv.) was used instead of DIPEA. 6.1 mg, total yield: 45% (based on the loading rate). Off-white powder. HRMS (ESI) Calcd. For $C_{35}H_{48}N_7O_{12}$ [M+H]$^+$: 758.3355. Found: 758.3355.

Ac-Lys(Boc)-Val-Cit-PABC-PNP (S12e).

11.1 mg, total yield: 67% (based on the loading rate). Off-white powder. HRMS (ESI) Calcd. For $C_{38}H_{55}N_8O_{12}$ [M+H]$^+$: 815.3934. Found: 815.3931.

t-Bu-OCH$_2$CO-Gly-Val-Cit-PABC-PNP　　　　　(S12f).

DMAP (2 equiv.) was used instead of DIPEA. 9.5 mg, total yield: 61% (based on the loading rate). Off-white powder. HRMS (ESI) Calcd. For $C_{33}H_{45}N_7O_{11}Na$ [M+Na]$^+$: 738.3069. Found: 738.3068.

Sarcosine-pyrene (S13)

To a solution of Fmoc-sarcosine-OH (14.0 mg, 0.045 mmol) in DMF (0.5 mL) were added HATU (25.7 mg, 0.0675 mmol), DIPEA (12 μL, 0.0675 mmol), and 1-pyrenemethylamine (13.3 mg, 0.0495 mmol). After being mixed at room temperature for 2 h, the solution was concentrated in vacuo and the crude products were dissolved in DMF (0.6 mL) and diethylamine (0.6 mL). After 1 h, the crude mixture was concentrated and purified by preparative RP-HPLC under acidic conditions to afford sarcosine-pyrene S13 (6.7 mg, 49% for the 2 steps). White powder. $^1$H NMR (300 MHz, DMSO-$d_6$) δ 8.82 (t, J=5.8 Hz, 1H), 8.40 (d, J=9.3 Hz, 1H), 8.35-8.23 (m, 4H), 8.17 (s, 2H), 8.14-8.02 (m, 2H), 5.08 (d, J=5.6 Hz, 2H), 3.49 (s, 2H), 2.88 (s, 1H), 2.43 (s, 3H); $^{13}$C NMR (75 MHz, DMSO-$d_6$) δ 167.9, 132.4, 130.8, 130.3, 130.2, 128.1, 127.6, 127.4, 127.1, 126.8, 126.3, 125.3, 125.2, 124.7, 124.0, 123.9, 123.1, 51.6, 39.4, 34.3; HRMS (ESI) Calcd. For $C_{20}H_{19}N_2O$ [M+H]$^+$: 303.1492. Found: 303.1492.

Ac-Val-Cit-PABC-Sar-pyrene (12a).

In a microtube were mixed Ac-Val-Cit-PABC-PNP S12a (6.3 mg, 10.7 μmol) in DMF (1 mL), 128.4 μL of 100 mM sarcosine-pyrene S13 in DMF (12.8 μmol), DIPEA (2.8 μL, 16.1 μmol), and DMAP (10 μL, 10 w/v % in DMF). After being stirred at room temperature for 2 h, the crude products were purified by preparative RP-HPLC under acidic conditions to afford analytically pure product 12a (2.7 mg, 34%). White powder. HRMS (ESI) Calcd. For $C_{41}H_{47}N_7O_7Na$ [M+Na]$^+$: 772.3429. Found: 772.3440.

Ac-Ser-Val-Cit-PABC-Sar-pyrene (12b).

In a microtube were mixed Ac-Ser(t-Bu)-Val-Cit-PABC-PNP S12b (6.6 mg, 9.1 μmol) in DMF (1 mL), 108.7 μL of 100 mM sarcosine-pyrene S13 in DMF (10.9 μmol), DIPEA (2.4 μL, 13.7 μmol), and DMAP (10 μL, 10 w/v % in DMF). After being stirred at room temperature for 2 h, the mixture was dried in vacuo and treated with a solution of TFA, DCM, and triisopropylsilane (45:50:5, 2 mL) at room temperature for 3 h. After the solution was concentrated, the crude products were purified by preparative RP-HPLC under acidic conditions to afford analytically pure product 12b (2.3 mg, 30% for the 2 steps). White powder. HRMS (ESI) Calcd. For $C_{44}H_{52}N_8O_9Na$ [M+Na]$^+$: 859.3749. Found: 859.3753. Probes 12c-f were synthesized from S12c-f in a similar manner.

Ac-Glu-Val-Cit-PABC-Sar-pyrene (12c).

2.6 mg, 31% for the 2 steps. White powder. HRMS (ESI) Calcd. For $C_{46}H_{54}N_8O_{10}Na$ [M+Na]$^+$: 901.3855. Found: 901.3870.

Ac-Asp-Val-Cit-PABC-Sar-pyrene (12d).

3.1 mg, 47% for the 2 steps. White powder. HRMS (ESI) Calcd. For $C_{45}H_{53}N_8O_{10}$ [M+H]$^+$: 865.3879. Found: 865.3877.

Ac-Lys-Val-Cit-PABC-Sar-pyrene (12e).

3.5 mg, 47% for the 2 steps. White powder. HRMS (ESI) Calcd. For $C_{47}H_{60}N_9O_8$ [M+H]$^+$: 878.4559. Found: 878.4553.

HOCH$_2$CO-Gly-Val-Cit-PABC-Sar-pyrene (12f).

2.7 mg, 47% for the 2 steps. White powder. HRMS (ESI) Calcd. For $C_{43}H_{50}N_8O_9Na$ [M+Na]$^+$: 845.3593. Found: 845.3589.

Scheme 9. Synthesis of branched linker 13.

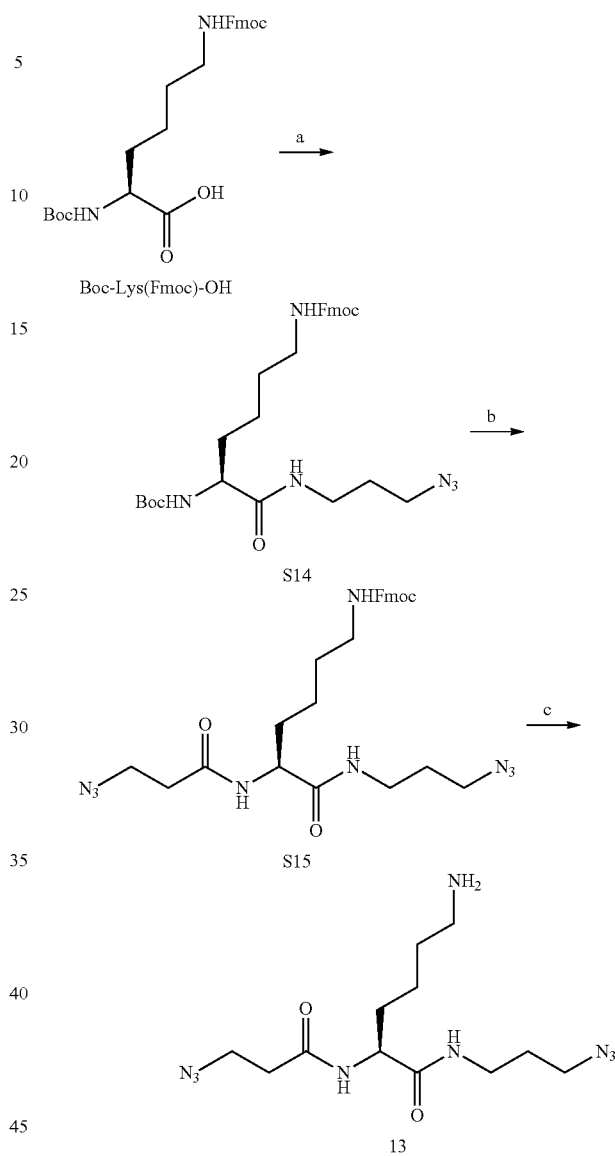

Reagents and conditions:
(a) 3-azidopropylamine, EDC•HCl, NHS, DMF, room temp, overnight;
(b) 50% TFA/DCM, room temp, 1 h then 3-azidopropionic acid, EDC•HCl, NHS, DIPEA, DMF, room temp, overnight;
(c) 50% diethylamine/DMF, room temp, 1 h.

Boc-Lys(Fmoc)-N$_3$ (S14).

Boc-Lys(Fmoc)-OH (120.4 mg, 0.257 mmol) in DMF (2 mL) was mixed with N-hydroxysuccinimide (NHS, 59.2 mg, 0.514 mmol) and N-(3-dimethylaminopropyl)-N'-ethylcarbodiimide hydrochloride (EDC·HCl, 98.5 mg, 0.514 mmol) at room temperature. To the solution was added 3-azidopropylamine (32.8 μL, 0.334 mmol) and the resulting mixture was stirred overnight at room temperature. The reaction was quenched with 15% citric acid and extracted with ethyl acetate. The organic layer was washed with brine, dried over Na$_2$SO$_4$, and concentrated. The residue was purified by column chromatography using a Biotage Isolera Flash Purification System (0-20% of DCM/MeOH, 20 mL/min, SNAP cartridge KP-Sil 10 g) to afford S14 (178.6 mg, 97%). White powder. $^1$H NMR (300 MHz, CD$_3$OD) δ 7.81 (d, J=7.4 Hz, 2H), 7.66 (d, J=7.4 Hz, 2H), 7.41 (t, J=7.3

Hz, 2H), 7.32 (t, J=7.4 Hz, 2H), 4.37 (d, J=6.8 Hz, 2H), 4.21 (t, J=6.9 Hz, 1H), 4.00-3.86 (m, 1H), 3.40-3.34 (m, 2H), 3.27 (td, J=6.6, 2.7 Hz, 2H), 3.12 (t, J=6.7 Hz, 2H), 1.82-1.68 (m, 3H), 1.66-1.48 (m, 3H), 1.44 (s, 9H), 1.40-1.15 (m, 2H); $^{13}$C NMR (75 MHz, CD$_3$OD) δ 175.4, 159.0, 145.4 (2 carbons), 145.3, 142.6 (2 carbons), 128.8 (2 carbons), 128.1 (2 carbons), 126.1 (2 carbons), 120.9 (2 carbons), 80.6, 67.6, 56.3, 50.0, 48.5, 41.3, 37.7, 32.9, 30.5, 29.7, 28.7 (3 carbons), 24.1; HRMS (ESI) Calcd. For C$_{29}$H$_{38}$N$_6$O$_5$Na [M+Na]$^+$: 573.2796. Found: 573.2802.

N$_3$-Lys(Fmoc)-N$_3$ (S15).

Compound S14 (79 mg, 0.144 mmol) was dissolved in DCM (500 μL) and then TFA (500 μL) was added to the solution at room temperature. After 1 h, the mixture was concentrated and used for the following reaction without purification. To the residue were added azidopropanoic acid (21.5 mg, 0.187 mmol, Advanced ChemBlocks), NHS (33.1 mg, 0.288 mmol), and EDC-HCl (55.2 mg, 0.288 mmol) in DMF (1 mL). DIPEA (50 μL, 0.288 mmol) was subsequently added to the mixture. After being stirred at room temperature overnight, the reaction mixture was quenched with 15% citric acid and extracted with ethyl acetate. The organic layer was washed with brine, dried over Na$_2$SO$_4$, and concentrated. The residue was purified by column chromatography using a Biotage Isolera Flash Purification System (0-20% of DCM/MeOH, 20 mL/min, SNAP cartridge KP-Sil 10 g) to afford S15 (54.9 mg, 70%). White powder. $^1$H NMR (300 MHz, CD$_3$OD) δ 8.18 (d, J=7.3 Hz, 1H), 8.03 (t, J=5.8 Hz, 1H), 7.80 (d, J=7.5 Hz, 2H), 7.64 (d, J=7.4 Hz, 2H), 7.39 (t, J=7.1 Hz, 2H), 7.31 (t, J=7.4 Hz, 2H), 4.35 (d, J=6.8 Hz, 2H), 4.32-4.14 (m, 2H), 3.55 (t, J=6.6 Hz, 2H), 3.37-3.32 (m, 2H), 3.25 (q, J=6.2 Hz, 2H), 3.11 (t, J=6.7 Hz, 2H), 2.49 (t, J=6.4 Hz, 2H), 1.82-1.69 (m, 3H), 1.67-1.43 (m, 3H), 1.43-1.27 (m, 2H); $^{13}$C NMR (75 MHz, CD$_3$OD) δ 174.4, 173.0, 159.0, 145.4 (2 carbons), 142.6 (2 carbons), 128.8 (2 carbons), 128.1 (2 carbons), 126.1 (2 carbons), 120.9 (2 carbons), 67.6, 55.0, 50.0, 48.54, 48.51, 41.4, 37.7, 36.0, 32.7, 30.5, 29.6, 24.1; HRMS (ESI) Calcd. For C$_{27}$H$_{33}$N$_9$O$_4$Na [M+Na]$^+$: 570.2548. Found: 570.2555.

Branched Linker (13).

Compound S15 (29.2 mg, 0.053 mmol) was dissolved in DMF (0.3 mL) and diethylamine (0.3 mL) was added to the solution at room temperature. After 1 h, the mixture was concentrated and purified by preparative RP-HPLC under acidic conditions (UV: 195 nm) to afford branched linker 13 (3.9 mg, 22%). Colorless oil. $^1$H NMR (300 MHz, DMSO-d$_6$) δ 8.17 (d, J=8.0 Hz, 1H), 8.01 (t, J=5.7 Hz, 1H), 7.73 (s, 2H), 4.20 (td, J=8.4, 5.3 Hz, 1H), 3.54-3.49 (m, 2H), 3.34 (t, J=6.8 Hz, 2H), 3.12 (q, J=6.5 Hz, 2H), 2.84-2.66 (m, 2H), 2.45 (t, J=6.4 Hz, 2H), 1.73-1.57 (m, 3H), 1.57-1.43 (m, 3H), 1.41-1.16 (m, 2H); $^{13}$C NMR (75 MHz, D$_2$O) δ 173.9, 173.8, 48.9, 48.6, 47.1, 39.2, 36.6, 34.7, 30.4, 27.6, 26.3, 22.1; HRMS (ESI) Calcd. For C$_{12}$H$_{23}$N$_9$O$_2$Na [M+Na]$^+$: 348.1867. Found: 348.1868.

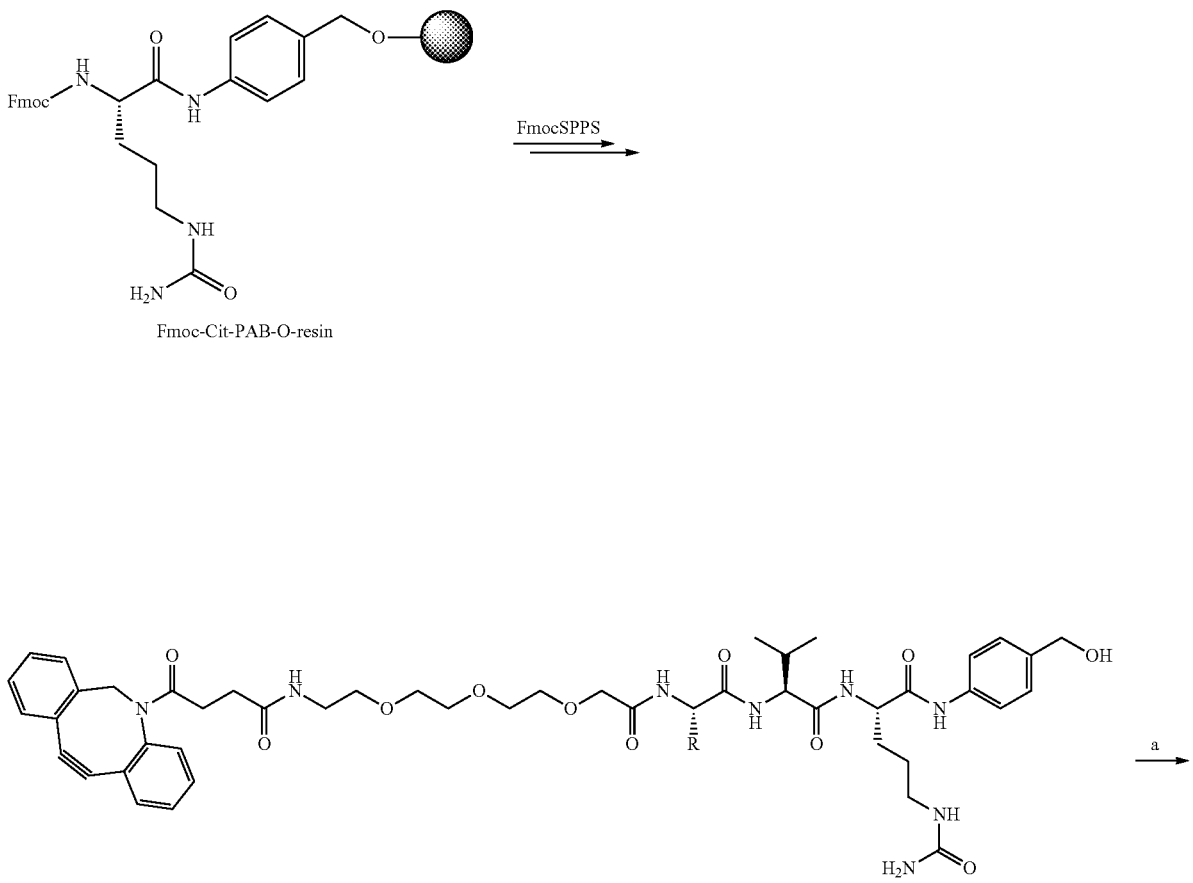

Scheme 10. Synthesis of DBCO-MMAF fragments S19a and S19b.

Fmoc-Cit-PAB-O-resin

S16a (R = CH$_2$O-t-Bu)
S16b (R = CH$_2$CH$_2$CO-t-Bu)

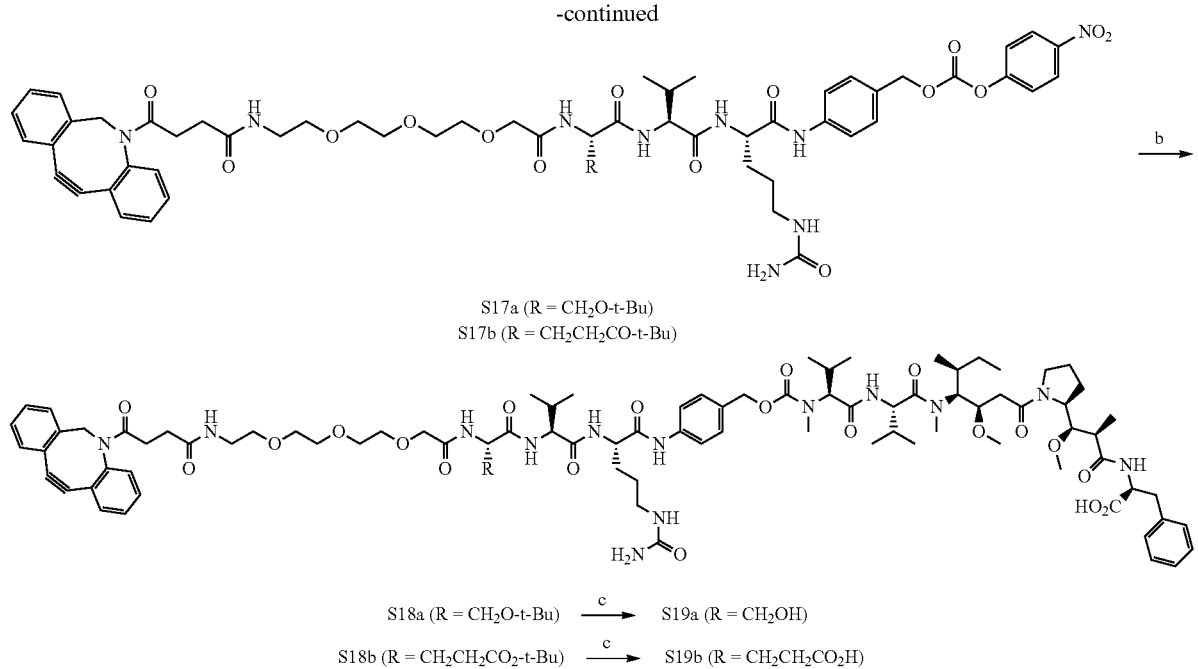

S17a (R = CH$_2$O-t-Bu)
S17b (R = CH$_2$CH$_2$CO-t-Bu)

S18a (R = CH$_2$O-t-Bu) →c S19a (R = CH$_2$OH)

S18b (R = CH$_2$CH$_2$CO$_2$-t-Bu) →c S19b (R = CH$_2$CH$_2$CO$_2$H)

Reagents and conditions: (a) bis(4-nitrophenyl) carbonate, DMAP, DMF, room temp, 2 h; (b) MMAF, DIPEA, HOAt, DMF, 37° C., overnight; (c) 20% TFA/DCM, 0° C., 4 h.

FmocSPPS

Conditions
Coupling: Fmoc-amino acid (4 equiv)
　　　　　HATU (4 equiv.)
　　　　　DIPEA (6 equiv.)
DBCO capping: DBCO acid (2 equiv.)
　　　　　HATU (2 equiv.)
　　　　　DIPEA (4 equiv.)
Fmoc deprotection: 20% piperidine in DMF
Resin cleavage: 1% TFA in DCM Fmoc Solid-Phase Peptide Synthesis (Fmoc SPPS) for DBCO-Capped Compounds (S16a) and (S16b).

After peptide elongation and pegylation, the resin was treated with DBCO acid (2 equiv., Broadpharm), HATU (2 equiv.), and DIPEA (3 equiv.) in DMF for 1 h and then washed with DMF (5×5 mL) and DCM (5×5 mL). The resin was treated with 1% TFA/DCM at room temperature for 1 h. The solution was concentrated in vacuo and the crude peptides were precipitated with cold diethyl ether (5-6 mL) followed by centrifugation at 1,000×g for 5 min (3 times). The crude products were purified by preparative RP-HPLC under basic conditions. Purity was confirmed by LC-MS under basic conditions.

S16a: 6.4 mg, total yield: 27% (based on the resin loading rate). White powder. HRMS (ESI) Calcd. For C$_{52}$H$_{70}$N$_8$O$_{12}$Na [M+Na]$^+$: 1021.5005. Found: 1021.4996.

S16b: 7.3 mg, total yield: 29% (based on the resin loading rate). White powder. HRMS (ESI) Calcd. For C$_{54}$H$_{72}$N$_8$O$_{13}$Na [M+Na]$^+$: 1063.5111. Found: 1063.5131.

DBCO-peg$_3$-Ser(tBu)-Val-Cit-PABC-PNP (S17a).

To a solution of S16a (6.2 mg, 0.0062 mmol) in DMF (500 µL) were added bis(2,4-dinitrophenyl) carbonate (9.4 mg, 0.031 mmol) and DMAP (1.5 mg, 0.0124 mmol). The resulting mixture was stirred at room temperature for 2.5 h under Ar. The reaction was quenched with 1% formic acid in ACN and a few drops of MeOH. The crude products were purified by preparative RP-HPLC to afford S17a (2.8 mg, 38%). White powder. HRMS (ESI) Calcd. For C$_{59}$H$_{73}$N$_9$O$_{16}$Na [M+Na]$^+$: 1186.5067. Found: 1186.5075. Peptide S17b was prepared from S16b in a similar manner.

DBCO-peg$_3$-Glu(tBu)-Val-Cit-PABC-PNP (S17b).

880 µg, 84%. White powder. HRMS (ESI) Calcd. For C$_{61}$H$_{76}$N$_9$O$_{17}$ [M+H]$^+$: 1206.5354. Found: 1206.5388.

DBCO-peg$_3$-Ser(tBu)-Val-Cit-PABC-MMAF (S18a).

A solution of S17a (2.8 mg, 0.00238 mmol) in DMF (238 µL) was mixed with monomethyl auristatin F TFA salt (3.0 mg, 0.00357 mmol, Levena Biopharma), 4.76 µL of 1M HOAt in DMF (0.00476 mmol), and DIPEA (2 µL, 0.012 mmol). The resulting mixture was stirred overnight at 37° C. The crude products were directly purified by preparative RP-HPLC under basic conditions to afford peptide S18a (1.1 mg, 26%). Purity was confirmed by LC-MS under basic conditions. White powder. HRMS (ESI) Calcd. For C$_{92}$H$_{133}$N$_{13}$O$_{21}$Na [M+Na]$^+$: 1778.9631. Found: 1778.9637. Peptide S18b was prepared from S17b in a similar manner.

DBCO-peg$_3$-Glu(tBu)-Val-Cit-PABC-MMAF (S18b).

1.4 mg, 33%. Purity was confirmed by LC-MS under basic conditions. White powder. HRMS (ESI) Calcd. For C$_{94}$H$_{135}$N$_{13}$O$_{22}$Na [M+Na]$^+$: 1820.9737. Found: 1820.9706.

DBCO-peg$_3$-Ser-Val-Cit-PABC-MMAF (S19a).

TFA (60 µL) was added to a DCM solution (240 µL) of compound S18a (1.1 mg, 0.6 µmol) at 0° C. After being stirred at 0° C. for 4 h, the reaction mixture was quenched with saturated NH$_4$OH (300 µL). The resulting mixture was directly purified by preparative RP-HPLC under basic conditions to afford peptide S19a (550 µg, 53%). Purity was confirmed by LC-MS under basic conditions. White powder. HRMS (ESI) Calcd. For $C_{88}H_{125}N_{13}O_{21}Na$ $[M+Na]^+$: 1722.9005. Found: 1722.9007. Peptide S19b was prepared from S18b in a similar manner.

DBCO-peg$_3$-Glu-Val-Cit-PABC-MMAF (S19b).

650 µg, 47%. Purity was confirmed by LC-MS under basic conditions. White powder. HRMS (ESI) Calcd. For $C_{90}H_{127}N_{13}O_{22}Na$ $[M+Na]^+$: 1764.9111. Found: 1764.9072.

Example 8—Assay Protocols, Biological Data, and Analysis

Cathepsin B-mediated cleavage assay using pyrene probes. Each test compound (10 mM in DMSO, 2 µL) was mixed with 97 µL of MES buffer (25 mM MES-Na, 1 mM DTT, pH 5.0) and 1 µL of 1-pyrenemethylamine (10 mM in DMSO, as an internal standard). The mixture was incubated at 37° C. for 10 min. Human liver cathepsin B (20 ng/µL, 100 µL, EMD Millipore) in MES buffer was added to the mixture, followed by incubation at 37° C. Aliquots (10 µL) were collected at each time point (0, 0.5, 1, 3, 24, and 48 h). Cold acetonitrile containing 1% formic acid (40 µL) was added to precipitate proteins. Precipitated proteins were separated by centrifugation (15,000 g, 4° C., 30 min) and supernatant of each sample was analyzed for quantification by analytical HPLC (UV absorption at 342 nm). The amount of each probe was normalized to the peak area of the internal standard. All assays were performed at least three times in technical duplicate, and data shown are representative of the replicates.

Plasma stability test using pyrene probes. Each test compound (10 mM in DMSO, 2 µL) was mixed with 1 µL of 1-pyrenemethylamine (10 mM in DMSO, as an internal standard) and incubated at 37° C. for 10 min. Pooled healthy human plasma or BALB/c mouse plasma (197 µL, Innovative Research) was added to the mixture, followed by incubation at 37° C. Aliquots (10 µL) were collected at each time point (0, 1, 6, 24, 48, and 96 h) and 40 µL of cold acetonitrile containing 1% formic acid was added to precipitate proteins. Supernatant of each sample was obtained and analyzed for quantification by analytical HPLC as described above. All assays were performed at least three times in technical duplicate, and data shown are representative of the replicates.

Cell culture. JIMT-1 (AddexBio), BT-474 (ATCC), and SKBR-3 (ATCC) were cultured in RPMI1640 (Corning) supplemented with 10% EquaFETAL® (Atlas Biologicals), 1% GlutaMAX® (Corning), 1% sodium pyruvate (Corning), and 1% penicillin-streptomycin (Gibco). KPL-4 (provided by Dr. Junichi Kurebayashi at Kawasaki Medical School, Kurebayshi et al., 1999) and MDA-MB-231 (ATCC) were cultured in DMEM (Corning) supplemented with 10% EquaFETAL®, 1% GlutaMAX®, and 1% penicillin-streptomycin. All cells were cultured at 37° C. under 5% $CO_2$ and passaged before becoming fully confluent up to 10 passages.

Expression and purification of monoclonal human antibodies. All antibodies were produced and validated prior to use according to the procedure reported previously (Anami et al., 2017 and Shi et al., 2014).

MTGase-mediated antibody-linker conjugation. Anti-HER2 IgG with a N297A mutation (291 µL in PBS, 11.79 mg/mL, 3.43 mg antibody) was incubated with branched linker 13 (18.3 µL of 100 mM stock in water, 80 equiv.) and 8% Activa TI® (77 µL, 40% solution in PBS, Ajinomoto, purchased from Modernist Pantry) at room temperature for 16-20 h. The reaction was monitored by LC-MS equipped with a MabPac RP column (3×50 mm, 4 µm, Thermo Scientific). Elution conditions were as follows: mobile phase A=water (0.1% formic acid); mobile phase B=acetonitrile (0.1% formic acid); gradient over 6.8 min from A:B=75:25 to 1:99; flow rate=0.4 mL/min. The conjugated antibody was purified by size exclusion chromatography (SEC, Superdex 200 increase 10/300 GL, GE Healthcare) with PBS (flow rate=0.6 mL/min) to afford antibody-linker conjugate (3.15 mg, 92% yield determined by bicinchoninic acid assay).

Strain-promoted azide-alkyne cycloaddition for payload installation. Strain-promoted azide-alkyne cycloaddition was performed according to the procedure reported previously (Anami et al., 2017). Purified ADCs were formulated in citrate buffer (20 mM sodium citrate and 1 mM citric acid, pH 6.6) containing 0.1% Tween 80 and trehalose (70 mg/mL, Dennler et al., 2014) and stored at 4° C.

Hydrophobic interaction chromatography (HIC) analysis. Each ADC (1 mg/mL, 10 µL in PBS) was analyzed using an Agilent 1100 HPLC system equipped with a MAbPac HIC-Butyl column (4.6×100 mm, 5 µm, Thermo Scientific). Elution conditions were as follows: mobile phase A=50 mM sodium phosphate supplemented with ammonium sulfate (1.5 M) and 5% isopropanol (pH 7.4); mobile phase B=50 mM sodium phosphate supplemented with 20% isopropanol (pH 7.4); gradient over 30 min from A:B=99:1 to 1:99; flow rate=0.5 mL/min.

Long-term stability test. Each ADC (1 mg/mL, 100 µL) in PBS was incubated at 37° C. Aliquots (10 µL) were taken at each time point (7, 14, and 28 days) and immediately stored at −80° C. until use. Samples were analyzed using an Agilent 1100 HPLC system equipped with a MAbPac SEC-1 analytical column (4.0×300 mm, 5 µm, Thermo Scientific). The conditions were as follows: flow rate=0.2 mL/min; solvent=PBS.

Plasma stability test using ADCs. stability in mouse plasma: Each ADC (100 µg/mL, 1.2 µL in PBS) was added to mouse plasma (118.8 µL) to a final concentration of 1 µg/mL. After incubation at 37° C. for varying time, the samples were taken (15 µL each) and stored at −80° C. until use. Samples were analyzed by sandwich ELISA assay. A high-binding 96 well plate (Corning) was coated with rabbit anti-MMAF antibody (100 ng/well, Levena Biopharma). After overnight coating, the plate was blocked with 100 µL of 2% BSA in PBS containing 0.05% Tween 20 (PBS-T) with agitation at room temperature for 1 h. Subsequently, the solution was removed and each ADC sample (100 µL in PBS-T containing 1% BSA) was added to each well of the plate, and the plate was incubated at room temperature for 2 h. After each well was washed three times with 100 µL of PBS-T, 100 µL of goat anti-human IgG Fab-HRP conjugate (1:10,000, Jackson ImmunoResearch) was added to each well. After being incubated at room temperature for 1 h, the plate was washed three times with 100 µL of PBS-T and 100 µL of TMB substrate (0.1 mg/mL) in phosphate-citrate buffer/30% $H_2O_2$ (1:0.0003 v/v, pH 5) was added. After color was developed for 10-30 min, 25 µL of 3N—HCl was added to each well and then the absorbance at 450 nm was recorded using a plate reader (Biotek Cytation 5). Concentrations were calculated based on a standard curve. [2] Stability in human plasma: assays were performed in the same manner using human HER2 (100 ng/well, ACROBiosystems) for plate coating, rabbit anti-MMAF antibody (1:5,000) and goat anti-rabbit IgG-HRP conjugate (1:10, 000) as secondary tertiary detection antibodies, respectively. All assays were performed in triplicate.

Human liver cathepsin B cleavage assay for ADCs. Each ADC (1 mg/mL) in 30 µL of MES buffer (10 mM MES-Na, 40 µM DTT, pH 5.0) was incubated at 37° C. for 10 min. Human liver cathepsin B in MES buffer (20 ng/µL, 30 µL, EMD Millipore) was added to the solution and the mixture was incubated at 37° C. Aliquots (20 µL) were collected at each time point (4, 12, and 24 h) and analyzed using an Agilent G1946C LC/ESI-MS equipped with a MabPac RP column (3×50 mm, 4 µm, Thermo Scientific). The analysis conditions were as follows: Mobile phase: 75:25 water (0.1% formic acid):acetonitrile (0.1% formic acid); gradient over 6.8 min (to 1:99 water (0.1% formic acid):acetonitrile (0.1% formic acid); flow rate=0.4 mL/min. Average DAR values were determined based on UV peak areas.

Cell-based ELISA. Cells (KPL-4 and MDA-MB-231) were seeded in a culture-treated 96-well clear plate (10,000 cells/well in 100 µL culture medium) and incubated at 37° C. with 5% $CO_2$ for 24 h. Paraformaldehyde (8%, 100 µL) was added to each well and incubated for 15 min at room temperature. The medium was aspirated and the cells were washed three times with 100 L of PBS. Cells were treated with 100 µL of blocking buffer (0.2% BSA in PBS) with agitation at room temperature for 2 h. After the blocking buffer was discarded, serially diluted samples (in 100 µL PBS containing 0.1% BSA) were added and the plate was incubated overnight at 4° C. with agitation. The buffer was discarded and the cells were washed three times with 100 µL of PBS containing 0.25% Tween 20. Cells were then incubated with 100 µL of donkey anti-human IgG-HRP conjugate (Jackson ImmunoResearch) (diluted 1:10,000 in PBS containing 0.1% BSA) was added and the plate was incubated at room temperature for 1 h. The plate was washed three times with PBS containing 0.25% Tween 20, and 100 µL of TMB substrate (0.1 mg/mL) in phosphate-citrate buffer/30% $H_2O_2$ (1:0.0003 v/v, pH 5) was added. After color was developed for 10-30 min, 25 µL of 3N—HCl was added to each well and then the absorbance at 450 nm was recorded using a plate reader (Biotek Cytation 5). Concentrations were calculated based on a standard curve. $K_D$ values were then calculated using Graph Pad Prism 7 software. All assays were performed in triplicate.

Cell viability assay. Cells were seeded in a culture-treated 96-well clear plate (5,000 cells/well in 50 µL culture medium) and incubated at 37° C. under 5% $CO_2$ for 24 h. Serially diluted samples (50 µL) were added to each well and the plate was incubated at 37° C. for 72 h (KPL-4 and SKBR-3) or 96 h (JIMT-1, MDA-MB-231, and BT-474). After the old medium was replaced with 100 µL fresh medium, 20 µL of a mixture of WST-8 (1.5 mg/mL, Cayman chemical) and 1-methoxy-5-methylphenazinium methylsulfate (1-methoxy PMS, 100 µM, Cayman Chemical) was added to each well, and the plate was incubated at 37° C. for 2 h. After gently agitating the plate, the absorbance at 460 nm was recorded using a plate reader. $EC_{50}$ values were calculated using Graph Pad Prism 7 software. All assays were performed in quadruplicate.

Animal experiments. All procedures were approved by the Animal Welfare Committee of the University of Texas Health Science Center at Houston and performed in accordance with the institutional guidelines for animal care and use.

In vivo pharmacokinetics study. Female BALB/c mice (6-8 weeks old, n=3/group, Jackson Laboratory) were injected with each mAb or ADC sample (100 µL) at a dose of 3 mg/kg via the retro-orbital sinus vein. After injection, blood (5-10 µL) was drawn through the tail vein at each time point (15 min, 6 h, 1 day, 2 days, 4 days, 9 days, and 14 days) and processed with 5 mM EDTA/PBS. Plasma samples were stored at −80° C. until use. All mice were humanely euthanized after last blood collection. Plasma samples were analyzed by sandwich ELISA. For determination of the total antibody concentration (both conjugated and unconjugated), goat anti-human IgG Fc antibody (500 ng/well) and goat anti-human IgG Fab-HRP conjugate (1:5,000, both from Jackson ImmunoResearch) were used for plate coating and detection, respectively. For determination of ADC concentration (conjugated only), rabbit anti-MMAF antibody (100 ng/well, Levena Biopharma) and goat anti-human IgG Fab-HRP conjugate (1:10,000) were used in the same manner. Assays were performed in the same manner as described above (see the section of the plasma stability test for ADCs). Concentrations were calculated based on a standard curve. Area under the curve (AUC, g day $mL^{-1}$) and half-lives at the elimination phase ($t_{1/2\beta}$) were determined using GraphPad Prism 7.

In vivo xenograft mouse models of human breast cancer. To produce KPL-4 or JIMT-1 tumors, female NCr nude mice (6-8 weeks old, Taconic Biosciences, were orthotopically injected into the mammary fat pad with 5-7×10⁶ cells suspended in 50 µL of 1:1 PBS/Cultrex® BME Type 3 (Trevigen). When the tumor volume reached ~100 mm³, mice were randomly assigned to three or four groups (n=4 for vehicle in the JIMT-1 model; n=3 for vehicle in the KPL-4 model; n=5 for ADCs) and preconditioned with sterile-filtered human IgG (30 mg/kg, Innovative Research) injected via the tail vein (Stefan et al., 2017 and Nanna et al., 2017). After 24 h, a single dose of 100 µL VCit-ADC 14a (3 mg/kg), EVCit-ADC 14c (1 or 3 mg/kg), or vehicle was administered to mice intravenously. The tumor volume was monitored every 3 days using a digital caliper. Mice were euthanized when the tumor volume exceeded 1000 mm³, the tumor size exceeded 2 cm in diameter, greater than 15% weight loss was observed, or mice showed signs of distress.

Data reporting. No statistical analysis was performed to determine sample size prior to experiments, but the sample size for ADC groups was determined according to similar experiments in the field reported previously. We used minimal sample sizes for vehicle control in the xenograft studies because we did not intend to use this group for statistical analysis. The investigators were not blinded to allocation during experiments. No samples or animals were excluded from the studies. For the in vivo PK analysis, a Welch's t-test (two-tailed, unpaired, uneven variance) was used to determine statistical significance of the observed differences. For the xenograft model studies, a Mann-Whitney U test (two-tailed, unpaired, non-parametric) was used. Kaplan-Meier survival curve statistics were analyzed with a log-rank (Mantel-Cox) test. To adjust the family wise error rate with a Bonferroni correction, P values less than [0.05/the number of comparisons] were considered statistically significant.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

V. REFERENCES

The following references, to the extent that they provide exemplary procedural or other details supplementary to those set forth herein, are specifically incorporated herein by reference:

U.S. Pat. No. 5,200,534
U.S. Pat. No. 5,202,448
U.S. Pat. No. 5,229,529
U.S. Pat. No. 5,274,137
U.S. Pat. No. 5,279,949
U.S. Pat. No. 5,283,253
U.S. Pat. No. 5,294,637
U.S. Pat. No. 5,415,869
U.S. Pat. No. 5,821,263
U.S. Pat. No. 5,824,701
U.S. Pat. No. 5,869,680
U.S. Pat. No. 6,214,345
U.S. Pat. No. 6,232,287
U.S. Pat. No. 6,323,315
U.S. Pat. No. 6,528,481
U.S. Pat. No. 6,570,040
U.S. Pat. No. 7,375,078
U.S. Pat. No. 7,452,964
U.S. Pat. No. 7,671,010
U.S. Pat. No. 7,691,962
U.S. Pat. No. 7,781,565
U.S. Pat. No. 8,450,278
U.S. Pat. No. 8,507,445
U.S. Pat. No. 9,487,556
U.S. Pub. No. 2003/0096743
U.S. Pub. No. 2004/0005647
U.S. Pub. No. 2006/0034925
U.S. Pub. No. 2006/0115537
U.S. Pub. No. 2006/0223114
U.S. Pub. No. 2006/0234299
U.S. Pub. No. 2007/0148095
U.S. Pub. No. 2008/0279868
U.S. Pub. No. 2011/0053435
U.S. Pub. No. 2012/0141550
U.S. Pub. No. 2013/0138032
U.S. Pub. No. 2014/0024610
U.S. Pub. No. 2014/0087413
EP 1391213
EP 590267
WO 2008/083312
WO 2008/121949
WO 81/01145
WO 93/10076
WO 93/23555
WO 94/07876
WO 94/07880
WO 94/07881
WO 94/07882
WO 96/14856
WO 96/33212
WO 98/13059
WO 98/22451
WO 98/28288
WO 98/58927
WO 99/09021
WO 99/14209
WO 99/18113
Adem et al., *Bioconjugate Chem.*, 25, 656-664, 2014.
Agard et al., *J. Am. Chem. Soc.*, 126, 15046-15047, 2004.
Anami et al., *Org. Biomol. Chem.* 15, 5635-5642 (2017).
Axup et al., *Proc. Natl. Acad. Sci. U.S.A.*, 109, 16101-16106, 2012.
Barclay, et al. (eds.), The Leucocyte Antigen Facts Book, Academic Press, 1993.
Beck et al., *Nat. Rev. Drug Discov.* 16, 315-337 (2017).
Beerli et al., *PLoS ONE* 10, e0131177 (2015).
Behrens et al., *Mol. Pharmaceutics* 12, 3986-3998 (2015).
Behrens et al., *Mol. Pharmaceutics*, 12, 3986-3998, 2015.
Bryden et al., *Bioconjugate Chem.*, 25, 611-617, 2014.
Burke, et al., *Mol. Cancer Ther.* 16(1):116-123, 2017.
Burkly, et al., 2007
Caculitan et al., *Cancer Res.* 77, 7027-7037 (2017).
Campbell, et al., 1991.
Carl et al., *J. Med. Chem.*, 24(3):479-480, 1981.
Cazzamalli et al., *J. Control. Release* 246, 39-45, 2017.
Chari et al. *Angew. Chem. Int. Ed.* 53, 3796-3827, 2014.
Chooniedass et al., *Molecules*, 21, 1741, 2016.
Christie et al., *Antibodies* 6, 20-18 (2017).
Dal Corso et al., *Bioconjugate Chem.* 28, 1826-1833 (2017).
Deghenghi et al., *Endocrine* 14:29, 2001.
Dennler et al., *Bioconjugate Chem.*, 25, 569-578, 2014.
Dennler et al., *ChemBioChem*, 16, 861-867, 2015.
Diamantis et al., *Br. J. Cancer* 114, 362-367 (2016).
Doronina et al., *Bioconjugate Chem.* 17, 114-124 (2006).
Doronina et al., *Nature Biotechnology* 21 (7), 778-784, 2003. (erratum, p. 941).
Dorywalska et al., *Bioconjugate Chem.* 26, 650-659 (2015).
Dorywalska et al., *Mol. Cancer Ther.* 15, 958-970 (2016).
Drake et al., *Bioconjugate Chem.* 25, 1331-1341 (2014).
Dubowchik et al., 1999.
Dubowchik et al., *Bioconjugate Chem.*, 13, 855-869, 2002.
Dubowchik et al., *Bioorg. Med. Chem. Lett.*, 12, 1529-1532, 2002.
Dubowchik et al., *Pharmacology & Therapeutics*, 83, 67-123, 1999.
Eggink et al., *J. Biol. Chem.* 284:26941, 2009.
Elgersma et al., *Mol. Pharmaceutics* 12, 1813-1835 (2015).
Godwin et al., *Leukemia* 31, 1855-1868 (2017).
Gordon et al., *Bioconjugate Chem.* 26, 2198-2215 (2015).
Greene and Wuts, *Protective Groups in Organic Chemistry*, 3rd Ed., 1999.
Gregson et al., *J. Med. Chem.* 60, 9490-9507 (2017).
Hamblett et al., *Clin. Cancer Res.*, 10, 7063-7070, 2004.
*Handbook of Pharmaceutical Salts: Properties, and Use* (P. H. Stahl & C. G. Wermuth eds., Verlag Helvetica Chimica Acta, 2002).
Jeger et al., *Angew. Chem. Int. Ed.*, 49, 9995-9997, 2010.
Junutula et al., *Nat. Biotechnol.*, 26, 925-932, 2008.
Katz et al., *Clin. Cancer Res.*, 17, 6428-6436, 2011.
Kern et al., *J. Am. Chem. Soc.* 138, 1430-1445 (2016).
King et al., *J. Med. Chem.*, 45, 4336-4343, 2002.
Kurebayashi et al., *Br. J. Cancer* 79, 707-717 (1999).
Lehar et al., *Nature* 527, 323-328 (2015).
Levengood et al., *Angew. Chem. Int. Ed.*, 56, 733-737, 2017.
Lhospice et al., *Mol. Pharmaceutics* 12, 1863-1871 (2015).
Liu et al. *Proc. Natl. Acad. Sci., USA* 93:8618-8623, 1996.
LoRusso et al., *Clin. Cancer Res.* 17, 6437-6447 (2011).
Lu et al., *Int. J. Mol. Sci.*, 17, 561, 2016.
Lyon et al., *Nat. Biotechnol.*, 33, 733-735, 2015.
*March's Advanced Organic Chemistry: Reactions, Mechanisms, and Structure*, 2007.
Maruani et al., *Nat. Commun.*, 6, 6645, 2015.
Maruani et al., *Org. Biomol. Chem.*, 14, 6165-6178, 2016.

Matos et al. 2010.
McCombs et al., *AAPS J* 17, 339-351 (2015).
Mendelsohn et al., *Bioconjugate Chem.* 28, 371-381 (2017).
Nanna et al., *Nat. Commun.* 8, 1112 (2017).
Nechushtan et al., 1997.
Onda, et al., 2004.
Panowski et al., *mAbs*, 6, 34-45, 2013.
Perez et al. *Drug Discovery Today* 19, 869-881 (2014).
Phillips et al., *Cancer Res.*, 68, 9280-9290, 2008.
Polakis, *Pharmacol. Rev.*, 68, 3-19, 2016.
Popp et al., *Curr Protoc Protein Sci*, 15, Unit 15.3.1-15.3.9, 2009.
Rabuka et al., *Nat. Protoc.* 7, 1052-1067 (2012).
Reddy et al., *Cancer Immunol. Immunother.* 46, 25-33 (1998).
Remington's Pharmaceutical Sciences," 15th Edition, pages 1035-1038 and 1570-1580.
Ricart et al., *Clin. Cancer Res.* 17, 6417-6427 (2011).
Robinson et al., *RSC Adv.*, 7, 9073-9077, 2017.
Senter et al. *Nat. Biotechnol.* 30, 631-637 (2012).
Senter et al., *Methods Enzymol*, 502, 123-138, 2012.
Shen et al., *Nat. Biotechnol.* 30, 184-189 (2012).
Shi et al., *Breast Cancer Res.*, 16, R33, 2014.
Sievers et al., *Annu. Rev. Med.* 64, 15-29 (2013).
Sjogren, *J. Gastroenterol. Hepatol.*, 19:S69, 2004.
Smith and =March, March's *Advanced Organic Chemistry: Reactions, Mechanisms, and Structure*, Fifth Edition. Wiley-Interscience, 2001.
Srinivasarao et al., *Nat. Rev. Drug Discov.* 14, 203-219 (2015).
Staben et al. *Nat. Chem.* 8, 1112-1119, 2016.
Stefan et al., *Mol. Cancer Ther.* 16, 879-892 (2017).
Strop et al., *Chem. Biol.*, 20, 161-167, 2013.
Strop et al., *Nat. Biotechnol.* 33, 694-696 (2015).
Sun et al., *Bioconjugate Chem.* 28, 1371-1381 (2017).
Thompson (ed.), The Cytokine Handbook, Academic Press, San Diego, 1994.
Tian et al., *Proc. Natl. Acad. Sci. U.S.A.*, 111, 1766-1771, 2014.
Told et al., *J. Org. Chem.* 67, 1866-1872, 2002.
Tsuchikama and An, *Protein Cell*, DOI:10.1007/s13238-016-0323-0, 2016.
Tsuchikama et al., *Protein Cell* 9, 33-46 (2018).
van Geel et al., *Bioconjugate Chem.*, 26, 2233-2242, 2015.
VanBrunt et al., *Bioconjugate Chem.*, 26, 2249-2260, 2015.
Verma et al., *N. Engl. J. Med.* 367, 1783-1791 (2012).
Vogel, *A Textbook of Practical Organic Chemistry, Including Qualitative Organic Analysis*, Fourth Edition, New York: Longman, 1978.
Weitman, et al., 1992.
Winkles, 2008
Winthrop, et al., 2003.
Younes et al., *N. Engl. J. Med.* 363, 1812-1821 (2010).
Zhou et al., *Bioconjugate Chem.*, 25, 510-520, 2014.
Zhou, et al., 2011
Zimmerman et al., *Bioconjugate Chem.*, 25, 351-361, 2014.

What is claimed is:
1. A compound of the formula:

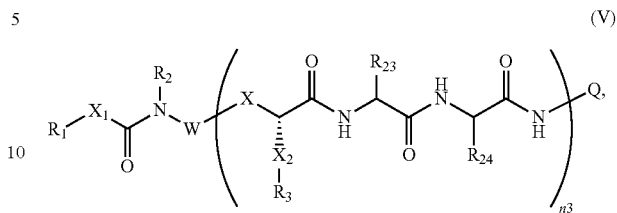

(V)

wherein:
X$_1$ is a covalent bond, alkanediyl$_{(C \leq 12)}$, or substituted alkanediyl$_{(C \leq 12)}$;
R$_1$ is hydrogen, —(OCH$_2$CH$_2$)$_{n1}$ZR$_6$, or substituted —(OCH$_2$CH$_2$)$_{n1}$ZR$_6$, wherein:
n1 is 0-50; and
R$_6$ is hydrogen, hydroxy, amine, mercapto, hydroxylamine, hydrazine, or azide; or
alkyl$_{(C \leq 12)}$, alkenyl$_{(C \leq 12)}$, alkynyl$_{(C \leq 12)}$, alkylhydrazine$_{(C \leq 12)}$, or a substituted version of any of these groups;
a polyglycine comprising from 1 to 6 glycine units; or
a substructure of the formula:

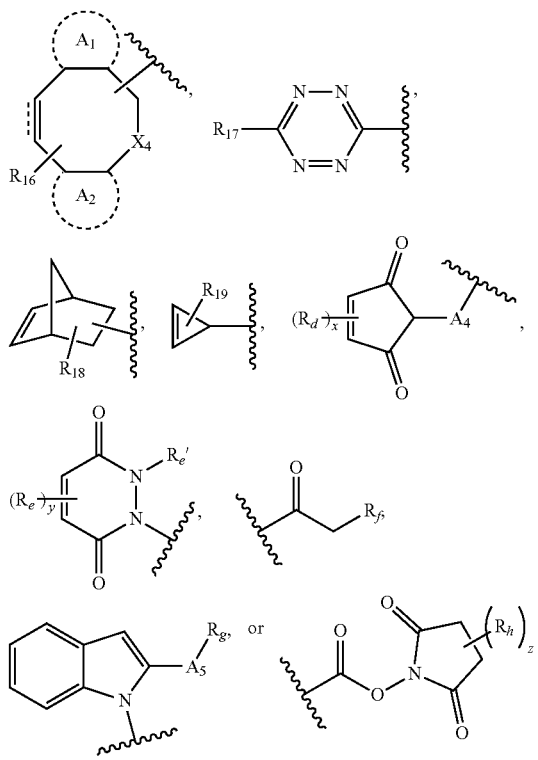

wherein:
A$_1$ and A$_2$ are each independently absent or arenediyl$_{(C \leq 12)}$, substituted arenediyl$_{(C \leq 12)}$, heteroarenediyl$_{(C \leq 12)}$, or substituted heteroarenediyl$_{(C \leq 12)}$, and form a fused arene$_{(C \leq 12)}$, substituted arene$_{(C \leq 12)}$, heteroarene$_{(C \leq 12)}$, or substituted heteroarene$_{(C \leq 12)}$;

$A_4$ or $A_5$ are each independently selected from a covalent bond, alkanediyl$_{(C\leq 8)}$, or substituted alkanediyl$_{(C\leq 8)}$;

$R_d$, $R_e$, $R_e'$, and $R_h$ are each independently selected from hydrogen, halo, sulfate, tosylate, mesylate, aryl$_{(C\leq 8)}$, or substituted aryl$_{(C\leq 8)}$;

$R_f$ is halo;

$R_g$ is amine, hydrazine, alkylamino$_{(C\leq 8)}$, substituted alkylamino$_{(C\leq 8)}$, dialkylamino$_{(C\leq 8)}$, substituted dialkylamino$_{(C\leq 8)}$, alkylhydrazine$_{(C\leq 8)}$, or substituted alkylhydrazine$_{(C\leq 8)}$;

$X_4$ is O, N, CH$_2$, or $X_4$ is alkanediyl$_{(C\leq 8)}$ or substituted alkanediyl$_{(C\leq 8)}$;

$R_{16}$ is hydroxy, amino, or oxo;

$R_{17}$ is carboxy; or
alkyl$_{(C\leq 12)}$, amido$_{(C\leq 12)}$, aryl$_{(C\leq 12)}$, heteroaryl$_{(C\leq 12)}$, —C(O)NR$_{20}$R$_{20}'$, or a substituted version of any of these groups wherein:
$R_{20}$ and $R_{20}'$ are each independently hydrogen; or
alkyl$_{(C\leq 12)}$, aryl$_{(C\leq 12)}$, or a substituted version of either of these groups;
$R_{18}$ and $R_{19}$ are each independently hydroxy, amino, halo; or
alkyl$_{(C\leq 12)}$, aryl$_{(C\leq 12)}$, or a substituted version of either of these groups;

Z is a covalent bond, alkanediyl$_{(C\leq 12)}$, —C(O)-alkanediyl$_{(C\leq 12)}$, —C(O)-alkanediyl$_{(C\leq 12)}$-C(O)NH—, or a substituted version of any of these groups;

$R_2$ is hydrogen, alkyl$_{(C\leq 12)}$, substituted alkyl$_{(C\leq 12)}$, acyl$_{(C\leq 12)}$, substituted acyl$_{(C\leq 12)}$, or a monovalent amino protecting group;

W is a covalent bond or a polyvalent polymer having 3-21 connection points;

n3 is 1 to 20 provided that when W is a covalent bond then n3 is 1 and when W is a polyvalent polymer then n3 is less than or equal to one less than the number of connection points;

each X is independently a covalent bond, alkanediyl$_{(C\leq 12)}$, or substituted alkanediyl$_{(C\leq 12)}$;

each $X_2$ is independently alkanediyl$_{(C\leq 12)}$ or substituted alkanediyl$_{(C\leq 12)}$;

each $R_3$ is independently hydroxy, or amino; or
alkoxy$_{(C\leq 12)}$, acyloxy$_{(C\leq 12)}$, alkylamino$_{(C\leq 12)}$, dialkylamino$_{(C\leq 12)}$, amido$_{(C\leq 12)}$, heteroaryl$_{(C\leq 12)}$, or a substituted version of any of these groups; or
—X$_9$—C(O)R$_7$, wherein:
$X_9$ is O, —NR$_b$—, or a covalent bond;
$R_b$ is hydrogen, alkyl$_{(C\leq 6)}$, substituted alkyl$_{(C\leq 6)}$, or a monovalent amino protecting group;
$R_7$ is hydroxy or amino; or
alkoxy$_{(C\leq 12)}$, alkylamino$_{(C\leq 12)}$, dialkylamino$_{(C\leq 12)}$, or a substituted version of any of these groups; or
-A$_3$SO$_2$NR$_{21}$R$_{21}'$, -A$_3$P(O)(OH)OR$_{22}$, or -A$_3$SO$_2$OR$_{22}'$, wherein:
$A_3$ is O, —NR$_c$—, or a covalent bond;
$R_c$ is hydrogen, alkyl$_{(C\leq 6)}$, substituted alkyl$_{(C\leq 6)}$, or a monovalent amino protecting group;
$R_{21}$, $R_{21}'$, $R_{22}$, and $R_{22}'$ are each independently hydrogen, alkyl$_{(C\leq 12)}$, cycloalkyl$_{(C\leq 12)}$, aryl$_{(C\leq 12)}$, heteroaryl$_{(C\leq 12)}$, aralkyl$_{(C\leq 12)}$, heteroaralkyl$_{(C\leq 12)}$, or a substituted version of any of these groups;

each $R_{23}$ is independently the side chain moiety of alanine, valine, leucine, isoleucine, phenylalanine, tyrosine, tryptophan, a hydroxyl-protected version of tyrosine, or an amino-protected version of tryptophan; and each $R_{24}$ is independently the side chain moiety of alanine, ornithine, lysine, arginine, citrulline, or an amino-protected version thereof;

each Q is independently a group of the formula:

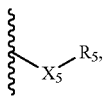

wherein:
each $R_5$ is independently hydrogen or —C(O)—R$_8$, wherein:
$R_8$ is a chemotherapeutic agent;
each $X_5$ is independently a covalent bond, O, S, —NH—, alkanediyl$_{(C\leq 12)}$, substituted alkanediyl$_{(C\leq 12)}$, —(OCH$_2$CH$_2$)$_{n2}$—, or substituted —(OCH$_2$CH$_2$)$_{n2}$—, wherein:
n2 is 0-50; or
a group of the formula:

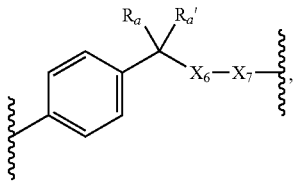

wherein:
$R_a$ and $R_a'$ are each independently hydrogen, alkyl$_{(C\leq 12)}$, or substituted alkyl$_{(C\leq 12)}$;
$X_6$ is O or —NR$_{26}$R$_{26}'$—, wherein:
$R_{26}$ and $R_{26}'$ are each independently alkyl$_{(C\leq 12)}$ or substituted alkyl$_{(C\leq 12)}$;
$X_7$ is a covalent bond, O, S, —NH—, —(OCH$_2$CH$_2$)$_{n3}$—, or substituted —(OCH$_2$CH$_2$)$_{n3}$—, wherein:
n3 is 0-50; or
a group of the formula:

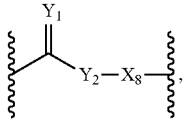

wherein:
Y is O or S;
$Y_2$ is O, S, —NH—, or —NR$_{27}$—, wherein:
$R_{27}$ is alkyl$_{(C\leq 12)}$ or substituted alkyl$_{(C\leq 12)}$; and
$X_8$ is a covalent bond, O, S, —NH—, —(OCH$_2$CH$_2$)$_{n3}$—, or substituted —(OCH$_2$CH$_2$)$_{n3}$—;

or a pharmaceutically acceptable salt thereof.

2. The compound of claim 1, wherein W is a polyvalent polymer.

3. The compound of claim 1, wherein X is a covalent bond.

4. The compound of claim 1, wherein $X_1$ is alkanediyl$_{(C \leq 12)}$, or substituted alkanediyl$_{(C \leq 12)}$.

5. The compound of claim 1, wherein $R_{24}$ is the side chain moiety of citrulline or an amino-protected version thereof.

6. The compound of claim 1, wherein $R_{23}$ is the side chain moiety of valine.

7. The compound of claim 1, wherein $X_2$ is alkanediyl$_{(C \leq 12)}$.

8. The compound of claim 1, wherein $R_3$ is hydroxy, amino, alkoxy$_{(C \leq 12)}$, substituted alkoxy$_{(C \leq 12)}$, alkylamino$_{(C \leq 12)}$, dialkylamino$_{(C \leq 12)}$, amido$_{(C \leq 12)}$, or —$X_9$—C(O)$R_7$.

9. The compound of claim 1, wherein $R_5$ is a —C(O)—$R_8$, wherein $R_8$ is a chemotherapeutic agent.

10. The compound of claim 9, wherein the chemotherapeutic agent is monomethyl auristatin E (MMAE), auristatin F (MMAF), or a derivative of auristatin, dolastatine, maytansine, duocarmycin, tubulysin, chalicheamicin, pyrrobenzodiazepine dimer, anthracycline, paclitaxel, vinblastine, or amanitin.

11. The compound of claim 1, wherein $X_5$ is a group of the formula:

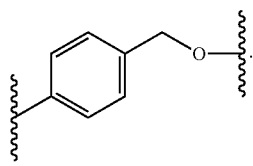 [SMILES: *OCc1ccc(*)cc1]

12. The compound of claim 1, wherein $R_1$ is —(OCH$_2$CH$_2$)$_{n1}$ZR$_6$, or substituted —(OCH$_2$CH$_2$)$_{n1}$ZR$_6$.

13. The compound of claim 1, wherein Z is —C(O)-alkanediyl$_{(C \leq 12)}$-C(O)NH— or a substituted —C(O)-alkanediyl$_{(C \leq 12)}$-C(O)NH—.

14. The compound of claim 1, wherein n1 is 0-10.

15. A conjugate of the formula:

T-L            (VI)

wherein:
T is a cell targeting moiety; and
L is a linker of claim 1.

16. The conjugate of claim 15, wherein T is an antibody.

17. A compound of the formula:

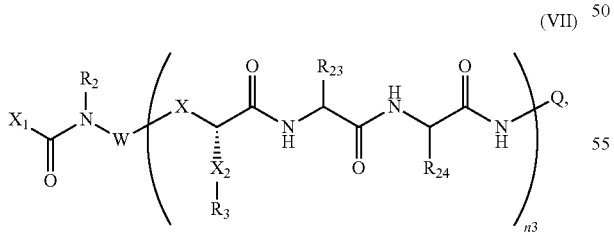
(VII)

wherein:
$X_1$ is alkyl$_{(C \leq 12)}$ or substituted alkyl$_{(C \leq 12)}$;
$R_2$ is hydrogen, alkyl$_{(C \leq 12)}$, substituted alkyl$_{(C \leq 12)}$, acyl$_{(C \leq 12)}$, substituted acyl$_{(C \leq 12)}$, or a monovalent amino protecting group;
W is a covalent bond or a polyvalent polymer having 3-21 connection points;

n3 is 1 to 20 provided that when W is a covalent bond n3 is 1 and when W is a polyvalent polymer n3 is less than or equal to one less than the number of connection points;

each X is independently a covalent bond, alkanediyl$_{(C \leq 12)}$, or substituted alkanediyl$_{(C \leq 12)}$;

each $X_2$ is independently alkanediyl$_{(C \leq 12)}$ or substituted alkanediyl$_{(C \leq 12)}$;

each $R_3$ is independently hydroxy, or amino; or alkoxy$_{(C \leq 12)}$, acyloxy$_{(C \leq 12)}$, alkylamino$_{(C \leq 12)}$, dialkylamino$_{(C \leq 12)}$, amido$_{(C \leq 12)}$, heteroaryl$_{(C \leq 12)}$, or a substituted version of any of these groups; or
—$X_9$—C(O)$R_7$, wherein:
$X_9$ is O, —NR$_b$—, or a covalent bond;
$R_b$ is hydrogen, alkyl$_{(C \leq 6)}$, substituted alkyl$_{(C \leq 6)}$, or a monovalent amino protecting group;
$R_7$ is hydroxy or amino; or
alkoxy$_{(C \leq 12)}$, alkylamino$_{(C \leq 12)}$, dialkylamino$_{(C \leq 12)}$, or a substituted version of any of these groups; or
-A$_3$SO$_2$NR$_{21}$R$_{21}$', -A$_3$P(O)(OH)OR$_{22}$, or -A$_3$SO$_2$OR$_{22}$', wherein:
$A_3$ is O, —NR$_c$—, or a covalent bond;
$R_c$ is hydrogen, alkyl$_{(C \leq 6)}$, substituted alkyl$_{(C \leq 6)}$, or a monovalent amino protecting group;
$R_{21}$, $R_{21}$', $R_{22}$, and $R_{22}$' are each independently hydrogen, alkyl$_{(C \leq 12)}$, cycloalkyl$_{(C \leq 12)}$, aryl$_{(C \leq 12)}$, heteroaryl$_{(C \leq 12)}$, aralkyl$_{(C \leq 12)}$, heteroaralkyl$_{(C \leq 12)}$, or a substituted version of any of these groups;

each $R_{23}$ is independently the side chain moiety of alanine, valine, leucine, isoleucine, phenylalanine, tyrosine, tryptophan, a hydroxyl-protected version of tyrosine, or an amino-protected version of tryptophan; and each $R_{24}$ is independently the side chain moiety of alanine, ornithine, lysine, arginine, citrulline, or an amino-protected version thereof;

each Q is independently a group of the formula:

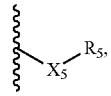

wherein:
each $R_5$ is independently hydrogen or —C(O)—$R_8$, wherein:
$R_8$ is a chemotherapeutic agent;
each $X_5$ is independently a covalent bond, O, S, —NH—, alkanediyl$_{(C \leq 12)}$, substituted alkanediyl$_{(C \leq 12)}$, —(OCH$_2$CH$_2$)$_{n2}$—, or substituted —(OCH$_2$CH$_2$)$_{n2}$—, wherein:
n2 is 0-50; or
a group of the formula:

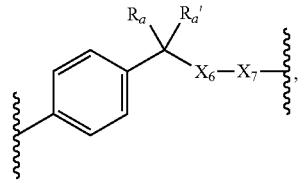

wherein:
$R_a$ and $R_a'$ are each independently hydrogen, alkyl$_{(C \leq 12)}$, or substituted alkyl$_{(C \leq 12)}$;
$X_6$ is O or —NR$_{26}$R$_{26}'$—, wherein:
$R_{26}$ and $R_{26}'$ are each independently alkyl$_{(C \leq 12)}$ or substituted alkyl$_{(C \leq 12)}$;
$X_7$ is a covalent bond, O, S, —NH—, —(OCH$_2$CH$_2$)$_{n3}$—, or substituted —(OCH$_2$CH$_2$)$_{n3}$—, wherein:
n3 is 0-50; or
a group of the formula:

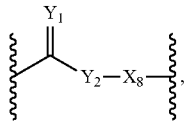

wherein:
Y is O or S;
$Y_2$ is O, S, —NH—, or —NR$_{27}$—, wherein:
$R_{27}$ is alkyl$_{(C \leq 12)}$ or substituted alkyl$_{(C \leq 12)}$; and
$X_8$ is a covalent bond, O, S, —NH—, —(OCH$_2$CH$_2$)$_{n3}$—, or substituted —(OCH$_2$CH$_2$)$_{n3}$—;
or a pharmaceutically acceptable salt thereof.

18. A pharmaceutical composition comprising a compound of claim 1 and an excipient.

19. A method of treating a disease or disorder in a patient comprising administering to the patient a therapeutically effective amount of a compound of claim 1.

* * * * *

UNITED STATES PATENT AND TRADEMARK OFFICE
CERTIFICATE OF CORRECTION

PATENT NO. : 12,084,403 B2
APPLICATION NO. : 18/173413
DATED : September 10, 2024
INVENTOR(S) : Kyoji Tsuchikama et al.

It is certified that error appears in the above-identified patent and that said Letters Patent is hereby corrected as shown below:

In the Claims

In Claim 1, Column 117, Line 55 and 56, delete "-$A_3SO_2NR_{21}R_{21}$', -$A_3P(O)(OH)OR_{22}$, or -$A_3SO_2OR_{22}$'" insert -- —$A_3SO_2NR_{21}R_{21}$', —$A_3P(O)(OH)OR_{22}$, or —$A_3SO_2OR_{22}$' -- thereof.

In Claim 1, Column 118, Line 57, delete "*Y is O or S*" insert -- *$Y_1$ is O or S* -- thereof.

In Claim 13, Column 119, Line 36 and 37, delete "*—C(O)-alkanediyl$_{(C≤12)}$-C(O)NH—*" insert -- *—C(O) —alkanediyl$_{(C≤12)}$—C(O)NH—* -- thereof.

In Claim 13, Column 119, Line 38, delete "*—C(O)-alkanediyl$_{(C≤12)}$-C(O)NH—*" insert -- *—C(O) —alkanediyl$_{(C≤12)}$—C(O)NH—* -- thereof.

In Claim 17, Column 120, Line 21 and 22, delete "-$A_3SO_2NR_{21}R_{21}$', -$A_3P(O)(OH)OR_{22}$, or -$A_3SO_2OR_{22}$'" insert -- —$A_3SO_2NR_{21}R_{21}$', —$A_3P(O)(OH)OR_{22}$, or —$A_3SO_2OR_{22}$' -- thereof.

Signed and Sealed this
Third Day of December, 2024

Katherine Kelly Vidal
*Director of the United States Patent and Trademark Office*